US012516056B2

(12) United States Patent
Rai et al.

(10) Patent No.: US 12,516,056 B2
(45) Date of Patent: Jan. 6, 2026

(54) COMPOUNDS FOR INHIBITION OF JANUS KINASE 1

(71) Applicant: MANKIND PHARMA LTD., New Delhi (IN)

(72) Inventors: Santosh Kumar Rai, Haryana (IN); Mahadev Bandgar, Haryana (IN); Sazid Ali, Haryana (IN); Himanshu Rai, Haryana (IN); Amol Pandurang Gunjal, Haryana (IN); Rakesh Iswar Patil, Haryana (IN); Srinivasa Reddy Bapuram, Haryana (IN); Anil Kumar, Haryana (IN)

(73) Assignee: MANKIND PHARMA LTD., New Delhi (IN)

( * ) Notice: Subject to any disclaimer, the term of this patent is extended or adjusted under 35 U.S.C. 154(b) by 976 days.

(21) Appl. No.: 17/614,114

(22) PCT Filed: May 26, 2020

(86) PCT No.: PCT/IN2020/050471
§ 371 (c)(1),
(2) Date: Nov. 24, 2021

(87) PCT Pub. No.: WO2020/240586
PCT Pub. Date: Dec. 3, 2020

(65) Prior Publication Data

US 2022/0235046 A1 Jul. 28, 2022

(30) Foreign Application Priority Data

May 28, 2019 (IN) ............................ 201911021098

(51) Int. Cl.
*C07D 471/04* (2006.01)
*A61P 1/00* (2006.01)
(Continued)

(52) U.S. Cl.
CPC .............. *C07D 471/04* (2013.01); *A61P 1/00* (2018.01); *A61P 17/06* (2018.01); *A61P 19/02* (2018.01)

(58) Field of Classification Search
CPC ........ C07D 471/04; A61P 17/06; A61P 19/02; A61P 1/00
(Continued)

(56) References Cited

U.S. PATENT DOCUMENTS 7,615,628 B2 * 11/2009 Hirao et al. ........... C07H 19/00 536/27.1
10,159,662 B2 * 12/2018 Xie ...................... A61K 31/437
(Continued)

FOREIGN PATENT DOCUMENTS

| | | |
|---|---|---|
| WO | 2009/099594 | 8/2009 |
| WO | 2013/116291 | 8/2013 |
| WO | 2019/076716 | 4/2019 |

OTHER PUBLICATIONS

International Search Report issued Aug. 28, 2020 in International (PCT) Application No. PCT/IN2020/050471.
(Continued)

*Primary Examiner* — Jeffrey S Lundgren
*Assistant Examiner* — Heather Dahlin
(74) *Attorney, Agent, or Firm* — Wenderoth, Lind & Ponack, L.L.P.

(57) ABSTRACT

An object of the invention is to provide compounds as selective JAK1 inhibitor, a process for preparation of the inhibitors, a composition containing the compounds and utility of the compounds.

14 Claims, 1 Drawing Sheet

(51) Int. Cl.
*A61P 17/06* (2006.01)
*A61P 19/02* (2006.01)

(58) Field of Classification Search
USPC .................................................... 514/210.18
See application file for complete search history.

(56) References Cited

U.S. PATENT DOCUMENTS

| | | | | |
|---|---|---|---|---|
| 2007/0135461 | A1 * | 6/2007 | Rodgers ............... | A61K 31/519 514/265.1 |
| 2018/0289680 | A1 | 10/2018 | Xie et al. | |

OTHER PUBLICATIONS

Vasbinder, Melissa M. et al., "Identification of azabenzimidazoles as potent JAK1 selective inhibitors", Bioorganic & Medicinal Chemistry Letters (2016), vol. 26, pp. 60-67.

CAS Registry Database (RN: 2177263-65-7), Entered STN: Feb. 20, 2018 (Feb. 20, 2018) Compound CAS RN: 2177263-65-7.

* cited by examiner

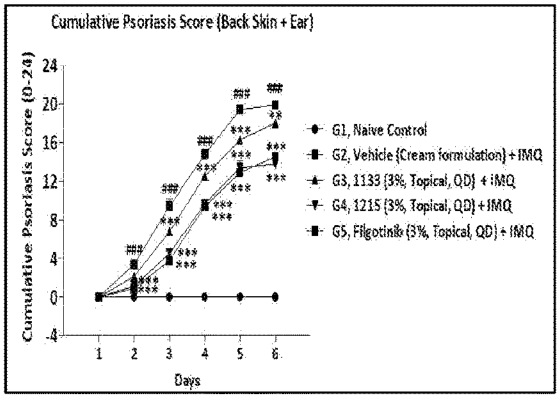
Figure 1a
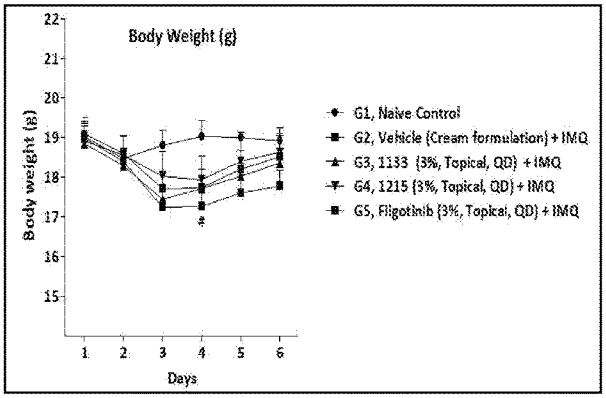
Figure 1b
Figure 1

COMPOUNDS FOR INHIBITION OF JANUS KINASE 1

FIELD OF THE INVENTION

The invention relates to inhibitors of Janus Kinase 1 (JAK1), a process for synthesis of the compounds of the present invention, composition comprising the compounds and use of the compounds for inhibition of JAK1.

BACKGROUND OF THE INVENTION

Cytokines are key drivers of several biological pathways and anti-cytokine therapy is indicated if there is any dysregulation in the pathway. Signalling pathways for Type I and Type II cytokine receptors, a family of receptors employed by over 50 cytokines, interleukins, interferons, colony stimulating factors, and hormones. Like other receptor super families, Type I and Type II cytokine receptors are related by their mode of intracellular signaling: they all employ JAKs. Janus Kinases (JAK) are intracellular tyrosine kinases linked to intracellular domains of many cytokine receptors. There are four JAK isoforms: JAK1, JAK2, JAK3 and TYK2. JAK1, JAK2, JAK3 and Tyrosine Kinase 2 (TYK2) bind directly to the intracellular domains of Type I/11 cytokine receptors and not to other classes of cytokine receptors. Different cytokine receptor families utilize specific JAK isoforms for signal transduction. Phosphorylation of JAK when cytokine binds to its cognate receptor leads to phosphorylation of other intracellular molecules that eventually leads to gene transcription. JAK-dependent cytokines are major contributors to immunopathology and that blocking such cytokines with biologics can be beneficial in immune-mediated diseases and in cancers and several other major disease and disorders.

Several inhibitors of JAK kinase exist. They block multiple JAKs and therefore inhibit the actions of a large variety of cytokines and several pan-JAK inhibitors continue to be developed. The JAK isoforms vary in function, and therefore there exists a need in the art for isoform-specific inhibitors that can reduce undesired effects from the administration of generalized JAK inhibitors. JAK1 plays a key role in types I and II interferon signaling and elicits signals from the interleukin-2, interleukin-4, gp130 and class II receptor families. As such, small molecule inhibition of JAK1 may intervene in the signaling pathways involved in oncology, inflammation and autoimmune diseases. However, to minimize adverse effects, especially those arising from JAK2 inhibition, the generation of selective inhibitors could in principle maintain efficacy and improve safety.

OBJECT OF THE INVENTION

An object of the invention is to provide compounds as selective JAK1 inhibitor, a process for preparation of the inhibitors, a composition containing the compounds and utility of the compounds.

SUMMARY OF THE INVENTION

The present invention discloses 1H-imidazo[4,5-b]pyridin-2(3H)-one as selective inhibitor of JAK 1 their pharmaceutically acceptable salts and isomers of formula I.

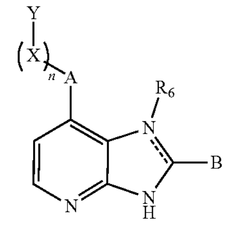

Wherein;

A is a 5 membered or a 6 membered carbocycle or heterocycle comprising 1 to 3 heteroatom selected from the group comprising O, N, S optionally substituted with $CH_3$, F or Cl;

B is H or alkoxy or O, —CO—, optionally substituted 3 to 8 carbocyclic ring, 3 to 8 membered heterocyclic ring containing 1 to 3 heteroatoms selected from the group comprising O, N, S, X is independently, H, $(CH_2)n$, —CO—, OCO, COO; $CO(CH_2)n$, $(NH_2)n$; $(CH_2)n(NH_2)n$; $(CH_2)n(NH_2)nCN$; CONH; $CONR_1R_2$, $CO(NH_2)n$; $(CH_2)nCO(NH_2)n$, $CO(NH_2)n(CH_2)CF_3$, $SO_2(CH_2)n$, $NH(CH_2)nCN$, unsubstituted or substituted 3-8 membered carbocylic ring or heterocyclic ring containing 1 to 3 heteroatoms selected from the group comprising O, N, S and $SO_2$, and substituents on the carboxylic or heterocyclic ring may be selected from Halogen, Alkoxy, CHMe, —$CH(CF_3)$, —$C(CF_3)(OH)$, $C(CF_3)(OMe)$, —CH(CN), CHOH, $CH(R_5)$, Y may be absent or may be selected from H, $R_1$, $R_2$, halo, $C_1$-$C_6$ Alkyl, $C_1$-$C_6$ Alkoxy CN, —CO—, $COR_1$, $(CH_2)n$, —$(CH_2)nCN$—, $CH_2CF_3$, COOH, $OR_1$, $NR_1R_2$, —$COOR_1$, —$CON(R_1)_2$, —$SO_2(CH_2)n$, —$SO_2N(R_1)_2$, —$OCOR_1$, $CONHCH(CH_3)$—$CF_3$, $CH_2CN$, $CH_2SO_2CH_3$—$NR_1COR_1$, —CONH, $CONR_1R_2$, —$CO(NH_2)n(CH_2)nSO_2$; —$CONH(CH_2)nOH$, $CONH(CH_2)nSO_2R_1R_2$, —CONH—$(CH_2)nCF_3$, —$CONH(CH_2)nCF_3$, —$NHCONH(CH_2)nCF_3$, $NHCONHR_1$, —$NHCOR_1R_2$, $NR_1CONR_1R_2$, $(NH_2)n$, —$NH_2CH_2$, $NH_2CH_2CF_3$, —$CH(CF_3)$—(CH)n-CO—N—$R_1R_2$, CH(CF3)-(CH)n-$SO_2$, (CH)n; CH(OH)$(CF_3)$(Heretocycle)$R_1$, optionally substituted 3 to 8 membered carbocyclic ring, or 3 to 8 membered saturated, mono-, fused- or bridged heterocyclic ring containing 1 to 3 heteroatoms, selected from the group comprising O, N, S or $SO_2$, optionally substituted 3 to 8 membered heterocyclic ring containing 1 to 3 heteroatoms, selected from the group comprising O, N, S or $SO_2$, wherein the substitution may independently be $R_1$ and $R_2$ at any position of the ring; $C_{1-6}$alk-aryl, Ar$C_{1-6}$alkyl;

$R_1$ and $R_2$ are independently selected from the group comprising H, halo, CN, CF3, hydroxyl, Amino, $SO_2$, $SO_2$, $C_1$-$C_6$ Alkyl, $SO_2$—$C_3$-$C_8$-cycloalkyl, $CH_2CN$, $CH_2CF_3$, unsubstituted or substituted $C_1$-$C_6$ straight or branched alkyl wherein the substituents are selected from halo, OH, CN, $C_1$-$C_6$ alkoxy, optionally substituted $NH_2$, $C_1$-$C_6$ alkylsulfonyl, optionally substituted $CONH_2$, unsubstituted or substituted $C_3$-$C_8$ carbocyclyl or 3-8 membered heterocyclic ring with 1-3 heteroatoms selected from O, N and S, $SO_2$, $C_1$-$C_6$ straight or branched alkenyl, $C_1$-$C_6$ straight or branched alkynyl, $C_1$-$C_6$ alkyloxy; $C_1$-$C_6$ alkylamino, $C_1$-$C_6$ alkylcarbonyl, C(O)—$C_3$-$C_8$-cycloalkyl, heteroalkyl, optionally substituted $CONH_2$, $C_3$-$C_8$ cycloalkyl, $C_3$-$C_8$cycloalkenyl, $C_3$-$C_8$heterocycloalkyl, $C_3$-$C_8$heterocycloalkenyl, carbocycyl, aryl, and heteroaryl, —$CH(CF_3)$—(CH)n-CO—N—$R_3R_4$, —CH $(CF_3)$—$(CH)n$-$SO_2$—$NR_3R_4$, $CH(CF_3)$—$(CH)n$-$NR_3R_4$, $CH(CF_3)$—$NR_3R_4$, $CH(CF_3)$—$(CH)n$-$SO_2$—$CHR_3R_4$, wherein cycloalkyl, cycloalkenyl, heterocycloalkyl, heterocycloalkenyl, carbocyclyl, aryl and heteroaryl groups are optionally substituted;

$R_3$ and $R_4$ are H, independently $CH_3$, $C_3$-$C_8$ cycloalkyl;

$R_5$ is unsubstituted or substituted 3-8 membered carbocylic ring or heterocyclic ring containing 1 to 3 heteroatoms selected from the group comprising O, N, S, $SO_2$;

$R_6$, is independently H, $C_1$-$C_6$ straight or branched alkyl, halogen;

X can be connected to Y at any atom so as to arrive at chemically viable bond;

n is 0 to 3.

The present invention also discloses a process for preparing the compounds of the present invention, a composition comprising the compounds of the present invention and utility of the compounds of the present invention as selective JAK1 inhibitors.

BRIEF DESCRIPTION OF FIGURES

FIG. 1 depicts cumulative Psoriasis Score and body weight of Example 1133 and 1215 in IMQ induced psoriasis mouse model. FIG. 1*a* is based on the Psoriasis Score. Data is shown as Mean±S.E.M. (n=8), * Significant difference as compared to Vehicle Control group. # Significant difference as compared to Naive Control group. Two-way ANOVA followed by Bonferroni Test. P<0.01 & ###/*P<0.001. FIG. 1(*b*) pertains to the body weight. Data is shown as Mean±S.E.M. (n=8), # Significant difference as compared to Naive control. Two-way ANOVA followed by Bonferroni Test #P<0.05.

DETAILED DESCRIPTION OF THE INVENTION

The present invention discloses 1H-imidazo[4,5-b]pyridin-2(3H)-one as selective inhibitor of JAK 1 their pharmaceutically acceptable salts and isomers of formula I.

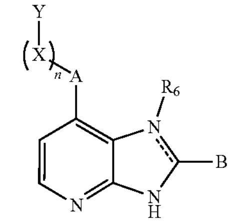

Wherein;

A is a 5 membered or a 6 membered carbocycle or heterocycle comprising 1 to 3 heteroatom selected from the group comprising O, N, S optionally substituted with $CH_3$, F or Cl;

B is H or alkoxy or O, —CO—, optionally substituted 3 to 8 carbocyclic ring, 3 to 8 membered heterocyclic ring containing 1 to 3 heteroatoms selected from the group comprising O, N, S, X is independently, H, $(CH_2)n$, —CO—, OCO, COO; $CO(CH_2)n$, $(NH_2)n$; $(CH_2)n(NH_2)n$; $(CH_2)n(NH_2)nCN$; CONH; $CONR_1R_2$, $CO(NH_2)n$; $(CH_2)nCO(NH_2)n$, $CO(NH_2)n(CH_2)CF_3$, $SO_2(CH_2)n$, $NH(CH_2)nCN$, unsubstituted or substituted 3-8 membered carbocylic ring or heterocyclic ring containing 1 to 3 heteroatoms selected from the group comprising O, N, S and $SO_2$, and substituents on the carboxylic or heterocyclic ring may be selected from Halogen, Alkoxy, CHMe, —$CH(CF_3)$, —$C(CF_3)(OH)$, $C(CF_3)(OMe)$, —CH(CN), CHOH, $CH(R_5)$, Y may be absent or may be selected from H, $R_1$, $R_2$, halo, $C_1$-$C_6$ Alkyl, $C_1$-$C_6$ Alkoxy CN, —CO—, $COR_1$, $(CH_2)n$, —$(CH_2)nCN$—, $CH_2CF_3$, COOH, $OR_1$, $NR_1R_2$, —$COOR_1$, —$CON(R_1)_2$, —$SO_2(CH_2)n$, —$SO_2N(R_1)_2$, —$OCOR_1$, $CONHCH(CH_3)$—$CF_3$, $CH_2CN$, $CH_2SO_2CH_3$—$NR_1COR_1$, —CONH, $CONR_1R_2$, —$CO(NH_2)n(CH_2)nSO_2$; —$CONH(CH_2)nOH$, $CONH(CH_2)nSO_2R_1R_2$, —CONH—$(CH_2)nCF_3$, —$CONH(CH_2)nCF_3$, —$NHCONH(CH_2)nCF_3$, $NHCONHR_1$, —$NHCOR_1R_2$, $NR_1CONR_1R_2$, $(NH_2)n$, —$NH_2CH_2$, $NH_2CH_2CF_3$, —$CH(CF_3)$—$(CH)n$-CO—N—$R_1R_2$, $CH(CF_3)$—$(CH)n$-$SO_2$, $(CH)n$; CH(OH)$(CF_3)$(Heretocycle)$R_1$, optionally substituted 3 to 8 membered carbocyclic ring, or 3 to 8 membered saturated, mono-, fused- or bridged heterocyclic ring containing 1 to 3 heteroatoms, selected from the group comprising O, N, S or $SO_2$, optionally substituted 3 to 8 membered heterocyclic ring containing 1 to 3 heteroatoms, selected from the group comprising O, N, S or $SO_2$, wherein the substitution may independently be $R_1$ and $R_2$ at any position of the ring; $C_{1-6}$alk-aryl, Ar$C_{1-6}$alkyl;

$R_1$ and $R_2$ are independently selected from the group comprising H, halo, CN, $CF_3$, hydroxyl, Amino, $SO_2$, $SO_2$, $C_1$-$C_6$ Alkyl, $SO_2$—$C_3$-$C_8$-cycloalkyl, $CH_2CN$, $CH_2CF_3$, unsubstituted or substituted $C_1$-$C_6$ straight or branched alkyl wherein the substituents are selected from halo, OH, CN, $C_1$-$C_6$ alkoxy, optionally substituted $NH_2$, $C_1$-$C_6$ alkylsulfonyl, optionally substituted $CONH_2$, unsubstituted or substituted $C_3$-$C_8$ carbocyclyl or 3-8 membered heterocyclic ring with 1-3 heteroatoms selected from O, N and S, $SO_2$, $C_1$-$C_6$ straight or branched alkenyl, $C_1$-$C_6$ straight or branched alkynyl, $C_1$-$C_6$ alkyloxy; $C_1$-$C_6$ alkylamino, $C_1$-$C_6$ alkylcarbonyl, C(O)—$C_3$-$C_8$-cycloalkyl, heteroalkyl, optionally substituted $CONH_2$, $C_3$-$C_8$ cycloalkyl, $C_3$-$C_8$cycloalkenyl, $C_3$-$C_8$heterocycloalkyl, $C_3$-$C_8$heterocycloalkenyl, carbocycyl, aryl, and heteroaryl, —$CH(CF_3)$—$(CH)n$-CO—N—$R_3R_4$, —CH(CF3)-(CH)n-$SO_2$—$NR_3R_4$, $CH(CF_3)$—$(CH)n$-$NR_3R_4$, $CH(CF_3)$—$NR_3R_4$, $CH(CF_3)$—$(CH)n$-$SO_2$—$CHR_3R_4$, wherein cycloalkyl, cycloalkenyl, heterocycloalkyl, heterocycloalkenyl, carbocyclyl, aryl and heteroaryl groups are optionally substituted;

$R_3$ and $R_4$ are H, independently $CH_3$, $C_3$-$C_8$ cycloalkyl;

$R_5$ is unsubstituted or substituted 3-8 membered carbocylic ring or heterocyclic ring containing 1 to 3 heteroatoms selected from the group comprising O, N, S, $SO_2$;

$R_6$, is independently H, $C_1$-$C_6$ straight or branched alkyl, halogen;

X can be connected to Y at any atom so as to arrive at chemically viable bond;

n is 0 to 3.

The compounds disclosed herein and their pharmaceutically acceptable salts can exist as single stereoisomers, racemates, and as mixtures of enantiomers and diastereomers. The compounds disclosed herein can also exist as geometric isomers. All such single stereoisomers, racemates and mixtures thereof, and geometric isomers are intended to be within the scope of the compounds disclosed herein.

Exemplary compounds of the present invention of Formula I are illustrated herein below at Table 1.

TABLE 1

| Exemplary compounds of the present invention | | |
|---|---|---|
| S. No | Structure | IUPAC Name |
| 1001. | 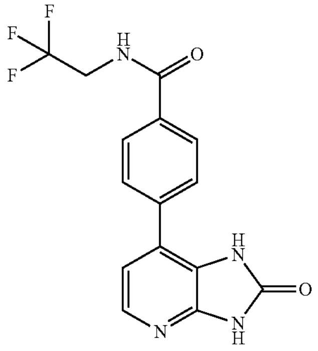 [SMILES: O=C(NCC(F)(F)F)c1ccc(-c2ccnc3[nH]c(=O)[nH]c23)cc1] | N-(2,2,2-trifluoroethyl)-4-(2,3-dihydro-2-oxo-1H-imidazo[4,5-b]pyridin-7-yl)benzamide |
| 1002. | 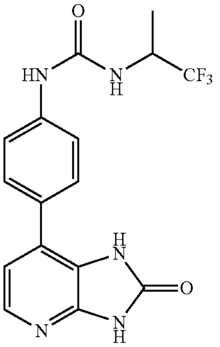 [SMILES: CC(NC(=O)Nc1ccc(-c2ccnc3[nH]c(=O)[nH]c23)cc1)C(F)(F)F] | 1-(1,1,1-trifluoropropan-2-yl)-3-(4-(2,3-dihydro-2-oxo-1H-imidazo[4,5-b]pyridin-7-yl)phenyl)urea |
| 1003. | 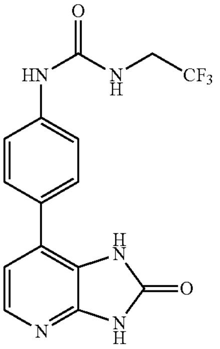 [SMILES: O=C(NCC(F)(F)F)Nc1ccc(-c2ccnc3[nH]c(=O)[nH]c23)cc1] | 1-(2,2,2-trifluoroethyl)-3-(4-(2,3-dihydro-2-oxo-1H-imidazo[4,5-b]pyridin-7-yl)phenyl)urea |
| 1004. | 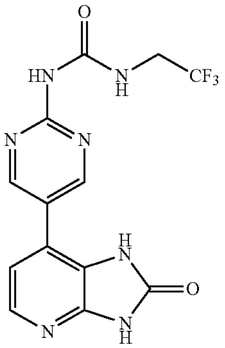 [SMILES: O=C(NCC(F)(F)F)Nc1ncc(-c2ccnc3[nH]c(=O)[nH]c23)cn1] | 1-(2,2,2-trifluoroethyl)-3-(5-(2,3-dihydro-2-oxo-1H-imidazo[4,5-b]pyridin-7-yl)pyrimidin-2-yl)urea |

TABLE 1-continued

| Exemplary compounds of the present invention | | |
|---|---|---|
| S. No | Structure | IUPAC Name |
| 1005. | 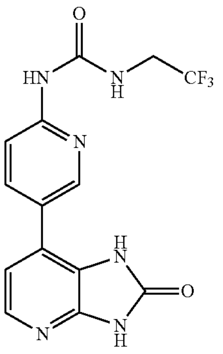 [SMILES: O=C(NCC(F)(F)F)Nc1ccc(-c2ccnc3[nH]c(=O)[nH]c23)cn1] | 1-(2,2,2-trifluoroethyl)-3-(5-(2,3-dihydro-2-oxo-1H-imidazo[4,5-b]pyridin-7-yl)pyridin-2-yl)urea |
| 1006. | 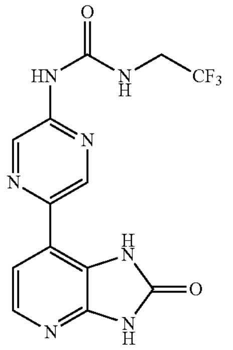 [SMILES: O=C(NCC(F)(F)F)Nc1cnc(-c2ccnc3[nH]c(=O)[nH]c23)cn1] | 1-(5-(2-oxo-2,3-dihydro-1H-imidazo[4,5-b]pyridin-7-yl)pyrazin-2-yl)-3-(2,2,2-trifluoroethyl)urea |
| 1007. | 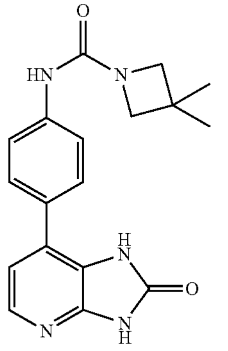 [SMILES: CC1(C)CN(C(=O)Nc2ccc(-c3ccnc4[nH]c(=O)[nH]c34)cc2)C1] | N-(4-(2,3-dihydro-2-oxo-1H-imidazo[4,5-b]pyridin-7-yl)phenyl)-3,3-dimethylazetidine-1-carboxamide |
| 1008. | 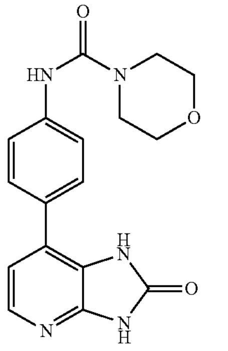 [SMILES: O=C(Nc1ccc(-c2ccnc3[nH]c(=O)[nH]c23)cc1)N1CCOCC1] | N-(4-(2,3-dihydro-2-oxo-1H-imidazo[4,5-b]pyridin-7-yl)phenyl)morpholine-4-carboxamide |

TABLE 1-continued
| Exemplary compounds of the present invention | | |
|---|---|---|
| S. No | Structure | IUPAC Name |
| 1009. | 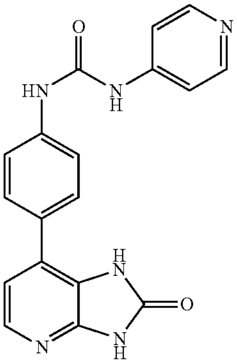 [SMILES: O=C(Nc1ccncc1)Nc1ccc(-c2ccnc3[nH]c(=O)[nH]c23)cc1] | 1-(4-(2,3-dihydro-2-oxo-1H-imidazo[4,5-b]pyridin-7-yl)phenyl)-3-(pyridin-4-yl)urea |
| 1010. | 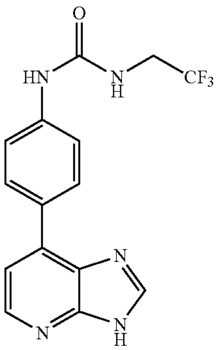 [SMILES: O=C(NCC(F)(F)F)Nc1ccc(-c2ccnc3[nH]cnc23)cc1] | 1-(4-(3H-imidazo[4,5-b]pyridin-7-yl)phenyl)-3-(2,2,2-trifluoroethyl)urea |
| 1011. | 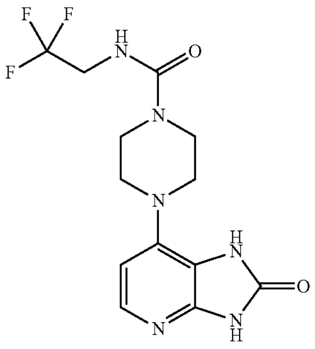 [SMILES: O=C(NCC(F)(F)F)N1CCN(c2ccnc3[nH]c(=O)[nH]c23)CC1] | N-(2,2,2-trifluoroethyl)-4-(2,3-dihydro-2-oxo-1H-imidazo[4,5-b]pyridin-7-yl)piperazine-1-carboxamide |
| 1012. | 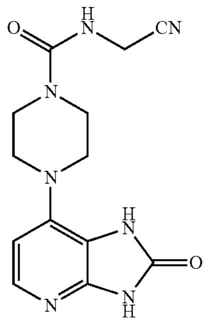 [SMILES: N#CCNC(=O)N1CCN(c2ccnc3[nH]c(=O)[nH]c23)CC1] | N-(cyanomethyl)-4-(2,3-dihydro-2-oxo-1H-imidazo[4,5-b]pyridin-7-yl)piperazine-1-carboxamide |

TABLE 1-continued

| Exemplary compounds of the present invention | | |
|---|---|---|
| S. No | Structure | IUPAC Name |
| 1013. | 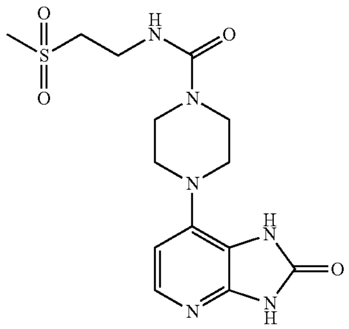 [SMILES: CS(=O)(=O)CCNC(=O)N1CCN(c2ccnc3[nH]c(=O)[nH]c23)CC1] | 4-(2,3-dihydro-2-oxo-1H-imidazo[4,5-b]pyridin-7-yl)-N-(2-(methylsulfonyl)ethyl)piperazine-1-carboxamide |
| 1014. | 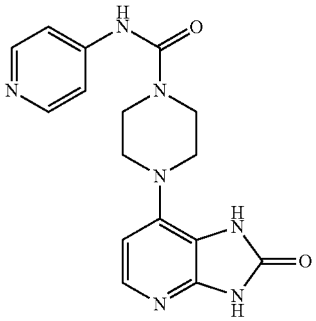 [SMILES: O=C(Nc1ccncc1)N1CCN(c2ccnc3[nH]c(=O)[nH]c23)CC1] | 4-(2,3-dihydro-2-oxo-1H-imidazo[4,5-b]pyridin-7-yl)-N-(pyridin-4-yl)piperazine-1-carboxamide |
| 1015. | 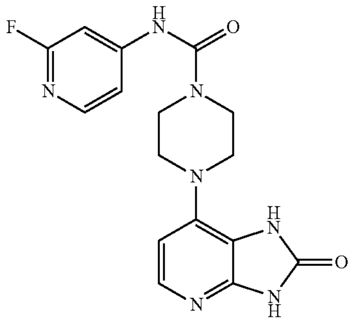 [SMILES: O=C(Nc1ccnc(F)c1)N1CCN(c2ccnc3[nH]c(=O)[nH]c23)CC1] | N-(2-fluoropyridin-4-yl)-4-(2,3-dihydro-2-oxo-1H-imidazo[4,5-b]pyridin-7-yl)piperazine-1-carboxamide |
| 1016. | 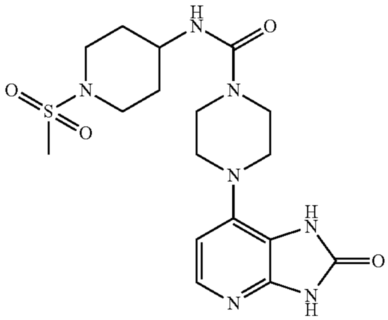 [SMILES: CS(=O)(=O)N1CCC(NC(=O)N2CCN(c3ccnc4[nH]c(=O)[nH]c34)CC2)CC1] | N-(1-(methylsulfonyl)piperidin-4-yl)-4-(2-oxo-2,3-dihydro-1H-imidazo[4,5-b]pyridin-7-yl)piperazine-1-carboxamide |

TABLE 1-continued

Exemplary compounds of the present invention

| S. No | Structure | IUPAC Name |
|---|---|---|
| 1017. | 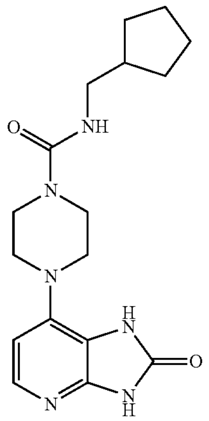 [SMILES: O=C(NCC1CCCC1)N1CCN(c2ccnc3[nH]c(=O)[nH]c23)CC1] | N-(cyclopentylmethyl)-4-(2,3-dihydro-2-oxo-1H-imidazo[4,5-b]pyridin-7-yl)piperazine-1-carboxamide |
| 1018. | 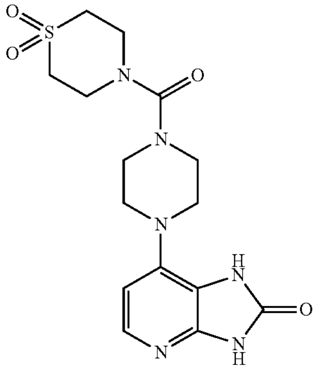 [SMILES: O=C(N1CCN(c2ccnc3[nH]c(=O)[nH]c23)CC1)N1CCS(=O)(=O)CC1] | 7-(4-(1,1-dioxidothiomorpholine-4-carbonyl)piperazin-1-yl)-1,3-dihydro-2H-imidazo[4,5-b]pyridin-2-one |
| 1019. | 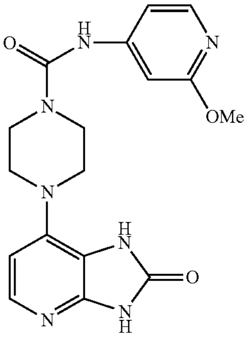 [SMILES: COc1cc(NC(=O)N2CCN(c3ccnc4[nH]c(=O)[nH]c34)CC2)ccn1] | 4-(2,3-dihydro-2-oxo-1H-imidazo[4,5-b]pyridin-7-yl)-N-(2-methoxypyridin-4-yl)piperazine-1-carboxamide |
| 1020. | 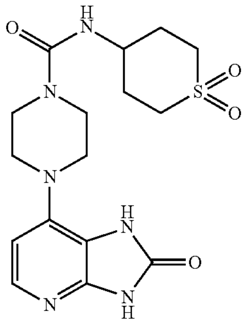 [SMILES: O=C(NC1CCS(=O)(=O)CC1)N1CCN(c2ccnc3[nH]c(=O)[nH]c23)CC1] | N-(1,1-dioxidotetrahydro-2H-thiopyran-4-yl)-4-(2-oxo-2,3-dihydro-1H-imidazo[4,5-b]pyridin-7-yl)piperazine-1-carboxamide |

TABLE 1-continued

| Exemplary compounds of the present invention | | |
|---|---|---|
| S. No | Structure | IUPAC Name |
| 1021. | 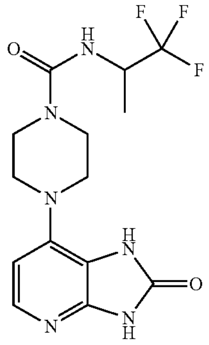 [SMILES: CC(NC(=O)N1CCN(c2ccnc3[nH]c(=O)[nH]c23)CC1)C(F)(F)F] | N-(1,1,1-trifluoropropan-2-yl)-4-(2,3-dihydro-2-oxo-1H-imidazo[4,5-b]pyridin-7-yl)piperazine-1-carboxamide |
| 1022. | 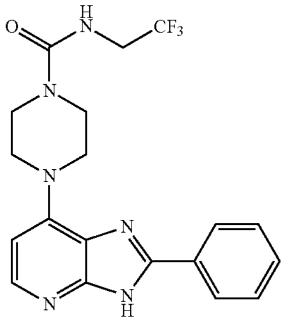 [SMILES: O=C(NCC(F)(F)F)N1CCN(c2ccnc3[nH]c(-c4ccccc4)nc23)CC1] | N-(2,2,2-trifluoroethyl)-4-(2-phenyl-3H-imidazo[4,5-b]pyridin-7-yl)piperazine-1-carboxamide |
| 1023. | 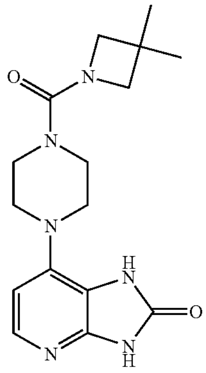 [SMILES: CC1(C)CN(C(=O)N2CCN(c3ccnc4[nH]c(=O)[nH]c34)CC2)C1] | 7-(4-(3,3-dimethylazetidine-1-carbonyl)piperazin-1-yl)-1,3-dihydro-2H-imidazo[4,5-b]pyridin-2-one |
| 1024. | 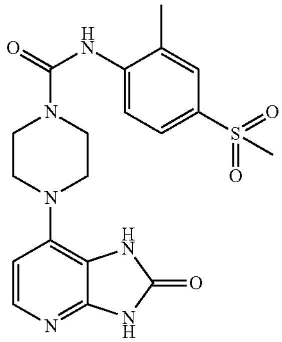 [SMILES: Cc1cc(S(C)(=O)=O)ccc1NC(=O)N1CCN(c2ccnc3[nH]c(=O)[nH]c23)CC1] | 4-(2,3-dihydro-2-oxo-1H-imidazo[4,5-b]pyridin-7-yl)-N-(2-methyl-4-(methylsulfonyl)phenyl)piperazine-1-carboxamide |

TABLE 1-continued

| Exemplary compounds of the present invention | | |
|---|---|---|
| S. No | Structure | IUPAC Name |
| 1025. | 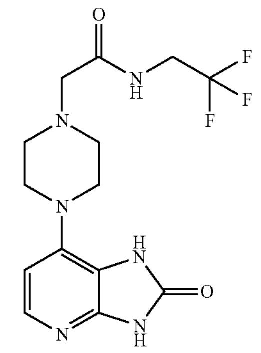 [SMILES: O=C(CN1CCN(c2ccnc3[nH]c(=O)[nH]c23)CC1)NCC(F)(F)F] | N-(2,2,2-trifluoroethyl)-2-(4-(2,3-dihydro-2-oxo-1H-imidazo[4,5-b]pyridin-7-yl)piperazin-1-yl)acetamide |
| 1026. | 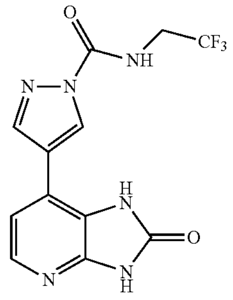 [SMILES: O=C(NCC(F)(F)F)n1cc(-c2ccnc3[nH]c(=O)[nH]c23)cn1] | N-(2,2,2-trifluoroethyl)-4-(2,3-dihydro-2-oxo-1H-imidazo[4,5-b]pyridin-7-yl)-1H-pyrazole-1-carboxamide |
| 1027. | 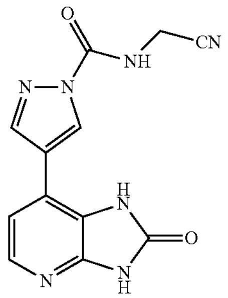 [SMILES: N#CCNC(=O)n1cc(-c2ccnc3[nH]c(=O)[nH]c23)cn1] | N-(cyanomethyl)-4-(2,3-dihydro-2-oxo-1H-imidazo[4,5-b]pyridin-7-yl)-1H-pyrazole-1-carboxamide |
| 1028. | 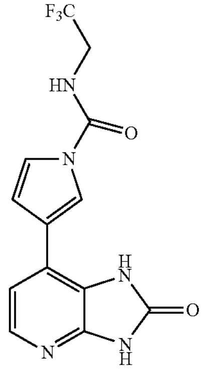 [SMILES: O=C(NCC(F)(F)F)n1ccc(-c2ccnc3[nH]c(=O)[nH]c23)c1] | N-(2,2,2-trifluoroethyl)-3-(2,3-dihydro-2-oxo-1H-imidazo[4,5-b]pyridin-7-yl)-1H-pyrrole-1-carboxamide |

TABLE 1-continued

| S. No | Structure | IUPAC Name |
|---|---|---|
| 1029. | 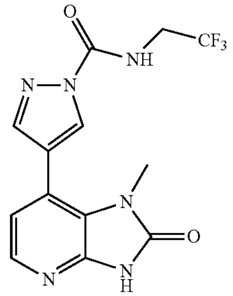 [SMILES: Cn1c(=O)[nH]c2nccc(-c3cnn(C(=O)NCC(F)(F)F)c3)c21] | N-(2,2,2-trifluoroethyl)-4-(2,3-dihydro-1-methyl-2-oxo-1H-imidazo[4,5-b]pyridin-7-yl)-1H-pyrazole-1-carboxamide |
| 1030. | 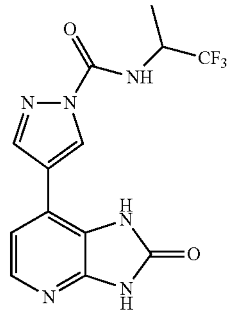 [SMILES: CC(NC(=O)n1cc(-c2ccnc3[nH]c(=O)[nH]c23)cn1)C(F)(F)F] | N-(1,1,1-trifluoropropan-2-yl)-4-(2,3-dihydro-2-oxo-1H-imidazo[4,5-b]pyridin-7-yl)-1H-pyrazole-1-carboxamide |
| 1031. | 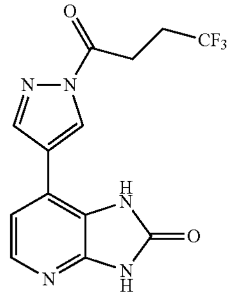 [SMILES: O=C(CCC(F)(F)F)n1cc(-c2ccnc3[nH]c(=O)[nH]c23)cn1] | 7-(1-(4,4,4-trifluorobutanoyl)-1H-pyrazol-4-yl)-1H-imidazo[4,5-b]pyridin-2(3H)-one |
| 1032. | 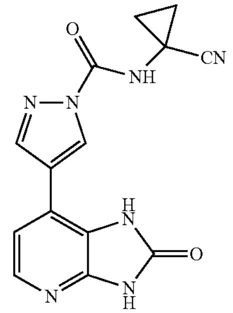 [SMILES: N#CC1(NC(=O)n2cc(-c3ccnc4[nH]c(=O)[nH]c34)cn2)CC1] | N-(1-cyanocyclopropyl)-4-(2,3-dihydro-2-oxo-1H-imidazo[4,5-b]pyridin-7-yl)-1H-pyrazole-1-carboxamide |
| 1033. | 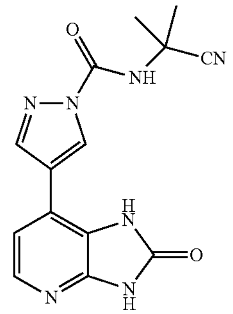 [SMILES: CC(C)(C#N)NC(=O)n1cc(-c2ccnc3[nH]c(=O)[nH]c23)cn1] | N-(2-cyanopropan-2-yl)-4-(2,3-dihydro-2-oxo-1H-imidazo[4,5-b]pyridin-7-yl)-1H-pyrazole-1-carboxamide |

Exemplary compounds of the present invention

TABLE 1-continued

| Exemplary compounds of the present invention | | |
|---|---|---|
| S. No | Structure | IUPAC Name |
| 1034. | 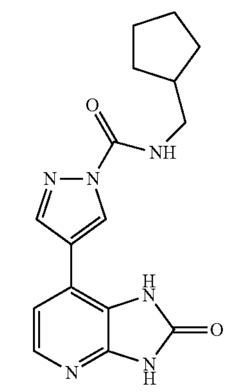 [SMILES: O=C(NCC1CCCC1)n1cc(-c2ccnc3[nH]c(=O)[nH]c23)cn1] | N-(cyclopentylmethyl)-4-(2,3-dihydro-2-oxo-1H-imidazo[4,5-b]pyridin-7-yl)-1H-pyrazole-1-carboxamide |
| 1035. | 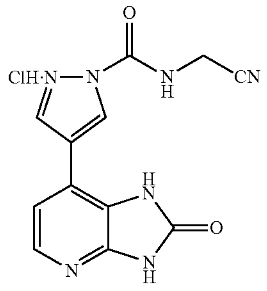 | N-(cyanomethyl)-4-(2,3-dihydro-2-oxo-1H-imidazo[4,5-b]pyridin-7-yl)-1H-pyrazole-1-carboxamide hydrochloride |
| 1036. | 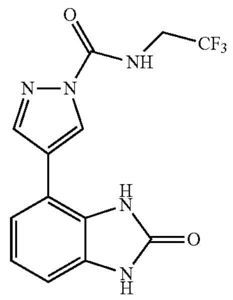 [SMILES: O=C(NCC(F)(F)F)n1cc(-c2cccc3[nH]c(=O)[nH]c23)cn1] | N-(2,2,2-trifluoroethyl)-4-(2,3-dihydro-2-oxo-1H-benzo[d]imidazol-4-yl)-1H-pyrazole-1-carboxamide |
| 1037. | 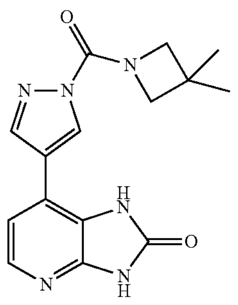 [SMILES: CC1(C)CN(C(=O)n2cc(-c3ccnc4[nH]c(=O)[nH]c34)cn2)C1] | 7-(1-(3,3-dimethylazetidine-1-carbonyl)-1H-pyrazol-4-yl)-1,3-dihydro-2H-imidazo[4,5-b]pyridin-2-one |

TABLE 1-continued

Exemplary compounds of the present invention

| S. No | Structure | IUPAC Name |
|---|---|---|
| 1038. | 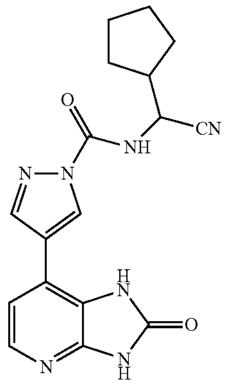 [SMILES: N#CC(NC(=O)n1cc(-c2ccnc3[nH]c(=O)[nH]c23)cn1)C1CCCC1] | N-(cyano(cyclopentyl)methyl)-4-(2,3-dihydro-2-oxo-1H-imidazo[4,5-b]pyridin-7-yl)-1H-pyrazole-1-carboxamide |
| 1039. | 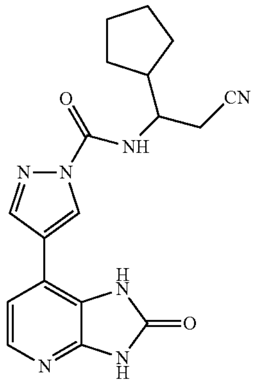 [SMILES: N#CCC(NC(=O)n1cc(-c2ccnc3[nH]c(=O)[nH]c23)cn1)C1CCCC1] | N-(2-cyano-1-cyclopentylethyl)-4-(2,3-dihydro-2-oxo-1H-imidazo[4,5-b]pyridin-7-yl)-1H-pyrazole-1-carboxamide |
| 1040. | 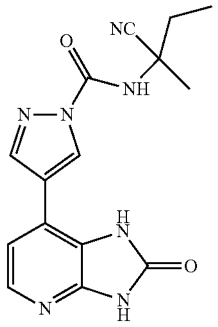 [SMILES: CCC(C)(C#N)NC(=O)n1cc(-c2ccnc3[nH]c(=O)[nH]c23)cn1] | N-(2-cyanobutan-2-yl)-4-(2,3-dihydro-2-oxo-1H-imidazo[4,5-b]pyridin-7-yl)-1H-pyrazole-1-carboxamide |
| 1041. | 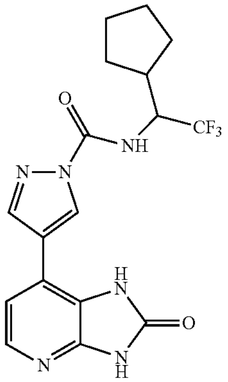 [SMILES: O=C(NC(C1CCCC1)C(F)(F)F)n1cc(-c2ccnc3[nH]c(=O)[nH]c23)cn1] | N-(1-cyclopentyl-2,2,2-trifluoroethyl)-4-(2,3-dihydro-2-oxo-1H-imidazo[4,5-b]pyridin-7-yl)-1H-pyrazole-1-carboxamide |

TABLE 1-continued

| Exemplary compounds of the present invention | | |
|---|---|---|
| S. No | Structure | IUPAC Name |
| 1042. | 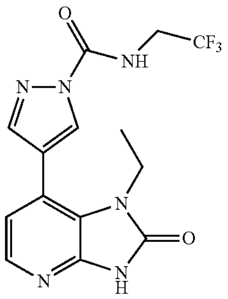 [SMILES: CCn1c(=O)[nH]c2nccc(-c3cnn(C(=O)NCC(F)(F)F)c3)c21] | 4-(1-ethyl-2,3-dihydro-2-oxo-1H-imidazo[4,5-b]pyridin-7-yl)-N-(2,2,2-trifluoroethyl)-1H-pyrazole-1-carboxamide |
| 1043. | 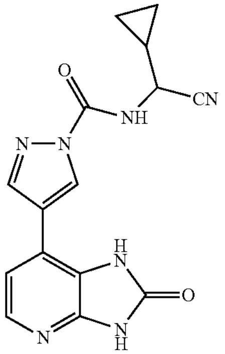 [SMILES: N#CC(NC(=O)n1cc(-c2ccnc3[nH]c(=O)[nH]c23)cn1)C1CC1] | N-(cyano(cyclopropyl)methyl)-4-(2,3-dihydro-2-oxo-1H-imidazo[4,5-b]pyridin-7-yl)-1H-pyrazole-1-carboxamide |
| 1044. | 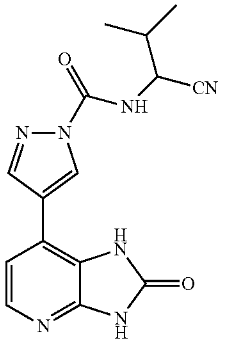 [SMILES: CC(C)C(C#N)NC(=O)n1cc(-c2ccnc3[nH]c(=O)[nH]c23)cn1] | N-(1-cyano-2-methylpropyl)-4-(2,3-dihydro-2-oxo-1H-imidazo[4,5-b]pyridin-7-yl)-1H-pyrazole-1-carboxamide |
| 1045. | 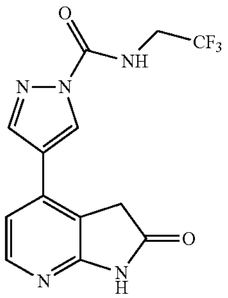 [SMILES: O=C1Cc2c(-c3cnn(C(=O)NCC(F)(F)F)c3)ccnc2N1] | N-(2,2,2-trifluoroethyl)-4-(2,3-dihydro-2-oxo-1H-pyrrolo[2,3-b]pyridin-4-yl)-1H-pyrazole-1-carboxamide |

TABLE 1-continued

| Exemplary compounds of the present invention | | |
|---|---|---|
| S. No | Structure | IUPAC Name |
| 1046. | 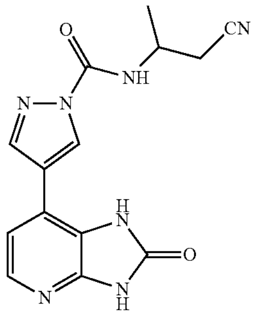 [SMILES: CC(CC#N)NC(=O)n1cc(-c2ccnc3[nH]c(=O)[nH]c23)cn1] | N-(1-cyanopropan-2-yl)-4-(2,3-dihydro-2-oxo-1H-imidazo[4,5-b]pyridin-7-yl)-1H-pyrazole-1-carboxamide |
| 1047. | 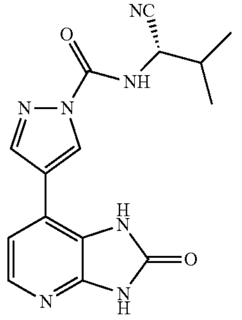 [SMILES: CC(C)[C@@H](C#N)NC(=O)n1cc(-c2ccnc3[nH]c(=O)[nH]c23)cn1] | N-((S)-1-cyano-2-methylpropyl)-4-(2,3-dihydro-2-oxo-1H-imidazo[4,5-b]pyridin-7-yl)-1H-pyrazole-1-carboxamide |
| 1048. | 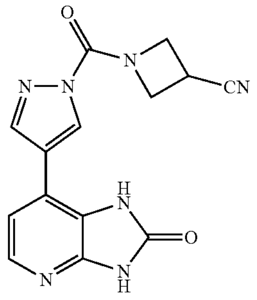 [SMILES: N#CC1CN(C(=O)n2cc(-c3ccnc4[nH]c(=O)[nH]c34)cn2)C1] | 1-(4-(2-oxo-2,3-dihydro-1H-imidazo[4,5-b]pyridin-7-yl)-1H-pyrazole-1-carbonyl)azetidine-3-carbonitrile |
| 1049. | 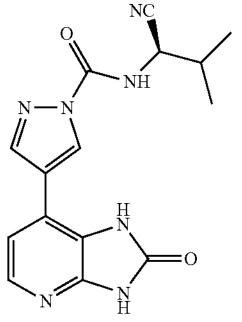 | N-((R)-1-cyano-2-methylpropyl)-4-(2,3-dihydro-2-oxo-1H-imidazo[4,5-b]pyridin-7-yl)-1H-pyrazole-1-carboxamide |

TABLE 1-continued

| Exemplary compounds of the present invention | | |
|---|---|---|
| S. No | Structure | IUPAC Name |
| 1050. | 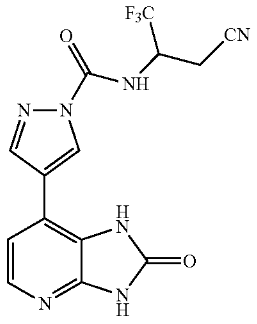 [SMILES: N#CCC(NC(=O)n1cc(-c2ccnc3[nH]c(=O)[nH]c23)cn1)C(F)(F)F] | N-(3-cyano-1,1,1-trifluoropropan-2-yl)-4-(2,3-dihydro-2-oxo-1H-imidazo[4,5-b]pyridin-7-yl)-1H-pyrazole-1-carboxamide |
| 1051. | 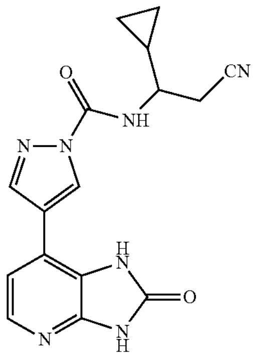 [SMILES: N#CCC(NC(=O)n1cc(-c2ccnc3[nH]c(=O)[nH]c23)cn1)C1CC1] | N-(2-cyano-1-cyclopropylethyl)-4-(2,3-dihydro-2-oxo-1H-imidazo[4,5-b]pyridin-7-yl)-1H-pyrazole-1-carboxamide |
| 1052. | 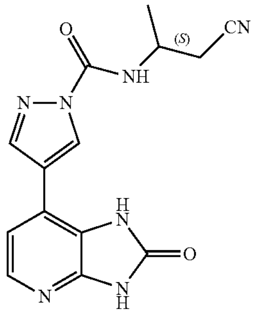 | N-(1-cyanopropan-2-yl)-4-(2,3-dihydro-2-oxo-1H-imidazo[4,5-b]pyridin-7-yl)-1H-pyrazole-1-carboxamide |
| 1053. | 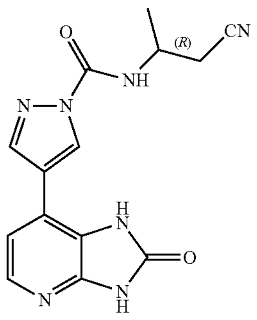 | N-(1-cyanopropan-2-yl)-4-(2,3-dihydro-2-oxo-1H-imidazo[4,5-b]pyridin-7-yl)-1H-pyrazole-1-carboxamide |

TABLE 1-continued

| Exemplary compounds of the present invention | | |
|---|---|---|
| S. No | Structure | IUPAC Name |
| 1054. | 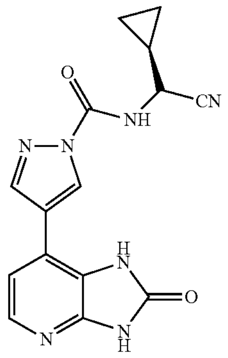 | N-((R)-cyano(cyclopropyl)methyl)-4-(2,3-dihydro-2-oxo-1H-imidazo[4,5-b]pyridin-7-yl)-1H-pyrazole-1-carboxamide |
| 1055. | 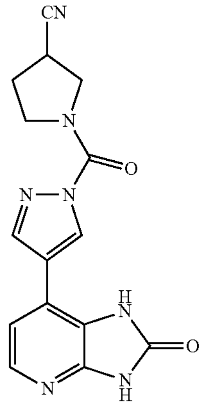 [SMILES: N#CC1CCN(C(=O)n2cc(-c3ccnc4[nH]c(=O)[nH]c34)cn2)C1] | 1-(4-(2-oxo-2,3-dihydro-1H-imidazo[4,5-b]pyridin-7-yl)-1H-pyrazole-1-carbonyl)pyrrolidine-3-carbonitrile |
| 1056. | 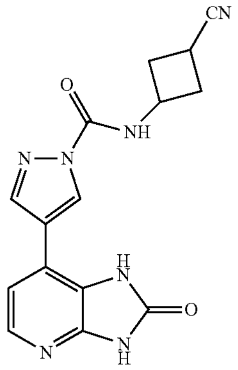 [SMILES: N#CC1CC(NC(=O)n2cc(-c3ccnc4[nH]c(=O)[nH]c34)cn2)C1] | N-(3-cyanocyclobutyl)-4-(2,3-dihydro-2-oxo-1H-imidazo[4,5-b]pyridin-7-yl)-1H-pyrazole-1-carboxamide |
| 1057. | 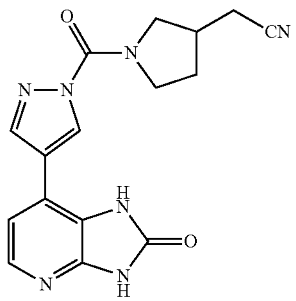 [SMILES: N#CCC1CCN(C(=O)n2cc(-c3ccnc4[nH]c(=O)[nH]c34)cn2)C1] | 2-(1-(4-(2-oxo-2,3-dihydro-1H-imidazo[4,5-b]pyridin-7-yl)-1H-pyrazole-1-carbonyl)pyrrolidin-3-yl)acetonitrile |

TABLE 1-continued

Exemplary compounds of the present invention

| S. No | Structure | IUPAC Name |
|---|---|---|
| 1058. | 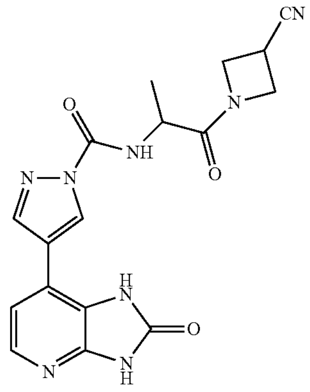 [SMILES: CC(NC(=O)n1cc(-c2ccnc3[nH]c(=O)[nH]c23)cn1)C(=O)N1CC(C#N)C1] | N-(1-(3-cyanoazetidin-1-yl)-1-oxopropan-2-yl)-4-(2-oxo-2,3-dihydro-1H-imidazo[4,5-b]pyridin-7-yl)-1H-pyrazole-1-carboxamide |
| 1059. | 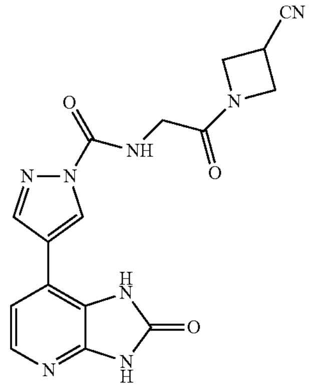 [SMILES: N#CC1CN(C(=O)CNC(=O)n2cc(-c3ccnc4[nH]c(=O)[nH]c34)cn2)C1] | N-(2-(3-cyanoazetidin-1-yl)-2-oxoethyl)-4-(2-oxo-2,3-dihydro-1H-imidazo[4,5-b]pyridin-7-yl)-1H-pyrazole-1-carboxamide |
| 1060. | 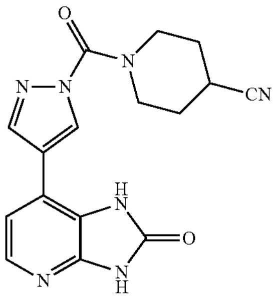 [SMILES: N#CC1CCN(C(=O)n2cc(-c3ccnc4[nH]c(=O)[nH]c34)cn2)CC1] | N-(2-(3-cyanoazetidin-1-yl)-2-oxoethyl)-4-(2-oxo-2,3-dihydro-1H-imidazo[4,5-b]pyridin-7-yl)-1H-pyrazole-1-carboxamide |
| 1061. | 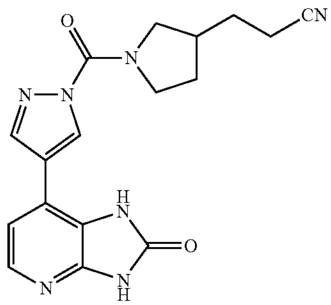 [SMILES: N#CCCC1CCN(C(=O)n2cc(-c3ccnc4[nH]c(=O)[nH]c34)cn2)C1] | 3-(1-(4-(2-oxo-2,3-dihydro-1H-imidazo[4,5-b]pyridin-7-yl)-1H-pyrazole-1-carbonyl)pyrrolidin-3-yl)propanenitrile |

TABLE 1-continued

Exemplary compounds of the present invention

| S. No | Structure | IUPAC Name |
|---|---|---|
| 1062. | 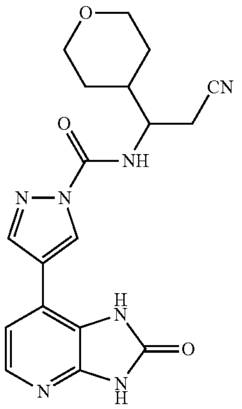 [SMILES: N#CCC(NC(=O)n1cc(-c2ccnc3[nH]c(=O)[nH]c23)cn1)C1CCOCC1] | N-(2-cyano-1-(tetrahydro-2H-pyran-4-yl)ethyl)-4-(2,3-dihydro-2-oxo-1H-imidazo[4,5-b]pyridin-7-yl)-1H-pyrazole-1-carboxamide |
| 1063. | 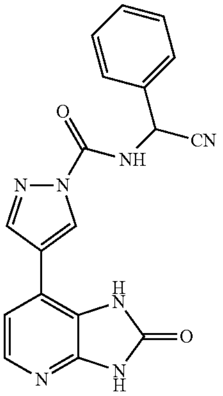 [SMILES: N#CC(NC(=O)n1cc(-c2ccnc3[nH]c(=O)[nH]c23)cn1)c1ccccc1] | N-(cyano(phenyl)methyl)-4-(2,3-dihydro-2-oxo-1H-imidazo[4,5-b]pyridin-7-yl)-1H-pyrazole-1-carboxamide |
| 1064. | 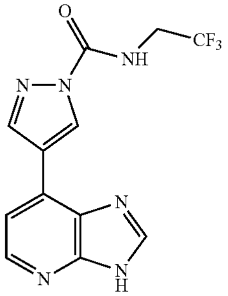 [SMILES: O=C(NCC(F)(F)F)n1cc(-c2ccnc3[nH]cnc23)cn1] | N-(2,2,2-trifluoroethyl)-4-(3H-imidazo[4,5-b]pyridin-7-yl)-1H-pyrazole-1-carboxamide |
| 1065. | 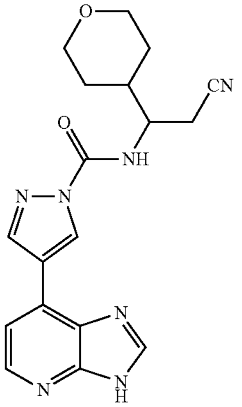 [SMILES: N#CCC(NC(=O)n1cc(-c2ccnc3[nH]cnc23)cn1)C1CCOCC1] | N-(2-cyano-1-(tetrahydro-2H-pyran-4-yl)ethyl)-4-(3H-imidazo[4,5-b]pyridin-7-yl)-1H-pyrazole-1-carboxamide |

TABLE 1-continued

| Exemplary compounds of the present invention | | |
|---|---|---|
| S. No | Structure | IUPAC Name |
| 1066. | 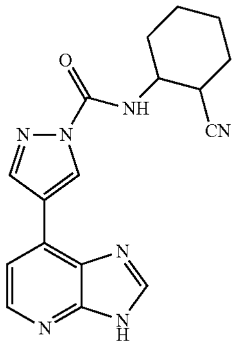 [SMILES: N#CC1CCCCC1NC(=O)n1cc(-c2ccnc3[nH]cnc23)cn1] | N-(2-cyanocyclohexyl)-4-(3H-imidazo[4,5-b]pyridin-7-yl)-1H-pyrazole-1-carboxamide |
| 1067. | 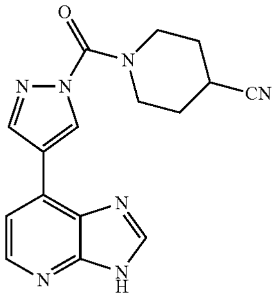 [SMILES: N#CC1CCN(C(=O)n2cc(-c3ccnc4[nH]cnc34)cn2)CC1] | 1-(4-(3H-imidazo[4,5-b]pyridin-7-yl)-1H-pyrazole-1-carbonyl)piperidine-4-carbonitrile |
| 1068. | 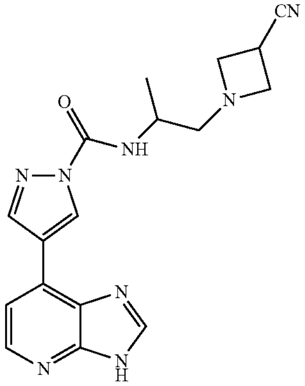 [SMILES: CC(CN1CC(C#N)C1)NC(=O)n1cc(-c2ccnc3[nH]cnc23)cn1] | N-(1-(3-cyanoazetidin-1-yl)propan-2-yl)-4-(3H-imidazo[4,5-b]pyridin-7-yl)-1H-pyrazole-1-carboxamide |
| 1069. | 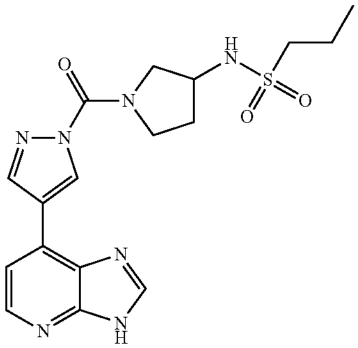 [SMILES: CCCS(=O)(=O)NC1CCN(C(=O)n2cc(-c3ccnc4[nH]cnc34)cn2)C1] | N-(1-(4-(3H-imidazo[4,5-b]pyridin-7-yl)-1H-pyrazole-1-carbonyl)pyrrolidin-3-yl)propane-1-sulfonamide |

TABLE 1-continued

Exemplary compounds of the present invention

| S. No | Structure | IUPAC Name |
|---|---|---|
| 1070. | 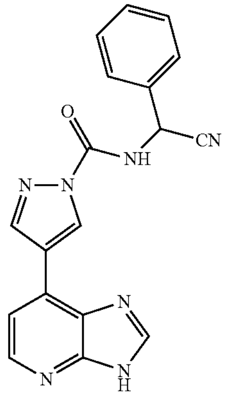 [SMILES: N#CC(NC(=O)n1cc(-c2ccnc3[nH]cnc23)cn1)c1ccccc1] | N-(cyano(phenyl)methyl)-4-(3H-imidazo[4,5-b]pyridin-7-yl)-1H-pyrazole-1-carboxamide |
| 1071. | 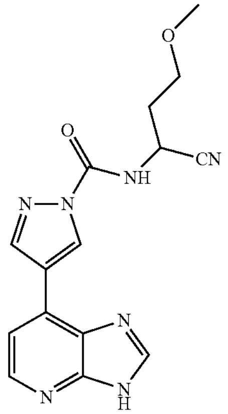 [SMILES: COCCC(C#N)NC(=O)n1cc(-c2ccnc3[nH]cnc23)cn1] | N-(1-cyano-3-methoxypropyl)-4-(3H-imidazo[4,5-b]pyridin-7-yl)-1H-pyrazole-1-carboxamide |
| 1072. | 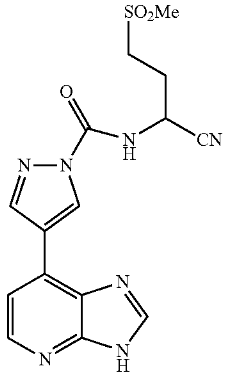 [SMILES: CS(=O)(=O)CCC(C#N)NC(=O)n1cc(-c2ccnc3[nH]cnc23)cn1] | N-(1-cyano-3-(methylsulfonyl)propyl)-4-(3H-imidazo[4,5-b]pyridin-7-yl)-1H-pyrazole-1-carboxamide |
| 1073. | 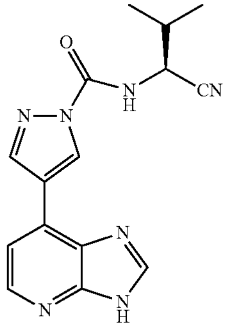 [SMILES: CC(C)[C@@H](C#N)NC(=O)n1cc(-c2ccnc3[nH]cnc23)cn1] | N-((S)-1-cyano-2-methylpropyl)-4-(3H-imidazo[4,5-b]pyridin-7-yl)-1H-pyrazole-1-carboxamide |

TABLE 1-continued
| Exemplary compounds of the present invention | | |
|---|---|---|
| S. No | Structure | IUPAC Name |
| 1074. | 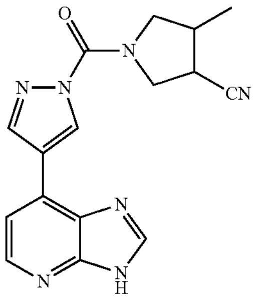 [SMILES: CC1CN(C(=O)n2cc(-c3ccnc4[nH]cnc34)cn2)CC1C#N] | 1-(4-(3H-imidazo[4,5-b]pyridin-7-yl)-1H-pyrazole-1-carbonyl)-4-methylpyrrolidine-3-carbonitrile |
| 1075. | 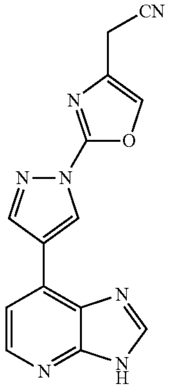 [SMILES: N#CCc1coc(-n2cc(-c3ccnc4[nH]cnc34)cn2)n1] | 2-(2-(4-(3H-imidazo[4,5-b]pyridin-7-yl)-1H-pyrazol-1-yl)oxazol-4-yl)acetonitrile |
| 1076. | 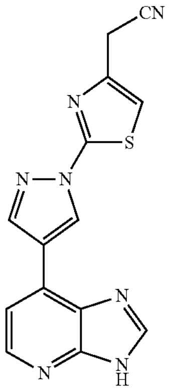 [SMILES: N#CCc1csc(-n2cc(-c3ccnc4[nH]cnc34)cn2)n1] | 2-(2-(4-(3H-imidazo[4,5-b]pyridin-7-yl)-1H-pyrazol-1-yl)thiazol-4-yl)acetonitrile |
| 1077. | 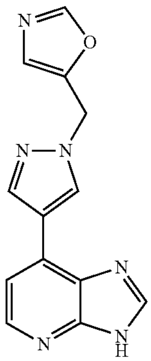 [SMILES: c1cc(-c2cnn(Cc3cnco3)c2)c2nc[nH]c2n1] | 7-(1-((oxazol-5-yl)methyl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1078. | 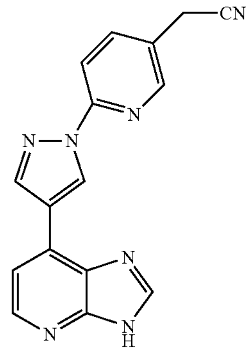 | 2-(6-(4-(3H-imidazo[4,5-b]pyridin-7-yl)-1H-pyrazol-1-yl)pyridin-3-yl)acetonitrile |
| 1079. | 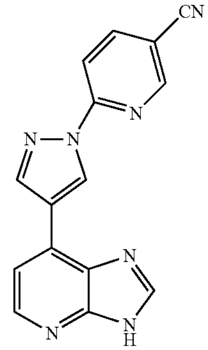 [SMILES: N#Cc1ccc(-n2cc(-c3ccnc4[nH]cnc34)cn2)nc1] | 6-(4-(3H-imidazo[4,5-b]pyridin-7-yl)-1H-pyrazol-1-yl)pyridine-3-carbonitrile |
| 1080. | 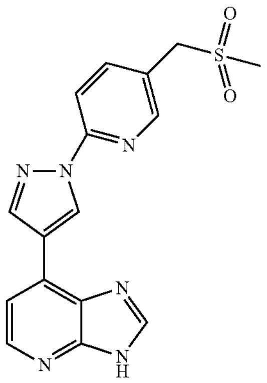 [SMILES: CS(=O)(=O)Cc1ccc(-n2cc(-c3ccnc4[nH]cnc34)cn2)nc1] | 7-(1-(5-((methylsulfonyl)methyl)pyridin-2-yl)-1H-pyrazol-4-yl)-3H-imidazo[4,5-b]pyridine |
| 1081. | 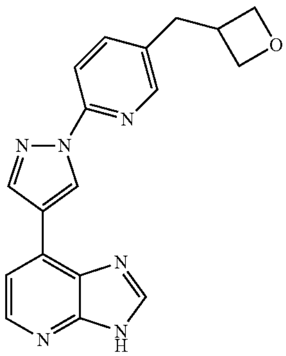 [SMILES: c1cc(-c2cnn(-c3ccc(CC4COC4)cn3)c2)c2nc[nH]c2n1] | 7-(1-(5-((oxetan-3-yl)methyl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1082. | 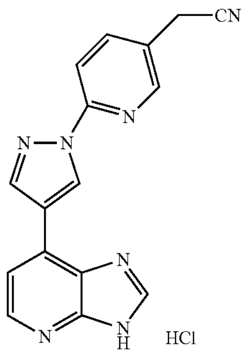 [SMILES: N#CCc1ccc(-n2cc(-c3ccnc4[nH]cnc34)cn2)nc1 ; Cl] | 2-(6-(4-(3H-imidazo[4,5-b]pyridin-7-yl)-1H-pyrazol-1-yl)pyridin-3-yl)acetonitrile hydrochloride |
| 1083. | 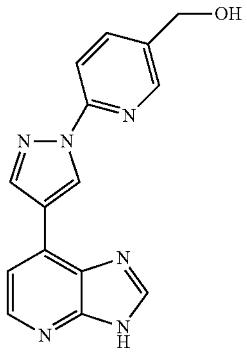 [SMILES: OCc1ccc(-n2cc(-c3ccnc4[nH]cnc34)cn2)nc1] | (6-(4-(3H-imidazo[4,5-b]pyridin-7-yl)-1H-pyrazol-1-yl)pyridin-3-yl)methanol |
| 1084. | 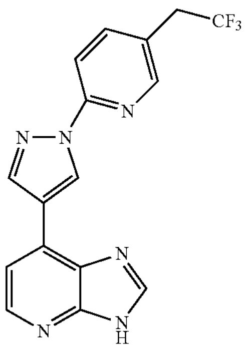 [SMILES: FC(F)(F)Cc1ccc(-n2cc(-c3ccnc4[nH]cnc34)cn2)nc1] | 7-(1-(5-(2,2,2-trifluoroethyl)pyridin-2-yl)-1H-pyrazol-4-yl)-3H-imidazo[4,5-b]pyridine |
| 1085. | 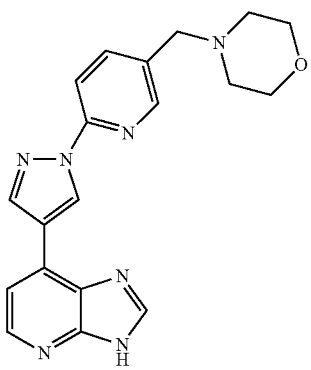 [SMILES: c1cc(-c2cnn(-c3ccc(CN4CCOCC4)cn3)c2)c2nc[nH]c2n1] | 7-(1-(5-(morpholinomethyl)pyridin-2-yl)-1H-pyrazol-4-yl)-3H-imidazo[4,5-b]pyridine |

TABLE 1-continued

| S. No | Structure | IUPAC Name |
|---|---|---|
| 1086. | 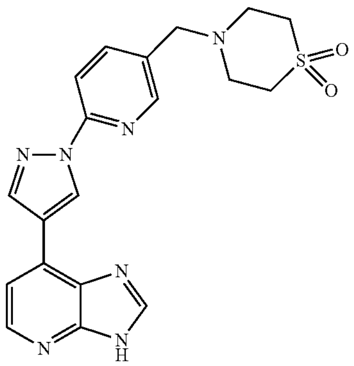 [SMILES: O=S1(=O)CCN(Cc2ccc(-n3cc(-c4ccnc5[nH]cnc45)cn3)nc2)CC1] | 4-((6-(4-(3H-imidazo[4,5-b]pyridin-7-yl)-1H-pyrazol-1-yl)pyridin-3-yl)methyl)thiomorpholine 1,1-dioxide |
| 1087. | 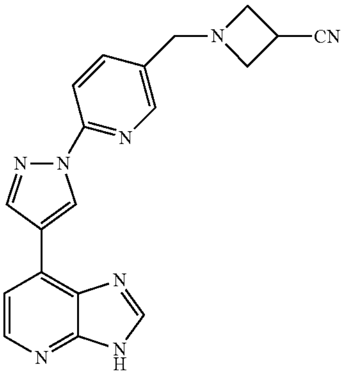 [SMILES: N#CC1CN(Cc2ccc(-n3cc(-c4ccnc5[nH]cnc45)cn3)nc2)C1] | 1-((6-(4-(3H-imidazo[4,5-b]pyridin-7-yl)-1H-pyrazol-1-yl)pyridin-3-yl)methyl)azetidine-3-carbonitrile |
| 1088. | 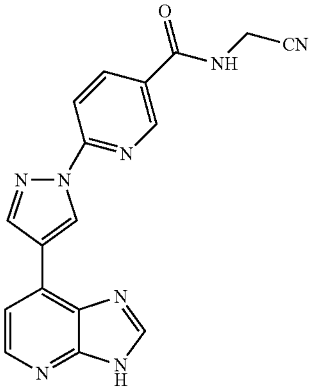 [SMILES: N#CCNC(=O)c1ccc(-n2cc(-c3ccnc4[nH]cnc34)cn2)nc1] | 6-(4-(3H-imidazo[4,5-b]pyridin-7-yl)-1H-pyrazol-1-yl)-N-(cyanomethyl)pyridine-3-carboxamide |
| 1089. | 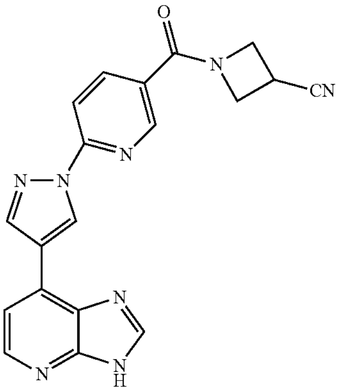 [SMILES: N#CC1CN(C(=O)c2ccc(-n3cc(-c4ccnc5[nH]cnc45)cn3)nc2)C1] | N-((6-(4-(3H-imidazo[4,5-b]pyridin-7-yl)-1H-pyrazol-1-yl)pyridin-3-yl)methyl)methanesulfonamide |

Exemplary compounds of the present invention

TABLE 1-continued
| Exemplary compounds of the present invention | | |
| --- | --- | --- |
| S. No | Structure | IUPAC Name |
| 1090. | 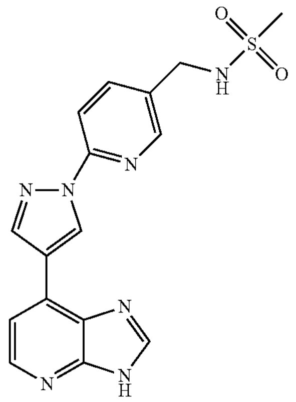 [SMILES: CS(=O)(=O)NCc1ccc(-n2cc(-c3ccnc4[nH]cnc34)cn2)nc1] | N-((6-(4-(3H-imidazo[4,5-b]pyridin-7-yl)-1H-pyrazol-1-yl)pyridin-3-yl)methyl)methanesulfonamide |
| 1091. | 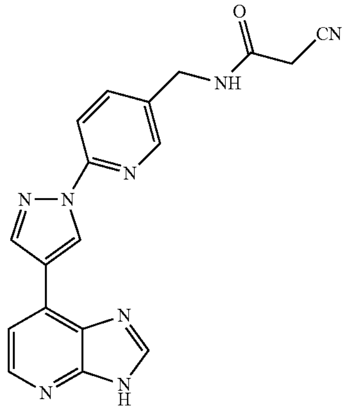 [SMILES: N#CCC(=O)NCc1ccc(-n2cc(-c3ccnc4[nH]cnc34)cn2)nc1] | N-((6-(4-(3H-imidazo[4,5-b]pyridin-7-yl)-1H-pyrazol-1-yl)pyridin-3-yl)methyl)-2-cyanoacetamide |
| 1092. | 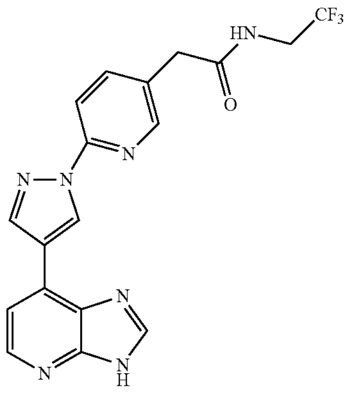 [SMILES: O=C(Cc1ccc(-n2cc(-c3ccnc4[nH]cnc34)cn2)nc1)NCC(F)(F)F] | 2-(6-(4-(3H-imidazo[4,5-b]pyridin-7-yl)-1H-pyrazol-1-yl)pyridin-3-yl)-N-(2,2,2-trifluoroethyl)acetamide |

TABLE 1-continued

| S. No | Structure | IUPAC Name |
| --- | --- | --- |
| 1093. | 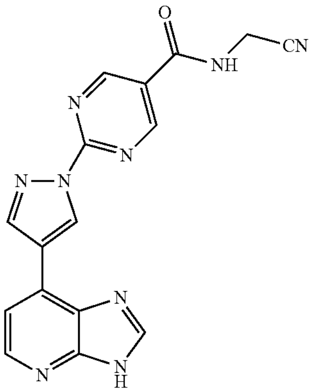 [SMILES: N#CCNC(=O)c1cnc(-n2cc(-c3ccnc4[nH]cnc34)cn2)nc1] | 2-(4-(3H-imidazo[4,5-b]pyridin-7-yl)-1H-pyrazol-1-yl)-N-(cyanomethyl)pyrimidine-5-carboxamide |
| 1094. | 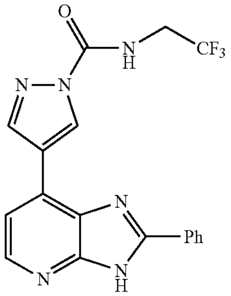 [SMILES: O=C(NCC(F)(F)F)n1cc(-c2ccnc3[nH]c(-c4ccccc4)nc23)cn1] | N-(2,2,2-trifluoroethyl)-4-(2-phenyl-3H-imidazo[4,5-b]pyridin-7-yl)-1H-pyrazole-1-carboxamide |
| 1095. | 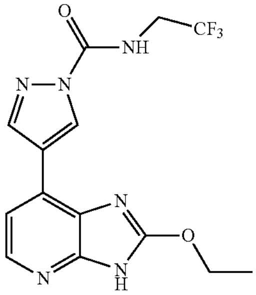 [SMILES: CCOc1nc2c(-c3cnn(C(=O)NCC(F)(F)F)c3)ccnc2[nH]1] | 4-(2-ethoxy-3H-imidazo[4,5-b]pyridin-7-yl)-N-(2,2,2-trifluoroethyl)-1H-pyrazole-1-carboxamide |
| 1096. | 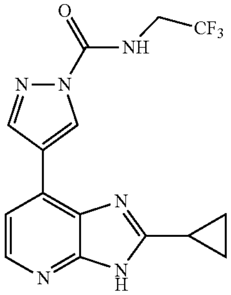 [SMILES: O=C(NCC(F)(F)F)n1cc(-c2ccnc3[nH]c(C4CC4)nc23)cn1] | 4-(2-cyclopropyl-3H-imidazo[4,5-b]pyridin-7-yl)-N-(2,2,2-trifluoroethyl)-1H-pyrazole-1-carboxamide |

Exemplary compounds of the present invention

TABLE 1-continued

| Exemplary compounds of the present invention | | |
|---|---|---|
| S. No | Structure | IUPAC Name |
| 1097. | 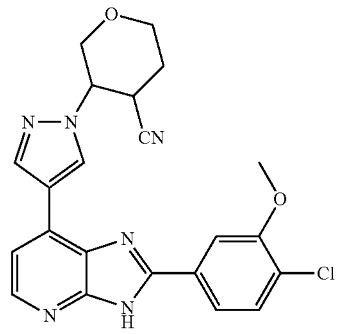 [SMILES: COc1cc(-c2nc3c(-c4cnn(C5COCCC5C#N)c4)ccnc3[nH]2)ccc1Cl] | 3-(4-(2-(4-chloro-3-methoxyphenyl)-3H-imidazo[4,5-b]pyridin-7-yl)-1H-pyrazol-1-yl)-tetrahydro-2H-pyran-4-carbonitrile |
| 1098. | 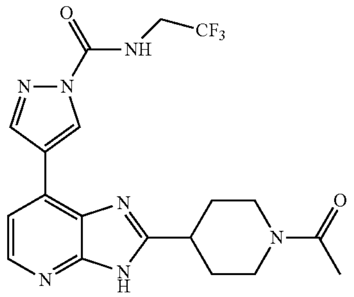 [SMILES: CC(=O)N1CCC(c2nc3c(-c4cnn(C(=O)NCC(F)(F)F)c4)ccnc3[nH]2)CC1] | 4-(2-(1-acetylpiperidin-4-yl)-3H-imidazo[4,5-b]pyridin-7-yl)-N-(2,2,2-trifluoroethyl)-1H-pyrazole-1-carboxamide |
| 1099. | 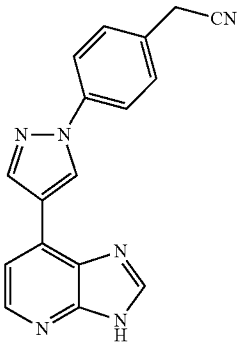 [SMILES: N#CCc1ccc(-n2cc(-c3ccnc4[nH]cnc34)cn2)cc1] | 2-(4-(4-(3H-imidazo[4,5-b]pyridin-7-yl)-1H-pyrazol-1-yl)phenyl)acetonitrile |
| 1100. | 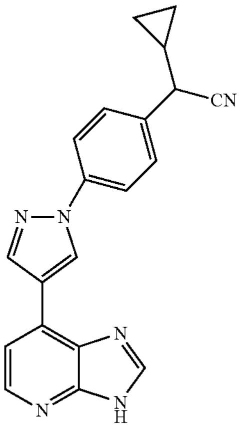 [SMILES: N#CC(c1ccc(-n2cc(-c3ccnc4[nH]cnc34)cn2)cc1)C1CC1] | 2-(4-(4-(3H-imidazo[4,5-b]pyridin-7-yl)-1H-pyrazol-1-yl)phenyl)-2-cyclopropylacetonitrile |

TABLE 1-continued
Exemplary compounds of the present invention
| S. No | Structure | IUPAC Name |
|---|---|---|
| 1101. | 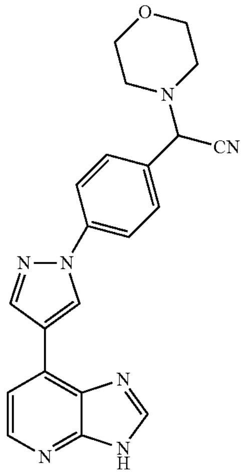 [SMILES: N#CC(c1ccc(-n2cc(-c3ccnc4[nH]cnc34)cn2)cc1)N1CCOCC1] | 2-(4-(4-(3H-imidazo[4,5-b]pyridin-7-yl)-1H-pyrazol-1-yl)phenyl)-2-morpholinoacetonitrile |
| 1102. | 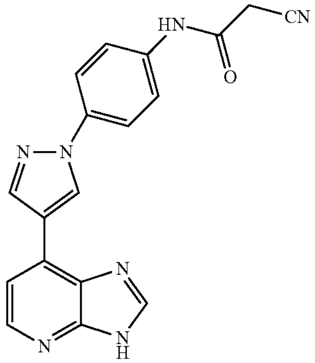 [SMILES: N#CCC(=O)Nc1ccc(-n2cc(-c3ccnc4[nH]cnc34)cn2)cc1] | N-(4-(4-(3H-imidazo[4,5-b]pyridin-7-yl)-1H-pyrazol-1-yl)phenyl)-2-cyanoacetamide |
| 1103. | 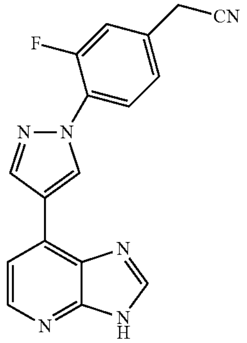 [SMILES: N#CCc1ccc(-n2cc(-c3ccnc4[nH]cnc34)cn2)c(F)c1] | 2-(4-(4-(3H-imidazo[4,5-b]pyridin-7-yl)-1H-pyrazol-1-yl)-3-fluorophenyl)acetonitrile |
| 1104. | 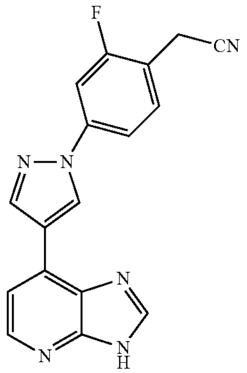 [SMILES: N#CCc1ccc(-n2cc(-c3ccnc4[nH]cnc34)cn2)cc1F] | 2-(4-(4-(3H-imidazo[4,5-b]pyridin-7-yl)-1H-pyrazol-1-yl)-2-fluorophenyl)acetonitrile |

TABLE 1-continued
| Exemplary compounds of the present invention | | |
|---|---|---|
| S. No | Structure | IUPAC Name |
| 1105. | 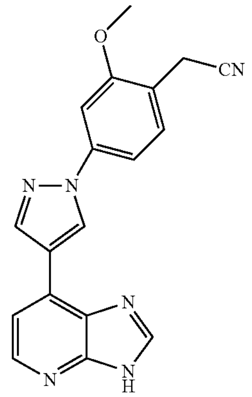 [SMILES: COc1cc(-n2cc(-c3ccnc4[nH]cnc34)cn2)ccc1CC#N] | 2-(4-(4-(3H-imidazo[4,5-b]pyridin-7-yl)-1H-pyrazol-1-yl)-2-methoxyphenyl)acetonitrile |
| 1106. | 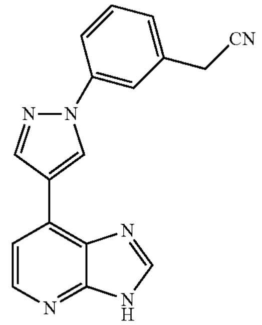 [SMILES: N#CCc1cccc(-n2cc(-c3ccnc4[nH]cnc34)cn2)c1] | 2-(3-(4-(3H-imidazo[4,5-b]pyridin-7-yl)-1H-pyrazol-1-yl)phenyl)acetonitrile |
| 1107. | 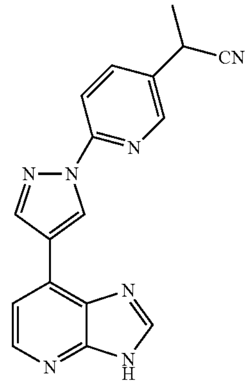 [SMILES: CC(C#N)c1ccc(-n2cc(-c3ccnc4[nH]cnc34)cn2)nc1] | 2-(6-(4-(3H-imidazo[4,5-b]pyridin-7-yl)-1H-pyrazol-1-yl)pyridin-3-yl)propanenitrile |
| 1108. | 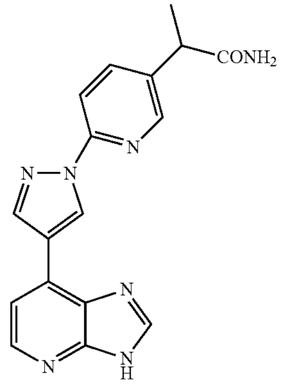 [SMILES: CC(C(N)=O)c1ccc(-n2cc(-c3ccnc4[nH]cnc34)cn2)nc1] | 2-(6-(4-(3H-imidazo[4,5-b]pyridin-7-yl)-1H-pyrazol-1-yl)pyridin-3-yl)propanamide |

TABLE 1-continued
| Exemplary compounds of the present invention | | |
|---|---|---|
| S. No | Structure | IUPAC Name |
| 1109. | 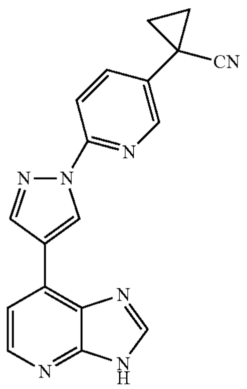 [SMILES: N#CC1(c2ccc(-n3cc(-c4ccnc5[nH]cnc45)cn3)nc2)CC1] | 1-(6-(4-(3H-imidazo[4,5-b]pyridin-7-yl)-1H-pyrazol-1-yl)pyridin-3-yl)cyclopropanecarbonitrile |
| 1110. | 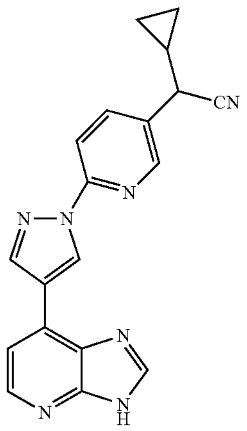 [SMILES: N#CC(c1ccc(-n2cc(-c3ccnc4[nH]cnc34)cn2)nc1)C1CC1] | 2-(6-(4-(3H-imidazo[4,5-b]pyridin-7-yl)-1H-pyrazol-1-yl)pyridin-3-yl)-2-cyclopropylacetonitrile |
| 1111. | 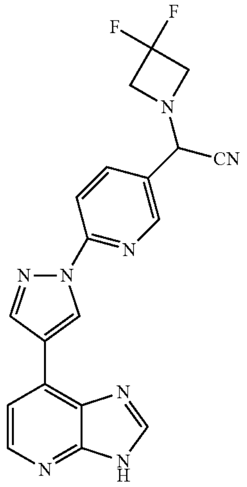 [SMILES: N#CC(c1ccc(-n2cc(-c3ccnc4[nH]cnc34)cn2)nc1)N1CC(F)(F)C1] | 2-(6-(4-(3H-imidazo[4,5-b]pyridin-7-yl)-1H-pyrazol-1-yl)pyridin-3-yl)-2-(3,3-difluoroazetidin-1-yl)acetonitrile |

TABLE 1-continued
| Exemplary compounds of the present invention | | |
|---|---|---|
| S. No | Structure | IUPAC Name |
| 1112. | 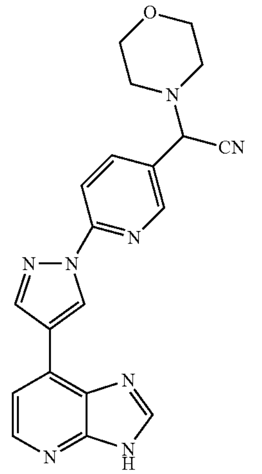 [SMILES: N#CC(c1ccc(-n2cc(-c3ccnc4[nH]cnc34)cn2)nc1)N1CCOCC1] | 2-(6-(4-(3H-imidazo[4,5-b]pyridin-7-yl)-1H-pyrazol-1-yl)pyridin-3-yl)-2-morpholinoacetonitrile |
| 1113. | 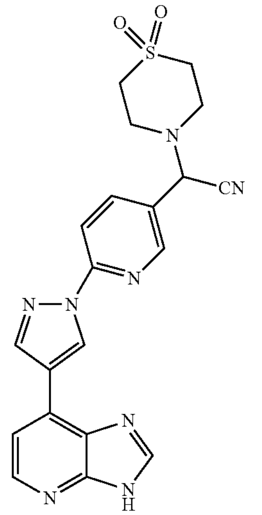 [SMILES: N#CC(c1ccc(-n2cc(-c3ccnc4[nH]cnc34)cn2)nc1)N1CCS(=O)(=O)CC1] | 2-(6-(4-(3H-imidazo[4,5-b]pyridin-7-yl)-1H-pyrazol-1-yl)pyridin-3-yl)-2-(1,1-dioxidothiomorpholino)acetonitrile |
| 1114. | 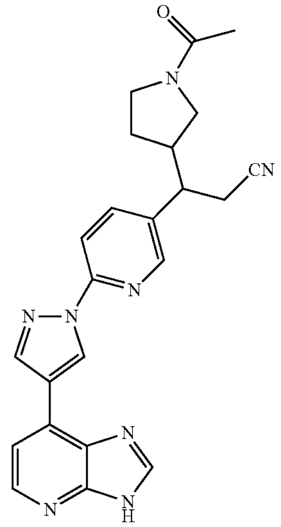 [SMILES: CC(=O)N1CCC(C(CC#N)c2ccc(-n3cc(-c4ccnc5[nH]cnc45)cn3)nc2)C1] | 2-(6-(4-(3H-imidazo[4,5-b]pyridin-7-yl)-1H-pyrazol-1-yl)pyridin-3-yl)-2-(1-(methylsulfonyl)azetidin-3-yl)acetonitrile |

TABLE 1-continued
| Exemplary compounds of the present invention | | |
|---|---|---|
| S. No | Structure | IUPAC Name |
| 1115. | 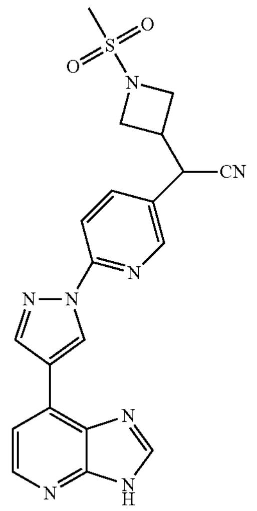 [SMILES: CS(=O)(=O)N1CC(C(C#N)c2ccc(-n3cc(-c4ccnc5[nH]cnc45)cn3)nc2)C1] | 2-(6-(4-(3H-imidazo[4,5-b]pyridin-7-yl)-1H-pyrazol-1-yl)pyridin-3-yl)-2-(1-(methylsulfonyl)azetidin-3-yl)acetonitrile |
| 1116. | 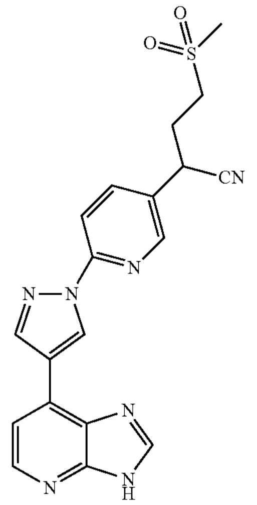 [SMILES: CS(=O)(=O)CCC(C#N)c1ccc(-n2cc(-c3ccnc4[nH]cnc34)cn2)nc1] | 2-(6-(4-(3H-imidazo[4,5-b]pyridin-7-yl)-1H-pyrazol-1-yl)pyridin-3-yl)-4-(methylsulfonyl)butanenitrile |
| 1117. | 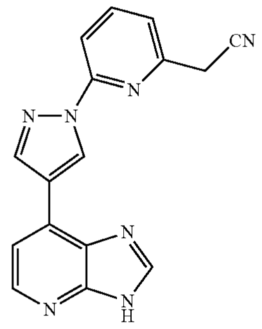 [SMILES: N#CCc1cccc(-n2cc(-c3ccnc4[nH]cnc34)cn2)n1] | 2-(6-(4-(3H-imidazo[4,5-b]pyridin-7-yl)-1H-pyrazol-1-yl)pyridin-2-yl)acetonitrile |

TABLE 1-continued
| Exemplary compounds of the present invention | | |
|---|---|---|
| S. No | Structure | IUPAC Name |
| 1118. | 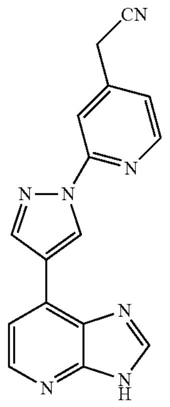 [SMILES: N#CCc1ccnc(-n2cc(-c3ccnc4[nH]cnc34)cn2)c1] | 2-(2-(4-(3H-imidazo[4,5-b]pyridin-7-yl)-1H-pyrazol-1-yl)pyridin-4-yl)acetonitrile |
| 1119. | 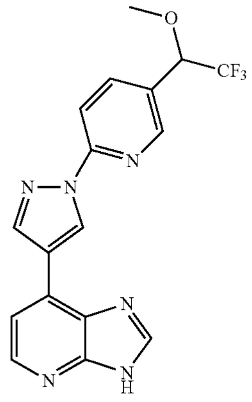 [SMILES: COC(c1ccc(-n2cc(-c3ccnc4[nH]cnc34)cn2)nc1)C(F)(F)F] | 7-(1-(5-(2,2,2-trifluoro-1-methoxyethyl)pyridin-2-yl)-1H-pyrazol-4-yl)-3H-imidazo[4,5-b]pyridine |
| 1120. | 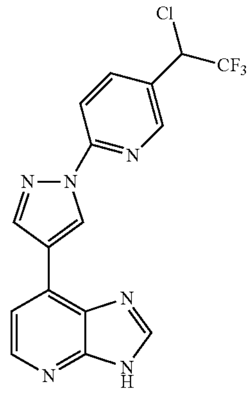 [SMILES: FC(F)(F)C(Cl)c1ccc(-n2cc(-c3ccnc4[nH]cnc34)cn2)nc1] | 7-(1-(5-(1-chloro-2,2,2-trifluoroethyl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1121. | 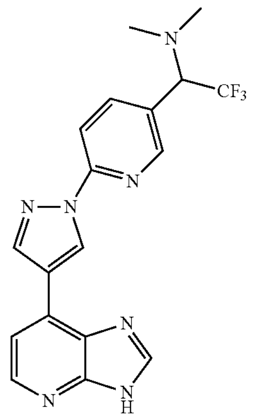 [SMILES: CN(C)C(c1ccc(-n2cc(-c3ccnc4[nH]cnc34)cn2)nc1)C(F)(F)F] | 1-(6-(4-(3H-imidazo[4,5-b]pyridin-7-yl)-1H-pyrazol-1-yl)pyridin-3-yl)-2,2,2-trifluoro-N,N-dimethylethanamine |
| 1122. | 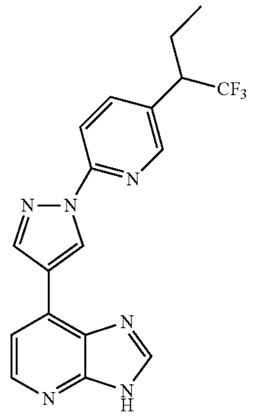 [SMILES: CCC(c1ccc(-n2cc(-c3ccnc4[nH]cnc34)cn2)nc1)C(F)(F)F] | 7-(1-(5-(1,1,1-trifluorobutan-2-yl)pyridin-2-yl)-1H-pyrazol-4-yl)-3H-imidazo[4,5-b]pyridine |
| 1123. | 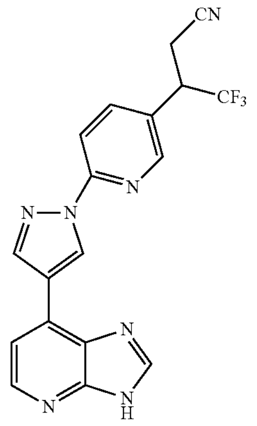 [SMILES: N#CCC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluorobutanenitrile |

TABLE 1-continued
| Exemplary compounds of the present invention | | |
|---|---|---|
| S. No | Structure | IUPAC Name |
| 1124. | 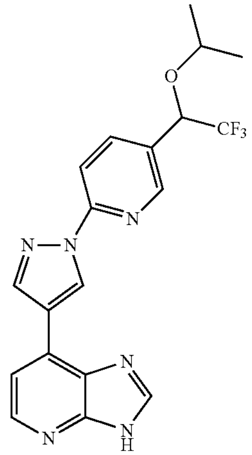 [SMILES: CC(C)OC(c1ccc(-n2cc(-c3ccnc4[nH]cnc34)cn2)nc1)C(F)(F)F] | 7-(1-(5-(2,2,2-trifluoro-1-isopropoxyethyl)pyridin-2-yl)-1H-pyrazol-4-yl)-3H-imidazo[4,5-b]pyridine |
| 1125. | 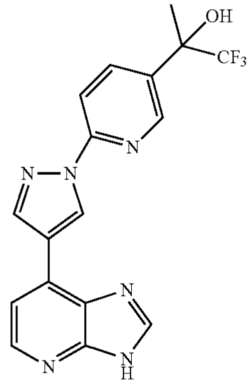 [SMILES: CC(O)(c1ccc(-n2cc(-c3ccnc4[nH]cnc34)cn2)nc1)C(F)(F)F] | 2-(6-(4-(3H-imidazo[4,5-b]pyridin-7-yl)-1H-pyrazol-1-yl)pyridin-3-yl)-1,1,1-trifluoropropan-2-ol |
| 1126. | 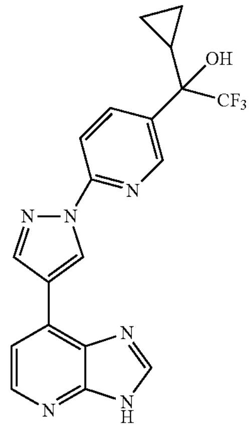 [SMILES: OC(c1ccc(-n2cc(-c3ccnc4[nH]cnc34)cn2)nc1)(C1CC1)C(F)(F)F] | 1-(6-(4-(3H-imidazo[4,5-b]pyridin-7-yl)-1H-pyrazol-1-yl)pyridin-3-yl)-1-cyclopropyl-2,2,2-trifluoroethanol |

TABLE 1-continued
| Exemplary compounds of the present invention | | |
|---|---|---|
| S. No | Structure | IUPAC Name |
| 1127. | 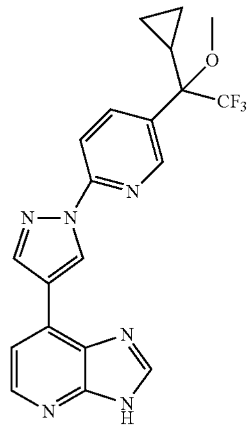 [SMILES: COC(c1ccc(-n2cc(-c3ccnc4[nH]cnc34)cn2)nc1)(C1CC1)C(F)(F)F] | 7-(1-(5-(1-cyclopropyl-2,2,2-trifluoro-1-methoxyethyl)pyridin-2-yl)-1H-pyrazol-4-yl)-3H-imidazo[4,5-b]pyridine |
| 1128. | 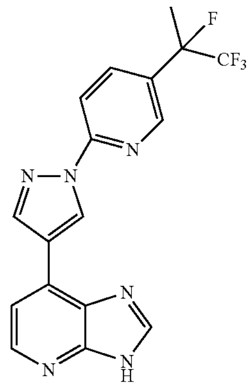 [SMILES: CC(F)(c1ccc(-n2cc(-c3ccnc4[nH]cnc34)cn2)nc1)C(F)(F)F] | 7-(1-(5-(1,1,1,2-tetrafluoropropan-2-yl)pyridin-2-yl)-1H-pyrazol-4-yl)-3H-imidazo[4,5-b]pyridine |
| 1129. | 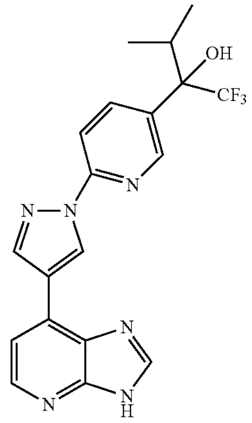 [SMILES: CC(C)C(O)(c1ccc(-n2cc(-c3ccnc4[nH]cnc34)cn2)nc1)C(F)(F)F] | 2-(6-(4-(3H-imidazo[4,5-b]pyridin-7-yl)-1H-pyrazol-1-yl)pyridin-3-yl)-1,1,1-trifluoro-3-methylbutan-2-ol |

TABLE 1-continued
| Exemplary compounds of the present invention | | |
|---|---|---|
| S. No | Structure | IUPAC Name |
| 1130. | 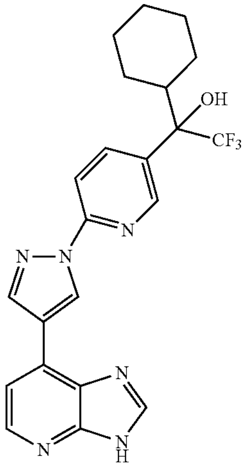 [SMILES: OC(c1ccc(-n2cc(-c3ccnc4[nH]cnc34)cn2)nc1)(C1CCCCC1)C(F)(F)F] | 1-(6-(4-(3H-imidazo[4,5-b]pyridin-7-yl)-1H-pyrazol-1-yl)pyridin-3-yl)-1-cyclohexyl-2,2,2-trifluoroethanol |
| 1131. | 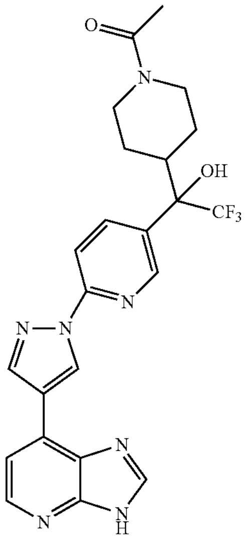 [SMILES: CC(=O)N1CCC(C(O)(c2ccc(-n3cc(-c4ccnc5[nH]cnc45)cn3)nc2)C(F)(F)F)CC1] | 1-(4-(1-(6-(4-(3H-imidazo[4,5-b]pyridin-7-yl)-1H-pyrazol-1-yl)pyridin-3-yl)-2,2,2-trifluoro-1-hydroxyethyl)piperidin-1-yl)ethanone |
| 1132. | 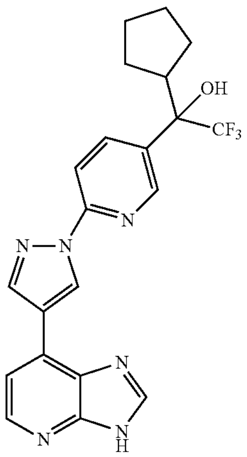 [SMILES: OC(c1ccc(-n2cc(-c3ccnc4[nH]cnc34)cn2)nc1)(C1CCCC1)C(F)(F)F] | 1-(6-(4-(3H-imidazo[4,5-b]pyridin-7-yl)-1H-pyrazol-1-yl)pyridin-3-yl)-1-cyclopentyl-2,2,2-trifluoroethanol |

TABLE 1-continued
| Exemplary compounds of the present invention | | |
|---|---|---|
| S. No | Structure | IUPAC Name |
| 1133. | 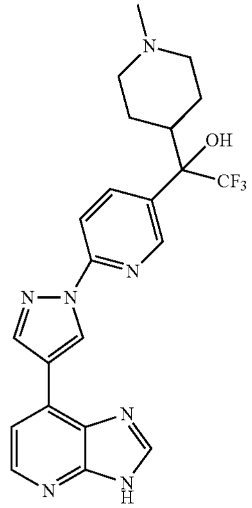 [SMILES: CN1CCC(C(O)(c2ccc(-n3cc(-c4ccnc5[nH]cnc45)cn3)nc2)C(F)(F)F)CC1] | 1-(6-(4-(3H-imidazo[4,5-b]pyridin-7-yl)-1H-pyrazol-1-yl)pyridin-3-yl)-2,2,2-trifluoro-1-(1-methylpiperidin-4-yl)ethanol |
| 1134. | 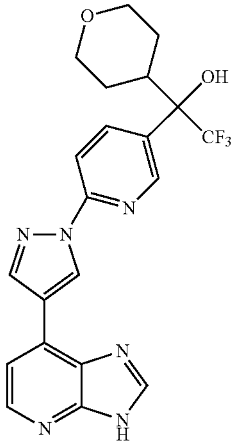 [SMILES: OC(c1ccc(-n2cc(-c3ccnc4[nH]cnc34)cn2)nc1)(C1CCOCC1)C(F)(F)F] | 1-(6-(4-(3H-imidazo[4,5-b]pyridin-7-yl)-1H-pyrazol-1-yl)pyridin-3-yl)-2,2,2-trifluoro-1-(tetrahydro-2H-pyran-4-yl)ethanol |
| 1135. | TFA 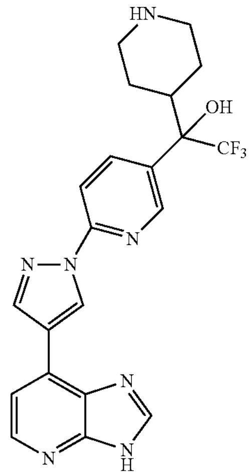 | 1-(6-(4-(3H-imidazo[4,5-b]pyridin-7-yl)-1H-pyrazol-1-yl)pyridin-3-yl)-2,2,2-trifluoro-1-(piperidin-4-yl)ethan-1-ol |

TABLE 1-continued
| Exemplary compounds of the present invention | | |
|---|---|---|
| S. No | Structure | IUPAC Name |
| 1136. | 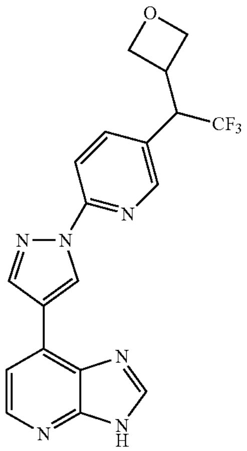 [SMILES: FC(F)(F)C(c1ccc(-n2cc(-c3ccnc4[nH]cnc34)cn2)nc1)C1COC1] | 7-(1-(5-(2,2,2-trifluoro-1-(oxetan-3-yl)ethyl)pyridin-2-yl)-1H-pyrazol-4-yl)-3H-imidazo[4,5-b]pyridine |
| 1137. | 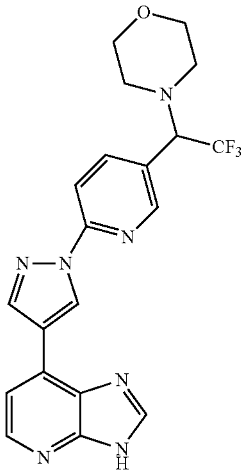 [SMILES: FC(F)(F)C(c1ccc(-n2cc(-c3ccnc4[nH]cnc34)cn2)nc1)N1CCOCC1] | 7-(1-(5-(2,2,2-trifluoro-1-morpholinoethyl)pyridin-2-yl)-1H-pyrazol-4-yl)-3H-imidazo[4,5-b]pyridine |
| 1138. | 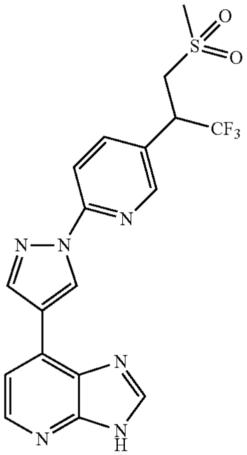 [SMILES: CS(=O)(=O)CC(c1ccc(-n2cc(-c3ccnc4[nH]cnc34)cn2)nc1)C(F)(F)F] | 7-(1-(5-(1,1,1-trifluoro-3-(methylsulfonyl)propan-2-yl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1139. | 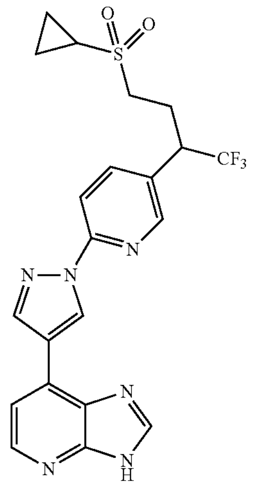 [SMILES: O=S(=O)(CCC(c1ccc(-n2cc(-c3ccnc4[nH]cnc34)cn2)nc1)C(F)(F)F)C1CC1] | 7-(1-(5-(4-(cyclopropylsulfonyl)-1,1,1-trifluorobutan-2-yl)pyridin-2-yl)-1H-pyrazol-4-yl)-3H-imidazo[4,5-b]pyridine |
| 1140. | 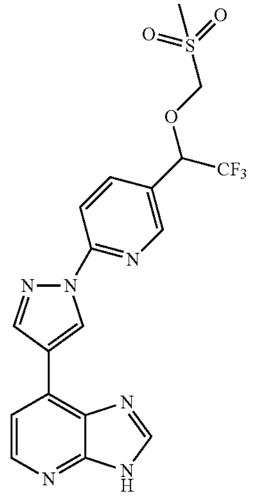 [SMILES: CS(=O)(=O)COC(c1ccc(-n2cc(-c3ccnc4[nH]cnc34)cn2)nc1)C(F)(F)F] | 7-(1-(5-(1-((methylsulfonyl)methoxy)-2,2,2-trifluoroethyl)pyridin-2-yl)-1H-pyrazol-4-yl)-3H-imidazo[4,5-b]pyridine |
| 1141. | 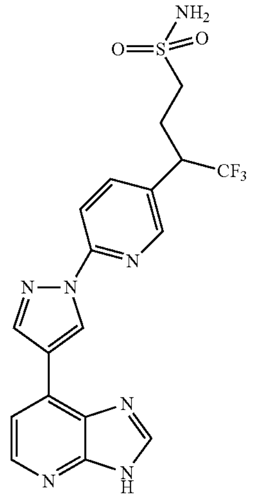 [SMILES: NS(=O)(=O)CCC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluorobutane-1-sulfonamide |

TABLE 1-continued
Exemplary compounds of the present invention
| S. No | Structure | IUPAC Name |
| --- | --- | --- |
| 1142. | 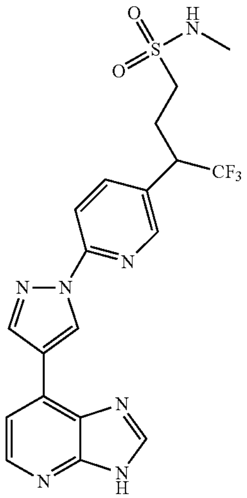 [SMILES: CNS(=O)(=O)CCC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluoro-N-methylbutane-1-sulfonamide |
| 1143. | 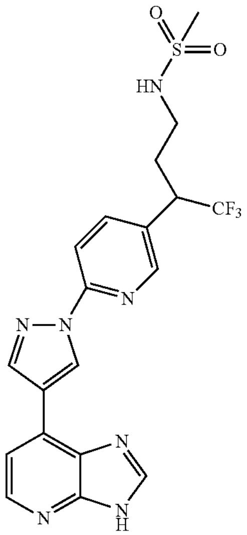 [SMILES: CS(=O)(=O)NCCC(c1ccc(-n2cc(-c3ccnc4[nH]cnc34)cn2)nc1)C(F)(F)F] | N-(3-(6-(4-(3H-imidazo[4,5-b]pyridin-7-yl)-1H-pyrazol-1-yl)pyridin-3-yl)-4,4,4-trifluorobutyl)methanesulfonamide |
| 1144. | 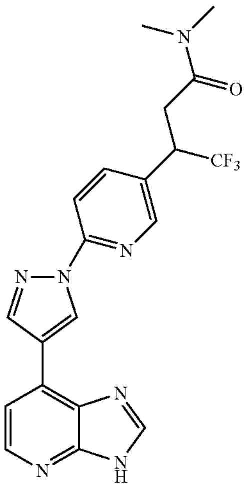 [SMILES: CN(C)C(=O)CC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluoro-N,N-dimethylbutanamide |

TABLE 1-continued
| S. No | Structure | IUPAC Name |
|---|---|---|
| Exemplary compounds of the present invention | | |
| 1145. | 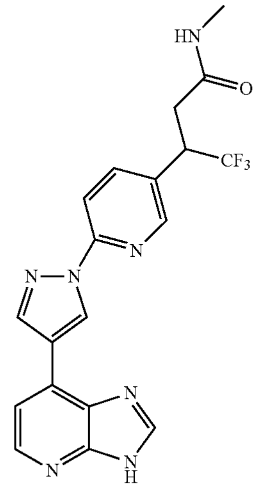 [SMILES: CNC(=O)CC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluoro-N-methylbutanamide |
| 1146. | 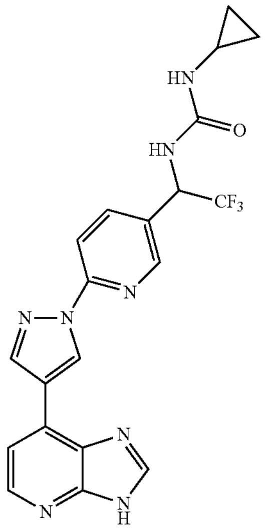 [SMILES: O=C(NC1CC1)NC(c1ccc(-n2cc(-c3ccnc4[nH]cnc34)cn2)nc1)C(F)(F)F] | 1-(1-(6-(4-(3H-imidazo[4,5-b]pyridin-7-yl)-1H-pyrazol-1-yl)pyridin-3-yl)-2,2,2-trifluoroethyl)-3-cyclopropylurea |
| 1147. | 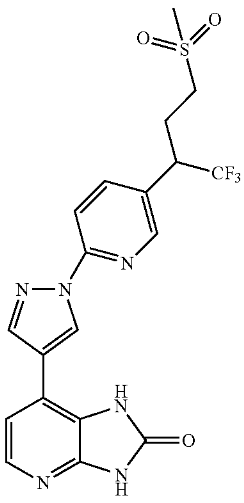 [SMILES: CS(=O)(=O)CCC(c1ccc(-n2cc(-c3ccnc4[nH]c(=O)[nH]c34)cn2)nc1)C(F)(F)F] | 7-(1-(5-(1,1,1-trifluoro-4-(methylsulfonyl)butan-2-yl)pyridin-2-yl)-1H-pyrazol-4-yl)-1H-imidazo[4,5-b]pyridin-2(3H)-one |

TABLE 1-continued
| Exemplary compounds of the present invention | | |
|---|---|---|
| S. No | Structure | IUPAC Name |
| 1148. | 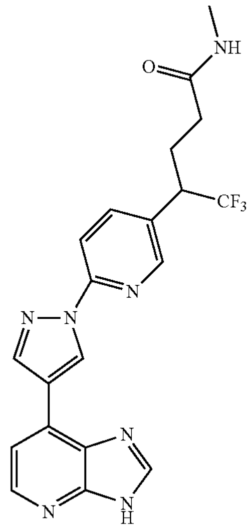 [SMILES: CNC(=O)CCC(c1ccc(-n2cc(-c3ccnc4[nH]cnc34)cn2)nc1)C(F)(F)F] | 4-(6-(4-(3H-imidazo[4,5-b]pyridin-7-yl)-1H-pyrazol-1-yl)pyridin-3-yl)-5,5,5-trifluoro-N-methylpentanamide |
| 1149. | 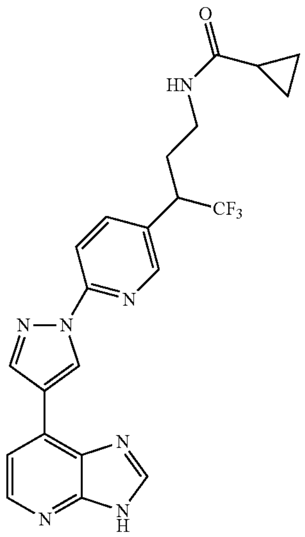 [SMILES: O=C(NCCC(c1ccc(-n2cc(-c3ccnc4[nH]cnc34)cn2)nc1)C(F)(F)F)C1CC1] | N-(3-(6-(4-(3H-imidazo[4,5-b]pyridin-7-yl)-1H-pyrazol-1-yl)pyridin-3-yl)-4,4,4-trifluorobutyl)cyclopropanecarboxamide |

TABLE 1-continued
| Exemplary compounds of the present invention | | |
|---|---|---|
| S. No | Structure | IUPAC Name |
| 1150. | 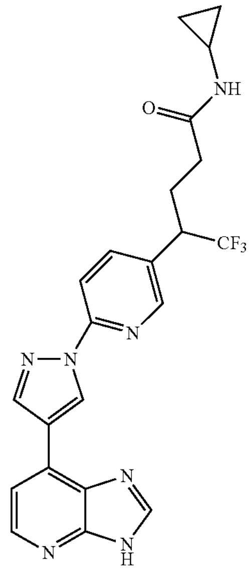 [SMILES: O=C(CCC(c1ccc(-n2cc(-c3ccnc4[nH]cnc34)cn2)nc1)C(F)(F)F)NC1CC1] | 4-(6-(4-(3H-imidazo[4,5-b]pyridin-7-yl)-1H-pyrazol-1-yl)pyridin-3-yl)-N-cyclopropyl-5,5,5-trifluoropentanamide |
| 1151. | 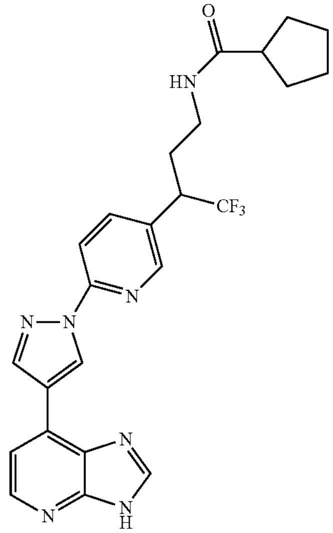 [SMILES: O=C(NCCC(c1ccc(-n2cc(-c3ccnc4[nH]cnc34)cn2)nc1)C(F)(F)F)C1CCCC1] | N-(3-(6-(4-(3H-imidazo[4,5-b]pyridin-7-yl)-1H-pyrazol-1-yl)pyridin-3-yl)-4,4,4-trifluorobutyl)cyclopentanecarboxamide |
| 1152. | 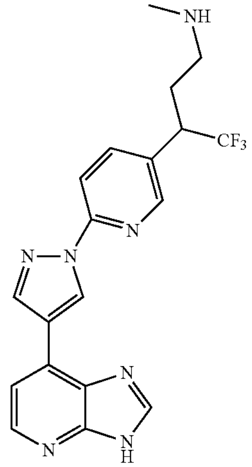 [SMILES: CNCCC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluoro-N-methylbutan-1-amine |

TABLE 1-continued
| Exemplary compounds of the present invention | | |
|---|---|---|
| S. No | Structure | IUPAC Name |
| 1153. | 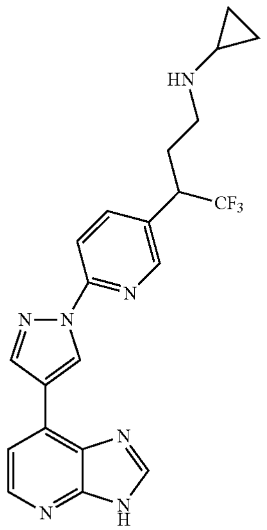 [SMILES: FC(F)(F)C(CCNC1CC1)c1ccc(-n2cc(-c3ccnc4[nH]cnc34)cn2)nc1] | N-(3-(6-(4-(3H-imidazo[4,5-b]pyridin-7-yl)-1H-pyrazol-1-yl)pyridin-3-yl)-4,4,4-trifluorobutyl)cyclopropanamine |
| 1154. | 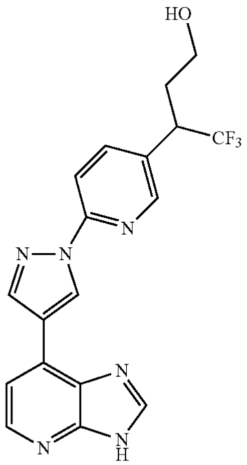 [SMILES: OCCC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluorobutan-1-ol |
| 1155. | 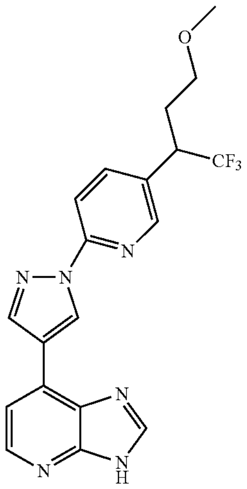 [SMILES: COCCC(c1ccc(-n2cc(-c3ccnc4[nH]cnc34)cn2)nc1)C(F)(F)F] | 7-(1-(5-(1,1,1-trifluoro-4-methoxybutan-2-yl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1156. | 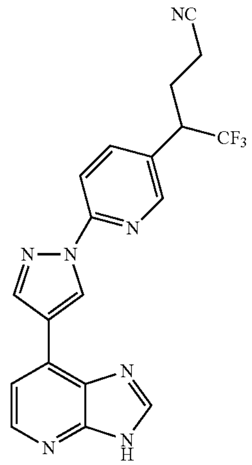 [SMILES: N#CCCC(c1ccc(-n2cc(-c3ccnc4[nH]cnc34)cn2)nc1)C(F)(F)F] | 4-(6-(4-(3H-imidazo[4,5-b]pyridin-7-yl)-1H-pyrazol-1-yl)pyridin-3-yl)-5,5,5-trifluoropentanenitrile |
| 1157. | 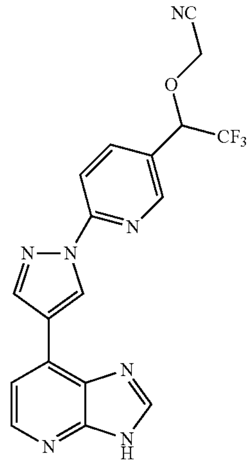 [SMILES: N#CCOC(c1ccc(-n2cc(-c3ccnc4[nH]cnc34)cn2)nc1)C(F)(F)F] | 2-(1-(6-(4-(3H-imidazo[4,5-b]pyridin-7-yl)-1H-pyrazol-1-yl)pyridin-3-yl)-2,2,2-trifluoroethoxy)acetonitrile |
| 1158. | 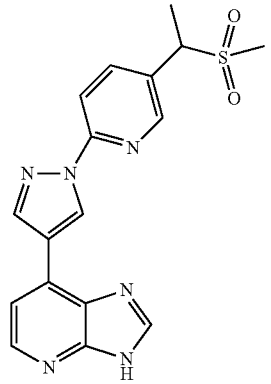 [SMILES: CC(c1ccc(-n2cc(-c3ccnc4[nH]cnc34)cn2)nc1)S(C)(=O)=O] | 7-(1-(5-(1-(methylsulfonyl)ethyl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1159. | 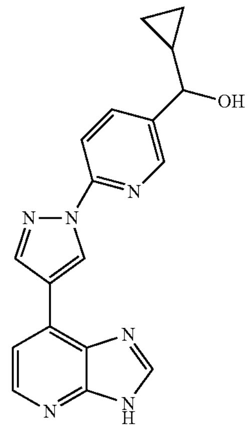 | (6-(4-(3H-imidazo[4,5-b]pyridin-7-yl)-1H-pyrazol-1-yl)pyridin-3-yl)(cyclopropyl)methanol |
| 1160. | 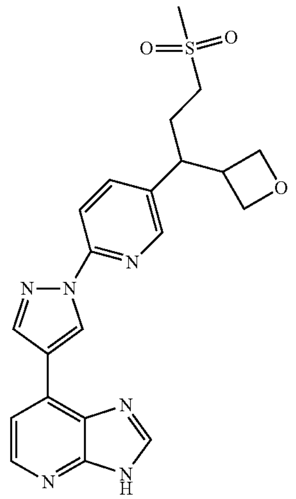 [SMILES: CS(=O)(=O)CCC(c1ccc(-n2cc(-c3ccnc4[nH]cnc34)cn2)nc1)C1COC1] | 7-(1-(5-(3-(methylsulfonyl)-1-(oxetan-3-yl)propyl)pyridin-2-yl)-1H-pyrazol-4-yl)-3H-imidazo[4,5-b]pyridine |
| 1161. | 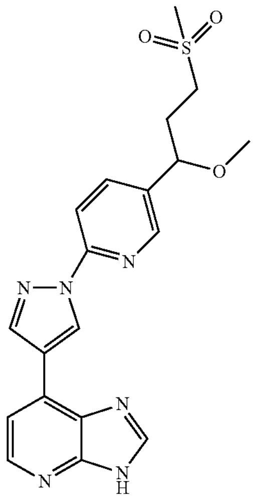 [SMILES: COC(CCS(C)(=O)=O)c1ccc(-n2cc(-c3ccnc4[nH]cnc34)cn2)nc1] | 7-(1-(5-(1-methoxy-3-(methylsulfonyl)propyl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1162. | 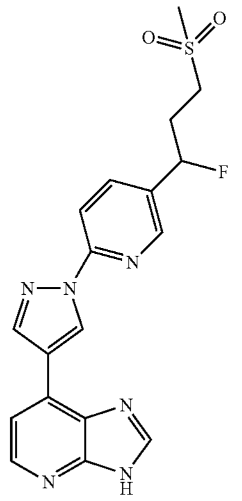 [SMILES: CS(=O)(=O)CCC(F)c1ccc(-n2cc(-c3ccnc4[nH]cnc34)cn2)nc1] | 7-(1-(5-(1-fluoro-3-(methylsulfonyl)propyl)pyridin-2-yl)-1H-pyrazol-4-yl)-3H-imidazo[4,5-b]pyridine |
| 1163. | 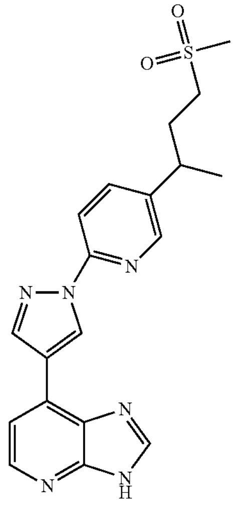 [SMILES: CC(CCS(C)(=O)=O)c1ccc(-n2cc(-c3ccnc4[nH]cnc34)cn2)nc1] | 7-(1-(5-(4-(methylsulfonyl)butan-2-yl)pyridin-2-yl)-1H-pyrazol-4-yl)-3H-imidazo[4,5-b]pyridine |
| 1164. | 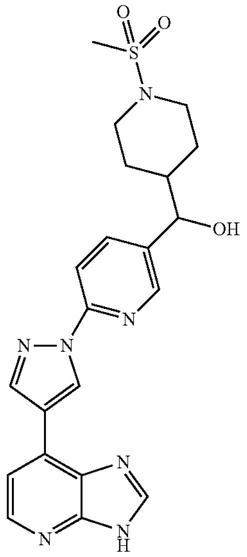 [SMILES: CS(=O)(=O)N1CCC(C(O)c2ccc(-n3cc(-c4ccnc5[nH]cnc45)cn3)nc2)CC1] | (6-(4-(3H-imidazo[4,5-b]pyridin-7-yl)-1H-pyrazol-1-yl)pyridin-3-yl)(1-(methylsulfonyl)piperidin-4-yl)methanol |

TABLE 1-continued
| Exemplary compounds of the present invention | | |
|---|---|---|
| S. No | Structure | IUPAC Name |
| 1165. | 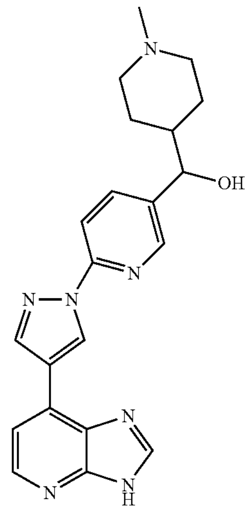 [SMILES: CN1CCC(C(O)c2ccc(-n3cc(-c4ccnc5[nH]cnc45)cn3)nc2)CC1] | (6-(4-(3H-imidazo[4,5-b]pyridin-7-yl)-1H-pyrazol-1-yl)pyridin-3-yl)(1-methylpiperidin-4-yl)methanol |
| 1166. | 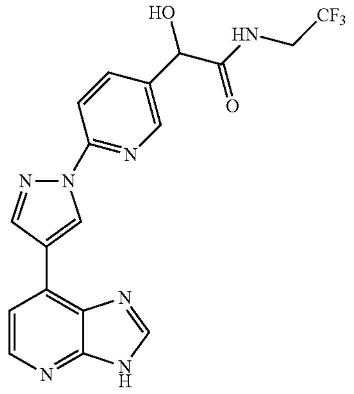 [SMILES: O=C(NCC(F)(F)F)C(O)c1ccc(-n2cc(-c3ccnc4[nH]cnc34)cn2)nc1] | 2-(6-(4-(3H-imidazo[4,5-b]pyridin-7-yl)-1H-pyrazol-1-yl)pyridin-3-yl)-N-(2,2,2-trifluoroethyl)-2-hydroxyacetamide |
| 1167. | 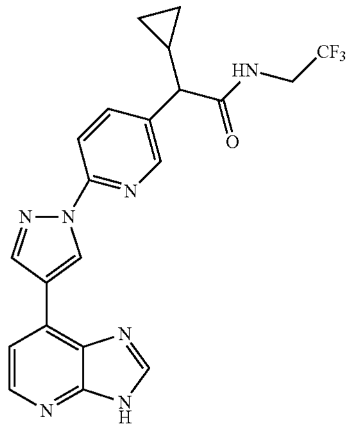 [SMILES: O=C(NCC(F)(F)F)C(c1ccc(-n2cc(-c3ccnc4[nH]cnc34)cn2)nc1)C1CC1] | 2-(6-(4-(3H-imidazo[4,5-b]pyridin-7-yl)-1H-pyrazol-1-yl)pyridin-3-yl)-2-cyclopropyl-N-(2,2,2-trifluoroethyl)acetamide |

TABLE 1-continued

| Exemplary compounds of the present invention | | |
|---|---|---|
| S. No | Structure | IUPAC Name |
| 1168. | 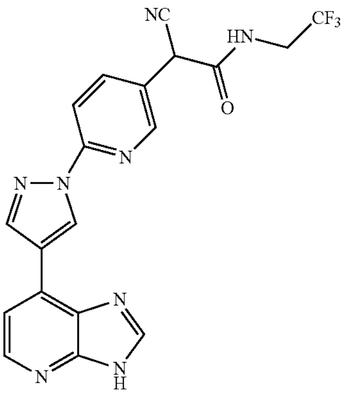 [SMILES: N#CC(C(=O)NCC(F)(F)F)c1ccc(-n2cc(-c3ccnc4[nH]cnc34)cn2)nc1] | 2-(6-(4-(3H-imidazo[4,5-b]pyridin-7-yl)-1H-pyrazol-1-yl)pyridin-3-yl)-2-cyano-N-(2,2,2-trifluoroethyl)acetamide |
| 1169. | 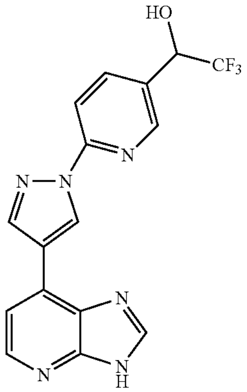 [SMILES: OC(c1ccc(-n2cc(-c3ccnc4[nH]cnc34)cn2)nc1)C(F)(F)F] | 1-(6-(4-(3H-imidazo[4,5-b]pyridin-7-yl)-1H-pyrazol-1-yl)pyridin-3-yl)-2,2,2-trifluoroethanol |
| 1170. | 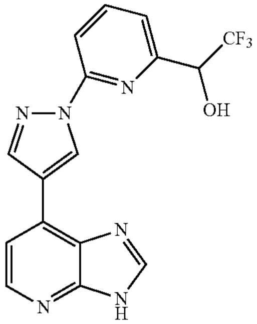 [SMILES: OC(c1cccc(-n2cc(-c3ccnc4[nH]cnc34)cn2)n1)C(F)(F)F] | 1-(6-(4-(3H-imidazo[4,5-b]pyridin-7-yl)-1H-pyrazol-1-yl)pyridin-2-yl)-2,2,2-trifluoroethanol |
| 1171. | 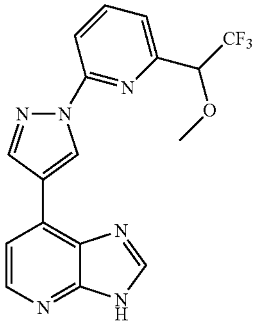 [SMILES: COC(c1cccc(-n2cc(-c3ccnc4[nH]cnc34)cn2)n1)C(F)(F)F] | 7-(1-(6-(2,2,2-trifluoro-1-methoxyethyl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1172. | 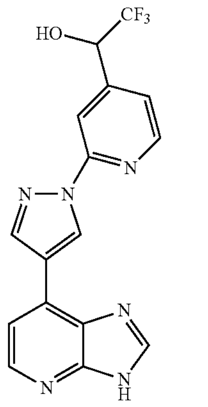 [SMILES: OC(c1ccnc(-n2cc(-c3ccnc4[nH]cnc34)cn2)c1)C(F)(F)F] | 1-(2-(4-(3H-imidazo[4,5-b]pyridin-7-yl)-1H-pyrazol-1-yl)pyridin-4-yl)-2,2,2-trifluoroethanol |
| 1173. | 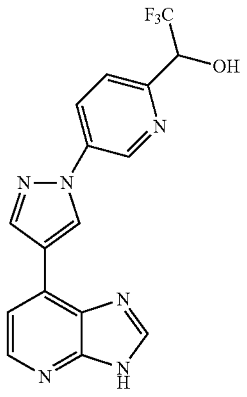 [SMILES: OC(c1ccc(-n2cc(-c3ccnc4[nH]cnc34)cn2)cn1)C(F)(F)F] | 1-(5-(4-(3H-imidazo[4,5-b]pyridin-7-yl)-1H-pyrazol-1-yl)pyridin-2-yl)-2,2,2-trifluoroethanol |
| 1174. | 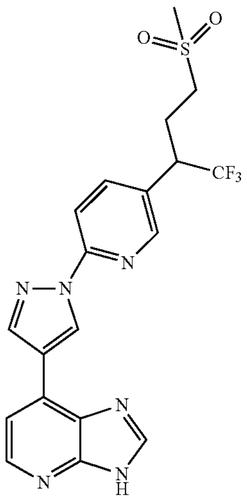 | 7-(1-(5-(1,1,1-trifluoro-4-(methylsulfonyl)butan-2-yl)pyridin-2-yl)-1H-pyrazol-4-yl)-3H-imidazo[4,5-b]pyridine |

TABLE 1-continued

| Exemplary compounds of the present invention | | |
|---|---|---|
| S. No | Structure | IUPAC Name |
| 1175. | 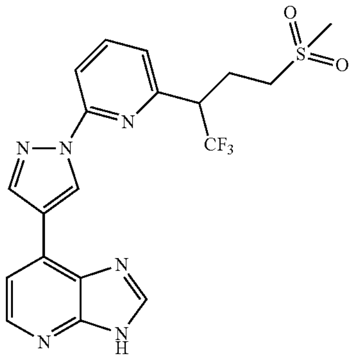 [SMILES: CS(=O)(=O)CCC(c1cccc(-n2cc(-c3ccnc4[nH]cnc34)cn2)n1)C(F)(F)F] | 7-(1-(6-(1,1,1-trifluoro-4-(methylsulfonyl)butan-2-yl)pyridin-2-yl)-1H-pyrazol-4-yl)-3H-imidazo[4,5-b]pyridine |
| 1176. | 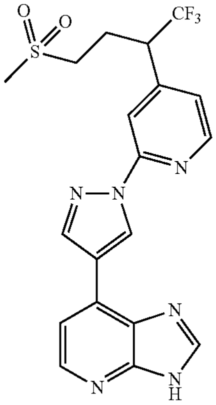 [SMILES: CS(=O)(=O)CCC(c1ccnc(-n2cc(-c3ccnc4[nH]cnc34)cn2)c1)C(F)(F)F] | 7-(1-(4-(1,1,1-trifluoro-4-(methylsulfonyl)butan-2-yl)pyridin-2-yl)-1H-pyrazol-4-yl)-3H-imidazo[4,5-b]pyridine |
| 1177. | 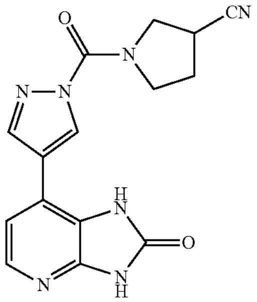 [SMILES: N#CC1CCN(C(=O)n2cc(-c3ccnc4[nH]c(=O)[nH]c34)cn2)C1] | 1-(4-(3H-imidazo[4,5-b]pyridin-7-yl)-1H-pyrazole-1-carbonyl)pyrrolidine-3-carbonitrile |
| 1178. | 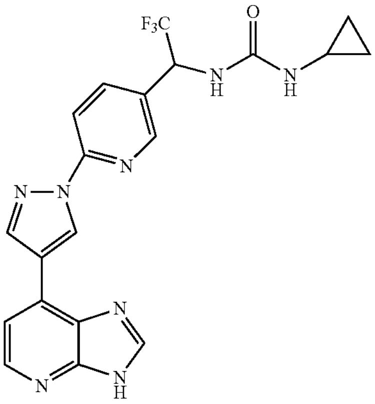 [SMILES: O=C(NC1CC1)NC(c1ccc(-n2cc(-c3ccnc4[nH]cnc34)cn2)nc1)C(F)(F)F] | 1-(1-(6-(4-(3H-imidazo[4,5-b]pyridin-7-yl)-1H-pyrazol-1-yl)pyridin-3-yl)-2,2,2-trifluoroethyl)-3-cyclopropylurea |

TABLE 1-continued
| Exemplary compounds of the present invention | | |
|---|---|---|
| S. No | Structure | IUPAC Name |
| 1179. | 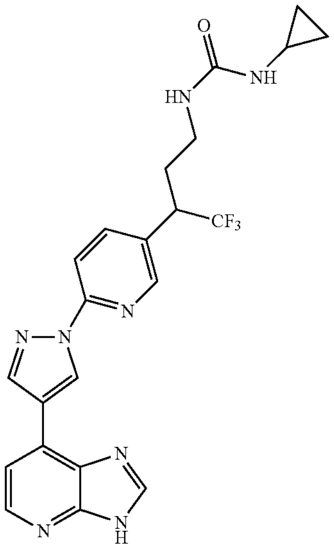 [SMILES: O=C(NCCC(c1ccc(-n2cc(-c3ccnc4[nH]cnc34)cn2)nc1)C(F)(F)F)NC1CC1] | 1-(3-(6-(4-(3H-imidazo[4,5-b]pyridin-7-yl)-1H-pyrazol-1-yl)pyridin-3-yl)-4,4,4-trifluorobutyl)-3-cyclopropylurea |
| 1180. | 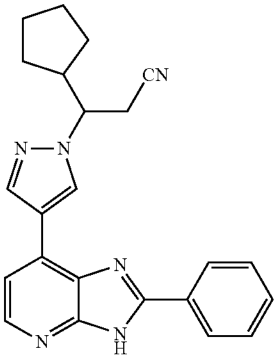 [SMILES: N#CCC(C1CCCC1)n1cc(-c2ccnc3[nH]c(-c4ccccc4)nc23)cn1] | 3-cyclopentyl-3-(4-(2-phenyl-3H-imidazo[4,5-b]pyridin-7-yl)-1H-pyrazol-1-yl)propanenitrile |
| 1181. | 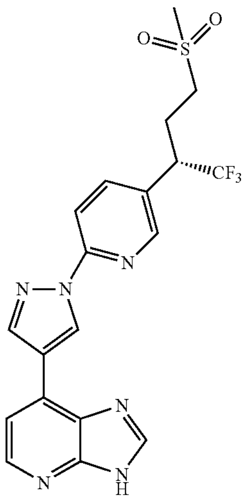 [SMILES: CS(=O)(=O)CC[C@@H](c1ccc(-n2cc(-c3ccnc4[nH]cnc34)cn2)nc1)C(F)(F)F] | 7-(1-(5-((S)-1,1,1-trifluoro-4-(methylsulfonyl)butan-2-yl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1182. | 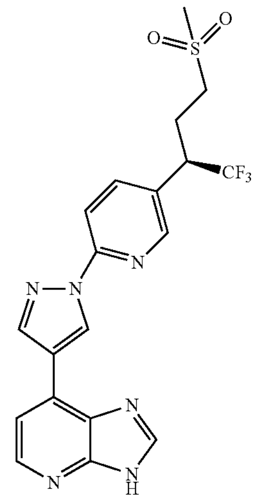 [SMILES: CS(=O)(=O)CC[C@H](c1ccc(-n2cc(-c3ccnc4[nH]cnc34)cn2)nc1)C(F)(F)F] | 7-(1-(5-((R)-1,1,1-trifluoro-4-(methylsulfonyl)butan-2-yl)pyridin-2-yl)-1H-pyrazol-4-yl)-3H-imidazo[4,5-b]pyridine |
| 1183. | 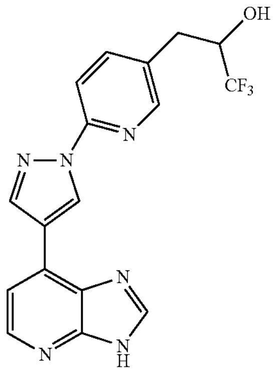 [SMILES: OC(Cc1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-1,1,1-trifluoropropan-2-ol |
| 1184. | 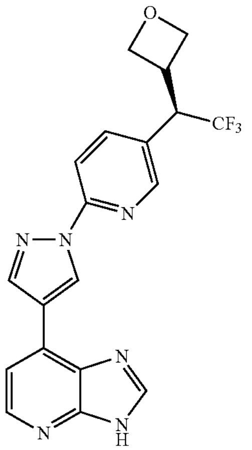 Peak-1 | 7-(1-(5-((R)-2,2,2-trifluoro-1-(oxetan-3-yl)ethyl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1185. | 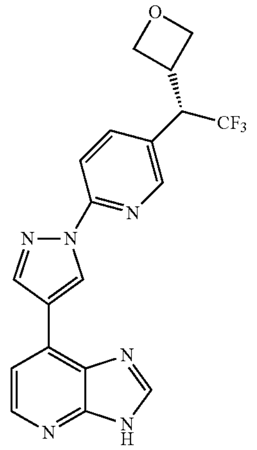 Peak-2 | 7-(1-(5-((S)-2,2,2-trifluoro-1-(oxetan-3-yl)ethyl)pyridin-2-yl)-1H-pyrazol-4-yl)-3H-imidazo[4,5-b]pyridine |
| 1186. | 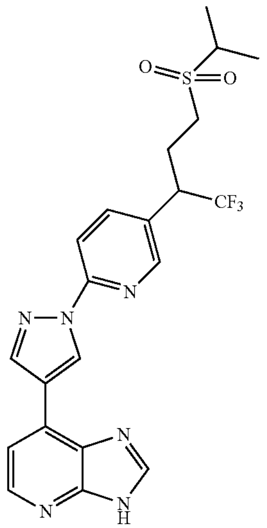 [SMILES: CC(C)S(=O)(=O)CCC(c1ccc(-n2cc(-c3ccnc4[nH]cnc34)cn2)nc1)C(F)(F)F] | 7-(1-(5-(1,1,1-trifluoro-4-(isopropylsulfonyl)butan-2-yl)pyridin-2-yl)-1H-pyrazol-4-yl)-3H-imidazo[4,5-b]pyridine |
| 1187. | 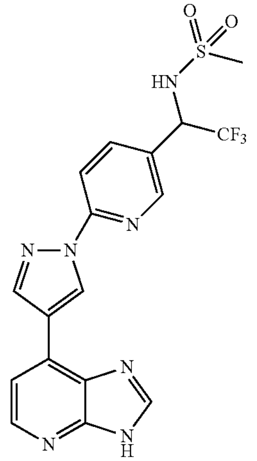 [SMILES: CS(=O)(=O)NC(c1ccc(-n2cc(-c3ccnc4[nH]cnc34)cn2)nc1)C(F)(F)F] | 1-(6-(4-(3H-imidazo[4,5-b]pyridin-7-yl)-(methylsulfonyl)1H-pyrazol-1-yl)pyridin-3-yl)-2,2,2-trifluoroethanamine |

TABLE 1-continued
| Exemplary compounds of the present invention | | |
|---|---|---|
| S. No | Structure | IUPAC Name |
| 1188. | 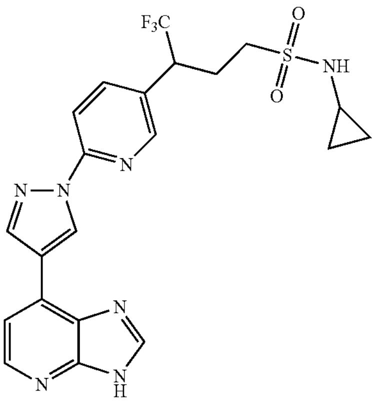 [SMILES: O=S(=O)(CCC(c1ccc(-n2cc(-c3ccnc4[nH]cnc34)cn2)nc1)C(F)(F)F)NC1CC1] | 7-(1-(5-(1,1,1-trifluoro-4-(methylsulfonyl)butan-2-yl)pyridin-2-yl)-(cyclopropylaminosulfonyl)1H-pyrazol-4-yl)-3H-imidazo[4,5-b]pyridine |
| 1189. | 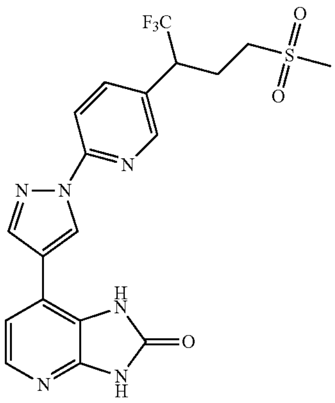 [SMILES: CS(=O)(=O)CCC(c1ccc(-n2cc(-c3ccnc4[nH]c(=O)[nH]c34)cn2)nc1)C(F)(F)F] | 7-(1-(5-(1,1,1-trifluoro-4-(methylsulfonyl)butan-2-yl)pyridin-2-yl)-1H-pyrazol-4-yl)-1H-imidazo[4,5-b]pyridin-2(3H)-one |
| 1190. | 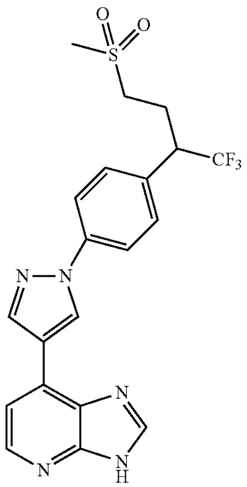 [SMILES: CS(=O)(=O)CCC(c1ccc(-n2cc(-c3ccnc4[nH]cnc34)cn2)cc1)C(F)(F)F] | 7-(1-(4-(1,1,1-trifluoro-4-(methylsulfonyl)butan-2-yl)phenyl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1191. | 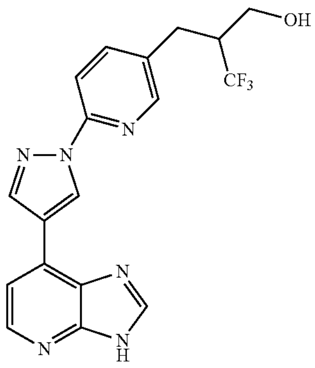 [SMILES: OCC(Cc1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-2-(trifluoromethyl)propan-1-ol |
| 1192. | 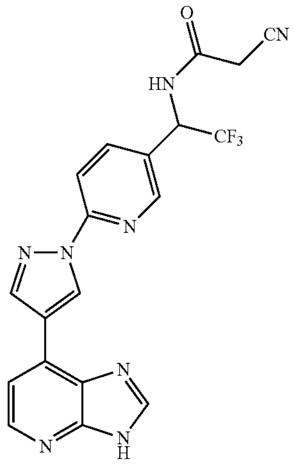 [SMILES: N#CCC(=O)NC(c1ccc(-n2cc(-c3ccnc4[nH]cnc34)cn2)nc1)C(F)(F)F] | N-(1-(6-(4-(3H-imidazo[4,5-b]pyridin-7-yl)-1H-pyrazol-1-yl)pyridin-3-yl)-2,2,2-trifluoroethyl)-2-cyanoacetamide |
| 1193. | 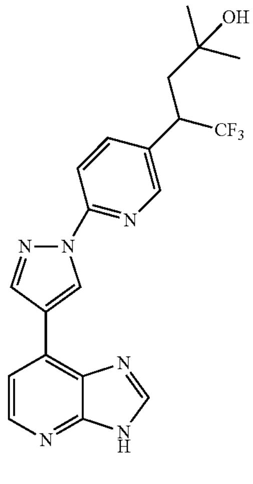 [SMILES: CC(C)(O)CC(c1ccc(-n2cc(-c3ccnc4[nH]cnc34)cn2)nc1)C(F)(F)F] | 4-(6-(4-(3H-imidazo[4,5-b]pyridin-7-yl)-1H-pyrazol-1-yl)pyridin-3-yl)-5,5,5-trifluoro-2-methylpentan-2-ol |

TABLE 1-continued
| Exemplary compounds of the present invention | | |
|---|---|---|
| S. No | Structure | IUPAC Name |
| 1194. | 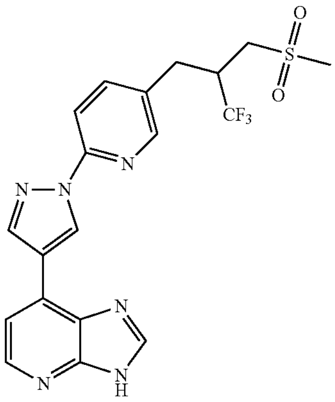 [SMILES: CS(=O)(=O)CC(Cc1ccc(-n2cc(-c3ccnc4[nH]cnc34)cn2)nc1)C(F)(F)F] | 7-(1-(5-(3,3,3-trifluoro-2-((methylsulfonyl)methyl)propyl)pyridin-2-yl)-1H-pyrazol-4-yl)-3H-imidazo[4,5-b]pyridine |
| 1195. | 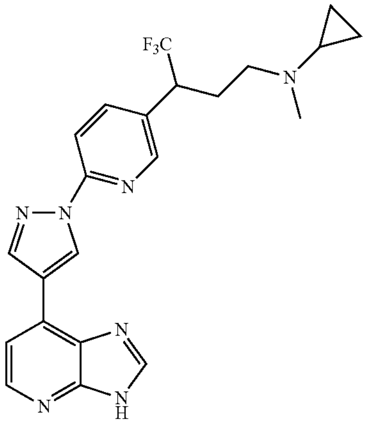 [SMILES: CN(CCC(c1ccc(-n2cc(-c3ccnc4[nH]cnc34)cn2)nc1)C(F)(F)F)C1CC1] | N-(3-(6-(4-(3H-imidazo[4,5-b]pyridin-7-yl)-1H-pyrazol-1-yl)pyridin-3-yl)-4,4,4-trifluorobutyl)-N-methylcyclopropanamine |
| 1196. | 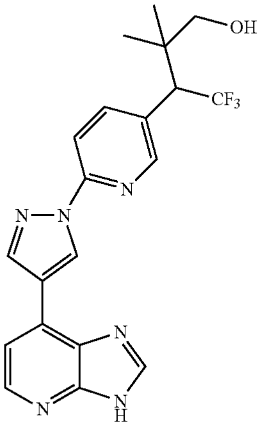 [SMILES: CC(C)(CO)C(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluoro-2,2-dimethylbutan-1-ol |

TABLE 1-continued
Exemplary compounds of the present invention
| S. No | Structure | IUPAC Name |
|---|---|---|
| 1197. | TFA 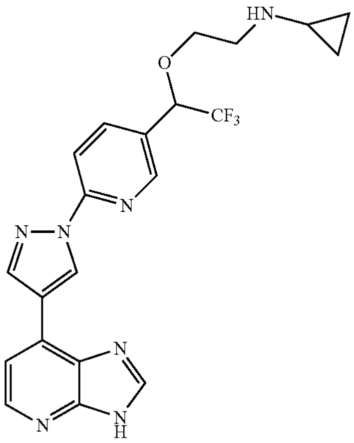 | N-(2-(1-(6-(4-(3H-imidazo[4,5-b]pyridin-7-yl)-1H-pyrazol-1-yl)pyridin-3-yl)-2,2,2-trifluoroethoxy)ethyl)cyclopropanamine |
| 1198. | 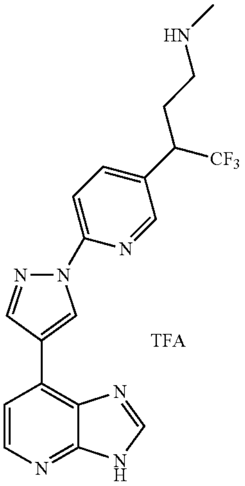 TFA | 3-(6-(4-(3H-imidazo[4,5-b]pyridin-7-yl)-1H-pyrazol-1-yl)pyridin-3-yl)-4,4,4-trifluoro-N-methylbutan-1-amine |
| 1199. | 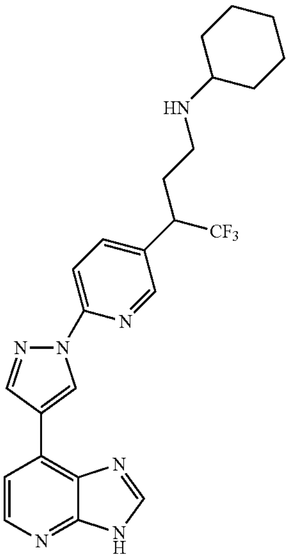 | N-(3-(6-(4-(3H-imidazo[4,5-b]pyridin-7-yl)-1H-pyrazol-1-yl)pyridin-3-yl)-4,4,4-trifluorobutyl)cyclohexanamine |

TABLE 1-continued
| Exemplary compounds of the present invention | | |
|---|---|---|
| S. No | Structure | IUPAC Name |
| 1200. | 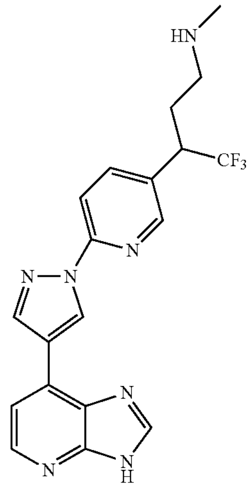 [SMILES: CNCCC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluoro-N-methylbutan-1-amine |
| 1201. | 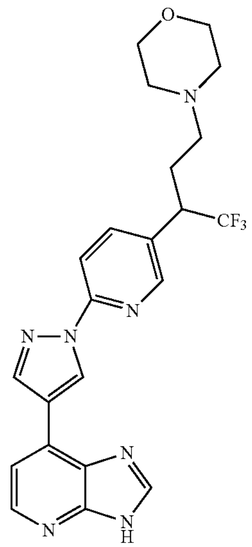 [SMILES: FC(F)(F)C(CCN1CCOCC1)c1ccc(-n2cc(-c3ccnc4[nH]cnc34)cn2)nc1] | 7-(1-(5-(1,1,1-trifluoro-4-morpholinobutan-2-yl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1202. | 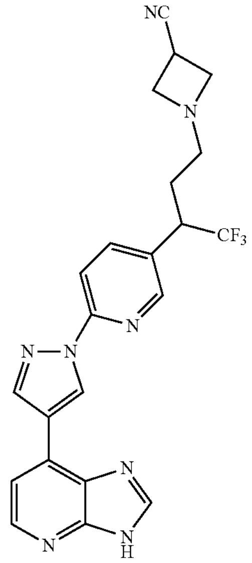 [SMILES: N#CC1CN(CCC(c2ccc(-n3cc(-c4ccnc5[nH]cnc45)cn3)nc2)C(F)(F)F)C1] | 1-(3-(6-(4-(3H-imidazo[4,5-b]pyridin-7-yl)-1H-pyrazol-1-yl)pyridin-3-yl)-4,4,4-trifluorobutyl)azetidine-3-carbonitrile |
| 1203. | 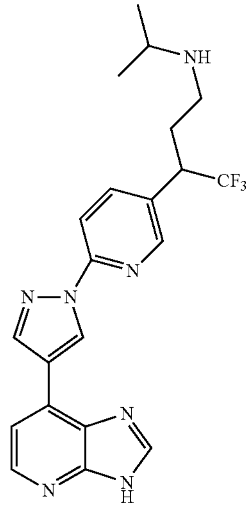 [SMILES: CC(C)NCCC(c1ccc(-n2cc(-c3ccnc4[nH]cnc34)cn2)nc1)C(F)(F)F] | 3-(6-(4-(3H-imidazo[4,5-b]pyridin-7-yl)-1H-pyrazol-1-yl)pyridin-3-yl)-4,4,4-trifluoro-N-isopropylbutan-1-amine |

TABLE 1-continued
| Exemplary compounds of the present invention | | |
|---|---|---|
| S. No | Structure | IUPAC Name |
| 1204. | 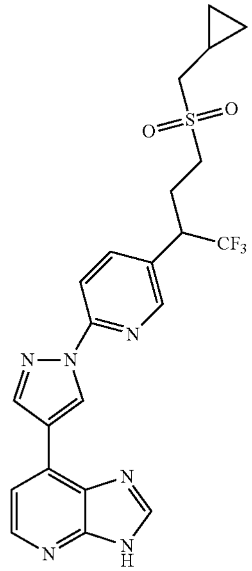 [SMILES: O=S(=O)(CCC(c1ccc(-n2cc(-c3ccnc4[nH]cnc34)cn2)nc1)C(F)(F)F)CC1CC1] | 7-(1-(5-(4-(cyclopropylmethylsulfonyl)-1,1,1-trifluorobutan-2-yl)pyridin-2-yl)-1H-pyrazol-4-yl)-3H-imidazo[4,5-b]pyridine |
| 1205. | 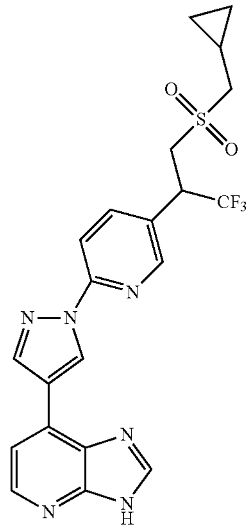 [SMILES: O=S(=O)(CC1CC1)CC(c1ccc(-n2cc(-c3ccnc4[nH]cnc34)cn2)nc1)C(F)(F)F] | 7-(1-(5-(3-(cyclopropylmethylsulfonyl)-1,1,1-trifluoropropan-2-yl)pyridin-2-yl)-1H-pyrazol-4-yl)-3H-imidazo[4,5-b]pyridine |
| 1206. | 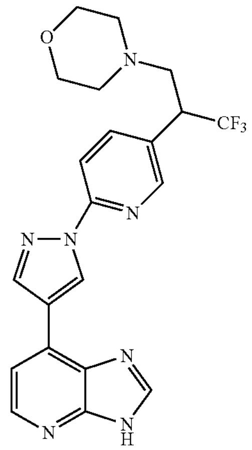 [SMILES: FC(F)(F)C(CN1CCOCC1)c1ccc(-n2cc(-c3ccnc4[nH]cnc34)cn2)nc1] | 7-(1-(5-(1,1,1-trifluoro-3-morpholinopropan-2-yl)pyridin-2-yl)-1H-pyrazol-4-yl)-3H-imidazo[4,5-b]pyridine |

TABLE 1-continued
| Exemplary compounds of the present invention | | |
|---|---|---|
| S. No | Structure | IUPAC Name |
| 1207. | 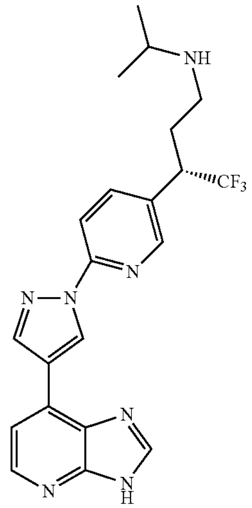 [SMILES: CC(C)NCC[C@@H](c1ccc(-n2cc(-c3ccnc4[nH]cnc34)cn2)nc1)C(F)(F)F] | (S)-3-(6-(4-(3H-imidazo[4,5-b]pyridin-7-yl)-1H-pyrazol-1-yl)pyridin-3-yl)-4,4,4-trifluoro-N-isopropylbutan-1-amine |
| 1208. | 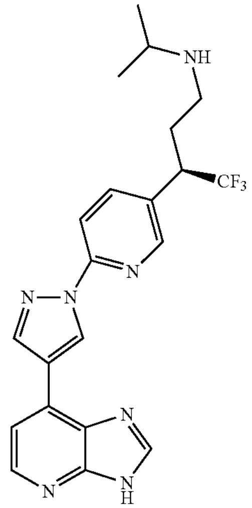 [SMILES: CC(C)NCC[C@H](c1ccc(-n2cc(-c3ccnc4[nH]cnc34)cn2)nc1)C(F)(F)F] | (R)-3-(6-(4-(3H-imidazo[4,5-b]pyridin-7-yl)-1H-pyrazol-1-yl)pyridin-3-yl)-4,4,4-trifluoro-N-isopropylbutan-1-amine |
| 1209. | 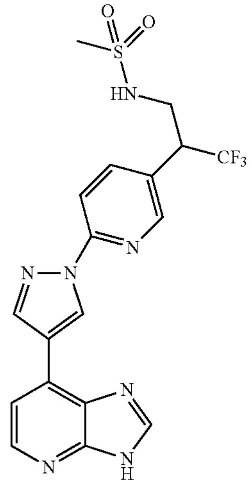 [SMILES: CS(=O)(=O)NCC(c1ccc(-n2cc(-c3ccnc4[nH]cnc34)cn2)nc1)C(F)(F)F] | 2-(6-(4-(3H-imidazo[4,5-b]pyridin-7-yl)-(Methylsulfonyl)1H-pyrazol-1-yl)pyridin-3-yl)-3,3,3-trifluoropropan-1-amine |

TABLE 1-continued
| Exemplary compounds of the present invention | | |
|---|---|---|
| S. No | Structure | IUPAC Name |
| 1210. | 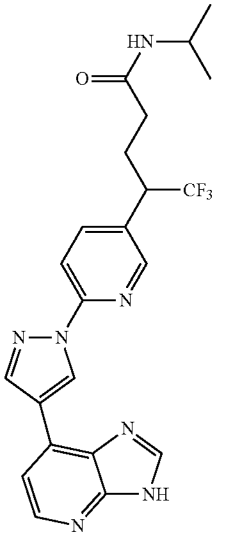 [SMILES: CC(C)NC(=O)CCC(c1ccc(-n2cc(-c3ccnc4[nH]cnc34)cn2)nc1)C(F)(F)F] | 4-(6-(4-(3H-imidazo[4,5-b]pyridin-7-yl)-1H-pyrazol-1-yl)pyridin-3-yl)-5,5,5-trifluoro-N-isopropylpentanamide |
| 1211. | 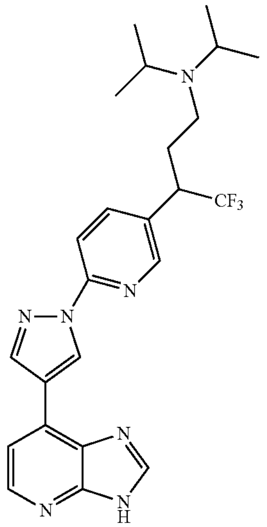 [SMILES: CC(C)N(CCC(c1ccc(-n2cc(-c3ccnc4[nH]cnc34)cn2)nc1)C(F)(F)F)C(C)C] | 3-(6-(4-(3H-imidazo[4,5-b]pyridin-7-yl)-1H-pyrazol-1-yl)pyridin-3-yl)-4,4,4-trifluoro-N,N-diisopropylbutan-1-amine |
| 1212. | 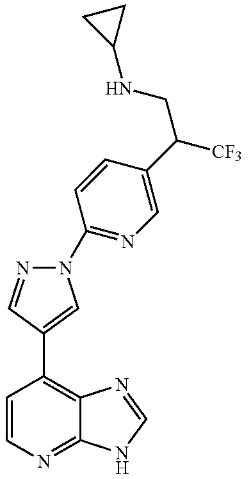 [SMILES: FC(F)(F)C(CNC1CC1)c1ccc(-n2cc(-c3ccnc4[nH]cnc34)cn2)nc1] | N-(2-(6-(4-(3H-imidazo[4,5-b]pyridin-7-yl)-1H-pyrazol-1-yl)pyridin-3-yl)-3,3,3-trifluoropropyl)cyclopropanamine |

TABLE 1-continued
| Exemplary compounds of the present invention | | |
|---|---|---|
| S. No | Structure | IUPAC Name |
| 1213. | 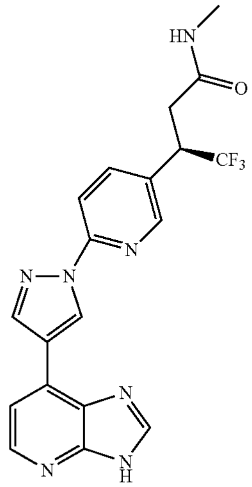 [SMILES: CNC(=O)C[C@H](c1ccc(-n2cc(-c3ccnc4[nH]cnc34)cn2)nc1)C(F)(F)F] | (R)-3-(6-(4-(3H-imidazo[4,5-b]pyridin-7-yl)-1H-pyrazol-1-yl)pyridin-3-yl)-4,4,4-trifluoro-N-methylbutanamide |
| 1214. | 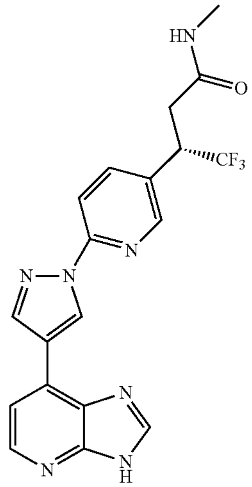 [SMILES: CNC(=O)C[C@@H](c1ccc(-n2cc(-c3ccnc4[nH]cnc34)cn2)nc1)C(F)(F)F] | (S)-3-(6-(4-(3H-imidazo[4,5-b]pyridin-7-yl)-1H-pyrazol-1-yl)pyridin-3-yl)-4,4,4-trifluoro-N-methylbutanamide |
| 1215. | 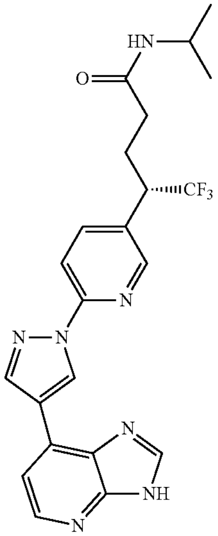 [SMILES: CC(C)NC(=O)CC[C@@H](c1ccc(-n2cc(-c3ccnc4[nH]cnc34)cn2)nc1)C(F)(F)F] | (S)-4-(6-(4-(3H-imidazo[4,5-b]pyridin-7-yl)-1H-pyrazol-1-yl)pyridin-3-yl)-5,5,5-trifluoro-N-isopropylpentanamide |

TABLE 1-continued
| Exemplary compounds of the present invention | | |
|---|---|---|
| S. No | Structure | IUPAC Name |
| 1216. | 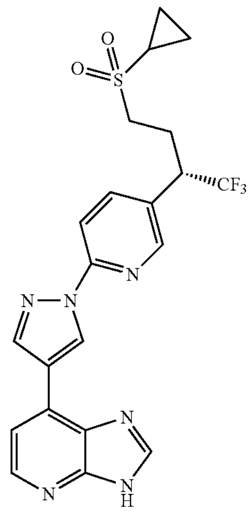 [SMILES: O=S(=O)(CC[C@@H](c1ccc(-n2cc(-c3ccnc4[nH]cnc34)cn2)nc1)C(F)(F)F)C1CC1] | 7-(1-(5-((S)-4-(cyclopropylsulfonyl)-1,1,1-trifluorobutan-2-yl)pyridin-2-yl)-1H-pyrazol-4-yl)-3H-imidazo[4,5-b]pyridine |
| 1217. | 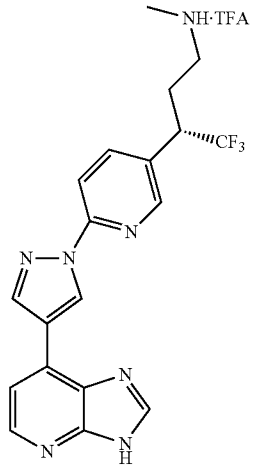 | (S)-3-(6-(4-(3H-imidazo[4,5-b]pyridin-7-yl)-1H-pyrazol-1-yl)pyridin-3-yl)-4,4,4-trifluoro-N-methylbutan-1-amine, TFA salt |
| 1218. | 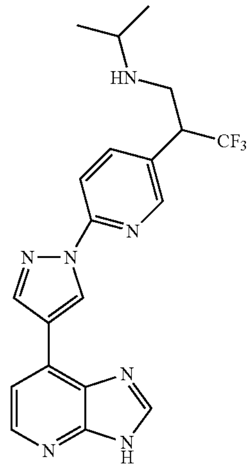 [SMILES: CC(C)NCC(c1ccc(-n2cc(-c3ccnc4[nH]cnc34)cn2)nc1)C(F)(F)F] | 2-(6-(4-(3H-imidazo[4,5-b]pyridin-7-yl)-1H-pyrazol-1-yl)pyridin-3-yl)-3,3,3-trifluoro-N-isopropylpropan-1-amine |

TABLE 1-continued
| Exemplary compounds of the present invention | | |
|---|---|---|
| S. No | Structure | IUPAC Name |
| 1219. | 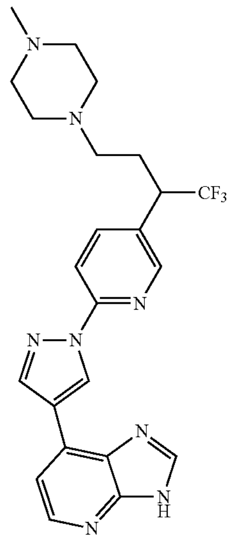 [SMILES: CN1CCN(CCC(c2ccc(-n3cc(-c4ccnc5[nH]cnc45)cn3)nc2)C(F)(F)F)CC1] | 7-(1-(5-(1,1,1-trifluoro-4-(4-methylpiperazin-1-yl)butan-2-yl)pyridin-2-yl)-1H-pyrazol-4-yl)-3H-imidazo[4,5-b]pyridine |
| 1220. | 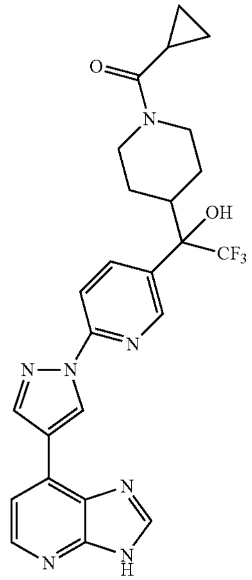 [SMILES: O=C(C1CC1)N1CCC(C(O)(c2ccc(-n3cc(-c4ccnc5[nH]cnc45)cn3)nc2)C(F)(F)F)CC1] | (4-(1-(6-(4-(3H-imidazo[4,5-b]pyridin-7-yl)-1H-pyrazol-1-yl)pyridin-3-yl)-2,2,2-trifluoro-1-hydroxyethyl)piperidin-1-yl)(cyclopropyl)methanone |

TABLE 1-continued
| Exemplary compounds of the present invention | | |
|---|---|---|
| S. No | Structure | IUPAC Name |
| 1221. | 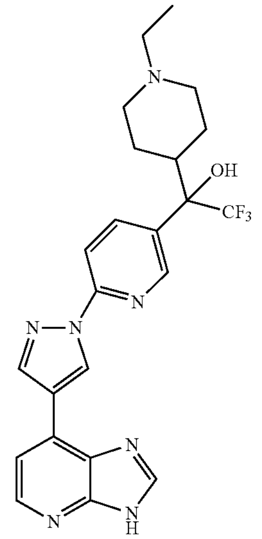 [SMILES: CCN1CCC(C(O)(c2ccc(-n3cc(-c4ccnc5[nH]cnc45)cn3)nc2)C(F)(F)F)CC1] | 1-(6-(4-(3H-imidazo[4,5-b]pyridin-7-yl)-1H-pyrazol-1-yl)pyridin-3-yl)-1-(1-ethylpiperidin-4-yl)-2,2,2-trifluoroethanol |
| 1222. | 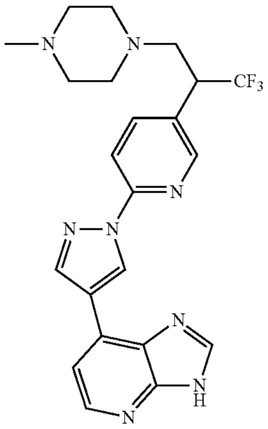 [SMILES: CN1CCN(CC(c2ccc(-n3cc(-c4ccnc5[nH]cnc45)cn3)nc2)C(F)(F)F)CC1] | 7-(1-(5-(1,1,1-trifluoro-3-(4-methylpiperazin-1-yl)propan-2-yl)pyridin-2-yl)-1H-pyrazol-4-yl)-3H-imidazo[4,5-b]pyridine |
| 1223. | 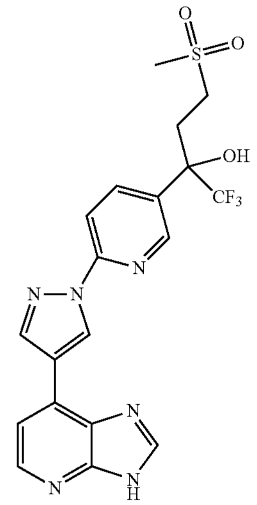 [SMILES: CS(=O)(=O)CCC(O)(c1ccc(-n2cc(-c3ccnc4[nH]cnc34)cn2)nc1)C(F)(F)F] | 2-(6-(4-(3H-imidazo[4,5-b]pyridin-7-yl)-1H-pyrazol-1-yl)pyridin-3-yl)-1,1,1-trifluoro-4-(methylsulfonyl)butan-2-ol |

TABLE 1-continued
| Exemplary compounds of the present invention | | |
|---|---|---|
| S. No | Structure | IUPAC Name |
| 1224. | 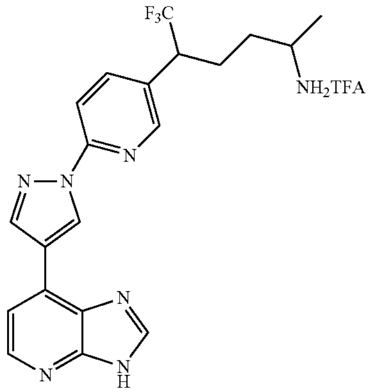 | 5-(6-(4-(3H-imidazo[4,5-b]pyridin-7-yl)-1H-pyrazol-1-yl)pyridin-3-yl)-6,6,6-trifluorohexan-2-amine, TFA salt |
| 1225. | 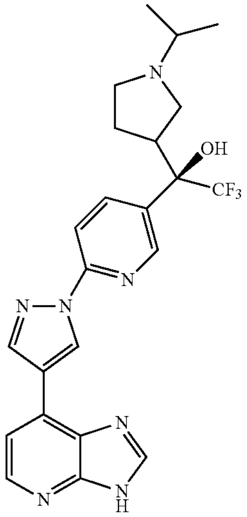 [SMILES: CC(C)N1CCC([C@@](O)(c2ccc(-n3cc(-c4ccnc5[nH]cnc45)cn3)nc2)C(F)(F)F)C1] | (R)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl)ethanol |
| 1226. | 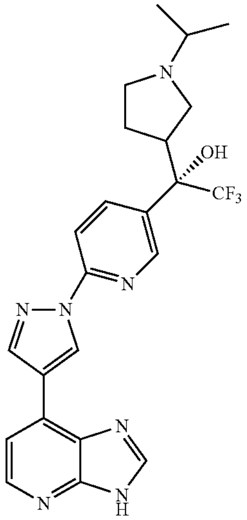 [SMILES: CC(C)N1CCC([C@](O)(c2ccc(-n3cc(-c4ccnc5[nH]cnc45)cn3)nc2)C(F)(F)F)C1] | (S)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl)ethanol |

TABLE 1-continued
| Exemplary compounds of the present invention | | |
|---|---|---|
| S. No | Structure | IUPAC Name |
| 1227. | 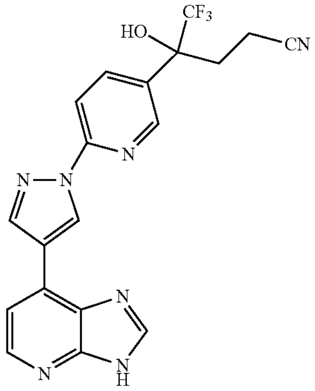 [SMILES: N#CCCC(O)(c1ccc(-n2cc(-c3ccnc4[nH]cnc34)cn2)nc1)C(F)(F)F] | 4-(6-(4-(3H-imidazo[4,5-b]pyridin-7-yl)-1H-pyrazol-1-yl)pyridin-3-yl)-5,5,5-trifluoro-4-hydroxypentanenitrile |
| 1228. | 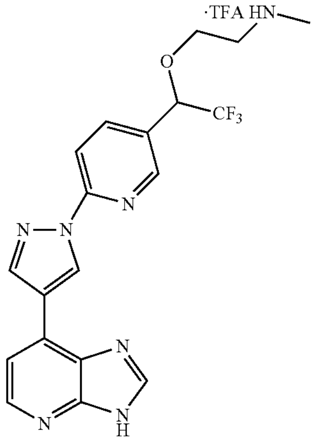 | 2-(1-(6-(4-(3H-imidazo[4,5-b]pyridin-7-yl)-1H-pyrazol-1-yl)pyridin-3-yl)-2,2,2-trifluoroethoxy)-N-methylethanamine |
| 1229. | 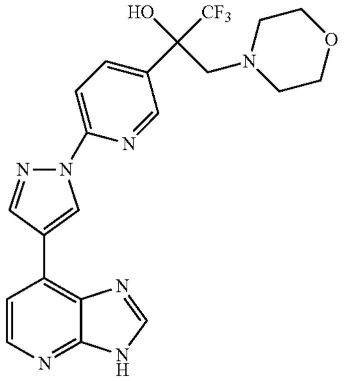 [SMILES: OC(CN1CCOCC1)(c1ccc(-n2cc(-c3ccnc4[nH]cnc34)cn2)nc1)C(F)(F)F] | 2-(6-(4-(3H-imidazo[4,5-b]pyridin-7-yl)-1H-pyrazol-1-yl)pyridin-3-yl)-1,1,1-trifluoro-3-morpholinopropan-2-ol |

TABLE 1-continued
| Exemplary compounds of the present invention | | |
|---|---|---|
| S. No | Structure | IUPAC Name |
| 1230. | 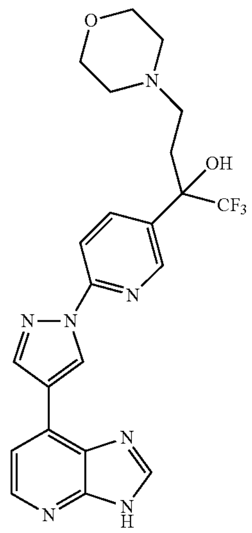 [SMILES: OC(CCN1CCOCC1)(c1ccc(-n2cc(-c3ccnc4[nH]cnc34)cn2)nc1)C(F)(F)F] | 2-(6-(4-(3H-imidazo[4,5-b]pyridin-7-yl)-1H-pyrazol-1-yl)pyridin-3-yl)-1,1,1-trifluoro-4-morpholinobutan-2-ol |
| 1231. | 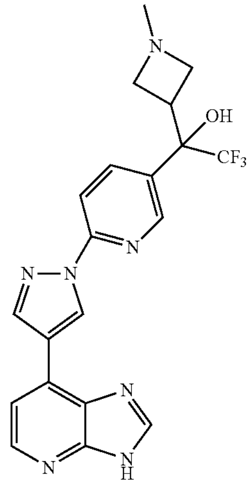 [SMILES: CN1CC(C(O)(c2ccc(-n3cc(-c4ccnc5[nH]cnc45)cn3)nc2)C(F)(F)F)C1] | 1-(6-(4-(3H-imidazo[4,5-b]pyridin-7-yl)-1H-pyrazol-1-yl)pyridin-3-yl)-2,2,2-trifluoro-1-(1-methylazetidin-3-yl)ethanol |
| 1232. | 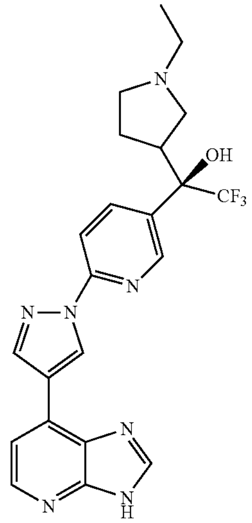 [SMILES: CCN1CCC([C@@](O)(c2ccc(-n3cc(-c4ccnc5[nH]cnc45)cn3)nc2)C(F)(F)F)C1] | (R)-1-(6-(4-(3H-imidazo[4,5-b]pyridin-7-yl)-1H-pyrazol-1-yl)pyridin-3-yl)-1-(1-ethylpyrrolidin-3-yl)-2,2,2-trifluoroethanol |

TABLE 1-continued
| Exemplary compounds of the present invention | | |
|---|---|---|
| S. No | Structure | IUPAC Name |
| 1233. | 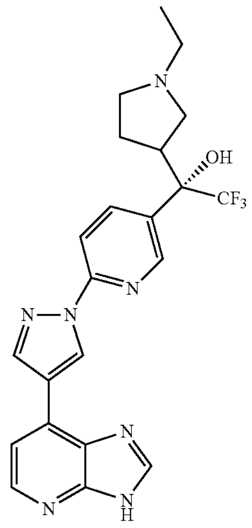 [SMILES: CCN1CCC([C@](O)(c2ccc(-n3cc(-c4ccnc5[nH]cnc45)cn3)nc2)C(F)(F)F)C1] | (S)-1-(6-(4-(3H-imidazo[4,5-b]pyridin-7-yl)-1H-pyrazol-1-yl)pyridin-3-yl)-1-(1-ethylpyrrolidin-3-yl)-2,2,2-trifluoroethanol |
| 1234. | 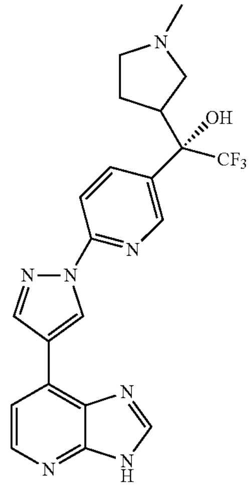 [SMILES: CN1CCC([C@](O)(c2ccc(-n3cc(-c4ccnc5[nH]cnc45)cn3)nc2)C(F)(F)F)C1] | (S)-1-(6-(4-(3H-imidazo[4,5-b]pyridin-7-yl)-1H-pyrazol-1-yl)pyridin-3-yl)-2,2,2-trifluoro-1-(1-methylpyrrolidin-3-yl)ethanol |
| 1235. | 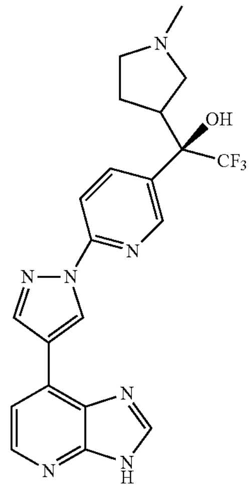 [SMILES: CN1CCC([C@@](O)(c2ccc(-n3cc(-c4ccnc5[nH]cnc45)cn3)nc2)C(F)(F)F)C1] | (R)-1-(6-(4-(3H-imidazo[4,5-b]pyridin-7-yl)-1H-pyrazol-1-yl)pyridin-3-yl)-2,2,2-trifluoro-1-(1-methylpyrrolidin-3-yl)ethanol |

TABLE 1-continued
Exemplary compounds of the present invention
| S. No | Structure | IUPAC Name |
|---|---|---|
| 1236. | 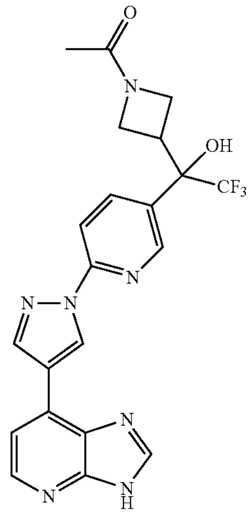 [SMILES: CC(=O)N1CC(C(O)(c2ccc(-n3cc(-c4ccnc5[nH]cnc45)cn3)nc2)C(F)(F)F)C1] | 1-(3-(1-(6-(4-(3H-imidazo[4,5-b]pyridin-7-yl)-1H-pyrazol-1-yl)pyridin-3-yl)-2,2,2-trifluoro-1-hydroxyethyl)azetidin-1-yl)ethanone |
| 1237. | 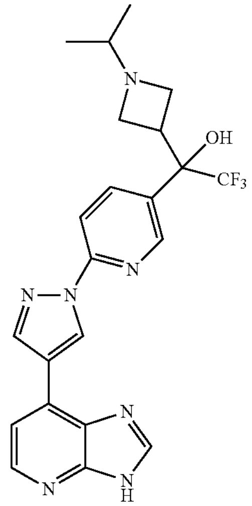 [SMILES: CC(C)N1CC(C(O)(c2ccc(-n3cc(-c4ccnc5[nH]cnc45)cn3)nc2)C(F)(F)F)C1] | 1-(6-(4-(3H-imidazo[4,5-b]pyridin-7-yl)-1H-pyrazol-1-yl)pyridin-3-yl)-2,2,2-trifluoro-1-(1-isopropylazetidin-3-yl)ethanol |
| 1238. | 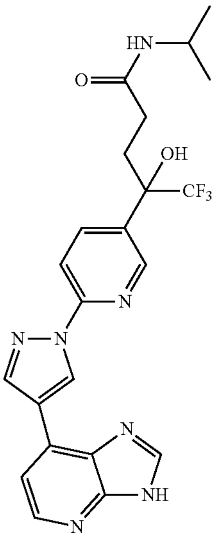 [SMILES: CC(C)NC(=O)CCC(O)(c1ccc(-n2cc(-c3ccnc4[nH]cnc34)cn2)nc1)C(F)(F)F] | 4-(6-(4-(3H-imidazo[4,5-b]pyridin-7-1H-pyrazol-1-yl)pyridin-3-yl)-5,5,5-trifluoro-4-hydroxy-N-isopropylpentanamide |

TABLE 1-continued
| Exemplary compounds of the present invention | | |
|---|---|---|
| S. No | Structure | IUPAC Name |
| 1239. | 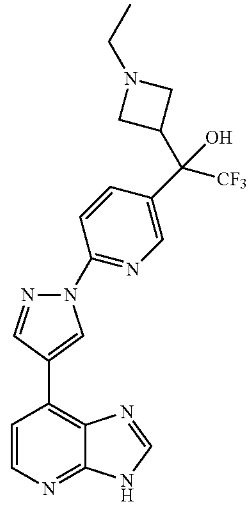 [SMILES: CCN1CC(C(O)(c2ccc(-n3cc(-c4ccnc5[nH]cnc45)cn3)nc2)C(F)(F)F)C1] | 1-(6-(4-(3H-imidazo[4,5-b]pyridin-7-yl)-1H-pyrazol-1-yl)pyridin-3-yl)-1-(1-ethylazetidin-3-yl)-2,2,2-trifluoroethanol |
| 1240. | 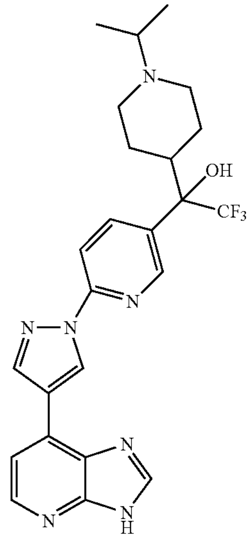 [SMILES: CC(C)N1CCC(C(O)(c2ccc(-n3cc(-c4ccnc5[nH]cnc45)cn3)nc2)C(F)(F)F)CC1] | 1-(6-(4-(3H-imidazo[4,5-b]pyridin-7-yl)-1H-pyrazol-1-yl)pyridin-3-yl)-2,2,2-trifluoro-1-(1-isopropylpiperidin-4-yl)ethanol |
| 1241. | 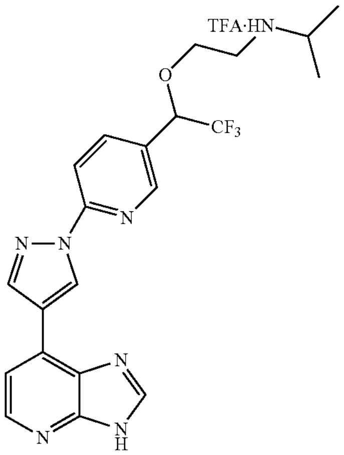 | N-(2-(1-(6-(4-(3H-imidazo[4,5-b]pyridin-7-yl)-1H-pyrazol-1-yl)pyridin-3-yl)-2,2,2-trifluoroethoxy)ethyl)propan-2-amine, TFA salt |

TABLE 1-continued
| Exemplary compounds of the present invention | | |
|---|---|---|
| S. No | Structure | IUPAC Name |
| 1242. | 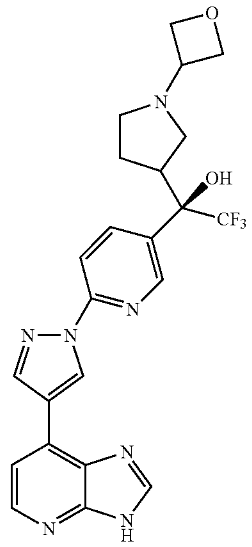 [SMILES: O[C@@](c1ccc(-n2cc(-c3ccnc4[nH]cnc34)cn2)nc1)(C1CCN(C2COC2)C1)C(F)(F)F] | (R)-1-(6-(4-(3H-imidazo[4,5-b]pyridin-7-yl)-1H-pyrazol-1-yl)pyridin-3-yl)-2,2,2-trifluoro-1-(1-(oxetan-3-yl)pyrrolidin-3-yl)ethanol |
| 1243. | 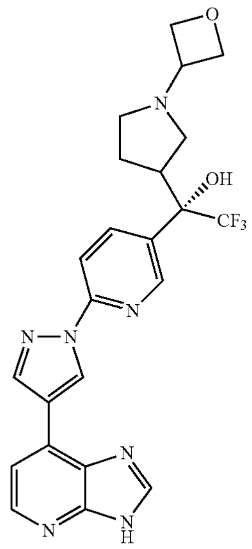 [SMILES: O[C@](c1ccc(-n2cc(-c3ccnc4[nH]cnc34)cn2)nc1)(C1CCN(C2COC2)C1)C(F)(F)F] | (S)-1-(6-(4-(3H-imidazo[4,5-b]pyridin-7-yl)-1H-pyrazol-1-yl)pyridin-3-yl)-2,2,2-trifluoro-1-(1-(oxetan-3-yl)pyrrolidin-3-yl)ethanol |

TABLE 1-continued

| S. No | Structure | IUPAC Name |
| --- | --- | --- |
| 1244. | 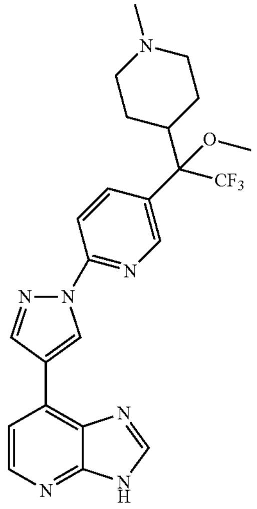 [SMILES: COC(c1ccc(-n2cc(-c3ccnc4[nH]cnc34)cn2)nc1)(C1CCN(C)CC1)C(F)(F)F] | 7-(1-(5-(2,2,2-trifluoro-1-methoxy-1-(1-methylpiperidin-4-yl)ethyl)pyridin-2-yl)-1H-pyrazol-4-yl)-3H-imidazo[4,5-b]pyridine |
| 1245. | 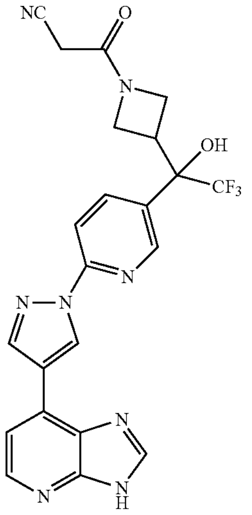 [SMILES: N#CCC(=O)N1CC(C(O)(c2ccc(-n3cc(-c4ccnc5[nH]cnc45)cn3)nc2)C(F)(F)F)C1] | 3-(3-(1-(6-(4-(3H-imidazo[4,5-b]pyridin-7-yl)-1H-pyrazol-1-yl)pyridin-3-yl)-2,2,2-trifluoro-1-hydroxyethyl)azetidin-1-yl)-3-oxopropanenitrile |
| 1246. | 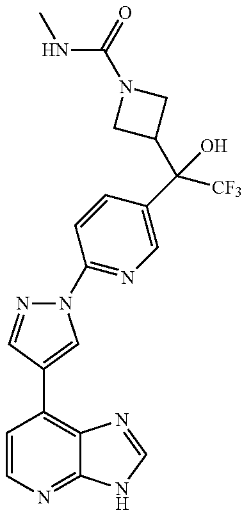 [SMILES: CNC(=O)N1CC(C(O)(c2ccc(-n3cc(-c4ccnc5[nH]cnc45)cn3)nc2)C(F)(F)F)C1] | 3-(1-(6-(4-(3H-imidazo[4,5-b]pyridin-7-yl)-1H-pyrazol-1-yl)pyridin-3-yl)-2,2,2-trifluoro-1-hydroxyethyl)-N-methylazetidine-1-carboxamide |

Exemplary compounds of the present invention

TABLE 1-continued
| Exemplary compounds of the present invention | | |
|---|---|---|
| S. No | Structure | IUPAC Name |
| 1247. | 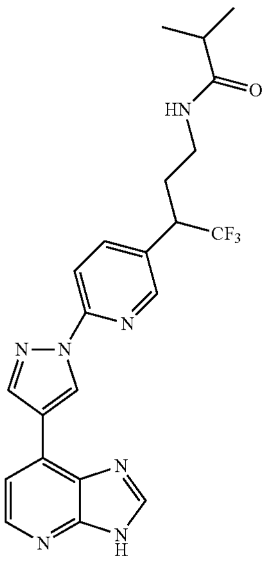 [SMILES: CC(C)C(=O)NCCC(c1ccc(-n2cc(-c3ccnc4[nH]cnc34)cn2)nc1)C(F)(F)F] | N-(3-(6-(4-(3H-imidazo[4,5-b]pyridin-7-yl)-1H-pyrazol-1-yl)pyridin-3-yl)-4,4,4-trifluorobutyl)isobutyramide |
| 1248. | 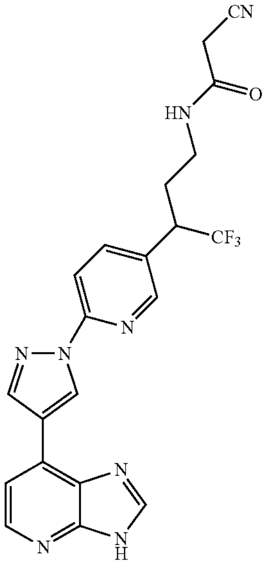 [SMILES: N#CCC(=O)NCCC(c1ccc(-n2cc(-c3ccnc4[nH]cnc34)cn2)nc1)C(F)(F)F] | N-(3-(6-(4-(3H-imidazo[4,5-b]pyridin-7-yl)-1H-pyrazol-1-yl)pyridin-3-yl)-4,4,4-trifluorobutyl)-2-cyanoacetamide |

TABLE 1-continued
| Exemplary compounds of the present invention | | |
|---|---|---|
| S. No | Structure | IUPAC Name |
| 1249. | 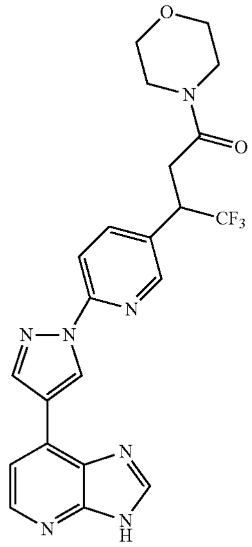 [SMILES: O=C(CC(c1ccc(-n2cc(-c3ccnc4[nH]cnc34)cn2)nc1)C(F)(F)F)N1CCOCC1] | 3-(6-(4-(3H-imidazo[4,5-b]pyridin-7-yl)-1H-pyrazol-1-yl)pyridin-3-yl)-4,4,4-trifluoro-1-morpholinobutan-1-one |
| 1250. | 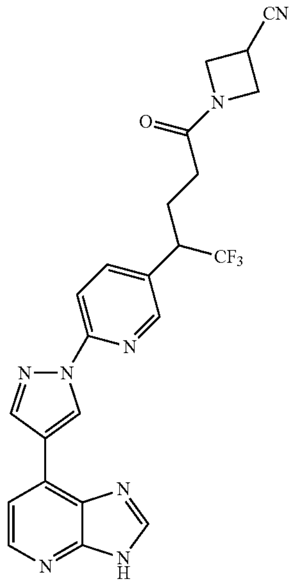 [SMILES: N#CC1CN(C(=O)CCC(c2ccc(-n3cc(-c4ccnc5[nH]cnc45)cn3)nc2)C(F)(F)F)C1] | 1-(4-(6-(4-(3H-imidazo[4,5-b]pyridin-7-yl)-1H-pyrazol-1-yl)pyridin-3-yl)-5,5,5-trifluoropentanoyl)azetidine-3-carbonitrile |

TABLE 1-continued

| Exemplary compounds of the present invention | | |
|---|---|---|
| S. No | Structure | IUPAC Name |
| 1251. | 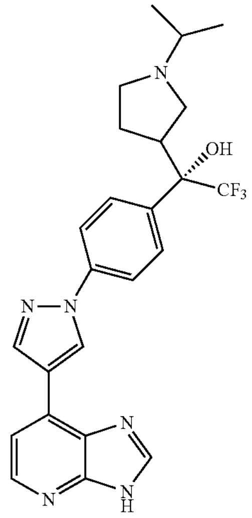 [SMILES: CC(C)N1CCC([C@](O)(c2ccc(-n3cc(-c4ccnc5[nH]cnc45)cn3)cc2)C(F)(F)F)C1] | (S)-1-(4-(4-(3H-imidazo[4,5-b]pyridin-7-yl)-1H-pyrazol-1-yl)phenyl)-2,2,2-trifluoro-1-(1-isopropylpyrrolidin-3-yl)ethanol |
| 1252. | 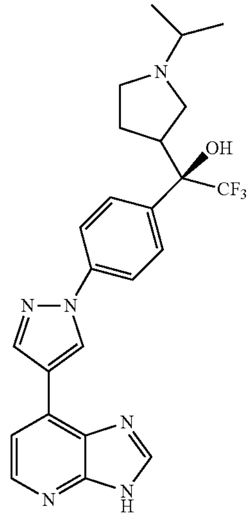 [SMILES: CC(C)N1CCC([C@@](O)(c2ccc(-n3cc(-c4ccnc5[nH]cnc45)cn3)cc2)C(F)(F)F)C1] | (R)-1-(4-(4-(3H-imidazo[4,5-b]pyridin-7-yl)-1H-pyrazol-1-yl)phenyl)-2,2,2-trifluoro-1-(1-isopropylpyrrolidin-3-yl)ethanol |

The compounds of the present invention include:

1001. N-(2,2,2-trifluoroethyl)-4-(2,3-dihydro-2-oxo-1H-imidazo[4,5-b]pyridin-7-yl)benzamide;

1002. 1-(1,1,1-trifluoropropan-2-yl)-3-(4-(2,3-dihydro-2-oxo-1H-imidazo[4,5-b]pyridin-7-yl)phenyl)urea;

1003. 1-(2,2,2-trifluoroethyl)-3-(4-(2,3-dihydro-2-oxo-1H-imidazo[4,5-b]pyridin-7-yl)phenyl)urea;

1004. 1-(2,2,2-trifluoroethyl)-3-(5-(2,3-dihydro-2-oxo-1H-imidazo[4,5-b]pyridin-7-yl)pyrimidin-2-yl)urea;

1005. 1-(2,2,2-trifluoroethyl)-3-(5-(2,3-dihydro-2-oxo-1H-imidazo[4,5-b]pyridin-7-yl)pyridin-2-yl)urea;

1006. 1-(5-(2-oxo-2,3-dihydro-1H-imidazo[4,5-b]pyridin-7-yl)pyrazin-2-yl)-3-(2,2,2-trifluoroethyl)urea;

1007. N-(4-(2,3-dihydro-2-oxo-1H-imidazo[4,5-b]pyridin-7-yl)phenyl)-3,3-dimethylazetidine-1-carboxamide;

1008. N-(4-(2,3-dihydro-2-oxo-1H-imidazo[4,5-b]pyridin-7-yl)phenyl)morpholine-4-carboxamide;

1009. 1-(4-(2,3-dihydro-2-oxo-1H-imidazo[4,5-b]pyridin-7-yl)phenyl)-3-(pyridin-4-yl)urea;

1010. 1-(4-(3H-imidazo[4,5-b]pyridin-7-yl)phenyl)-3-(2,2,2-trifluoroethyl)urea;

1011. N-(2,2,2-trifluoroethyl)-4-(2,3-dihydro-2-oxo-1H-imidazo[4,5-b]pyridin-7-yl)piperazine-1-carboxamide;

1012. N-(cyanomethyl)-4-(2,3-dihydro-2-oxo-1H-imidazo[4,5-b]pyridin-7-yl)piperazine-1-carboxamide;

1013. 4-(2,3-dihydro-2-oxo-1H-imidazo[4,5-b]pyridin-7-yl)-N-(2-(methylsulfonyl)ethyl)piperazine-1-carboxamide;

1014. 4-(2,3-dihydro-2-oxo-1H-imidazo[4,5-b]pyridin-7-yl)-N-(pyridin-4-yl)piperazine-1-carboxamide;

1015. N-(2-fluoropyridin-4-yl)-4-(2,3-dihydro-2-oxo-1H-imidazo[4,5-b]pyridin-7-yl)piperazine-1-carboxamide;

1016. N-(1-(methylsulfonyl)piperidin-4-yl)-4-(2-oxo-2,3-dihydro-1H-imidazo[4,5-b]pyridin-7-yl)piperazine-1-carboxamide;

1017. N-(cyclopentylmethyl)-4-(2,3-dihydro-2-oxo-1H-imidazo[4,5-b]pyridin-7-yl)piperazine-1-carboxamide;

1018. 7-(4-(1,1-dioxidothiomorpholine-4-carbonyl)piperazin-1-yl)-1,3-dihydro-2H-imidazo[4,5-b]pyridin-2-one;

1019. 4-(2,3-dihydro-2-oxo-1H-imidazo[4,5-b]pyridin-7-yl)-N-(2-methoxypyridin-4-yl)piperazine-1-carboxamide;

1020. N-(1,1-dioxidotetrahydro-2H-thiopyran-4-yl)-4-(2-oxo-2,3-dihydro-1H-imidazo[4,5-b]pyridin-7-yl)piperazine-1-carboxamide;

1021. N-(1,1,1-trifluoropropan-2-yl)-4-(2,3-dihydro-2-oxo-1H-imidazo[4,5-b]pyridin-7-yl)piperazine-1-carboxamide;

1022. N-(2,2,2-trifluoroethyl)-4-(2-phenyl-3H-imidazo[4,5-b]pyridin-7-yl)piperazine-1-carboxamide;

1023. 7-(4-(3,3-dimethylazetidine-1-carbonyl)piperazin-1-yl)-1,3-dihydro-2H-imidazo[4,5-b]pyridin-2-one;

1024. 4-(2,3-dihydro-2-oxo-1H-imidazo[4,5-b]pyridin-7-yl)-N-(2-methyl-4-(methylsulfonyl)phenyl)piperazine-1-carboxamide;

1025. N-(2,2,2-trifluoroethyl)-2-(4-(2,3-dihydro-2-oxo-1H-imidazo[4,5-b]pyridin-7-yl)piperazin-1-yl)acetamide;

1026. N-(2,2,2-trifluoroethyl)-4-(2,3-dihydro-2-oxo-1H-imidazo[4,5-b]pyridin-7-yl)-1H-pyrazole-1-carboxamide;

1027. N-(cyanomethyl)-4-(2,3-dihydro-2-oxo-1H-imidazo[4,5-b]pyridin-7-yl)-1H-pyrazole-1-carboxamide;

1028. N-(2,2,2-trifluoroethyl)-3-(2,3-dihydro-2-oxo-1H-imidazo[4,5-b]pyridin-7-yl)-1H-pyrrole-1-carboxamide;

1029. N-(2,2,2-trifluoroethyl)-4-(2,3-dihydro-1-methyl-2-oxo-1H-imidazo[4,5-b]pyridin-7-yl)-1H-pyrazole-1-carboxamide;

1030. N-(1,1,1-trifluoropropan-2-yl)-4-(2,3-dihydro-2-oxo-1H-imidazo[4,5-b]pyridin-7-yl)-1H-pyrazole-1-carboxamide;

1031. 7-(1-(4,4,4-trifluorobutanoyl)-1H-pyrazol-4-yl)-1H-imidazo[4,5-b]pyridin-2(3H)-one;

1032. N-(1-cyanocyclopropyl)-4-(2,3-dihydro-2-oxo-1H-imidazo[4,5-b]pyridin-7-yl)-1H-pyrazole-1-carboxamide;

1033. N-(2-cyanopropan-2-yl)-4-(2,3-dihydro-2-oxo-1H-imidazo[4,5-b]pyridin-7-yl)-1H-pyrazole-1-carboxamide;

1034. N-(cyclopentylmethyl)-4-(2,3-dihydro-2-oxo-1H-imidazo[4,5-b]pyridin-7-yl)-1H-pyrazole-1-carboxamide;

1035. N-(cyanomethyl)-4-(2,3-dihydro-2-oxo-1H-imidazo[4,5-b]pyridin-7-yl)-1H-pyrazole-1-carboxamide hydrochloride;

1036. N-(2,2,2-trifluoroethyl)-4-(2,3-dihydro-2-oxo-1H-benzo[d]imidazol-4-yl)-1H-pyrazole-1-carboxamide;

1037. 7-(1-(3,3-dimethylazetidine-1-carbonyl)-1H-pyrazol-4-yl)-1,3-dihydro-2H-imidazo[4,5-b]pyridin-2-one;

1038. N-(cyano(cyclopentyl)methyl)-4-(2,3-dihydro-2-oxo-1H-imidazo[4,5-b]pyridin-7-yl)-1H-pyrazole-1-carboxamide;

1039. N-(2-cyano-1-cyclopentylethyl)-4-(2,3-dihydro-2-oxo-1H-imidazo[4,5-b]pyridin-7-yl)-1H-pyrazole-1-carboxamide;

1040. N-(2-cyanobutan-2-yl)-4-(2,3-dihydro-2-oxo-1H-imidazo[4,5-b]pyridin-7-yl)-1H-pyrazole-1-carboxamide;

1041. N-(1-cyclopentyl-2,2,2-trifluoroethyl)-4-(2,3-dihydro-2-oxo-1H-imidazo[4,5-b]pyridin-7-yl)-1H-pyrazole-1-carboxamide;

1042. 4-(1-ethyl-2,3-dihydro-2-oxo-1H-imidazo[4,5-b]pyridin-7-yl)-N-(2,2,2-trifluoroethyl)-1H-pyrazole-1-carboxamide;

1043. N-(cyano(cyclopropyl)methyl)-4-(2,3-dihydro-2-oxo-1H-imidazo[4,5-b]pyridin-7-yl)-1H-pyrazole-1-carboxamide;

1044. N-(1-cyano-2-methylpropyl)-4-(2,3-dihydro-2-oxo-1H-imidazo[4,5-b]pyridin-7-yl)-1H-pyrazole-1-carboxamide;

1045. N-(2,2,2-trifluoroethyl)-4-(2,3-dihydro-2-oxo-1H-pyrrolo[2,3-b]pyridin-4-yl)-1H-pyrazole-1-carboxamide;

1046. N-(1-cyanopropan-2-yl)-4-(2,3-dihydro-2-oxo-1H-imidazo[4,5-b]pyridin-7-yl)-1H-pyrazole-1-carboxamide;

1047. N—((S)-1-cyano-2-methylpropyl)-4-(2,3-dihydro-2-oxo-1H-imidazo[4,5-b]pyridin-7-yl)-1H-pyrazole-1-carboxamide;

1048. 1-(4-(2-oxo-2,3-dihydro-1H-imidazo[4,5-b]pyridin-7-yl)-1H-pyrazole-1-carbonyl)azetidine-3-carbonitrile;

1049. N—((R)-1-cyano-2-methylpropyl)-4-(2,3-dihydro-2-oxo-1H-imidazo[4,5-b]pyridin-7-yl)-1H-pyrazole-1-carboxamide;

1050. N-(3-cyano-1,1,1-trifluoropropan-2-yl)-4-(2,3-dihydro-2-oxo-1H-imidazo[4,5-b]pyridin-7-yl)-1H-pyrazole-1-carboxamide;

1051. N-(2-cyano-1-cyclopropylethyl)-4-(2,3-dihydro-2-oxo-1H-imidazo[4,5-b]pyridin-7-yl)-1H-pyrazole-1-carboxamide;

1052. N-(1-cyanopropan-2-yl)-4-(2,3-dihydro-2-oxo-1H-imidazo[4,5-b]pyridin-7-yl)-1H-pyrazole-1-carboxamide;

1053. N-(1-cyanopropan-2-yl)-4-(2,3-dihydro-2-oxo-1H-imidazo[4,5-b]pyridin-7-yl)-1H-pyrazole-1-carboxamide;

1054. N—((R)-cyano(cyclopropyl)methyl)-4-(2,3-dihydro-2-oxo-1H-imidazo[4,5-b]pyridin-7-yl)-1H-pyrazole-1-carboxamide;

1055. 1-(4-(2-oxo-2,3-dihydro-1H-imidazo[4,5-b]pyridin-7-yl)-1H-pyrazole-1-carbonyl)pyrrolidine-3-carbonitrile;

1056. N-(3-cyanocyclobutyl)-4-(2,3-dihydro-2-oxo-1H-imidazo[4,5-b]pyridin-7-yl)-1H-pyrazole-1-carboxamide;

1057. 2-(1-(4-(2-oxo-2,3-dihydro-1H-imidazo[4,5-b]pyridin-7-yl)-1H-pyrazole-1-carbonyl)pyrrolidin-3-yl)acetonitrile;

1058. N-(1-(3-cyanoazetidin-1-yl)-1-oxopropan-2-yl)-4-(2-oxo-2,3-dihydro-1H-imidazo[4,5-b]pyridin-7-yl)-1H-pyrazole-1-carboxamide;

1059. N-(2-(3-cyanoazetidin-1-yl)-2-oxoethyl)-4-(2-oxo-2,3-dihydro-1H-imidazo[4,5-b]pyridin-7-yl)-1H-pyrazole-1-carboxamide;

1060. N-(2-(3-cyanoazetidin-1-yl)-2-oxoethyl)-4-(2-oxo-2,3-dihydro-1H-imidazo[4,5-b]pyridin-7-yl)-1H-pyrazole-1-carboxamide;

1061. 3-(1-(4-(2-oxo-2,3-dihydro-1H-imidazo[4,5-b]pyridin-7-yl)-1H-pyrazole-1-carbonyl)pyrrolidin-3-yl)propanenitrile;

1062. N-(2-cyano-1-(tetrahydro-2H-pyran-4-yl)ethyl)-4-(2,3-dihydro-2-oxo-1H-imidazo[4,5-b]pyridin-7-yl)-1H-pyrazole-1-carboxamide;

1063. N-(cyano(phenyl)methyl)-4-(2,3-dihydro-2-oxo-1H-imidazo[4,5-b]pyridin-7-yl)-1H-pyrazole-1-carboxamide;

1064. N-(2,2,2-trifluoroethyl)-4-(3H-imidazo[4,5-b]pyridin-7-yl)-1H-pyrazole-1-carboxamide;

1065. N-(2-cyano-1-(tetrahydro-2H-pyran-4-yl)ethyl)-4-(3H-imidazo[4,5-b]pyridin-7-yl)-1H-pyrazole-1-carboxamide;

1066. N-(2-cyanocyclohexyl)-4-(3H-imidazo[4,5-b]pyridin-7-yl)-1H-pyrazole-1-carboxamide;

1067. 1-(4-(3H-imidazo[4,5-b]pyridin-7-yl)-1H-pyrazole-1-carbonyl)piperidine-4-carbonitrile;

1068. N-(1-(3-cyanoazetidin-1-yl)propan-2-yl)-4-(3H-imidazo[4,5-b]pyridin-7-yl)-1H-pyrazole-1-carboxamide;

1069. N-(1-(4-(3H-imidazo[4,5-b]pyridin-7-yl)-1H-pyrazole-1-carbonyl)pyrrolidin-3-yl)propane-1-sulfonamide;

1070. N-(cyano(phenyl)methyl)-4-(3H-imidazo[4,5-b]pyridin-7-yl)-1H-pyrazole-1-carboxamide;
1071. N-(1-cyano-3-methoxypropyl)-4-(3H-imidazo[4,5-b]pyridin-7-yl)-1H-pyrazole-1-carboxamide;
1072. N-(1-cyano-3-(methylsulfonyl)propyl)-4-(3H-imidazo[4,5-b]pyridin-7-yl)-1H-pyrazole-1-carboxamide;
1073. N—((S)-1-cyano-2-methylpropyl)-4-(3H-imidazo[4,5-b]pyridin-7-yl)-1H-pyrazole-1-carboxamide;
1074. 1-(4-(3H-imidazo[4,5-b]pyridin-7-yl)-1H-pyrazole-1-carbonyl)-4-methylpyrrolidine-3-carbonitrile;
1075. 2-(2-(4-(3H-imidazo[4,5-b]pyridin-7-yl)-1H-pyrazol-1-yl)oxazol-4-yl)acetonitrile;
1076. 2-(2-(4-(3H-imidazo[4,5-b]pyridin-7-yl)-1H-pyrazol-1-yl)thiazol-4-yl)acetonitrile;
1077. 7-(1-((oxazol-5-yl)methyl)-1H-pyrazol-4-yl)-3H-imidazo[4,5-b]pyridine;
1078. 2-(6-(4-(3H-imidazo[4,5-b]pyridin-7-yl)-1H-pyrazol-1-yl)pyridin-3-yl)acetonitrile;
1079. 6-(4-(3H-imidazo[4,5-b]pyridin-7-yl)-1H-pyrazol-1-yl)pyridine-3-carbonitrile;
1080. 7-(1-(5-((methylsulfonyl)methyl)pyridin-2-yl)-1H-pyrazol-4-yl)-3H-imidazo[4,5-b]pyridine;
1081. 7-(1-(5-((oxetan-3-yl)methyl)pyridin-2-yl)-1H-pyrazol-4-yl)-3H-imidazo[4,5-b]pyridine;
1082. 2-(6-(4-(3H-imidazo[4,5-b]pyridin-7-yl)-1H-pyrazol-1-yl)pyridin-3-yl)acetonitrile hydrochloride;
1083. (6-(4-(3H-imidazo[4,5-b]pyridin-7-yl)-1H-pyrazol-1-yl)pyridin-3-yl)methanol;
1084. 7-(1-(5-(2,2,2-trifluoroethyl)pyridin-2-yl)-1H-pyrazol-4-yl)-3H-imidazo[4,5-b]pyridine;
1085. 7-(1-(5-(morpholinomethyl)pyridin-2-yl)-1H-pyrazol-4-yl)-3H-imidazo[4,5-b]pyridine;
1086. 4-((6-(4-(3H-imidazo[4,5-b]pyridin-7-yl)-1H-pyrazol-1-yl)pyridin-3-yl)methyl)thiomorpholine 1,1-dioxide;
1087. 1-((6-(4-(3H-imidazo[4,5-b]pyridin-7-yl)-1H-pyrazol-1-yl)pyridin-3-yl)methyl)azetidine-3-carbonitrile;
1088. 6-(4-(3H-imidazo[4,5-b]pyridin-7-yl)-1H-pyrazol-1-yl)-N-(cyanomethyl)pyridine-3-carboxamide;
1089. N-((6-(4-(3H-imidazo[4,5-b]pyridin-7-yl)-1H-pyrazol-1-yl)pyridin-3-yl)methyl)methanesulfonamide;
1090. N-((6-(4-(3H-imidazo[4,5-b]pyridin-7-yl)-1H-pyrazol-1-yl)pyridin-3-yl)methyl)methanesulfonamide;
1091. N-((6-(4-(3H-imidazo[4,5-b]pyridin-7-yl)-1H-pyrazol-1-yl)pyridin-3-yl)methyl)-2-cyanoacetamide;
1092. 2-(6-(4-(3H-imidazo[4,5-b]pyridin-7-yl)-1H-pyrazol-1-yl)pyridin-3-yl)-N-(2,2,2-trifluoroethyl)acetamide;
1093. 2-(4-(3H-imidazo[4,5-b]pyridin-7-yl)-1H-pyrazol-1-yl)-N-(cyanomethyl)pyrimidine-5-carboxamide;
1094. N-(2,2,2-trifluoroethyl)-4-(2-phenyl-3H-imidazo[4,5-b]pyridin-7-yl)-1H-pyrazole-1-carboxamide;
1095. 4-(2-ethoxy-3H-imidazo[4,5-b]pyridin-7-yl)-N-(2,2,2-trifluoroethyl)-1H-pyrazole-1-carboxamide;
1096. 4-(2-cyclopropyl-3H-imidazo[4,5-b]pyridin-7-yl)-N-(2,2,2-trifluoroethyl)-1H-pyrazole-1-carboxamide;
1097. 3-(4-(2-(4-chloro-3-methoxyphenyl)-3H-imidazo[4,5-b]pyridin-7-yl)-1H-pyrazol-1-yl)-tetrahydro-2H-pyran-4-carbonitrile;
1098. 4-(2-(1-acetylpiperidin-4-yl)-3H-imidazo[4,5-b]pyridin-7-yl)-N-(2,2,2-trifluoroethyl)-1H-pyrazole-1-carboxamide;
1099. 2-(4-(4-(3H-imidazo[4,5-b]pyridin-7-yl)-1H-pyrazol-1-yl)phenyl)acetonitrile;
1100. 2-(4-(4-(3H-imidazo[4,5-b]pyridin-7-yl)-1H-pyrazol-1-yl)phenyl)-2-cyclopropylacetonitrile;
1101. 2-(4-(4-(3H-imidazo[4,5-b]pyridin-7-yl)-1H-pyrazol-1-yl)phenyl)-2-morpholinoacetonitrile;
1102. N-(4-(4-(3H-imidazo[4,5-b]pyridin-7-yl)-1H-pyrazol-1-yl)phenyl)-2-cyanoacetamide;
1103. 2-(4-(4-(3H-imidazo[4,5-b]pyridin-7-yl)-1H-pyrazol-1-yl)-3-fluorophenyl)acetonitrile;
1104. 2-(4-(4-(3H-imidazo[4,5-b]pyridin-7-yl)-1H-pyrazol-1-yl)-2-fluorophenyl)acetonitrile;
1105. 2-(4-(4-(3H-imidazo[4,5-b]pyridin-7-yl)-1H-pyrazol-1-yl)-2-methoxyphenyl)acetonitrile;
1106. 2-(3-(4-(3H-imidazo[4,5-b]pyridin-7-yl)-1H-pyrazol-1-yl)phenyl)acetonitrile;
1107. 2-(6-(4-(3H-imidazo[4,5-b]pyridin-7-yl)-1H-pyrazol-1-yl)pyridin-3-yl)propanenitrile;
1108. 2-(6-(4-(3H-imidazo[4,5-b]pyridin-7-yl)-1H-pyrazol-1-yl)pyridin-3-yl)propanamide;
1109. 1-(6-(4-(3H-imidazo[4,5-b]pyridin-7-yl)-1H-pyrazol-1-yl)pyridin-3-yl)cyclopropanecarbonitrile;
1110. 2-(6-(4-(3H-imidazo[4,5-b]pyridin-7-yl)-1H-pyrazol-1-yl)pyridin-3-yl)-2-cyclopropylacetonitrile;
1111. 2-(6-(4-(3H-imidazo[4,5-b]pyridin-7-yl)-1H-pyrazol-1-yl)pyridin-3-yl)-2-(3,3-difluoroazetidin-1-yl)acetonitrile;
1112. 2-(6-(4-(3H-imidazo[4,5-b]pyridin-7-yl)-1H-pyrazol-1-yl)pyridin-3-yl)-2-morpholinoacetonitrile;
1113. 2-(6-(4-(3H-imidazo[4,5-b]pyridin-7-yl)-1H-pyrazol-1-yl)pyridin-3-yl)-2-(1,1-dioxidothiomorpholino)acetonitrile;
1114. 2-(6-(4-(3H-imidazo[4,5-b]pyridin-7-yl)-1H-pyrazol-1-yl)pyridin-3-yl)-2-(1-(methylsulfonyl)azetidin-3-yl)acetonitrile;
1115. 2-(6-(4-(3H-imidazo[4,5-b]pyridin-7-yl)-1H-pyrazol-1-yl)pyridin-3-yl)-2-(1-(methylsulfonyl)azetidin-3-yl)acetonitrile;
1116. 2-(6-(4-(3H-imidazo[4,5-b]pyridin-7-yl)-1H-pyrazol-1-yl)pyridin-3-yl)-4-(methylsulfonyl)butanenitrile;
1117. 2-(6-(4-(3H-imidazo[4,5-b]pyridin-7-yl)-1H-pyrazol-1-yl)pyridin-2-yl)acetonitrile;
1118. 2-(2-(4-(3H-imidazo[4,5-b]pyridin-7-yl)-1H-pyrazol-1-yl)pyridin-4-yl)acetonitrile;
1119. 7-(1-(5-(2,2,2-trifluoro-1-methoxyethyl)pyridin-2-yl)-1H-pyrazol-4-yl)-3H-imidazo[4,5-b]pyridine;
1120. 7-(1-(5-(1-chloro-2,2,2-trifluoroethyl)pyridin-2-yl)-1H-pyrazol-4-yl)-3H-imidazo[4,5-b]pyridine;
1121. 1-(6-(4-(3H-imidazo[4,5-b]pyridin-7-yl)-1H-pyrazol-1-yl)pyridin-3-yl)-2,2,2-trifluoro-N,N-dimethylethanamine;
1122. 7-(1-(5-(1,1,1-trifluorobutan-2-yl)pyridin-2-yl)-1H-pyrazol-4-yl)-3H-imidazo[4,5-b]pyridine;
1123. 3-(6-(4-(3H-imidazo[4,5-b]pyridin-7-yl)-1H-pyrazol-1-yl)pyridin-3-yl)-4,4,4-trifluorobutanenitrile;
1124. 7-(1-(5-(2,2,2-trifluoro-1-isopropoxyethyl)pyridin-2-yl)-1H-pyrazol-4-yl)-3H-imidazo[4,5-b]pyridine;
1125. 2-(6-(4-(3H-imidazo[4,5-b]pyridin-7-yl)-1H-pyrazol-1-yl)pyridin-3-yl)-1,1,1-trifluoropropan-2-ol;
1126. 1-(6-(4-(3H-imidazo[4,5-b]pyridin-7-yl)-1H-pyrazol-1-yl)pyridin-3-yl)-1-cyclopropyl-2,2,2-trifluoroethanol;
1127. 7-(1-(5-(1-cyclopropyl-2,2,2-trifluoro-1-methoxyethyl)pyridin-2-yl)-1H-pyrazol-4-yl)-3H-imidazo[4,5-b]pyridine;
1128. 7-(1-(5-(1,1,1,2-tetrafluoropropan-2-yl)pyridin-2-yl)-1H-pyrazol-4-yl)-3H-imidazo[4,5-b]pyridine;
1129. 2-(6-(4-(3H-imidazo[4,5-b]pyridin-7-yl)-1H-pyrazol-1-yl)pyridin-3-yl)-1,1,1-trifluoro-3-methylbutan-2-ol;
1130. 1-(6-(4-(3H-imidazo[4,5-b]pyridin-7-yl)-1H-pyrazol-1-yl)pyridin-3-yl)-1-cyclohexyl-2,2,2-trifluoroethanol;
1131. 1-(4-(1-(6-(4-(3H-imidazo[4,5-b]pyridin-7-yl)-1H-pyrazol-1-yl)pyridin-3-yl)-2,2,2-trifluoro-1-hydroxyethyl)piperidin-1-yl)ethanone;

1132. 1-(6-(4-(3H-imidazo[4,5-b]pyridin-7-yl)-1H-pyrazol-1-yl)pyridin-3-yl)-1-cyclopentyl-2,2,2-trifluoroethanol;
1133. 1-(6-(4-(3H-imidazo[4,5-b]pyridin-7-yl)-1H-pyrazol-1-yl)pyridin-3-yl)-2,2,2-trifluoro-1-(1-methylpiperidin-4-yl)ethanol;
1134. 1-(6-(4-(3H-imidazo[4,5-b]pyridin-7-yl)-1H-pyrazol-1-yl)pyridin-3-yl)-2,2,2-trifluoro-1-(tetrahydro-2H-pyran-4-yl)ethanol;
1135. 1-(6-(4-(3H-imidazo[4,5-b]pyridin-7-yl)-1H-pyrazol-1-yl)pyridin-3-yl)-2,2,2-trifluoro-1-(piperidin-4-yl)ethan-1-ol
1135. 7-(1-(5-(2,2,2-trifluoro-1-(oxetan-3-yl)ethyl)pyridin-2-yl)-1H-pyrazol-4-yl)-3H-imidazo[4,5-b]pyridine;
1136. 7-(1-(5-(2,2,2-trifluoro-1-morpholinoethyl)pyridin-2-yl)-1H-pyrazol-4-yl)-3H-imidazo[4,5-b]pyridine;
1137. 7-(1-(5-(1,1,1-trifluoro-3-(methylsulfonyl)propan-2-yl)pyridin-2-yl)-1H-pyrazol-4-yl)-3H-imidazo[4,5-b]pyridine;
1138. 7-(1-(5-(4-(cyclopropylsulfonyl)-1,1,1-trifluorobutan-2-yl)pyridin-2-yl)-1H-pyrazol-4-yl)-3H-imidazo[4,5-b]pyridine;
1139. 7-(1-(5-(1-((methylsulfonyl)methoxy)-2,2,2-trifluoroethyl)pyridin-2-yl)-1H-pyrazol-4-yl)-3H-imidazo[4,5-b]pyridine;
1140. 3-(6-(4-(3H-imidazo[4,5-b]pyridin-7-yl)-1H-pyrazol-1-yl)pyridin-3-yl)-4,4,4-trifluorobutane-1-sulfonamide;
1141. 3-(6-(4-(3H-imidazo[4,5-b]pyridin-7-yl)-1H-pyrazol-1-yl)pyridin-3-yl)-4,4,4-trifluoro-N-methylbutane-1-sulfonamide;
1142. N-(3-(6-(4-(3H-imidazo[4,5-b]pyridin-7-yl)-1H-pyrazol-1-yl)pyridin-3-yl)-4,4,4-trifluorobutyl)methanesulfonamide;
1143. 3-(6-(4-(3H-imidazo[4,5-b]pyridin-7-yl)-1H-pyrazol-1-yl)pyridin-3-yl)-4,4,4-trifluoro-N,N-dimethylbutanamide;
1144. 3-(6-(4-(3H-imidazo[4,5-b]pyridin-7-yl)-1H-pyrazol-1-yl)pyridin-3-yl)-4,4,4-trifluoro-N-methylbutanamide;
1145. 1-(1-(6-(4-(3H-imidazo[4,5-b]pyridin-7-yl)-1H-pyrazol-1-yl)pyridin-3-yl)-2,2,2-trifluoroethyl)-3-cyclopropylurea;
1146. 7-(1-(5-(1,1,1-trifluoro-4-(methylsulfonyl)butan-2-yl)pyridin-2-yl)-1H-pyrazol-4-yl)-1H-imidazo[4,5-b]pyridin-2(3H)-one;
1147. 4-(6-(4-(3H-imidazo[4,5-b]pyridin-7-yl)-1H-pyrazol-1-yl)pyridin-3-yl)-5,5,5-trifluoro-N-methylpentanamide;
1148. N-(3-(6-(4-(3H-imidazo[4,5-b]pyridin-7-yl)-1H-pyrazol-1-yl)pyridin-3-yl)-4,4,4-trifluorobutyl)cyclopropanecarboxamide;
1149. 4-(6-(4-(3H-imidazo[4,5-b]pyridin-7-yl)-1H-pyrazol-1-yl)pyridin-3-yl)-N-cyclopropyl-5,5,5-trifluoropentanamide;
1150. N-(3-(6-(4-(3H-imidazo[4,5-b]pyridin-7-yl)-1H-pyrazol-1-yl)pyridin-3-yl)-4,4,4-trifluorobutyl)cyclopentanecarboxamide;
1151. 3-(6-(4-(3H-imidazo[4,5-b]pyridin-7-yl)-1H-pyrazol-1-yl)pyridin-3-yl)-4,4,4-trifluoro-N-methylbutan-1-amine;
1152. N-(3-(6-(4-(3H-imidazo[4,5-b]pyridin-7-yl)-1H-pyrazol-1-yl)pyridin-3-yl)-4,4,4-trifluorobutyl)cyclopropanamine;
1153. 3-(6-(4-(3H-imidazo[4,5-b]pyridin-7-yl)-1H-pyrazol-1-yl)pyridin-3-yl)-4,4,4-trifluorobutan-1-ol;
1154. 7-(1-(5-(1,1,1-trifluoro-4-methoxybutan-2-yl)pyridin-2-yl)-1H-pyrazol-4-yl)-3H-imidazo[4,5-b]pyridine;
1155. 4-(6-(4-(3H-imidazo[4,5-b]pyridin-7-yl)-1H-pyrazol-1-yl)pyridin-3-yl)-5,5,5-trifluoropentanenitrile;
1156. 2-(1-(6-(4-(3H-imidazo[4,5-b]pyridin-7-yl)-1H-pyrazol-1-yl)pyridin-3-yl)-2,2,2-trifluoroethoxy)acetonitrile;
1157. 7-(1-(5-(1-(methylsulfonyl)ethyl)pyridin-2-yl)-1H-pyrazol-4-yl)-3H-imidazo[4,5-b]pyridine;
1158. (6-(4-(3H-imidazo[4,5-b]pyridin-7-yl)-1H-pyrazol-1-yl)pyridin-3-yl)(cyclopropyl)methanol;
1159. 7-(1-(5-(3-(methylsulfonyl)-1-(oxetan-3-yl)propyl)pyridin-2-yl)-1H-pyrazol-4-yl)-3H-imidazo[4,5-b]pyridine;
1160. 7-(1-(5-(1-methoxy-3-(methylsulfonyl)propyl)pyridin-2-yl)-1H-pyrazol-4-yl)-3H-imidazo[4,5-b]pyridine;
1161. 7-(1-(5-(1-fluoro-3-(methylsulfonyl)propyl)pyridin-2-yl)-1H-pyrazol-4-yl)-3H-imidazo[4,5-b]pyridine;
1162. 7-(1-(5-(4-(methylsulfonyl)butan-2-yl)pyridin-2-yl)-1H-pyrazol-4-yl)-3H-imidazo[4,5-b]pyridine;
1163. (6-(4-(3H-imidazo[4,5-b]pyridin-7-yl)-1H-pyrazol-1-yl)pyridin-3-yl)(1-(methylsulfonyl)piperidin-4-yl)methanol;
1164. (6-(4-(3H-imidazo[4,5-b]pyridin-7-yl)-1H-pyrazol-1-yl)pyridin-3-yl)(1-methylpiperidin-4-yl)methanol;
1165. 2-(6-(4-(3H-imidazo[4,5-b]pyridin-7-yl)-1H-pyrazol-1-yl)pyridin-3-yl)-N-(2,2,2-trifluoroethyl)-2-hydroxyacetamide;
1166. 2-(6-(4-(3H-imidazo[4,5-b]pyridin-7-yl)-1H-pyrazol-1-yl)pyridin-3-yl)-2-cyclopropyl-N-(2,2,2-trifluoroethyl)acetamide;
1167. 2-(6-(4-(3H-imidazo[4,5-b]pyridin-7-yl)-1H-pyrazol-1-yl)pyridin-3-yl)-2-cyano-N-(2,2,2-trifluoroethyl)acetamide;
1168. 1-(6-(4-(3H-imidazo[4,5-b]pyridin-7-yl)-1H-pyrazol-1-yl)pyridin-3-yl)-2,2,2-trifluoroethanol;
1169. 1-(6-(4-(3H-imidazo[4,5-b]pyridin-7-yl)-1H-pyrazol-1-yl)pyridin-2-yl)-2,2,2-trifluoroethanol;
1170. 7-(1-(6-(2,2,2-trifluoro-1-methoxyethyl)pyridin-2-yl)-1H-pyrazol-4-yl)-3H-imidazo[4,5-b]pyridine;
1171. 1-(2-(4-(3H-imidazo[4,5-b]pyridin-7-yl)-1H-pyrazol-1-yl)pyridin-4-yl)-2,2,2-trifluoroethanol;
1172. 1-(5-(4-(3H-imidazo[4,5-b]pyridin-7-yl)-1H-pyrazol-1-yl)pyridin-2-yl)-2,2,2-trifluoroethanol;
1173. 7-(1-(5-(1,1,1-trifluoro-4-(methylsulfonyl)butan-2-yl)pyridin-2-yl)-1H-pyrazol-4-yl)-3H-imidazo[4,5-b]pyridine;
1174. 7-(1-(6-(1,1,1-trifluoro-4-(methylsulfonyl)butan-2-yl)pyridin-2-yl)-1H-pyrazol-4-yl)-3H-imidazo[4,5-b]pyridine;
1175. 7-(1-(4-(1,1,1-trifluoro-4-(methylsulfonyl)butan-2-yl)pyridin-2-yl)-1H-pyrazol-4-yl)-3H-imidazo[4,5-b]pyridine;
1176. 1-(4-(3H-imidazo[4,5-b]pyridin-7-yl)-1H-pyrazole-1-carbonyl)pyrrolidine-3-carbonitrile
1177. 1-(1-(6-(4-(3H-imidazo[4,5-b]pyridin-7-yl)-1H-pyrazol-1-yl)pyridin-3-yl)-2,2,2-trifluoroethyl)-3-cyclopropylurea
1178. 1-(3-(6-(4-(3H-imidazo[4,5-b]pyridin-7-yl)-1H-pyrazol-1-yl)pyridin-3-yl)-4,4,4-trifluorobutyl)-3-cyclopropylurea
1179. 3-cyclopentyl-3-(4-(2-phenyl-3H-imidazo[4,5-b]pyridin-7-yl)-1H-pyrazol-1-yl)propanenitrile
1180. 3-cyclopentyl-3-(4-(2-phenyl-3H-imidazo[4,5-b]pyridin-7-yl)-1H-pyrazol-1-yl)propanenitrile
1181. 7-(1-(5-((S)-1,1,1-trifluoro-4-(methylsulfonyl)butan-2-yl)pyridin-2-yl)-1H-pyrazol-4-yl)-3H-imidazo[4,5-b]pyridine
1182. 7-(1-(5-((R)-1,1,1-trifluoro-4-(methylsulfonyl)butan-2-yl)pyridin-2-yl)-1H-pyrazol-4-yl)-3H-imidazo[4,5-b]pyridine 1183. 3-(6-(4-(3H-imidazo[4,5-b]pyridin-7-yl)-1H-pyrazol-1-yl)pyridin-3-yl)-1,1,1-trifluoropropan-2-ol 1184. 7-(1-(5-((R)-2,2,2-trifluoro-1-(oxetan-3-yl)ethyl)pyridin-2-yl)-1H-pyrazol-4-yl)-3H-imidazo[4,5-b]pyridine 1185. 7-(1-(5-((S)-2,2,2-trifluoro-1-(oxetan-3-yl)ethyl)pyridin-2-yl)-1H-pyrazol-4-yl)-3H-imidazo[4,5-b]pyridine 1186. 7-(1-(5-(1,1,1-trifluoro-4-(isopropylsulfonyl)butan-2-yl)pyridin-2-yl)-1H-pyrazol-4-yl)-3H-imidazo[4,5-b] pyridine 1187. 1-(6-(4-(3H-imidazo[4,5-b]pyridin-7-yl)-(methyl sulfonyl) 1H-pyrazol-1-yl)pyridin-3-yl)-2,2,2-trifluoroethanamine 1188. 7-(1-(5-(1,1,1-trifluoro-4-(methylsulfonyl)butan-2-yl) pyridin-2-yl)-(cyclopropyl amino sulfonyl) 1H-pyrazol-4-yl)-3H-imidazo[4,5-b]pyridine 1189. 7-(1-(5-(1,1,1-trifluoro-4-(methylsulfonyl)butan-2-yl) pyridin-2-yl)-1H-pyrazol-4-yl)-1H-imidazo[4,5-b]pyridin-2(3H)-one 1190. 7-(1-(4-(1,1,1-trifluoro-4-(methylsulfonyl)butan-2-yl) phenyl)-1H-pyrazol-4-yl)-3H-imidazo[4,5-b]pyridine 1191. 3-(6-(4-(3H-imidazo[4,5-b]pyridin-7-yl)-1H-pyrazol-1-yl)pyridin-3-yl)-2-(trifluoromethyl)propan-1-ol 1192. N-(1-(6-(4-(3H-imidazo[4,5-b]pyridin-7-yl)-1H-pyrazol-1-yl)pyridin-3-yl)-2,2,2-trifluoroethyl)-2-cyanoacetamide 1193. 4-(6-(4-(3H-imidazo[4,5-b]pyridin-7-yl)-1H-pyrazol-1-yl)pyridin-3-yl)-5,5,5-trifluoro-2-methylpentan-2-ol 1194. 7-(1-(5-(3,3,3-trifluoro-2-((methylsulfonyl)methyl) propyl)pyridin-2-yl)-1H-pyrazol-4-yl)-3H-imidazo[4,5-b]pyridine 1195. N-(3-(6-(4-(3H-imidazo[4,5-b]pyridin-7-yl)-1H-pyrazol-1-yl)pyridin-3-yl)-4,4,4-trifluorobutyl)-N-methylcyclopropanamine 1196. 3-(6-(4-(3H-imidazo[4,5-b]pyridin-7-yl)-1H-pyrazol-1-yl)pyridin-3-yl)-4,4,4-trifluoro-2,2-dimethylbutan-1-ol 1197. N-(2-(1-(6-(4-(3H-imidazo[4,5-b]pyridin-7-yl)-1H-pyrazol-1-yl)pyridin-3-yl)-2,2,2-trifluoroethoxy)ethyl) cyclopropanamine 1198. 3-(6-(4-(3H-imidazo[4,5-b]pyridin-7-yl)-1H-pyrazol-1-yl)pyridin-3-yl)-4,4,4-trifluoro-N-methylbutan-1-amine 1199. N-(3-(6-(4-(3H-imidazo[4,5-b]pyridin-7-yl)-1H-pyrazol-1-yl)pyridin-3-yl)-4,4,4-trifluorobutyl)cyclohexanamine 1200. 3-(6-(4-(3H-imidazo[4,5-b]pyridin-7-yl)-1H-pyrazol-1-yl)pyridin-3-yl)-4,4,4-trifluoro-N-methylbutan-1-amine 1201. 7-(1-(5-(1,1,1-trifluoro-4-morpholinobutan-2-yl)pyridin-2-yl)-1H-pyrazol-4-yl)-3H-imidazo[4,5-b]pyridine 1202. 1-(3-(6-(4-(3H-imidazo[4,5-b]pyridin-7-yl)-1H-pyrazol-1-yl)pyridin-3-yl)-4,4,4-trifluorobutyl)azetidine-3-carbonitrile 1203. 3-(6-(4-(3H-imidazo[4,5-b]pyridin-7-yl)-1H-pyrazol-1-yl)pyridin-3-yl)-4,4,4-trifluoro-N-isopropylbutan-1-amine 1204. 7-(1-(5-(4-(cyclopropylmethylsulfonyl)-1,1,1-trifluorobutan-2-yl)pyridin-2-yl)-1H-pyrazol-4-yl)-3H-imidazo [4,5-b]pyridine 1205. 7-(1-(5-(3-(cyclopropylmethylsulfonyl)-1,1,1-trifluoropropan-2-yl)pyridin-2-yl)-1H-pyrazol-4-yl)-3H-imidazo[4,5-b]pyridine 1206. 7-(1-(5-(1,1,1-trifluoro-3-morpholinopropan-2-yl) pyridin-2-yl)-1H-pyrazol-4-yl)-3H-imidazo[4,5-b]pyridine 1207. (S)-3-(6-(4-(3H-imidazo[4,5-b]pyridin-7-yl)-1H-pyrazol-1-yl)pyridin-3-yl)-4,4,4-trifluoro-N-isopropylbutan-1-amine 1208. (R)-3-(6-(4-(3H-imidazo[4,5-b]pyridin-7-yl)-1H-pyrazol-1-yl)pyridin-3-yl)-4,4,4-trifluoro-N-isopropylbutan-1-amine 1209. 2-(6-(4-(3H-imidazo[4,5-b]pyridin-7-yl)-(Methyl sulfonyl)1H-pyrazol-1-yl)pyridin-3-yl)-3,3,3-trifluoropropan-1-amine 1210. 4-(6-(4-(3H-imidazo[4,5-b]pyridin-7-yl)-1H-pyrazol-1-yl)pyridin-3-yl)-5,5,5-trifluoro-N-isopropylpentanamide 1211. 3-(6-(4-(3H-imidazo[4,5-b]pyridin-7-yl)-1H-pyrazol-1-yl)pyridin-3-yl)-4,4,4-trifluoro-N,N-diisopropylbutan-1-amine 1212. N-(2-(6-(4-(3H-imidazo[4,5-b]pyridin-7-yl)-1H-pyrazol-1-yl)pyridin-3-yl)-3,3,3-trifluoropropyl)cyclopropanamine 1213. (R)-3-(6-(4-(3H-imidazo[4,5-b]pyridin-7-yl)-1H-pyrazol-1-yl)pyridin-3-yl)-4,4,4-trifluoro-N-methylbutanamide 1214. (S)-3-(6-(4-(3H-imidazo[4,5-b]pyridin-7-yl)-1H-pyrazol-1-yl)pyridin-3-yl)-4,4,4-trifluoro-N-methylbutanamide 1215. (S)-4-(6-(4-(3H-imidazo[4,5-b]pyridin-7-yl)-1H-pyrazol-1-yl)pyridin-3-yl)-5,5,5-trifluoro-N-isopropylpentanamide 1216. 7-(1-(5-((S)-4-(cyclopropylsulfonyl)-1,1,1-trifluorobutan-2-yl)pyridin-2-yl)-1H-pyrazol-4-yl)-3H-imidazo [4,5-b]pyridine 1217. (S)-3-(6-(4-(3H-imidazo[4,5-b]pyridin-7-yl)-1H-pyrazol-1-yl)pyridin-3-yl)-4,4,4-trifluoro-N-methylbutan-1-amine, TFA salt 1218. 2-(6-(4-(3H-imidazo[4,5-b]pyridin-7-yl)-1H-pyrazol-1-yl)pyridin-3-yl)-3,3,3-trifluoro-N-isopropylpropan-1-amine 1219. 7-(1-(5-(1,1,1-trifluoro-4-(4-methylpiperazin-1-yl) butan-2-yl)pyridin-2-yl)-1H-pyrazol-4-yl)-3H-imidazo [4,5-b]pyridine 1220. (4-(1-(6-(4-(3H-imidazo[4,5-b]pyridin-7-yl)-1H-pyrazol-1-yl)pyridin-3-yl)-2,2,2-trifluoro-1-hydroxyethyl)piperidin-1-yl)(cyclopropyl)methanone 1221. 1-(6-(4-(3H-imidazo[4,5-b]pyridin-7-yl)-1H-pyrazol-1-yl)pyridin-3-yl)-1-(1-ethylpiperidin-4-yl)-2,2,2-trifluoroethanol 1222. 7-(1-(5-(1,1,1-trifluoro-3-(4-methylpiperazin-1-yl) propan-2-yl)pyridin-2-yl)-1H-pyrazol-4-yl)-3H-imidazo [4,5-b]pyridine 1223. 2-(6-(4-(3H-imidazo[4,5-b]pyridin-7-yl)-1H-pyrazol-1-yl)pyridin-3-yl)-1,1,1-trifluoro-4-(methylsulfonyl)butan-2-ol 1224. 5-(6-(4-(3H-imidazo[4,5-b]pyridin-7-yl)-1H-pyrazol-1-yl)pyridin-3-yl)-6,6,6-trifluorohexan-2-amine, TFA salt 1225. (R)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl)ethanol 1226. (S)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl)ethanol 1227. 4-(6-(4-(3H-imidazo[4,5-b]pyridin-7-yl)-1H-pyrazol-1-yl)pyridin-3-yl)-5,5,5-trifluoro-4-hydroxypentanenitrile 1228. 2-(1-(6-(4-(3H-imidazo[4,5-b]pyridin-7-yl)-1H-pyrazol-1-yl)pyridin-3-yl)-2,2,2-trifluoroethoxy)-N-methylethanamine 1229. 2-(6-(4-(3H-imidazo[4,5-b]pyridin-7-yl)-1H-pyrazol-1-yl)pyridin-3-yl)-1,1,1-trifluoro-3-morpholinopropan-2-ol 1230. 2-(6-(4-(3H-imidazo[4,5-b]pyridin-7-yl)-1H-pyrazol-1-yl)pyridin-3-yl)-1,1,1-trifluoro-4-morpholinobutan-2-ol 1231. 1-(6-(4-(3H-imidazo[4,5-b]pyridin-7-yl)-1H-pyrazol-1-yl)pyridin-3-yl)-2,2,2-trifluoro-1-(1-methylazetidin-3-yl)ethanol 1232. (R)-1-(6-(4-(3H-imidazo[4,5-b]pyridin-7-yl)-1H-pyrazol-1-yl)pyridin-3-yl)-1-(1-ethylpyrrolidin-3-yl)-2,2,2-trifluoroethanol 1233. (S)-1-(6-(4-(3H-imidazo[4,5-b]pyridin-7-yl)-1H-pyrazol-1-yl)pyridin-3-yl)-1-(1-ethylpyrrolidin-3-yl)-2,2,2-trifluoroethanol 1234. (S)-1-(6-(4-(3H-imidazo[4,5-b]pyridin-7-yl)-1H-pyrazol-1-yl)pyridin-3-yl)-2,2,2-trifluoro-1-(1-methylpyrrolidin-3-yl)ethanol 1235. (R)-1-(6-(4-(3H-imidazo[4,5-b]pyridin-7-yl)-1H-pyrazol-1-yl)pyridin-3-yl)-2,2,2-trifluoro-1-(1-methylpyrrolidin-3-yl)ethanol 1236. 1-(3-(1-(6-(4-(3H-imidazo[4,5-b]pyridin-7-yl)-1H-pyrazol-1-yl)pyridin-3-yl)-2,2,2-trifluoro-1-hydroxyethyl)azetidin-1-yl)ethanone 1237. 1-(6-(4-(3H-imidazo[4,5-b]pyridin-7-yl)-1H-pyrazol-1-yl)pyridin-3-yl)-2,2,2-trifluoro-1-(1-isopropylazetidin-3-yl)ethanol 1238. 4-(6-(4-(3H-imidazo[4,5-b]pyridin-7-yl)-1H-pyrazol-1-yl)pyridin-3-yl)-5,5,5-trifluoro-4-hydroxy-N-isopropylpentanamide 1239. 1-(6-(4-(3H-imidazo[4,5-b]pyridin-7-yl)-1H-pyrazol-1-yl)pyridin-3-yl)-1-(1-ethylazetidin-3-yl)-2,2,2-trifluoroethanol 1240. 1-(6-(4-(3H-imidazo[4,5-b]pyridin-7-yl)-1H-pyrazol-1-yl)pyridin-3-yl)-2,2,2-trifluoro-1-(1-isopropylpiperidin-4-yl)ethanol 1241. N-(2-(1-(6-(4-(3H-imidazo[4,5-b]pyridin-7-yl)-1H-pyrazol-1-yl)pyridin-3-yl)-2,2,2-trifluoroethoxy)ethyl)propan-2-amine, TFA salt 1242. (R)-1-(6-(4-(3H-imidazo[4,5-b]pyridin-7-yl)-1H-pyrazol-1-yl)pyridin-3-yl)-2,2,2-trifluoro-1-(1-(oxetan-3-yl)pyrrolidin-3-yl)ethanol 1243. (S)-1-(6-(4-(3H-imidazo[4,5-b]pyridin-7-yl)-1H-pyrazol-1-yl)pyridin-3-yl)-2,2,2-trifluoro-1-(1-(oxetan-3-yl)pyrrolidin-3-yl)ethanol 1244. 7-(1-(5-(2,2,2-trifluoro-1-methoxy-1-(1-methylpiperidin-4-yl)ethyl)pyridin-2-yl)-1H-pyrazol-4-yl)-3H-imidazo[4,5-b]pyridine 1245. 3-(3-(1-(6-(4-(3H-imidazo[4,5-b]pyridin-7-yl)-1H-pyrazol-1-yl)pyridin-3-yl)-2,2,2-trifluoro-1-hydroxyethyl)azetidin-1-yl)-3-oxopropanenitrile 1246. 3-(1-(6-(4-(3H-imidazo[4,5-b]pyridin-7-yl)-1H-pyrazol-1-yl)pyridin-3-yl)-2,2,2-trifluoro-1-hydroxyethyl)-N-methylazetidine-1-carboxamide 1247. N-(3-(6-(4-(3H-imidazo[4,5-b]pyridin-7-yl)-1H-pyrazol-1-yl)pyridin-3-yl)-4,4,4-trifluorobutyl)isobutyramide 1248. N-(3-(6-(4-(3H-imidazo[4,5-b]pyridin-7-yl)-1H-pyrazol-1-yl)pyridin-3-yl)-4,4,4-trifluorobutyl)-2-cyanoacetamide 1249. 3-(6-(4-(3H-imidazo[4,5-b]pyridin-7-yl)-1H-pyrazol-1-yl)pyridin-3-yl)-4,4,4-trifluoro-1-morpholinobutan-1-one 1250. 1-(4-(6-(4-(3H-imidazo[4,5-b]pyridin-7-yl)-1H-pyrazol-1-yl)pyridin-3-yl)-5,5,5-trifluoropentanoyl)azetidine-3-carbonitrile 1251. (S)-1-(4-(4-(3H-imidazo[4,5-b]pyridin-7-yl)-1H-pyrazol-1-yl)phenyl)-2,2,2-trifluoro-1-(1-isopropylpyrrolidin-3-yl)ethanol 1252. (R)-1-(4-(4-(3H-imidazo[4,5-b]pyridin-7-yl)-1H-pyrazol-1-yl)phenyl)-2,2,2-trifluoro-1-(1-isopropylpyrrolidin-3-yl)ethanol The present invention discloses novel compounds of 1H-imidazo[4,5-b]pyridin-2(3H)-one their pharmaceutically acceptable salts and isomers of formula II:

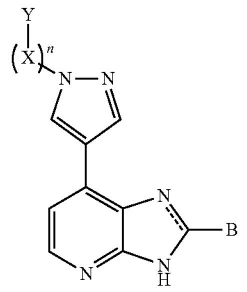

Wherein;

B is H;

X is independently, H, $(CH_2)n$, —CO—, OCO, COO; $CO(CH_2)n$, $(NH_2)n$; $(CH_2)n(NH_2)n$; $(CH_2)n(NH_2)nCN$; CONH; $CONR_1R_2$, $CO(NH_2)n$; $(CH_2)nCO(NH_2)n$, $CO(NH_2)n(CH_2)CF_3$, $SO_2(CH_2)n$, $NH(CH_2)nCN$, unsubstituted or substituted 3-8 membered carbocylic ring or heterocyclic ring containing 1 to 3 heteroatoms selected from the group comprising O, N, S and $SO_2$, and substituents on the carboxylic or heterocyclic ring may be selected from Halogen, Alkoxy, CHMe, $—CH(CF_3)$, $—C(CF_3)(OH)$, $C(CF_3)(OMe)$, —CH(CN), CHOH, $CH(R_5)$, H, $R_1$, $R_2$, halo, $C_1$-$C_6$ Alkyl, $C_1$-$C_6$ Alkoxy CN, —CO—, $COR_1$, $(CH_2)n$, $—(CH_2)nCN—$, $CH_2CF_3$, COOH, $OR_1$, $NR_1R_2$, $—COOR_1$, $—CON(R_1)_2$, $—SO_2(CH_2)n$, $—SO_2N(R_1)_2$, $—OCOR_1$, $CONHCH(CH_3)—CF_3$, $CH_2CN$, $CH_2SO_2CH_3—NR_1COR_1$, —CONH, $CONR_1R_2$, $—CO(NH_2)n(CH_2)nSO_2$; $—CONH(CH_2)nOH$, $CONH(CH_2)nSO_2R_1R_2$, $—CONH—(CH_2)nCF_3$, $—CONH(CH_2)nCF_3$, $—NHCONH(CH_2)nCF_3$, $NHCONHR_1$, $—NHCOR_1R_2$, $NR_1CONR_1R_2$, $(NH_2)n$, $—NH_2CH_2$, $NH_2CH_2CF_3$, $—CH(CF_3)—(CH)n$-CO—N—$R_1R_2$, CH(CF3)-(CH)n-$SO_2$, (CH)n; CH(OH)$(CF_3)$(Heretocycle)$R_1$, optionally substituted 3 to 8 membered carbocyclic ring, or 3 to 8 membered saturated, mono-, fused- or bridged heterocyclic ring containing 1 to 3 heteroatoms, selected from the group comprising O, N, S or $SO_2$, optionally substituted 3 to 8 membered heterocyclic ring containing 1 to 3 heteroatoms, selected from the group comprising O, N, S or $SO_2$, wherein the substitution may independently be $R_1$ and $R_2$ at any position of the ring; $C_{1-6}$alk-aryl, Ar$C_{1-6}$alkyl;

$R_1$ and $R_2$ are independently selected from the group comprising H, halo, CN, $CF_3$, hydroxyl, Amino, $SO_2$, $SO_2$, $C_1$-$C_6$ Alkyl, $SO_2$—$C_3$-$C_8$-cycloalkyl, $CH_2CN$, $CH_2CF_3$, unsubstituted or substituted $C_1$-$C_6$ straight or branched alkyl wherein the substituents are selected from halo, OH, CN, $C_1$-$C_6$ alkoxy, optionally substituted $NH_2$, $C_1$-$C_6$ alkylsulfonyl, optionally substituted $CONH_2$, unsubstituted or substituted $C_3$-$C_8$ carbocyclyl or 3-8 membered heterocyclic ring with 1-3 heteroatoms selected from O, N and S, $SO_2$, $C_1$-$C_6$ straight or branched alkenyl, $C_1$-$C_6$ straight or branched alkynyl, $C_1$-$C_6$ alkyloxy; $C_1$-$C_6$ alkylamino, $C_1$-$C_6$ alkylcarbonyl, C(O)—$C_3$-$C_8$-cycloalkyl, heteroalkyl, optionally substituted $CONH_2$, $C_3$-$C_8$ cycloalkyl, $C_3$-$C_8$cycloalkenyl, $C_3$-$C_8$heterocycloalkyl, $C_3$-$C_8$heterocycloalkenyl, carbocycyl, aryl, and heteroaryl, $—CH(CF_3)—(CH)n$-CO—N—$R_3R_4$, —CH(CF3)-(CH)n-$SO_2$—$NR_3R_4$, $CH(CF_3)—(CH)n$-

$NR_3R_4$, $CH(CF_3)—NR_3R_4$, $CH(CF_3)—(CH)n-SO_2—CHR_3R_4$, wherein cycloalkyl, cycloalkenyl, heterocycloalkyl, heterocycloalkenyl, carbocyclyl, aryl and heteroaryl groups are optionally substituted;

$R_3$ and $R_4$ are H, independently $CH_3$, $C_3$-$C_8$ cycloalkyl;

$R_5$ is unsubstituted or substituted 3-8 membered carbocylic ring or heterocyclic ring containing 1 to 3 heteroatoms selected from the group comprising O, N, S, $SO_2$;

$R_6$, is independently H, $C_1$-$C_6$ straight or branched alkyl, halogen;

X can be connected to Y at any atom so as to arrive at chemically viable bond;

n is 0 to 3.

The present invention discloses novel compounds of 1H-imidazo[4,5-b]pyridin-2(3H)-one their pharmaceutically acceptable salts and isomers of formula III:

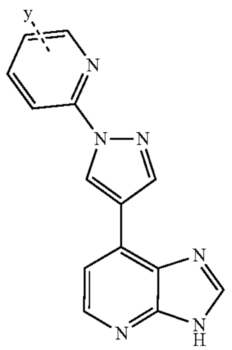

Wherein;

Y may be present at any position of the pyridine ring, preferably, at 4$^{th}$ or 5$^{th}$ position of pyridine;

Y is H, $R_1$, $R_2$, halo, CN, —CO—, $COR_1$, $(CH_2)n$, $—(CH_2)nCN—$, $CH_2CF_3$, COOH, $—COOR_1$, $—CON(R_1)_2$, $—SO_2(CH_2)n$, $—SO_2N(R_1)_2$, $—OCOR_1$, $—NR_1COR_1$, —CONH, $CONR_1R_2$, $—CO(NH_2)n(CH_2)nSO_2$; $—CONH(CH_2)nOH$, $CONH(CH_2)nSO_2R_1R_2$, $—CONH—(CH_2)nCF_3$, $—CONH(CH_2)nCF_3$, $—NHCONH(CH_2)nCF_3$, $—CH(CF_3)—(CH)n-CO—N—R_1R_2$, $CH(CF_3)—(CH)n-SO_2—(CH)n$; $CH(OH)(CF_3)(Heretocycle)R_1$, $NHCONHR_1$, $—NHCOR_1R_2$, $NR_1CONR_1R_2$, $(NH_2)n$, $—NH_2CH_2—$, $NH_2CH_2CF_3$, wherein the heterocycle is optionally substituted 3 to 8 membered saturated, mono-, fused- or bridged heterocyclic ring containing 1 to 3 heteroatoms, selected from the group comprising O, N, S.

wherein the substitution may independently be $R_1$ and $R_2$ at any position of the heterocyclic ring; $C_{1-6}$alk-aryl, Ar $C_{1-6}$ alkyl;

$R_1$ and $R_2$ are absent or independently selected from the group comprising H, halo, CN, $CF_3$, hydroxyl, Amino, $SO_2$, $SO_2C_1$-$C_6$ Alkyl, $CH_2CF_3$, $C_1$-$C_6$ straight or branched alkyl, $C_1$-$C_6$ straight or branched alkenyl, $C_1$-$C_6$ straight or branched alkynyl, halo-$C_1$-$C_6$ alkyl, $C_1$-$C_6$ alkyloxy; $C_1$-$C_6$ alkylamino, n is 0 to 3.

The present invention discloses exemplary compounds of formula III as below:

1133.1-(6-(4-(3H-imidazo[4,5-b]pyridin-7-yl)-1H-pyrazol-1-yl)pyridin-3-yl)-2,2,2-trifluoro-1-(1-methylpiperidin-4-yl)ethanol;

1134.1-(6-(4-(3H-imidazo[4,5-b]pyridin-7-yl)-1H-pyrazol-1-yl)pyridin-3-yl)-2,2,2-trifluoro-1-(tetrahydro-2H-pyran-4-yl)ethanol;

1176.1-(4-(3H-imidazo[4,5-b]pyridin-7-yl)-1H-pyrazole-1-carbonyl)pyrrolidine-3-carbonitrile 1181.7-(1-(5-((S)-1,1,1-trifluoro-4-(methylsulfonyl)butan-2-yl)pyridin-2-yl)-1H-pyrazol-4-yl)-3H-imidazo[4,5-b]pyridine 1182.7-(1-(5-((R)-1,1,1-trifluoro-4-(methylsulfonyl)butan-2-yl)pyridin-2-yl)-1H-pyrazol-4-yl)-3H-imidazo[4,5-b]pyridine 1225. (R)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl)ethanol 1226. (S)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl)ethanol 1231. 1-(6-(4-(3H-imidazo[4,5-b]pyridin-7-yl)-1H-pyrazol-1-yl)pyridin-3-yl)-2,2,2-trifluoro-1-(1-methylazetidin-3-yl)ethanol In an embodiment, the present invention also discloses a process of preparing the compounds of the present invention. The compounds of the present invention can be prepared by the general synthetic schemes 1 to 4, presented here below:

General Synthetic Scheme 1:

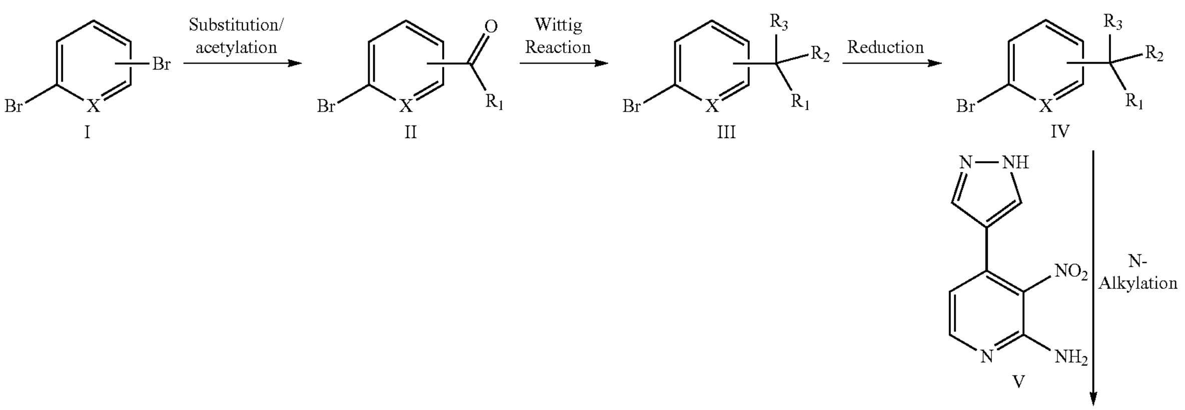

-continued
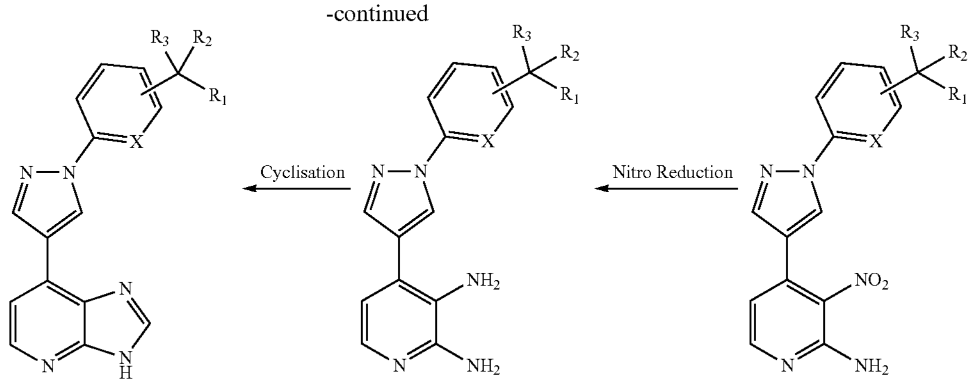
VIII VII VI
Wherein,
X is C, N,
$R_2$ and $R_3$ is H,
$R_1$:
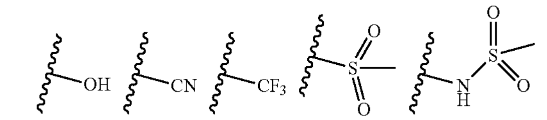
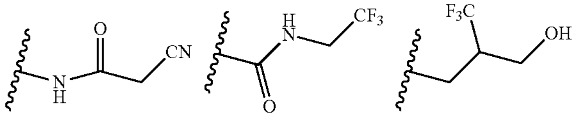
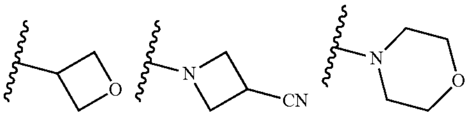
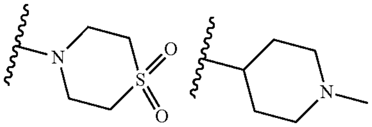
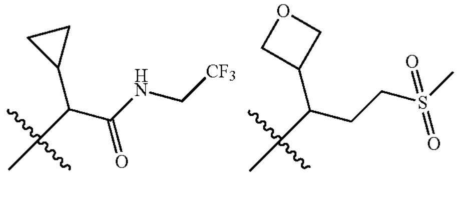
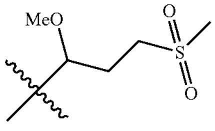
Wherein,
X is C, N,
$R_1$ is CN and $R_2$ is H
R3;
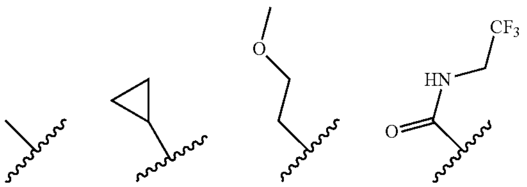
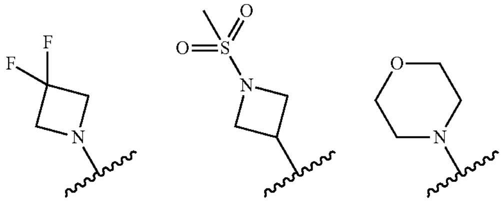
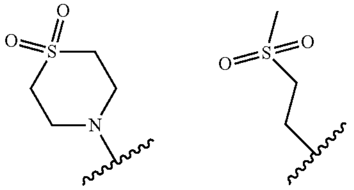
Wherein,
X is C, N,
$R_1$ $CF_3$ and $R_2$ is H,
$R_3$;
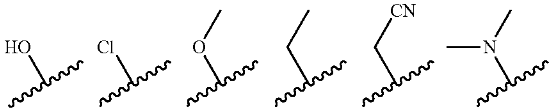
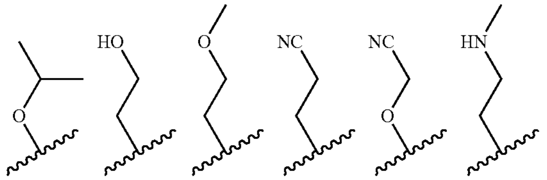

-continued
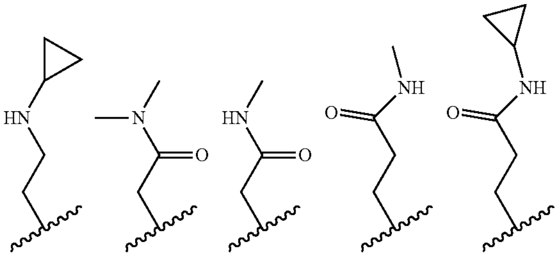
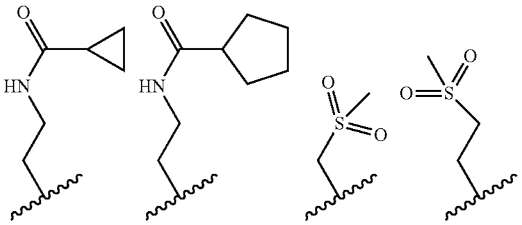
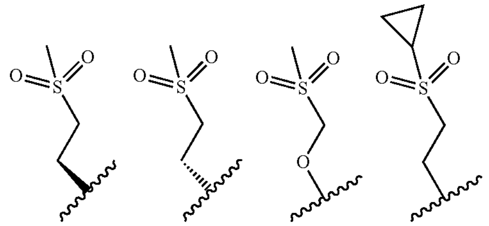
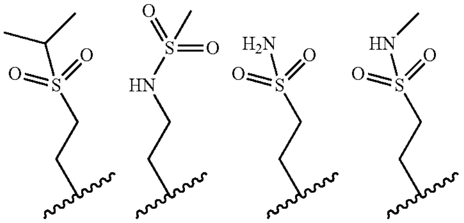
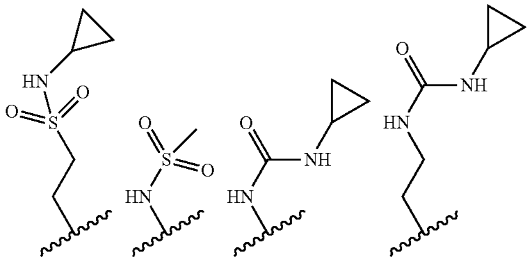
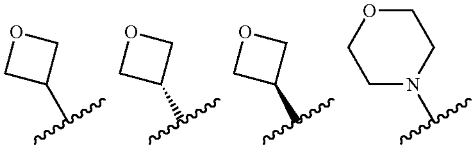
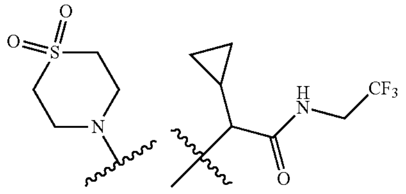
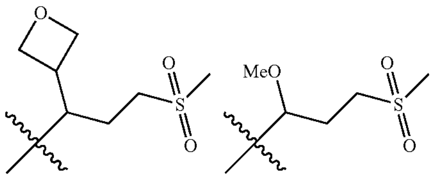
-continued
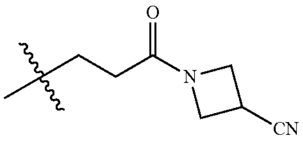
Wherein,
X is C, N,
$R_1$ is $CF_3$ and $R_2$ is OH
$R_3$
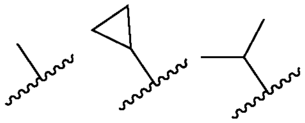
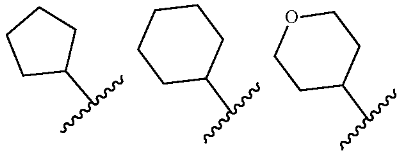
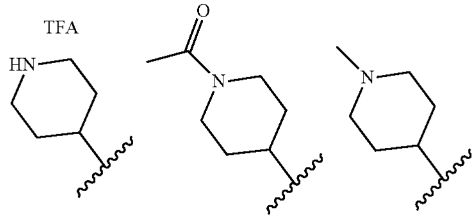
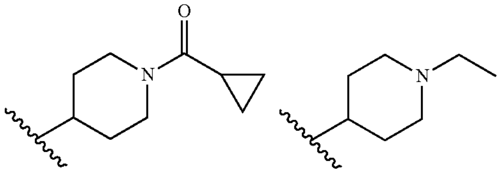
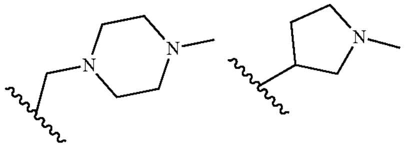
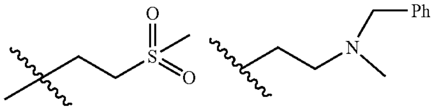
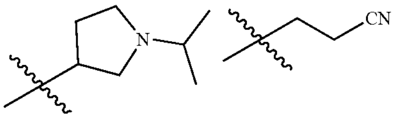
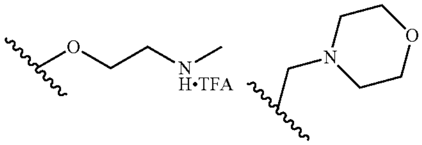
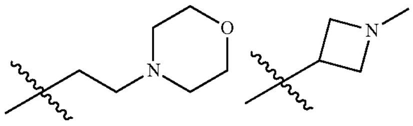

-continued
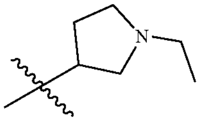
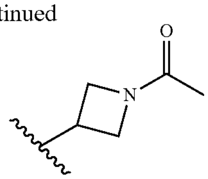
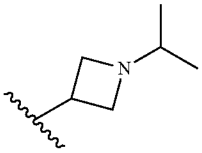
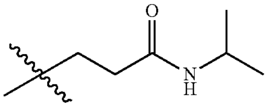
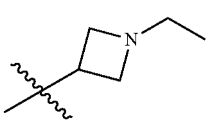
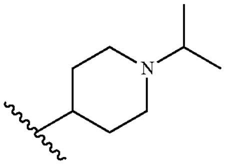
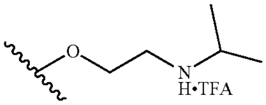
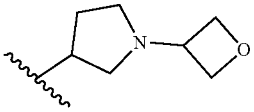
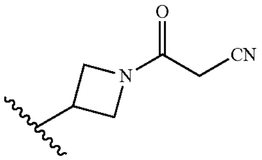
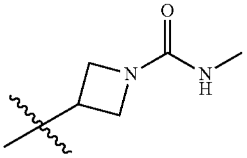
-continued
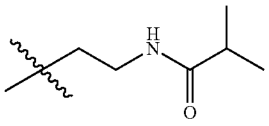
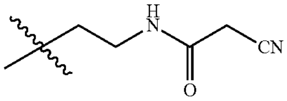
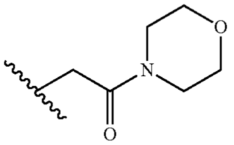
X is C, N,
$R_1$ is $CF_3$ and $R_2$ is $OCH_3$
$R_3$
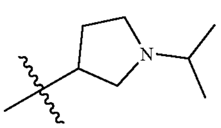
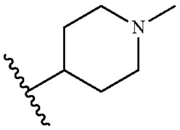
General Synthetic Scheme 2:
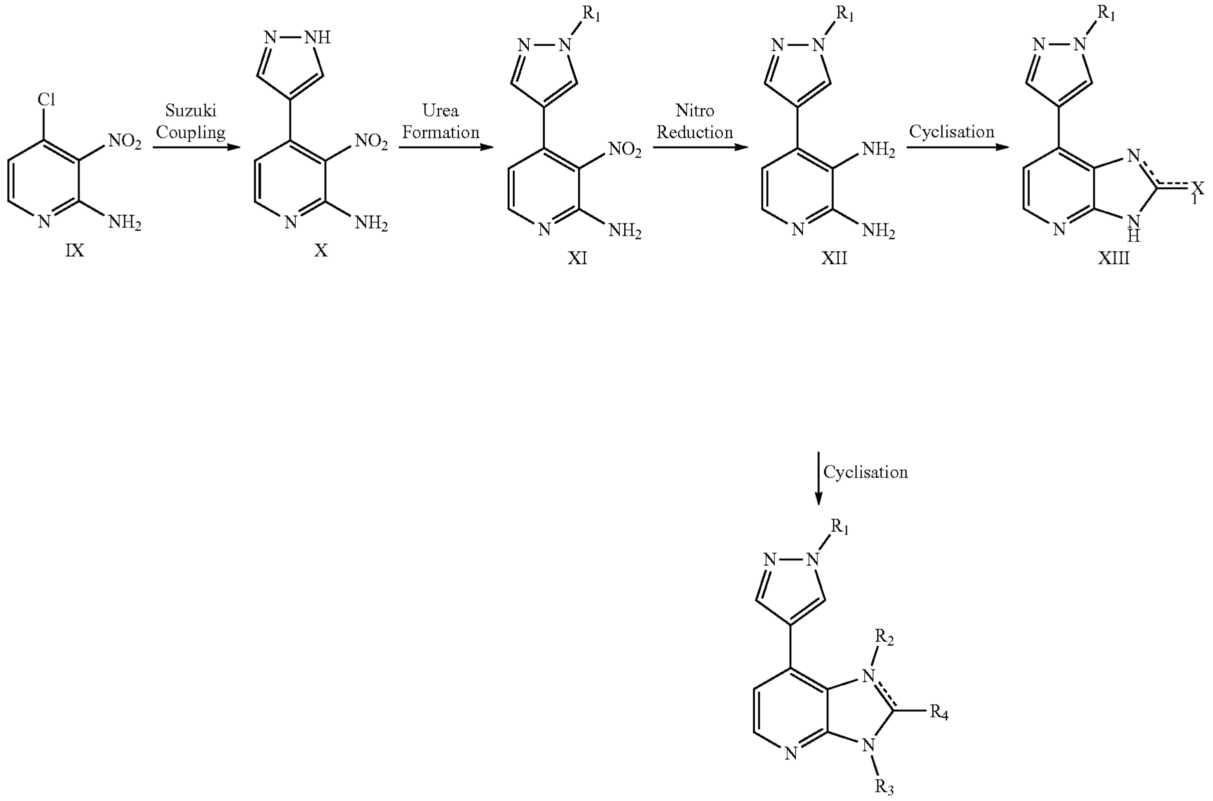
IX X XI XII XIII XIV $X_1$=O or H $R_2$=H or —$CH_3$ $R_3$=H or —$CH_3$
$R_1$;
$R_1$ =
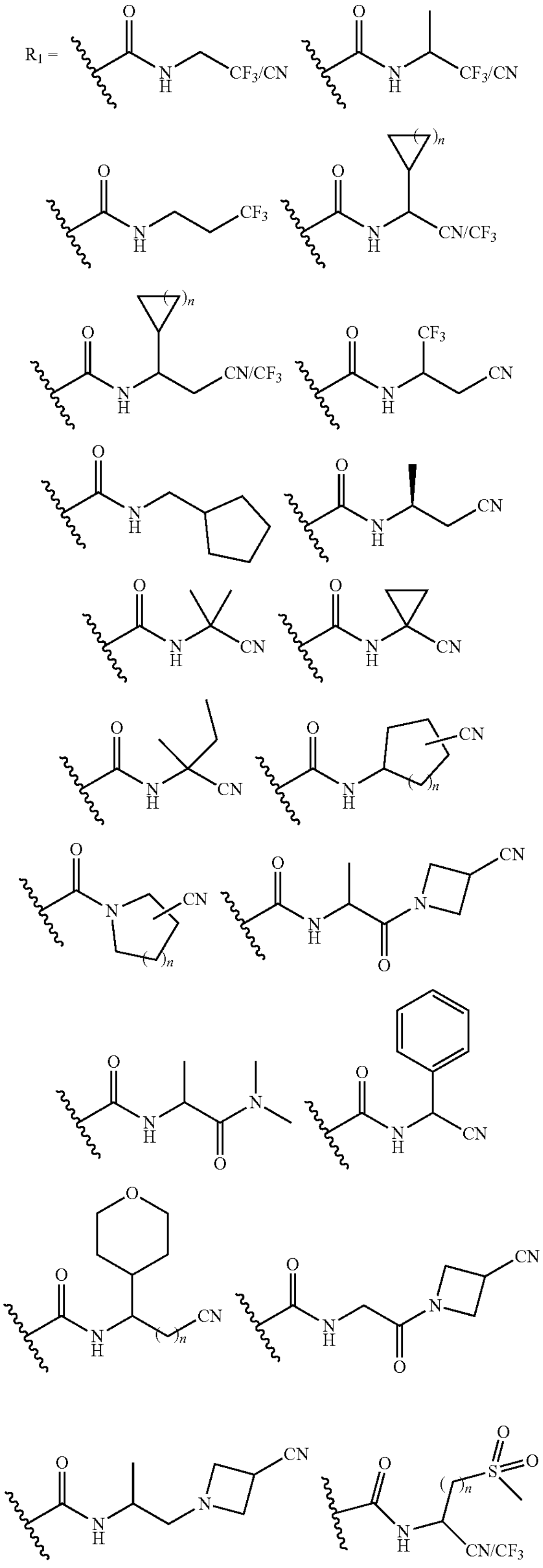
-continued
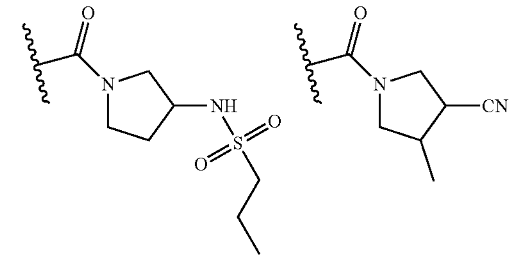 [SMILES: *C(=O)N1CCC(NS(=O)(=O)CCC)C1 ; *C(=O)N1CC(C)C(C#N)C1]
$R_4$;
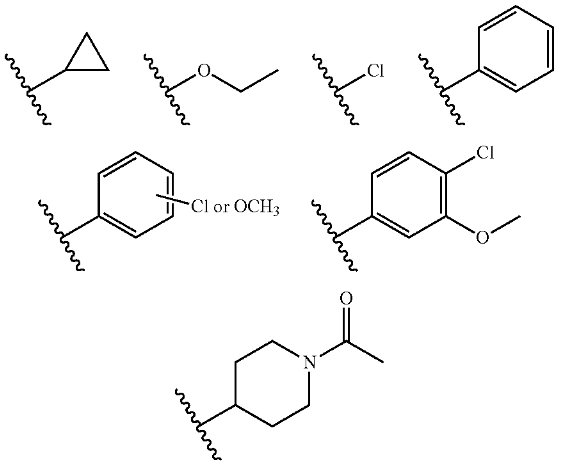
General Synthetic Scheme 3:
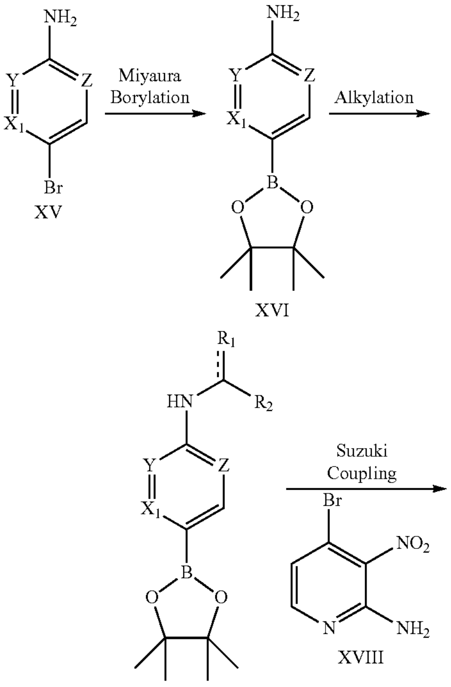
XV XVI XVII XVIII -continued
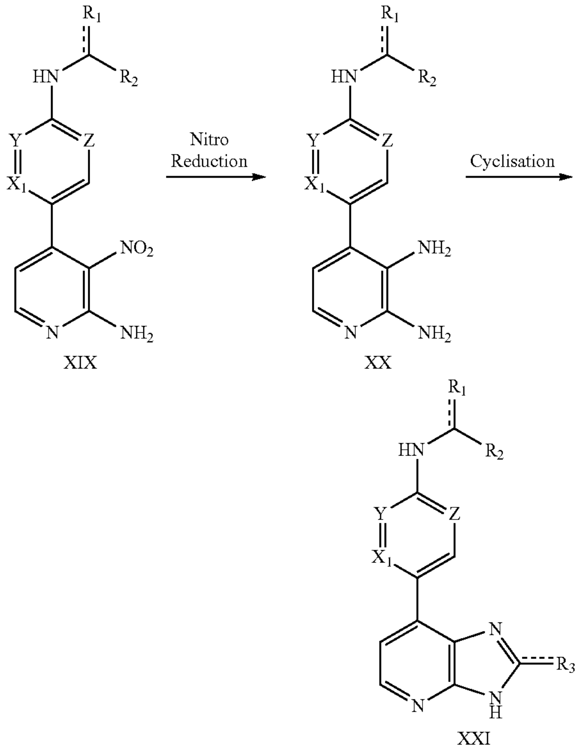
X1, Y, Z is C, N.
$R_3$ is H, O, carbocycle,
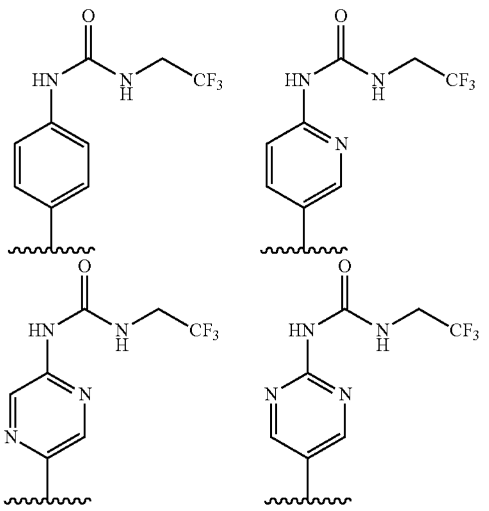
General Synthetic Scheme 4:
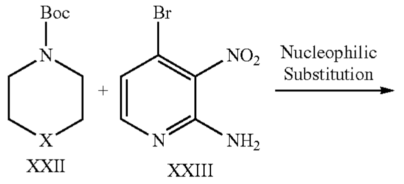
-continued
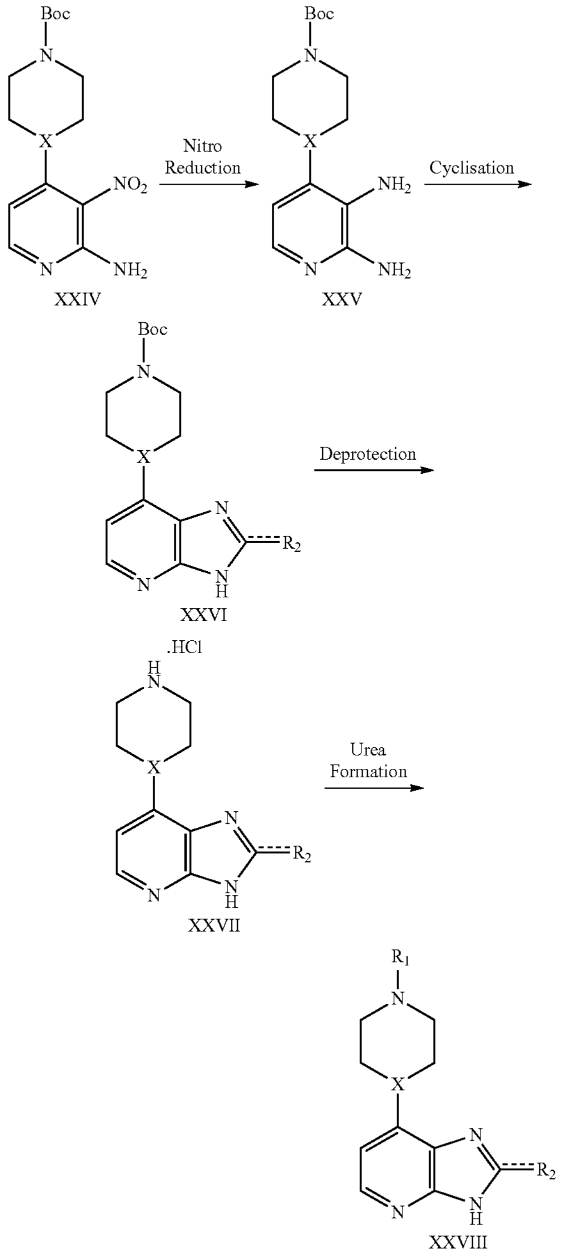
X is C, N.
$R_2$ is H, O, carbocycle,
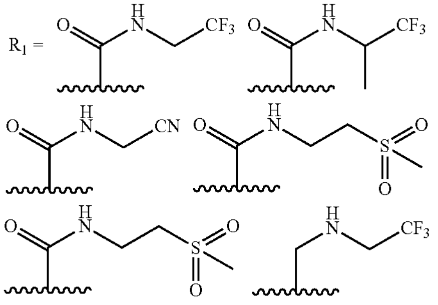

-continued

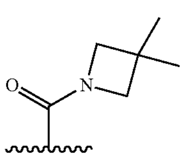
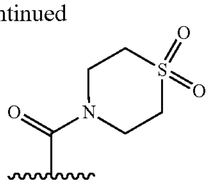
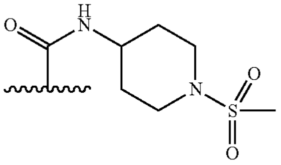
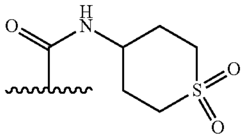
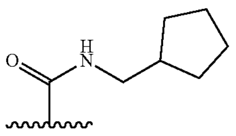
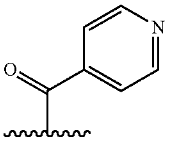
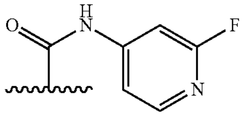
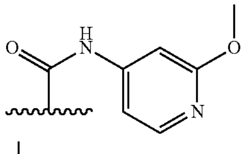
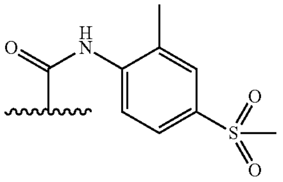

The invention also comprises as another embodiment, a composition comprising a JAK1 inhibitor compound according to any one of the preceding embodiments together with a pharmaceutically acceptable diluent, excipient, and/or carrier. The compositions will include a conventional pharmaceutical carrier, excipient, and/or diluent and a compound of this disclosure as the/an active agent, and, in addition, can include carriers and adjuvants, etc. The pharmaceutically acceptable compositions will contain about 1% to about 99% by weight of a compound(s) of this disclosure, or a pharmaceutically acceptable salt thereof, and 99% to 1% by weight of a suitable pharmaceutical excipient.

Administration of the compounds of this disclosure, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

Solid dosage forms for oral administration include capsules, tablets, pills, powders, and granules. Solid dosage forms, as described above, can be prepared with coatings and shells, such as enteric coatings. Liquid dosage forms for oral administration include pharmaceutically acceptable emulsions, solutions, suspensions, syrups, and elixirs. Compositions for rectal administrations are, for example, suppositories that can be prepared by mixing the compounds of this disclosure with, for example, suitable non-irritating excipients or carriers. They are also be parenteral and administered as sterile powders for reconstitution into sterile injectable solutions or dispersions. Dosage forms for topical administration of a compound of this disclosure include ointments, powders, sprays. Ophthalmic formulations, eye ointments, powders, inhalation formulations and solutions are also contemplated for the compounds in this disclosure. Compressed gases can be used to disperse a compound of this disclosure in aerosol form.

The invention comprises as a further embodiment a method for treating a disease JAK1 mediates or is implicated in a subject in need thereof comprising administrating to the subject a therapeutically effective amount of a JAK1 inhibitor compound according to any one of the preceding embodiments, or a composition comprising a JAK1 inhibitor according to any one of the preceding embodiments together with a pharmaceutically acceptable diluent, excipient, and/or carrier. The diseases JAK1 mediates or is implicated in that may be treated includes, without limitation, cancer, inflammatory disorders, and autoimmune diseases.

The selective JAK1 inhibitors of the present invention may be effective in treating cancer, including, but not limited to, carcinomas, sarcomas, lymphomas, leukemias, myelomas, germ cell tumors, blastomas, tumors of the central and peripheral nervous system and other tumors including melanomas, seminoma and Kaposi's sarcoma and the like.

The compounds of the present invention may also be useful in disorder and diseases pertaining to acquired immunodeficiency syndrome (AIDS), Addison's disease, adult respiratory distress syndrome, allergies, ankylosing spondylitis, amyloidosis, asthma, autoimmune hemolytic anemia, autoimmune thyroiditis, Crohn's disease, episodic lymphopenia with lymphocytotoxins, erythroblastosis fetalis, Goodpasture's syndrome, Graves' disease, Hashimoto's thyroiditis, hypereosinophilia, irritable bowel syndrome and other interbowel diseases, Lupus, myasthenia gravis, myocardial or pericardial inflammation, pancreatitis, polymyositis, psoriasis, Reiter's syndrome, scleroderma, systemic anaphylaxis, ulcerative colitis, nephritis (including glomerulonephritis), gout, arthritis (such as rheumatoid arthritis and osteoarthritis), erythema, dermatitis, dermatomyositis, bronchitis, cholecystitis, sepsis and gastritis.

Without being limited by theory, the compounds of the present invention exhibit selective inhibition of JAK1 with respect to JAK 2, JAK 3 and TYK 2. Therefore, it is submitted that the compounds of the present invention demonstrate selective inhibition and therefore are more specific and advantageous than other compounds in prior art, as they are expected to result in less adverse effects.

The examples and scheme below depict the general synthetic procedure for the compounds disclosed herein. Synthesis of the compounds of Formulae I disclosed herein, and embodiments thereof, are not limited by these examples and schemes. One skilled in the art will know that other procedures can be used to synthesize the compounds of Formulae I disclosed herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure. All intermediate compounds described below, for which there is no description of how to synthesize such intermediates within these examples below, are commercially available compounds unless otherwise specified.

Synthesis of Compound no. 1177: 2-(6-(4-(3H-imidazo[4,5-b]pyridin-7-yl)-1H-pyrazol-1-yl)pyridin-3-yl)acetonitrile

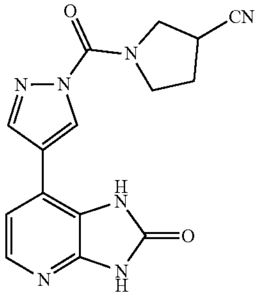 [SMILES: N#CC1CCN(C(=O)n2cc(-c3ccnc4[nH]c(=O)[nH]c34)cn2)C1]

Step-1: Synthesis of tert-butyl 3-hydroxypyrrolidine-1-carboxylate

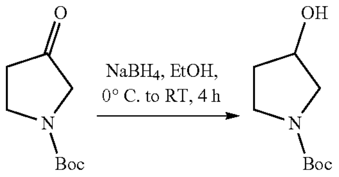

1 2

To a stirred solution of tert-butyl 3-oxopyrrolidine-1-carboxylate (0.50 g, 2.699 mmol) in ethanol (5 mL) was added sodium borohydride (0.20 g, 5.399 mmol) at 0° C. and the mixture was stirred at room temperature for 4 h. Progress of reaction was monitored by TLC. After reaction completion water (10 mL) was added to the reaction mixture and the product extracted with ethyl acetate. The organic layer was dried over sodium sulphate, concentrated under reduced pressure to give tert-butyl 3-hydroxypyrrolidine-1-carboxylate (0.5 g, 99%) as yellow solid.

MS: 188.24 [M+1]

Step-2: Synthesis of 1-(tert-butoxycarbonyl)pyrrolidin-3-yl methanesulfonate

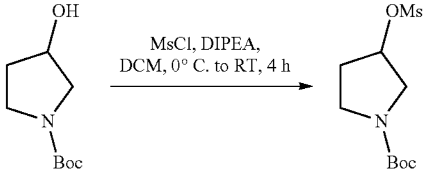

3 4

To a stirred solution of tert-butyl 3-hydroxypyrrolidine-1-carboxylate (1.0 g, 5.347 mmol) in DCM (10.0 mL) at 0° C. was added MsCl (0.673 g, 5.882 mmol) under nitrogen. To resultant reaction mixture DIPEA (0.898 g, 6.951 mmol) solution in DCM (1.0 mL) was added drop wise, stirred for 4 h at RT and progress of reaction was monitored by TLC. On completion, quenched with water, extracted with ethyl acetate. Organic layer was dried over sodium sulphate, concentrated under reduced pressure. Crude was purified by silica gel (100-200 mesh) column chromatography using 10% ethyl acetate in hexane as eluent to 1-(tert-butoxycarbonyl)pyrrolidin-3-yl methanesulfonate (0.25 g, 25%) as crude yellow oily mass.

MS: 266.33 [M+1]

Step-3: Synthesis of tert-butyl 3-cyanopyrrolidine-1-carboxylate

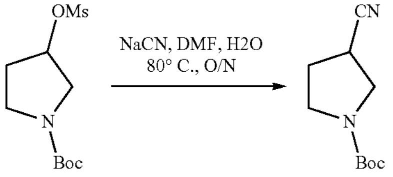

5 6

To a stirred solution of 1-(tert-butoxycarbonyl) pyrrolidin-3-yl methanesulfonate (0.25 g, 0.9432 mmol) in DMF (5 mL) and water (1 mL) was added KCN (0.138 g, 2.830 mmol) under nitrogen and the resulted solution heated overnight at 80° C. Progress of reaction was monitored by TLC. After reaction completion reaction mass was cooled to 0° C. and quenched with water. Product was extracted with ethyl acetate. The organic layer was washed with brine, dried over sodium sulphate and concentrated under reduced pressure. Crude was purified by silica gel (100-200 mesh) column chromatography using 6% acetone/hexane as eluent to obtain tert-butyl 3-cyanopyrrolidine-1-carboxylate (0.15 g, 81%) as yellow oil. MS: 197.25 [M+1]

Step-4: Synthesis of pyrrolidine-3-carbonitrile trifluoroacetate

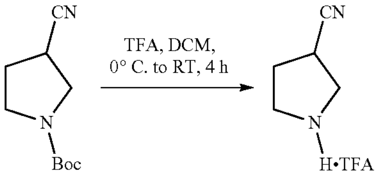

7 8

To a stirred solution of tert-butyl 3-cyanopyrrolidine-1-carboxylate (0.15 g, 0.765 mmol) in DCM (5 mL) was added TFA (0.8 mL) at 0° C. and reaction allowed to stir at room temperature for 4 h. Reaction was monitored by TLC. On completion all volatiles were evaporated under reduced pressure, residue was triturated with diethyl ether, filtered and dried to obtained pyrrolidine-3-carbonitrile trifluoroacetate (0.1 g, 62.2%) as off brown solid.

MS: 194.15 [M+1]

Step-5: Synthesis of 4-nitrophenyl 3-cyanocyclopentanecarboxylate

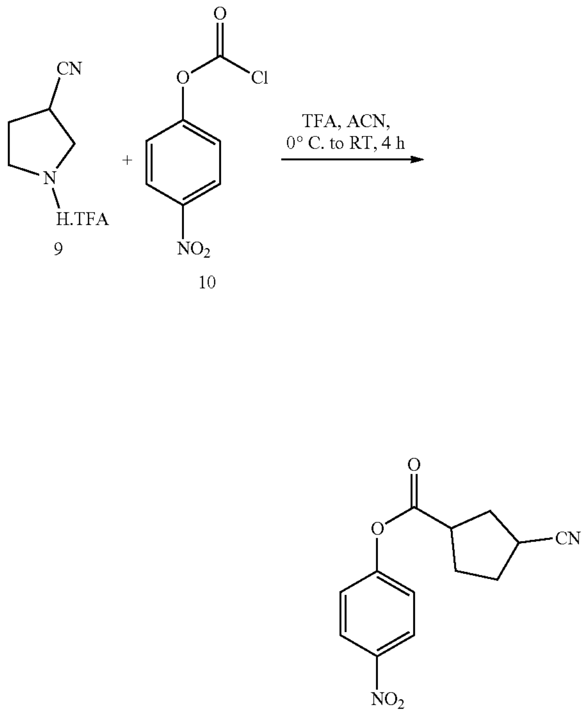

9 10

11

To a stirred solution of pyrrolidine-3-carbonitrile trifluoroacetate (0.05 g, 0.238 mmol) in ACN (5.0 mL), trimethylamine (0.072 g, 0.714 mmol) was added followed by 4-nitrophenyl chloroformate (0.047 g, 0.238 mmol) at 0° C. The resultant reaction mixture was stirred for 4 h at room temperature. Completion of reaction was monitored by TLC. On completion product was extracted with ethyl acetate. The organic layer was washed with brine, dried over sodium sulphate and concentrated under reduced pressure to give 4-nitrophenyl 3-cyanocyclopentanecarboxylate (0.05 g, 80.5%) as white solid MS: 261.25 [M+1]

Step-6: Synthesis of 1-(4-(2-amino-3-nitropyridin-4-yl)-1H-pyrazole-1-carbonyl)pyrrolidine-3-carbonitrile

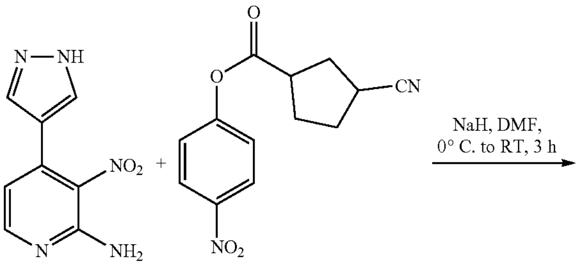

12 13

-continued

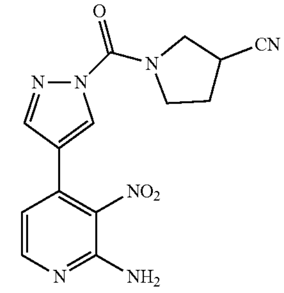

14

To a stirred solution of 3-nitro-4-(1H-pyrazol-4-yl)pyridin-2-amine (0.05 g, 0.2439 mmol) in DMF (2 mL) at 0° C. was added NaH (0.02 g, 0.4878 mmol) under nitrogen and stirred for 30 min. at same temperature. To resultant reaction mass solution of 4-nitrophenyl 3-cyanocyclopentanecarboxylate (0.094 g, 0.7894 mmol) in DMF was added at 0° C. and stirred for 4 h at RT. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 0.5% Methanol in DCM as eluent to obtain 1-(4-(2-amino-3-nitropyridin-4-yl)-1H-pyrazole-1-carbonyl)pyrrolidine-3-carbonitrile (0.03 g, 37.6%) as yellow solid.

MS: 328.3 [M+1]

Step-7: Synthesis of 1-(4-(2,3-diaminopyridin-4-yl)-1H-pyrazole-1-carbonyl)pyrrolidine-3-carbonitrile

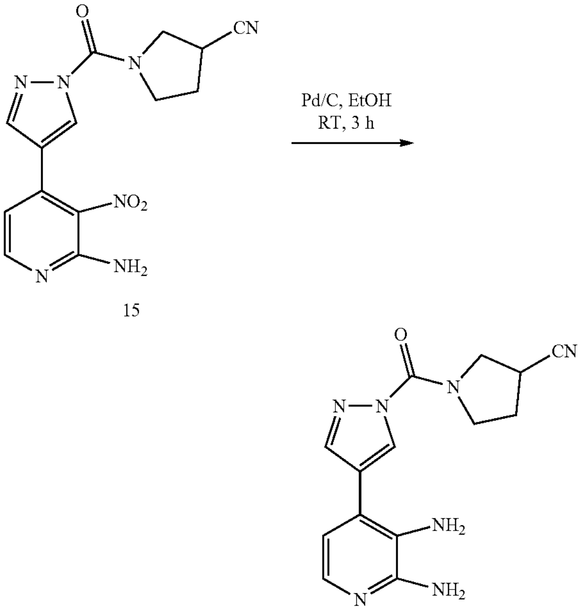

15

16

To a stirred solution of 1-(4-(2-amino-3-nitropyridin-4-yl)-1H-pyrazole-1-carbonyl)pyrrolidine-3-carbonitrile (0.03 g, 0.0917 mmol) in methanol (5 mL) was hydrogenated by 10% Pd/C (0.003 g, 10% wt/wt) using hydrogen balloon. Progress of the reaction was monitored by TLC. After reaction completion reaction mass filtered through celite and filtrate was evaporated under reduced pressure to give 2-(6-(4-(2,3-diaminopyridin-4-yl)-1H-pyrazol-1-yl)pyridin-3-yl)acetonitrile (0.02 g, 73.5%) as brown solid.

MS: 298.3 [M+1]

Step-8: Synthesis of 1-(4-(3H-imidazo[4,5-b]pyridin-7-yl)-1H-pyrazole-1-carbonyl)pyrrolidine-3-carbonitrile

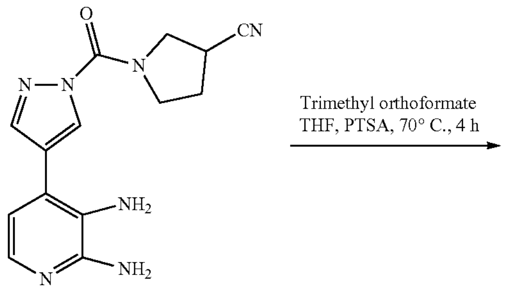

17

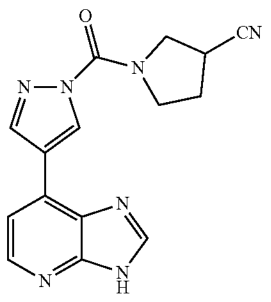

1177

To a stirred solution of 2-(6-(4-(2,3-diaminopyridin-4-yl)-1H-pyrazol-1-yl)pyridin-3-yl)acetonitrile (0.025 g, 0.0841 mmol) in trimethyl orthoformate (1.0 mL) was added. To resultant reaction mixture, PTSA (0.004 g) was added and stirred for 4 h at 70° C. Completion of reaction was monitored by TLC. On completion, quenched with aq. sodium bicarbonate solution, extracted with ethyl acetate. The organic layer was washed with water, brine, dried over sodium sulphate and concentrated under reduced pressure to give crude desired product that was purified by silica gel (100 to 200 Mesh) column chromatography: eluent at 3% to 5% MeOH in DCM to obtain 1-(4-(3H-imidazo[4,5-b]pyridin-7-yl)-1H-pyrazole-1-carbonyl)pyrrolidine-3-carbonitrile (0.01 g, 40%) as off white solid.

MS: 308.3 [M+1]

Synthesis of Compound No: 1056: N-(3-cyanocyclobutyl)-4-(2,3-dihydro-2-oxo-1H-imidazo[4,5-b]pyridin-7-yl)-1H-Pyrazole-1-carboxamide

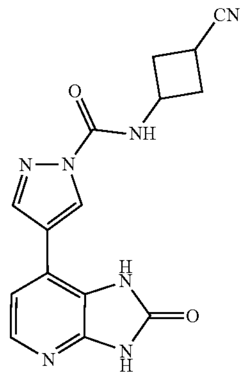 [SMILES: N#CC1CC(NC(=O)n2cc(-c3ccnc4[nH]c(=O)[nH]c34)cn2)C1]

Step-1: Synthesis of tert-butyl 3-carbamoylcyclobutylcarbamate

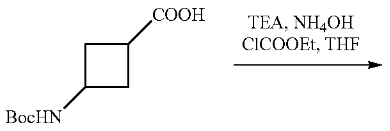

18

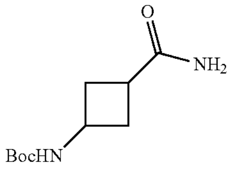

19

To a stirred solution of tert-butyl 3-cyanopyrrolidine-1-carboxylate (0.500 g, 2.325 mmol) in THE (15 mL) was added ethyl chloroformate (0.301 mg, 2.79 mmol) at 0° C. and reaction allowed to stir at room temperature for 1 h. To resultant reaction mass solution of ammonium hydroxide (5.0 mL) was added at 0° C. and stirred for 4 h at RT. Reaction was monitored by TLC. On completion product was extracted with ethyl acetate. The organic layer was washed with brine, dried over sodium sulphate and concentrated under reduced pressure to give to obtained tert-butyl 3-carbamoylcyclobutylcarbamate (0.430 g, 85.65%) as colourless liquid.

MS: 215.12 [M+1]

Step-2: Synthesis of tert-butyl 3-cyanocyclobutylcarbamate

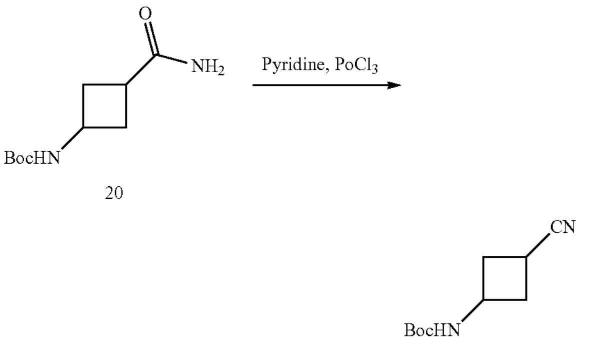

20

21

To a stirred solution of tert-butyl 3-carbamoylcyclobutylcarbamate (0.400 g, 1.869 mmol) in pyridine (5.0 mL) was added POCl3 (1.84 g, 1.200 mmol) at 0° C. and reaction allowed to stir at room temperature for 1 h. Reaction was monitored by TLC. On completion product was extracted with ethyl acetate. The organic layer was washed with brine, dried over sodium sulphate and concentrated under reduced pressure to give to obtained tert-butyl 3-cyanocyclobutylcarbamate (0.340 g, 98.8%) as colourless liquid.

MS: 197.15 [M+1]

Step-3: Synthesis of 3-aminocyclobutanecarbonitrile hydrochloride

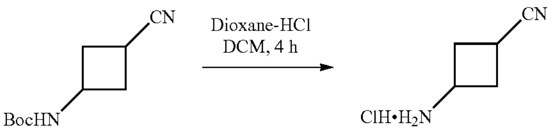

22

23

To a stirred solution of tert-butyl 3-cyanocyclobutylcarbamate (0.300 g, 1.522 mmol) in DCM (5 mL) was added Dioxane-HCl (2.5 mL) at 0° C. and reaction allowed to stir at room temperature for 4 h. Reaction was monitored by TLC. On completion all volatiles were evaporated under reduced pressure, residue was triturated with di-ethyl ether, filtered and dried to obtained 3-aminocyclobutanecarbonitrile hydrochloride (0.240 g, 94.63%) as off white solid.

MS: 133.05 [M+1]

Step-4: Synthesis of 4-nitrophenyl 3-cyanocyclobutylcarbamate

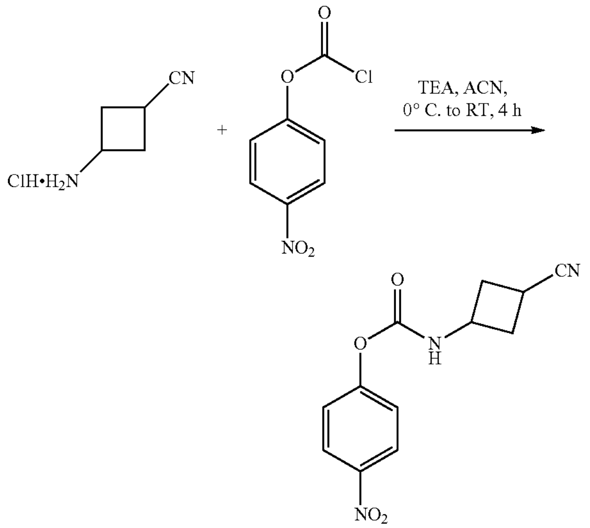

To a stirred solution of 3-aminocyclobutanecarbonitrile hydrochloride (0.300 g, 2.247 mmol) in ACN (5.0 mL), trimethylamine (0.493 g, 4.89 mmol) was added followed by 4-nitrophenyl chloroformate (0.544 g, 2.706 mmol) at 0° C. The resultant reaction mixture was stirred for 4 h at room temperature. Completion of reaction was monitored by TLC. On completion product was extracted with ethyl acetate. The organic layer was washed with brine, dried over sodium sulphate and concentrated under reduced pressure to give 4-nitrophenyl 3-cyanocyclobutylcarbamate (0.250 g, 42.23%) as yellowish solid.

MS: 262.05 [M+1]

Step-5: Synthesis of N-(3-cyanocyclobutyl)-4-(2,3-dihydro-2-oxo-1H-imidazo[4,5-b]pyridin-7-yl)-1H-pyrazole-1-carboxamide

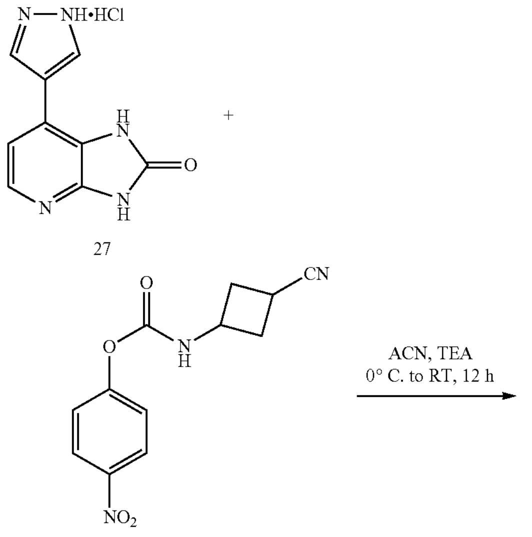

27

28

-continued

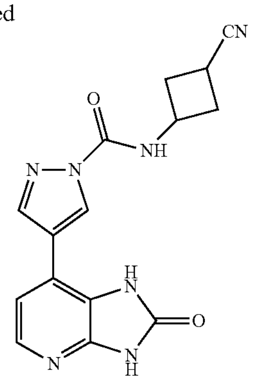

1056

To a stirred solution of 7-(1H-pyrazol-4-yl)-1H-imidazo[4,5-b]pyridin-2(3H)-one hydrochloride (0.05 g, 0.210 mmol) in ACN (2.5 mL) at 0° C. was added TEA (0.053 g, 0.527 mmol) under nitrogen and stirred for 30 min. at same temperature. To resultant reaction mass solution of 4-nitrophenyl 3-cyanocyclobutylcarbamate (0.081 g, 0.315 mmol) in ACN was added at 0° C. followed by TEA (0.035 g, 0.315 mmol) under nitrogen and stirred for 4 h at RT. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 3-5% Methanol in DCM as eluent to obtain N-(3-cyanocyclobutyl)-4-(2,3-dihydro-2-oxo-1H-imidazo[4,5-b]pyridin-7-yl)-1H-pyrazole-1-carboxamide (0.03 g, 37.6%) as off white solid.

MS: 324.11 [M+1]

Synthesis of compound No. 1063: N-(cyano(phenyl)methyl)-4-(2,3-dihydro-2-oxo-1H-imidazo[4,5-b]pyridin-7-yl)-1H-pyrazole-1-carboxamide

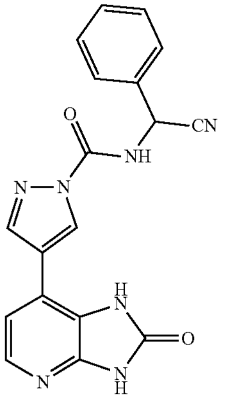 [SMILES: N#CC(NC(=O)n1cc(-c2ccnc3[nH]c(=O)[nH]c23)cn1)c1ccccc1]

Step-1: 2-amino-2-phenylacetonitrile

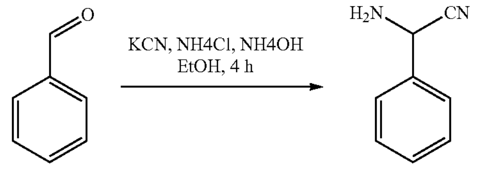

29 30

To a stirred solution of benzaldehyde (1.0 g, 0.934 mmol) in Ethanol (20 mL) was added ammonium chloride (0.99 g, 1.86 mmol), ammonium hydroxide (12.5 ml, 25%) and potassium cyanide (078 g, 1.21 mmol) at room temperature. The resultant reaction mixture was stirred at same temperature for 4 h. Completion of reaction was monitored by TLC. On completion, quenched with ice water, extracted with ethyl acetate. The organic layer was washed with water, brine, dried over sodium sulphate, concentrated under reduced pressure to obtained 2-amino-2-phenylacetonitrile (0.600 g, 48.3%) as orange solid.

MS: 133.04 [M+1]

Step-2: 4-nitrophenyl cyano(phenyl)methylcarbamate

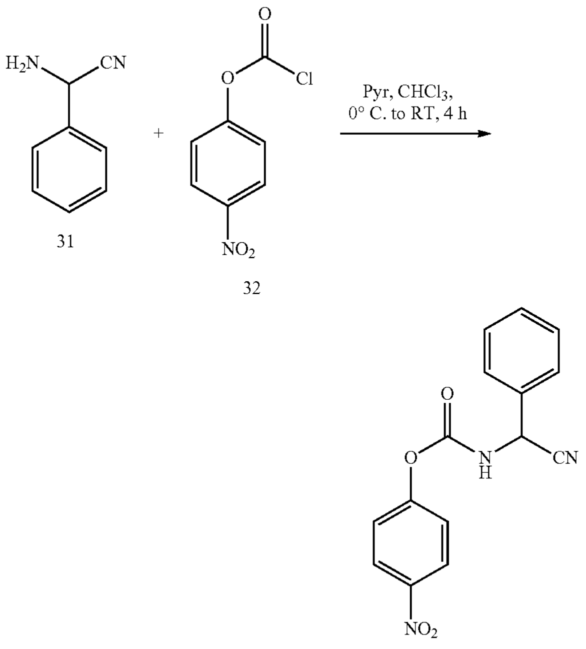

31 32 33

To a stirred solution of 2-amino-2-phenylacetonitrile (0.200 g, 1.515 mmol) in chloroform (5.0 mL), pyridine (0.3 g, 3.03 mmol) was added followed by 4-nitrophenyl chloroformate (0.3 g, 1.515 mmol) at 0° C. The resultant reaction mixture was stirred for 4 h at room temperature. Completion of reaction was monitored by TLC. On completion product was extracted with ethyl acetate. The organic layer was washed with brine, dried over sodium sulphate and concentrated under reduced pressure to give 4-nitrophenyl cyano (phenyl)methylcarbamate (0.200 g, 44.4%) as white solid

MS: 298.25 [M+1]

Step-3: 3 Synthesis of N-(cyano(phenyl)methyl)-4-(2,3-dihydro-2-oxo-1H-imidazo[4,5-b]pyridin-7-yl)-1H-pyrazole-1-carboxamide

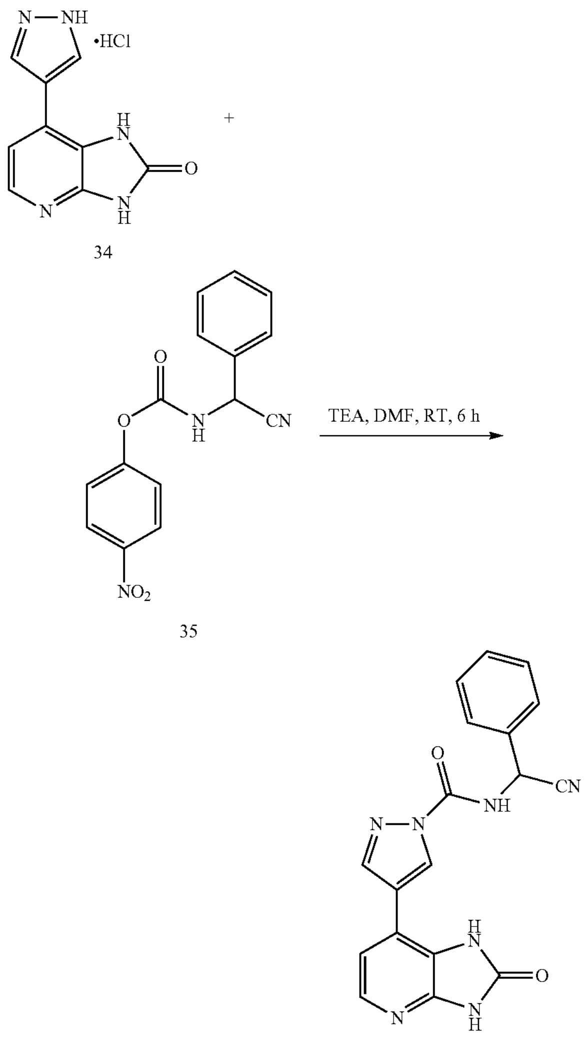

34

35

1063

To a stirred solution of 7-(1H-pyrazol-4-yl)-1H-imidazo [4,5-b]pyridin-2(3H)-one hydrochloride (0.030 g, 0.0127 mmol) in DMF (2.0 mL), trimethylamine (0.038 g, 0.0381) and 4-nitrophenyl cyano(phenyl)methylcarbamate (0.037 g, 0.0127 mmol) was added. The resultant reaction mixture was stirred 6 h at room temperature. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtain N-(cyano(phenyl)methyl)-4-(2,3-dihydro-2-oxo-1H-imidazo[4,5-b]pyridin-7-yl)-1H-pyrazole-1-carboxamide (0.004 g, 8.7%) as off white solid.

MS: 360.1[M+1]

Synthesis of Compound No. 1064: —N-(2,2,2-trifluoroethyl)-4-(3H-imidazo[4,5-b]pyridin-7-yl)-1H-pyrazole-1-carboxamide

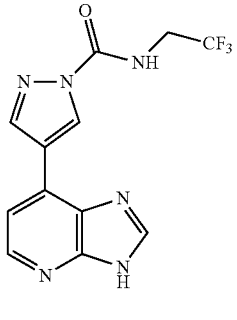 [SMILES: O=C(NCC(F)(F)F)n1cc(-c2ccnc3[nH]cnc23)cn1]

Step-1: Synthesis of 4-(2-amino-3-nitropyridin-4-yl)-N-(2,2,2-trifluoroethyl)-1H-pyrazole-1-carboxamide

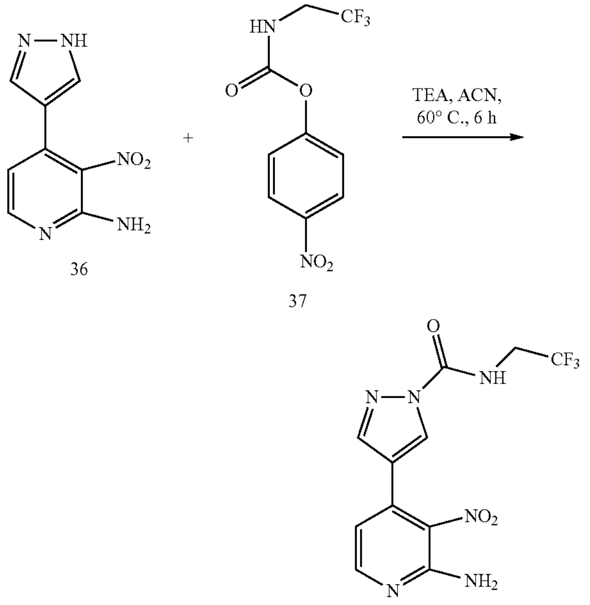

36

37

38

To a stirred solution of 3-nitro-4-(1H-pyrazol-4-yl)pyridin-2-amine (0.150 g, 0.073 mmol) in acetonitrile (10 mL) and trimethylamine (0.147 g, 0.146 mmol), was added 4-nitrophenyl 2,2,2-trifluoroethylcarbamate (0.231 g, 0.087 mmol) at room temperature. The resultant reaction mixture was stirred at 60° C. temperature for 6 h. Completion of reaction was monitored by TLC. On completion, quenched with ice water, extracted with ethyl acetate. The organic layer was washed with water, brine, dried over sodium sulphate, concentrated under reduced pressure obtained crude reaction mass. Purification of the crude was done via silica gel (100-200 Mesh) column chromatography and desired compound eluted at 3 to 4% methanol in DCM to obtained 4-(2-amino-3-nitropyridin-4-yl)-N-(2,2,2-trifluoroethyl)-1H-pyrazole-1-carboxamide (0.160 g, 67%) as yellow solid.

MS: 331.04 [M+1]

Step-2: Synthesis of 4-(2,3-diaminopyridin-4-yl)-N-(2,2,2-trifluoroethyl)-1H-pyrazole-1-carboxamide

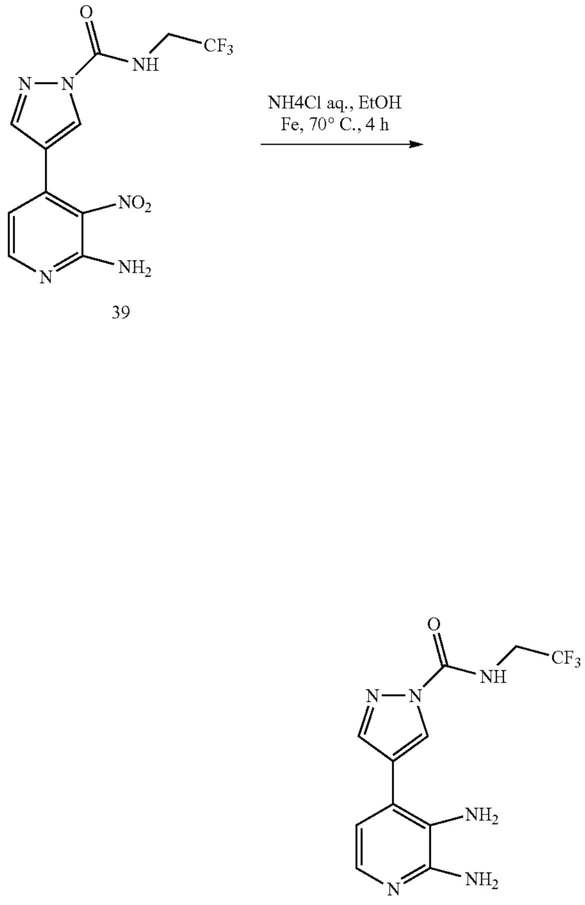

39

40

To a stirred solution of 4-(2-amino-3-nitropyridin-4-yl)-N-(2,2,2-trifluoroethyl)-1H-pyrazole-1-carboxamide (0.080 g, 0.024 mmol) in EtOH (3.0 mL), $NH_4Cl$ (2.0 mL) was added at room temperature. To resultant reaction mixture, Fe powder (0.064 g, 0.12 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained 4-(2,3-diaminopyridin-4-yl)-N-(2,2,2-trifluoroethyl)-1H-pyrazole-1-carboxamide (0.045 g, 62.5%) as dark brown solid mass.

MS: 301.2 [M+1]

Step-: 3 Synthesis of N-(2,2,2-trifluoroethyl)-4-(3H-imidazo[4,5-b]pyridin-7-yl)-1H-Pyrazole-1-carboxamide

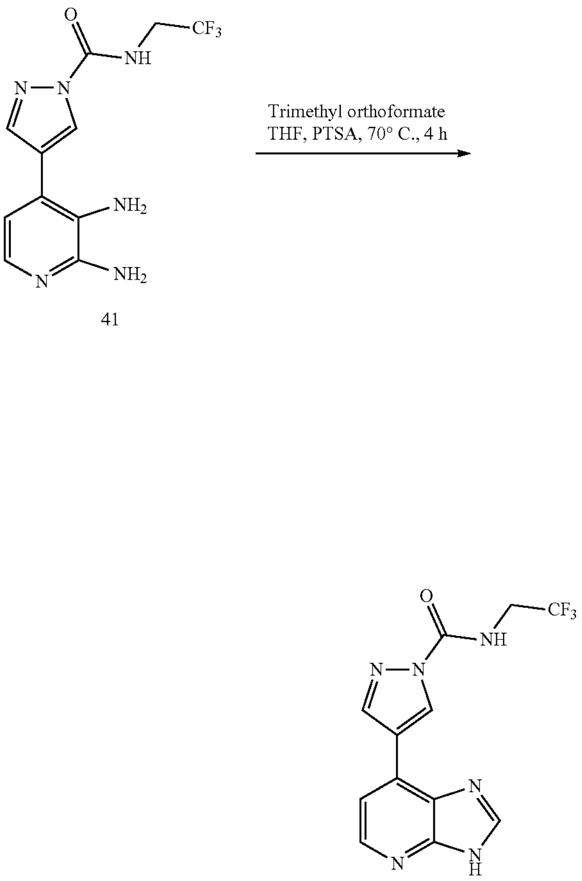

41

1064

To a stirred solution of 4-(2,3-diaminopyridin-4-yl)-N-(2,2,2-trifluoroethyl)-1H-pyrazole-1-carboxamide (0.045 g, 0.015 mmol) in THF (1.0 mL), trimethyl orthoformate (2.0 mL) was added. To resultant reaction mixture, PTSA (0.0051 g, 0.0030 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained N-(2,2,2-trifluoroethyl)-4-(3H-imidazo[4,5-b]pyridin-7-yl)-1H-pyrazole-1-carboxamide (0.023 g, 50%) as off white solid.

MS: 311.1[M+1]

Synthesis of Compound No. 1119: 7-(1-(5-(2,2,2-trifluoro-1-methoxy ethyl)pyridin-2-yl)-1H-pyrazol-4-yl)-3H-imidazo[4,5-b]pyridine

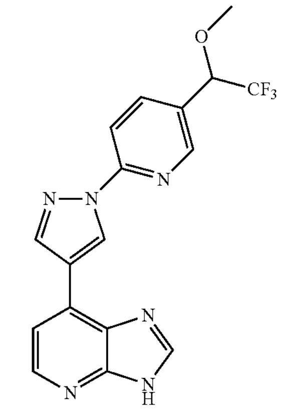 [SMILES: COC(c1ccc(-n2cc(-c3ccnc4[nH]cnc34)cn2)nc1)C(F)(F)F]

Step-1: Synthesis of 6-bromopyridine-3-carbaldehyde

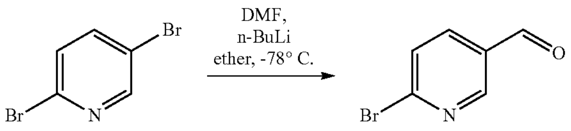

42 43

To a stirred solution of 2,5-dibromopyridine (26.0 g, 109.75 mmol) in diethyl ether (500 mL) at −78° C. was added n-Butyl lithium (2.5M in hexane) (66 mL, 164.63 mmol) under nitrogen and stirred for 1 h at same temperature. DMF (13 mL, 164.63 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 4% ethyl acetate in hexane as eluent to obtain 6-bromopyridine-3-carbaldehyde (12.20 g, 59.8%) as yellow oil.

MS: 187.0 [M+1]

Step-2: Synthesis of 1-(6-bromopyridin-3-yl)-2,2,2-trifluoroethanol

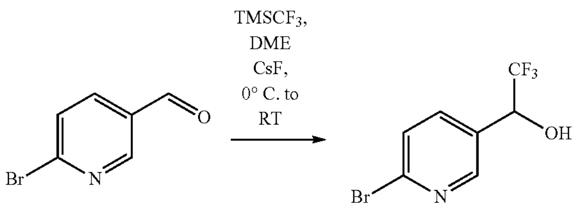

44 45

To a stirred solution of 6-bromopyridine-3-carbaldehyde (2.0 g, 10.75 mmol) in DME (50 mL) at 0° C. was added $TMSCF_3$ (1.61 g, 16.12 mmol) under nitrogen, followed by portion wise addition of CsF (2.44 g, 16.12 mmol) and stirred for 1 h at same temperature. Allow to warm to RT and Stirred for 6 h. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) on flash column chromatography using 20% ethyl acetate in hexane as eluent to obtain 1-(6-bromopyridin-3-yl)-2,2,2-trifluoroethanol (1.24 g, 47.69%) as yellow oil.

MS: 257.8 [M+1]

Step-3: Synthesis of 2-bromo-5-(2,2,2-trifluoro-1-methoxyethyl)pyridine

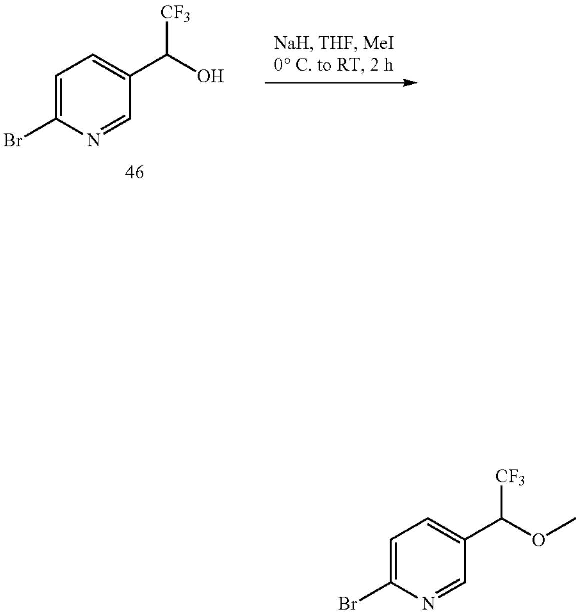

46 47

To a stirred solution of 1-(6-bromopyridin-3-yl)-2,2,2-trifluoroethanol (0.40 g, 15.56 mmol) in THF (5.0 mL) at 0° C. was added NaH (0.081 g, 20.23 mmol) under nitrogen and stirred for 1 h at same temperature. To resultant reaction mass MeI (0.232 g, 20.23 mmol) solution in THF (3.0 mL) was added Allow to warm to RT and Stirred for 1 h. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 10% acetone in hexane as eluent to obtain 2-bromo-5-(2,2,2-trifluoro-1-methoxyethyl)pyridine (0.39 g, 92.19%) as colourless oil.

MS: 271.0 [M+1]

Step-4: Synthesis of 4-(1-(5-(2,2,2-trifluoro-1-methoxyethyl)pyridin-2-yl)-1H-pyrazol-4-yl)-3-nitropyridin-2-amine

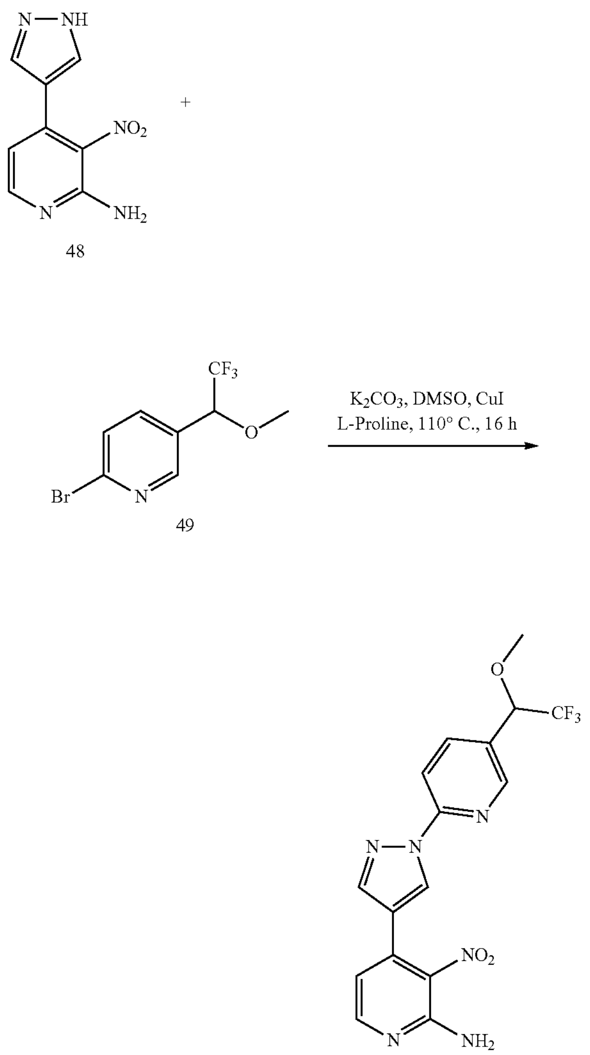

48

49

50

To a stirred solution of 3-nitro-4-(1H-pyrazol-4-yl)pyridin-2-amine (0.15 g, 0.73 mmol) and compound 2-bromo-5-(2,2,2-trifluoro-1-methoxyethyl)pyridine (0.278 g, 1.02 mmol) in DMSO (5 ml) was added $K_2CO_3$ (0.251 g, 1.825 mmol) followed by CuI (0.013 g, 0.073 mmol) and L-Proline (0.056 g, 0.365 mmol). Reaction was heated at 110° C. for 16 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 40-60% acetone in n-hexane to obtained 4-(1-(5-(2,2,2-trifluoro-1-methoxyethyl)pyridin-2-yl)-1H-pyrazol-4-yl)-3-nitropyridin-2-amine (0.075 g, 37.87%) as yellow solid.

MS: 394.4[M+1]

Step-5: Synthesis of 4-(1-(5-(2,2,2-trifluoro-1-methoxyethyl)pyridin-2-yl)-1H-pyrazol-4-yl)pyridine-2,3-diamine

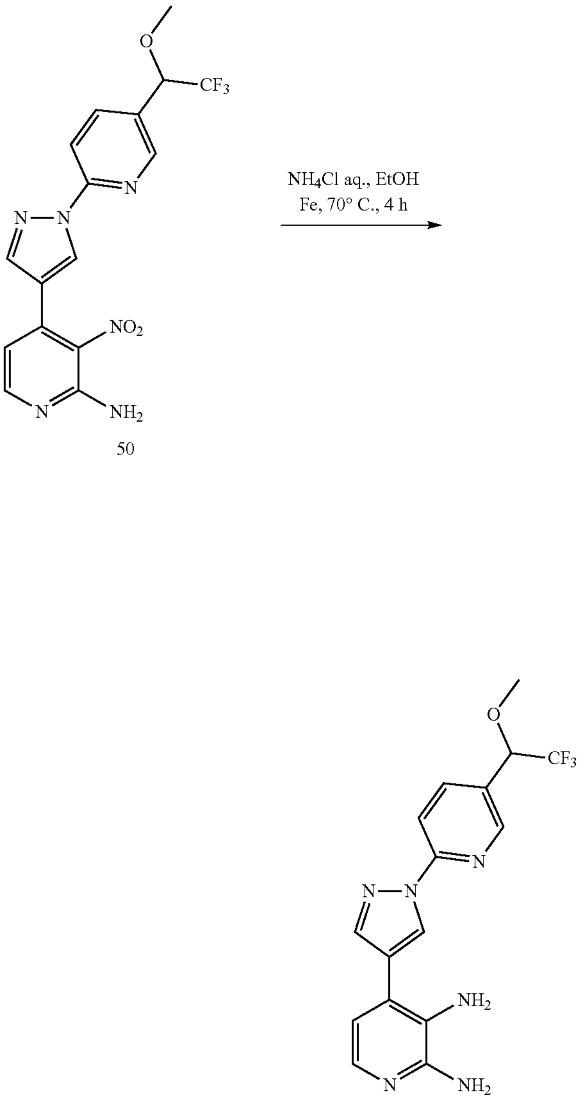

50

52

To a stirred solution of 4-(1-(5-(2,2,2-trifluoro-1-methoxyethyl)pyridin-2-yl)-1H-pyrazol-4-yl)-3-nitropyridin-2-amine (0.070 g, 1.77 mmol) in EtOH (3.0 mL), $NH_4Cl$ (2.5 mL) was added at room temperature. To resultant reaction mixture, Fe powder (0.025 g, 0.45 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 4-(1-(5-(2,2,2-trifluoro-1-methoxy ethyl)pyridin-2-yl)-1H-pyrazol-4-yl)pyridine-2,3-diamine (0.035 g, 53.03%) as dark brown solid mass.

MS: 364.2 [M+1]

Step-6: Synthesis of 7-(1-(5-(2,2,2-trifluoro-1-methoxyethyl)pyridin-2-yl)-1H-pyrazol-4-yl)-3H-imidazo[4,5-b]pyridine

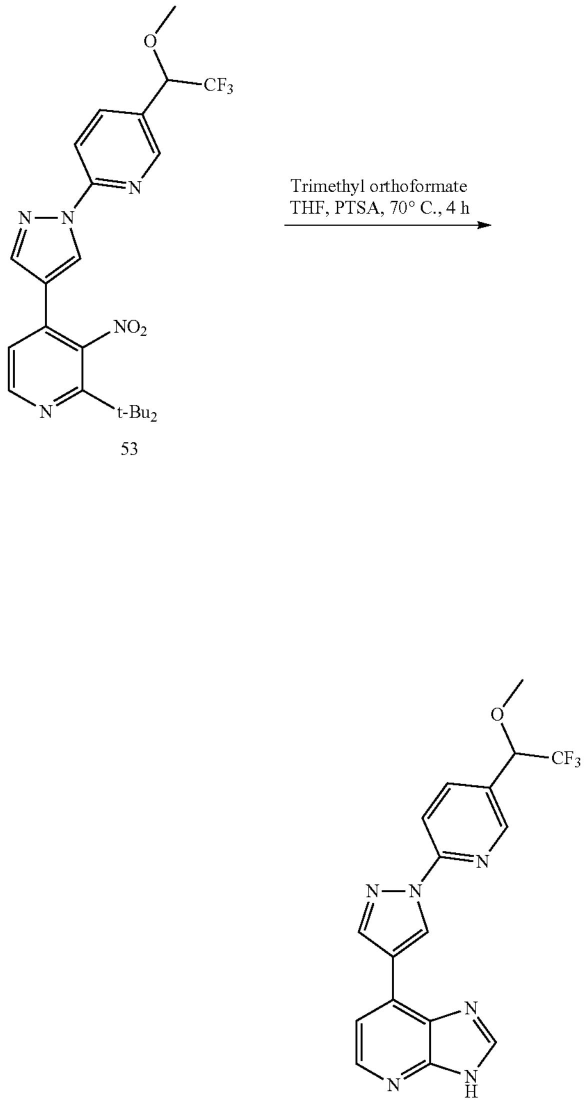

53

1119

To a stirred solution of 4-(1-(5-(2,2,2-trifluoro-1-methoxy ethyl)pyridin-2-yl)-1H-pyrazol-4-yl)pyridine-2,3-diamine (0.035 g, 0.093 mmol) in THF (1.0 mL), Trimethyl orthoformate (1.5 mL) was added. To resultant reaction mixture, PTSA (0.002 g, 0.018 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 3% to 5% MeOH in DCM to obtained 7-(1-(5-(2,2,2-trifluoro-1-methoxy ethyl)pyridin-2-yl)-1H-pyrazol-4-yl)-3H-imidazo[4,5-b]pyridine (0.07 g, 19.44%) as off white solid.

MS: 375.9[M+1]

Synthesis of Compound No. 1126: 1-(6-(4-(3H-imidazo[4,5-b]pyridin-7-yl)-1H-pyrazol-1-yl)pyridin-3-yl)-1-cyclopropyl-2,2,2-trifluoroethanol

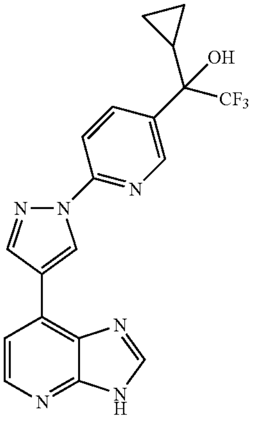 [SMILES: OC(c1ccc(-n2cc(-c3ccnc4[nH]cnc34)cn2)nc1)(C1CC1)C(F)(F)F]

Step-1: Synthesis of N-methoxy-N-methyl cyclopropane carboxamide

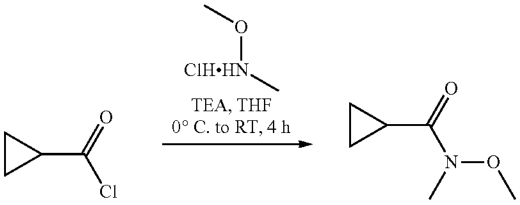

54 55

To a stirred solution of cyclopropane carbonyl chloride (10.0 g, 961.5 mmol) and N-methoxy methanamine hydrochloride (11.20 g, 1153.8 mmol) in THE (150 mL), TEA (24.20 g, 2403.8 mmol) was added drop-wise at 0° C. and allow to stirred for 30 min. Resultant reaction mass was then placed at RT and stirred for 4 h. Completion of reaction was monitored by TLC. On completion, concentrated under reduced pressure to obtained crude mass. Purification of the crude was done via silica gel (100-200 Mesh) column chromatography and desired compound eluted at 5% ether/n-Hexane to obtained N-methoxy-N-methyl cyclopropane carboxamide (7.45 g, 60%) as colourless oily mass.

MS: 130.07 [M+1]

Step-2: Synthesis of (6-bromopyridin-3-yl)(cyclopropyl)methanone

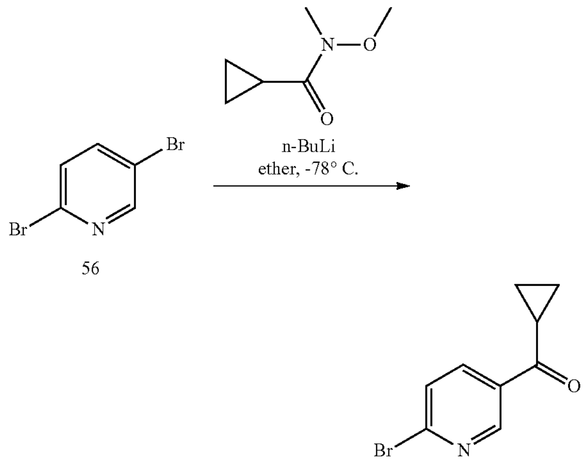

56

57

To a stirred solution of 2,5-dibromopyridine (12.0 g, 50.63 mmol) in diethyl ether (250 mL) at −78° C. was added n-Butyl lithium (2.5M in hexane) (24.30 mL, 65.81 mmol) under nitrogen and stirred for 1 h at same temperature. N-methoxy-N-methyl cyclopropane carboxamide (7.1 g, 55.69 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 4% ethyl acetate in hexane as eluent to obtain (6-bromopyridin-3-yl) (cyclopropyl)methanone (6.46 g, 68.07%) as yellow oil.

MS: 227.1 [M+1]

Step-3: Synthesis of 1-(6-bromopyridin-3-yl)-1-cyclopropyl-2,2,2-trifluoroethanol

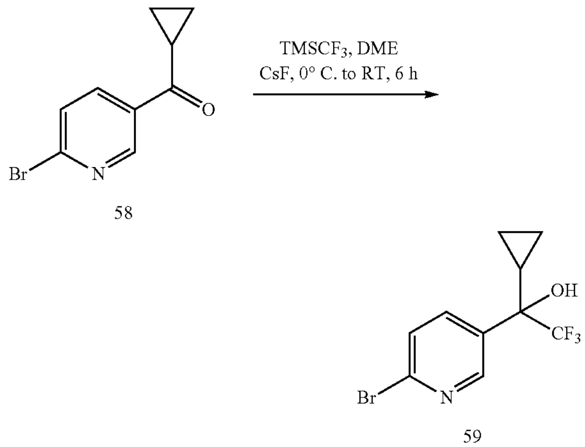

58

59

To a stirred solution of (6-bromopyridin-3-yl) (cyclopropyl) methanone (2.0 g, 88.49 mmol) in DME (25 mL) at 0° C. was added $TMSCF_3$ (1.86 g, 132.74 mmol) under nitrogen, followed by portion wise addition of CsF (2.01 g, 132.74 mmol) and stirred for 1 h at same temperature. Allow to warm to RT and Stirred for 6 h. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) on flash column chromatography using 15-20% ethyl acetate in hexane as eluent to obtain 1-(6-bromopyridin-3-yl)-1-cyclopropyl-2,2,2-trifluoroethanol (1.45 g, 55.76%) as yellow oil.

MS: 297.4 [M+1]

Step-4: Synthesis of 1-(6-(4-(2-amino-3-nitropyridin-4-yl)-1H-pyrazol-1-yl)pyridin-3-yl)-1-cyclopropyl-2,2,2-trifluoroethanol

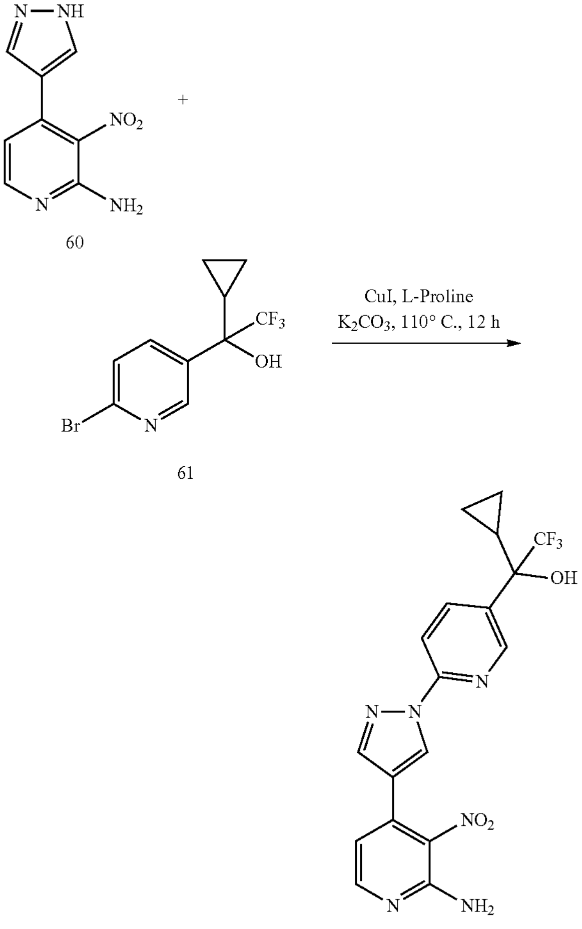

60

61

62

To a stirred solution of 3-nitro-4-(1H-pyrazol-4-yl)pyridin-2-amine (0.15 g, 0.73 mmol) and compound 1-(6-bromopyridin-3-yl)-1-cyclopropyl-2,2,2-trifluoroethanol (0.320 g, 1.02 mmol) in DMSO (5 ml) was added $K_2CO_3$ (0.251 g, 1.825 mmol) followed by CuI (0.013 g, 0.073 mmol) and L-Proline (0.056 g, 0.365 mmol). Reaction was heated at 110° C. for 12 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 40-60% acetone in n-hexane to obtained 1-(6-(4-(2-amino-3-nitropyridin-4-yl)-1H-pyrazol-1-yl)pyridin-3-yl)-1-cyclopropyl-2,2,2-trifluoroethanol (0.065 g, 21.10%) as yellow solid.

MS: 421.37 [M+1]

Step-5: Synthesis of 1-(6-(4-(2,3-diaminopyridin-4-yl)-1H-pyrazol-1-yl)pyridin-3-yl)-1-cyclopropyl-2,2,2-trifluoroethanol

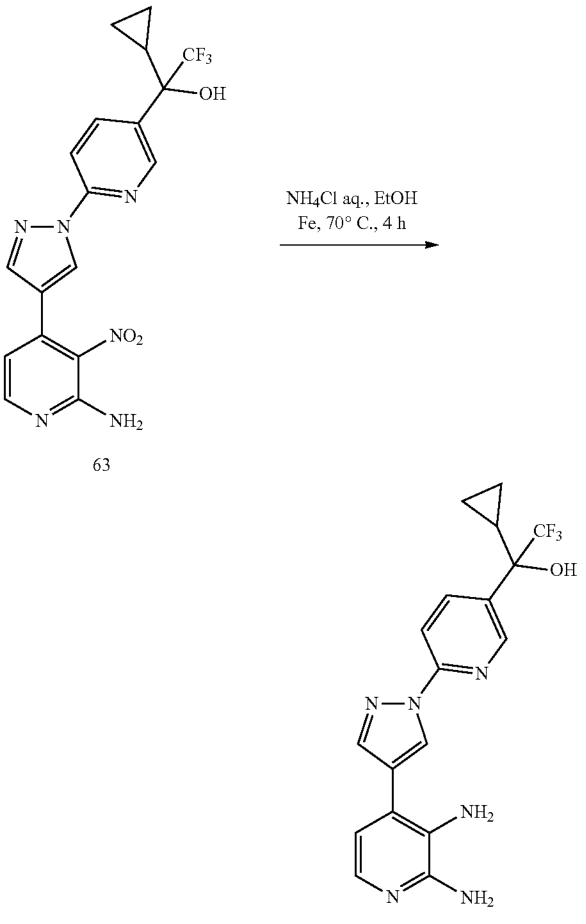

63

64

To a stirred solution of 1-(6-(4-(2-amino-3-nitropyridin-4-yl)-1H-pyrazol-1-yl)pyridin-3-yl)-1-cyclopropyl-2,2,2-trifluoroethanol (0.065 g, 1.54 mmol) in EtOH (3.0 mL), $NH_4Cl$ (2.5 mL) was added at room temperature. To resultant reaction mixture, Fe powder (0.043 g, 7.8 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained 1-(6-(4-(2,3-diamino pyridin-4-yl)-1H-pyrazol-1-yl)pyridin-3-yl)-1-cyclopropyl-2,2,2-trifluoroethanol (0.035 g, 57.37%) as dark brown solid mass.

MS: 391.2 [M+1]

Step-6: Synthesis of 1-(6-(4-(3H-imidazo[4,5-b]pyridin-7-yl)-1H-pyrazol-1-yl)pyridin-3-yl)-1-cyclopropyl-2,2,2-trifluoroethanol

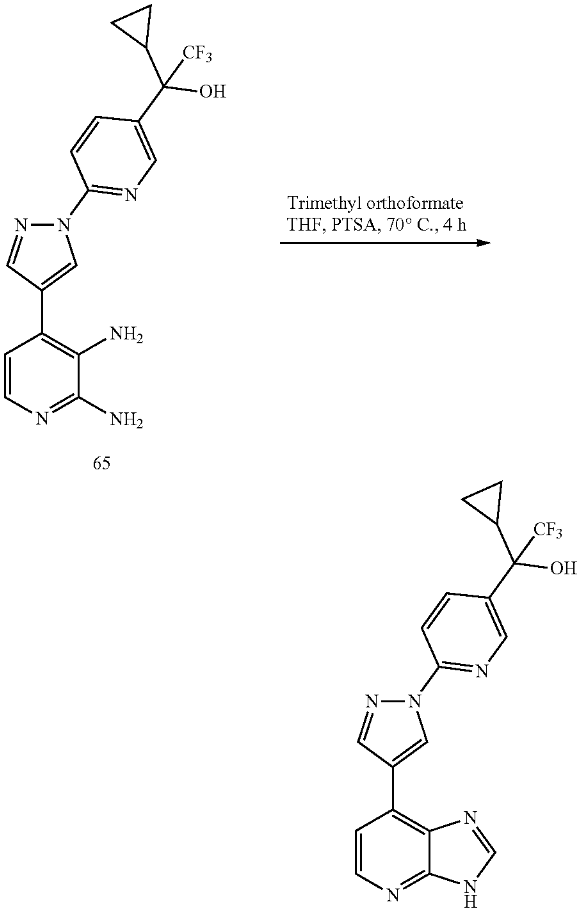

65

1126

To a stirred solution of 1-(6-(4-(2,3-diamino pyridin-4-yl)-1H-pyrazol-1-yl)pyridin-3-yl)-1-cyclopropyl-2,2,2-trifluoroethanol (0.035 g, 0.089 mmol) in THF (1.0 mL), Trimethyl orthoformate (1.5 mL) was added. To resultant reaction mixture, PTSA (0.003 g, 0.0017 mmol) was added and stirred for 4 h at 70° C. Completion of reaction was monitored by TLC. On completion, quenched with bicarbonate water and extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 3% to 5% MeOH in DCM to obtained 7-(1-(5-(2,2,2-trifluoro-1-methoxy ethyl)pyridin-2-yl)-1H-pyrazol-4-yl)-3H-imidazo[4,5-b]pyridine (0.06 g, 17.19%) as off white solid.

MS: 400.9[M+1]

Synthesis of Compound No. 1128: 7-(1-(5-(1,1,1,2-tetrafluoropropan-2-yl)pyridin-2-yl)-1H-pyrazol-4-yl)-3H-imidazo[4,5-b]pyridine

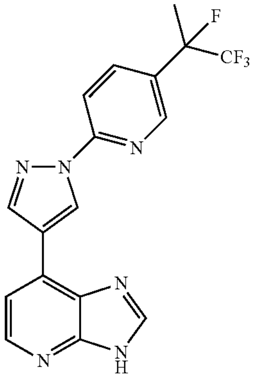 [SMILES: CC(F)(c1ccc(-n2cc(-c3ccnc4[nH]cnc34)cn2)nc1)C(F)(F)F]

Step-1: Synthesis of 1-(6-bromopyridin-3-yl)ethanone

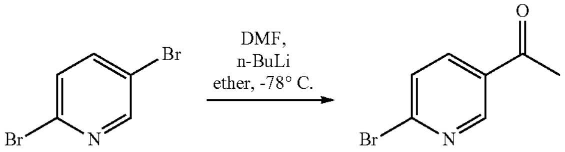

66 67

To a stirred solution of 2,5-dibromopyridine (12.0 g, 50.63 mmol) in diethyl ether (250 mL) at −78° C. was added n-Butyl lithium (2.5M in hexane) (24.30 mL, 65.81 mmol) under nitrogen and stirred for 1 h at same temperature. DMA (7.89 g, 60.75 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 4% ethyl acetate in hexane as eluent to obtain 1-(6-bromopyridin-3-yl)ethanone (4.5 g, 44.03%) as yellow oil.

MS: 201.1 [M+1]

Step-2: Synthesis of 2-(6-bromopyridin-3-yl)-1,1,1-trifluoropropan-2-ol

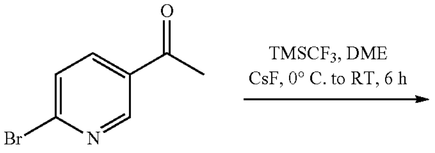

68

-continued

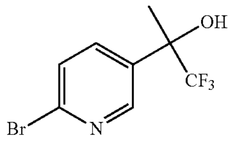

69

To a stirred solution of 1-(6-bromopyridin-3-yl)ethanone (2.0 g, 11.00 mmol) in DME (50 mL) at 0° C. was added $TMSCF_3$ (2.33 g, 14.30 mmol) under nitrogen, followed by portion wise addition of CsF (2.50 g, 16.50 mmol) and stirred for 1 h at same temperature. Allow to warm to RT and Stirred for 6 h. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) on flash column chromatography using 15-20% ethyl acetate in hexane as eluent to obtain 2-(6-bromopyridin-3-yl)-1,1,1-trifluoropropan-2-ol (1.45 g, 53.50%) as yellow oil.

MS: 271.0 [M+1]

Step-3: Synthesis of 2-bromo-5-(1,1,1,2-tetrafluoropropan-2-yl)pyridine

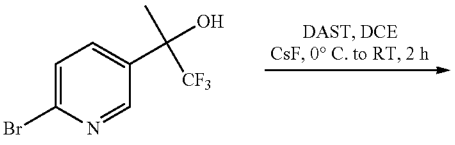

70

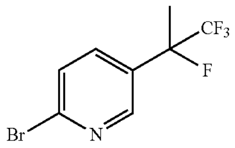

71

To a stirred solution of 2-(6-bromopyridin-3-yl)-1,1,1-trifluoropropan-2-ol (1.45 g, 53.70 mmol) in DCE (35 mL) at 0° C. was added DAST (1.12 g, 69.81 mmol) under nitrogen, followed by stirred for 15 min at same temperature. Allow to warm to RT and Stirred for 1 h. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) on flash column chromatography using 15-20% ethyl acetate in hexane as eluent to obtain 2-bromo-5-(1,1,1,2-tetrafluoropropan-2-yl)pyridine (1.1 g, 75.86%) as yellow oil.

MS: 273.04 [M+1]

Step-4: Synthesis of 4-(1-(5-(1,1,1,2-tetrafluoropropan-2-yl)pyridin-2-yl)-1H-pyrazol-4-yl)-3-nitropyridin-2-amine

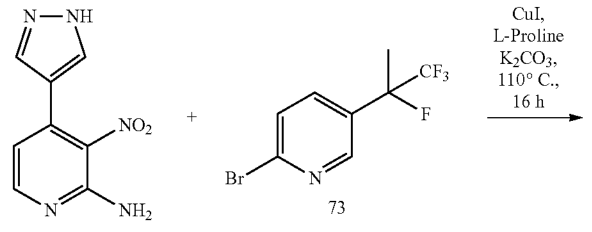

72

73

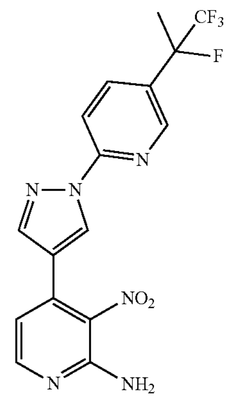

74

To a stirred solution of 3-nitro-4-(1H-pyrazol-4-yl)pyridin-2-amine (0.15 g, 0.73 mmol) and compound 2-bromo-5-(1,1,1,2-tetrafluoropropan-2-yl)pyridine (0.298 g, 1.09 mmol) in DMSO (5 ml) was added $K_2CO_3$ (0.251 g, 1.825 mmol) followed by CuI (0.013 g, 0.073 mmol) and L-Proline (0.056 g, 0.365 mmol). Reaction was heated at 110° C. for 16 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography, eluent at 40-60% acetone in n-hexane to obtained 4-(1-(5-(1,1,1,2-tetrafluoropropan-2-yl)pyridin-2-yl)-1H-pyrazol-4-yl)-3-nitropyridin-2-amine (0.065 g, 22.49%) as yellow solid.

MS: 397.1 [M+1]

Step-5: Synthesis of 4-(1-(5-(1,1,1,2-tetrafluoropropan-2-yl)pyridin-2-yl)-1H-pyrazol-4-yl)pyridine-2,3-diamine

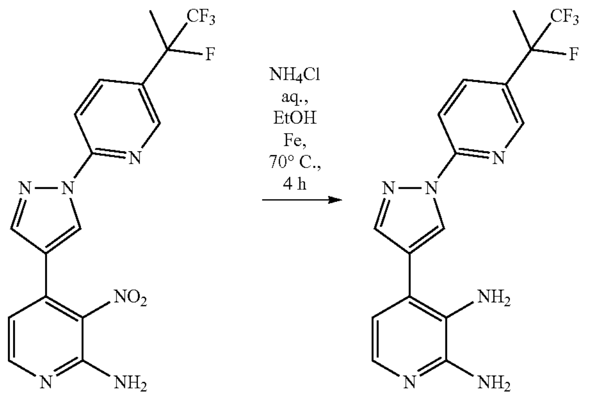

75

76

To a stirred solution of 4-(1-(5-(1,1,1,2-tetrafluoropropan-2-yl)pyridin-2-yl)-1H-pyrazol-4-yl)-3-nitropyridin-2-amine (0.065 g, 0.16 mmol) in EtOH (3.0 mL), $NH_4Cl$ (2.5 mL) was added at room temperature. To resultant reaction mixture, Fe powder (0.041 g, 0.82 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained 4-(1-(5-(1,1,2-tetrafluoropropan-2-yl)pyridin-2-yl)-1H-pyrazol-4-yl)pyridine-2,3-diamine (0.035 g, 58.32%) as dark brown solid mass.

MS: 367.4 [M+1]

Step-6: Synthesis of 7-(1-(5-(1,1,1,2-tetrafluoropropan-2-yl)pyridin-2-yl)-1H-pyrazol-4-yl)-3H-imidazo[4,5-b]pyridine

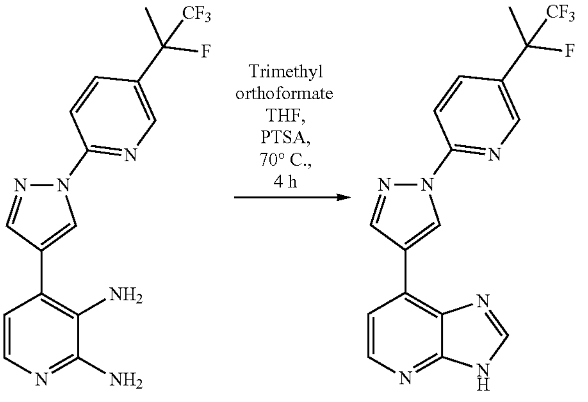

77

1128

To a stirred solution of 4-(1-(5-(1,1,1,2-tetrafluoropropan-2-yl)pyridin-2-yl)-1H-pyrazol-4-yl)pyridine-2,3-diamine (0.035 g, 0.095 mmol) in THF (1.0 mL), Trimethyl orthoformate (1.5 mL) was added. To resultant reaction mixture, PTSA (0.003 g, 0.0017 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 3% to 5% MeOH in DCM to obtained 7-(1-(5-(1,1,1,2-tetrafluoropropan-2-yl)pyridin-2-yl)-1H-pyrazol-4-yl)-3H-imidazo[4,5-b]pyridine (0.06 g, 16.67%) as off white solid.

MS: 377.2 [M+1]

Synthesis of Compound No. 1164: (6-(4-(3H-imidazo[4,5-b]pyridin-7-yl)-1H-pyrazol-1-yl)pyridin-3-yl)(1-(methylsulfonyl)piperidin-4-yl)methanol

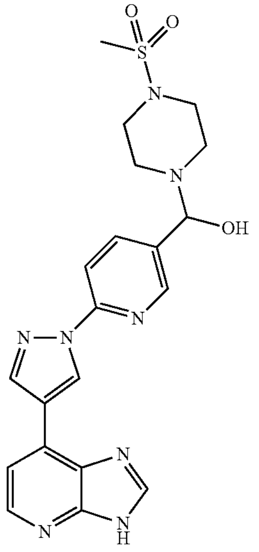 [SMILES: CS(=O)(=O)N1CCN(C(O)c2ccc(-n3cc(-c4ccnc5[nH]cnc45)cn3)nc2)CC1]

Step-1: Synthesis of N-methoxy-N-methyl cyclopropane carboxamide

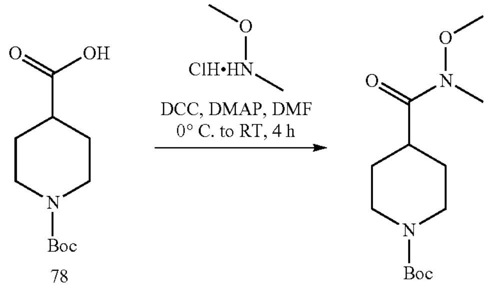

78
79

To a stirred solution of 1-(tert-butoxy carbonyl)piperidine-4-carboxylic acid (10.0 g, 43.66 mmol) and N-methoxy methanamine hydrochloride (5.56 g, 56.76 mmol) in DMF (35 mL), DCC (13.51 g, 65.49 mmol) and DMAP (1.60 g, 13.98 mmol) was added successively at 0° C. and allow to stirred for 30 min. Resultant reaction mass was allow to warm to RT and stirred for 4 h. Completion of reaction was monitored by TLC. On completion, quenched reaction mixture with 1N HCl water and extracted with EtOAc. The organic layer was washed with bicarbonate water, brine, dried over sodium sulphate and concentrated under reduced pressure to give crude desired product that was purified by silica gel (100 to 200 Mesh) column chromatography: eluent at 20% acetone in n-hexane to obtained tert-butyl 4-(N-methoxy-N-methylcarbamoyl)piperidine-1-carboxylate (7.45 g, 60%) as colourless oily mass.

MS: 273.1 [M+1]

Step-2: Synthesis of tert-butyl 4-(6-bromonicotinoyl)piperidine-1-carboxylate

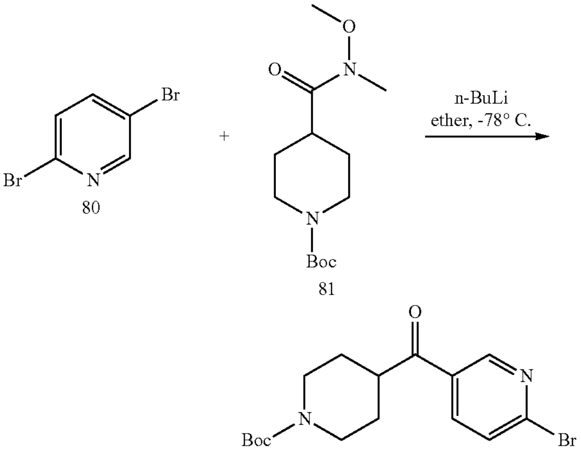

80
81
82

To a stirred solution of 2,5-dibromopyridine (5.0 g, 21.18 mmol) in diethyl ether (100 mL) at −78° C. was added n-Butyl lithium (2.5M in hexane) (8.47 mL, 21.18 mmol) under nitrogen and stirred for 1 h at same temperature. tert-butyl 4-(N-methoxy-N-methylcarbamoyl)piperidine-1-carboxylate (6.36 g, 23.29 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with 10% MeOH in DCM. The organic layer was washed with brine, dried over sodium sulphate and concentrated under reduced pressure to obtained tert-butyl 4-(6-bromonicotinoyl)piperidine-1-carboxylate (5.8 g, 67.12%) as colourless oily mass.

MS: 371.0 [M+1]

Step-3: Synthesis of (6-bromopyridin-3-yl)(piperidin-4-yl)methanone

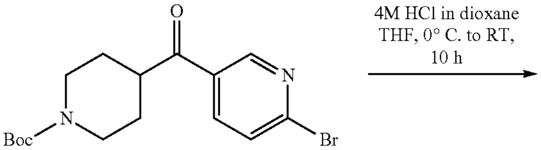

83

-continued

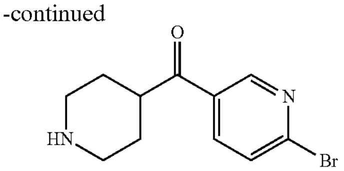

84

To a stirred solution of tert-butyl 4-(6-bromonicotinoyl) piperidine-1-carboxylate (5.0 g, 13.51 mmol) in THF (50 mL), 4M HCl in Dioxane (25 mL) was added at 0° C. under nitrogen. Allow to warm reaction mixture to RT and stirred for 10 h. On completion, reaction mixture quenched with bicarbonate solution and extracted with 10% MeOH in DCM. The organic layer was washed with brine, dried over sodium sulphate and concentrated under reduced pressure. Crude was purified by silica gel (100-200 mesh) column chromatography using 4-5% MeOH in DCM as eluent to obtain (6-bromopyridin-3-yl)(piperidin-4-yl)methanone (3.45 g, 94.52%) as colourless crystalline solid.

MS: 271.0 [M+1]

Step-4: Synthesis of (6-bromopyridin-3-yl)(1-(methylsulfonyl)piperidin-4-yl)methanone

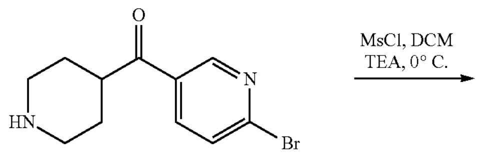

85

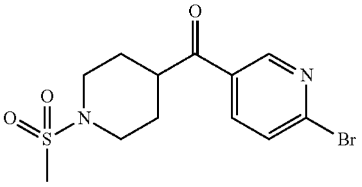

86

To a stirred solution of (6-bromopyridin-3-yl)(piperidin-4-yl)methanone (2.0 g, 7.44 mmol) in dry DCM (20 mL) at 0° C. was added MsCl (1.11 g, 9.66 mmol) under nitrogen. To resultant reaction mixture TEA (1.12 g, 11.16 mmol) was added drop wise to the reaction mixture, stirred for 1 h at 0° C. Allow to warm to RT and Stirred for 1 h. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) on flash column chromatography using 2-3% ethyl MeOH in DCM as eluent to obtain (6-bromopyridin-3-yl)(1-(methylsulfonyl)piperidin-4-yl)methanone (1.40 g, 56.00%) as off white solid.

MS: 349.01 [M+1]

Step-5: Synthesis of (6-(4-(2-amino-3-nitropyridin-4-yl)-1H-pyrazol-1-yl)pyridin-3-yl)(1-(methylsulfonyl)piperidin-4-yl)methanone

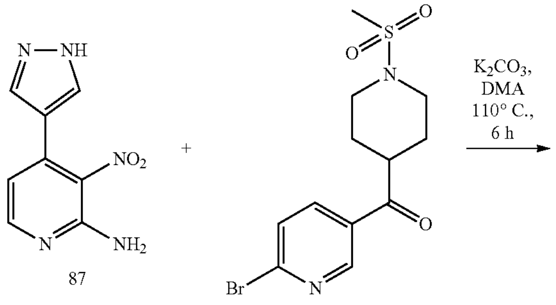

87

88

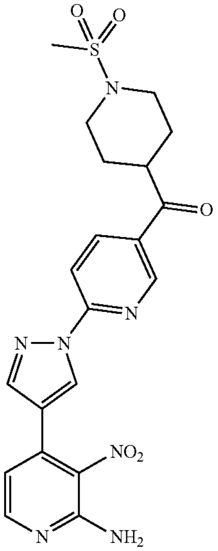

89

To a stirred solution of 3-nitro-4-(1H-pyrazol-4-yl)pyridin-2-amine (0.15 g, 0.73 mmol) and compound (6-bromopyridin-3-yl)(1-(methylsulfonyl)piperidin-4-yl)methanone (0.254 g, mmol) in DMA (5 ml) was added $K_2CO_3$ (0.251 g, 1.825 mmol). Reaction was heated at 110° C. for 6 h. Reaction was monitored by TLC. On completion reaction mixture was quenched with water and extracted with EtOAc. The organic layer was washed with water, brine, dried over sodium sulphate and concentrated under reduced pressure. Crude was purified by silica gel (100-200 mesh) on flash column chromatography using 4-5% MeOH in DCM as eluent to obtained (6-(4-(2-amino-3-nitropyridin-4-yl)-1H-pyrazol-1-yl)pyridin-3-yl)(1-(methylsulfonyl) piperidin-4-yl)methanone (0.065 g, 18.84%) as yellow solid.

MS: 472.02 [M+1]

Step-6: Synthesis of 1-(6-(4-(2,3-diaminopyridin-4-yl)-1H-pyrazol-1-yl)pyridin-3-yl)-1-cyclopropyl-2,2,2-trifluoroethanol

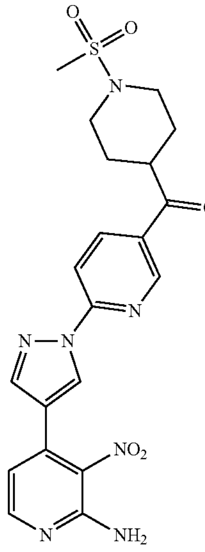

90

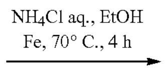

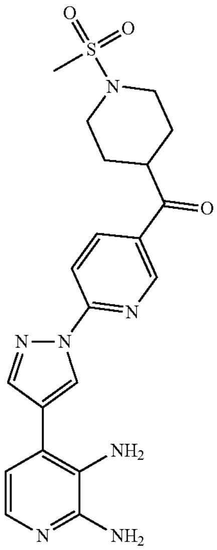

91

To a stirred solution of 1-(6-(4-(2-amino-3-nitropyridin-4-yl)-1H-pyrazol-1-yl)pyridin-3-yl)-1-cyclopropyl-2,2,2-trifluoroethanol (0.065 g, 1.37 mmol) in EtOH (3.0 mL), $NH_4Cl$ (2.5 mL) was added at room temperature. To resultant reaction mixture, Fe powder (0.037 g, 6.8 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained 1-(6-(4-(2,3-diamino pyridin-4-yl)-1H-pyrazol-1-yl)pyridin-3-yl)-1-cyclopropyl-2,2,2-trifluoroethanol (0.035 g, 57.37%) as dark brown solid mass.

MS: 442.0 [M+1]

Step-7: Synthesis of (6-(4-(3H-imidazo[4,5-b]pyridin-7-yl)-1H-pyrazol-1-yl)pyridin-3-yl)(1-(methylsulfonyl)piperidin-4-yl)methanone

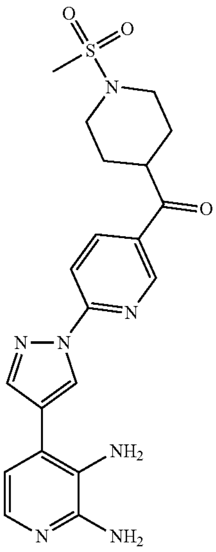

92

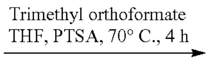

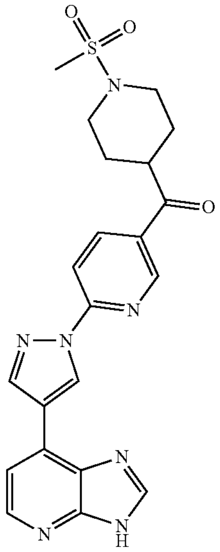

93

To a stirred solution of 1-(6-(4-(2,3-diamino pyridin-4-yl)-1H-pyrazol-1-yl)pyridin-3-yl)-1-cyclopropyl-2,2,2-trifluoroethanol (0.035 g, 7.93 mmol) in THF (1.0 mL), trimethyl orthoformate (1.5 mL) was added. To resultant reaction mixture, PTSA (0.003 g, 0.0017 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure. Crude was purified by silica gel (100-200 mesh) on flash column chromatography using 5-6% MeOH in DCM as eluent to obtained (6-(4-(3H-imidazo[4,5-b]pyridin-7-yl)-

1H-pyrazol-1-yl)pyridin-3-yl)(1-(methylsulfonyl)piperidin-4-yl)methanone (0.006 g, 17.41%) as off white solid.

MS: 452.0 [M+1]

Step-8: Synthesis of 1-(6-(4-(3H-imidazo[4,5-b]pyridin-7-yl)-1H-pyrazol-1-yl)pyridin-3-VI)-1-cyclopropyl-2,2,2-trifluoroethanol

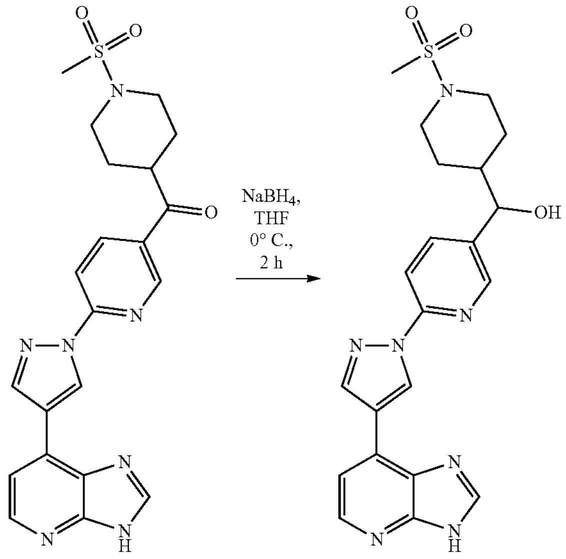

94 1164

To a stirred solution of (6-(4-(3H-imidazo[4,5-b]pyridin-7-yl)-1H-pyrazol-1-yl)pyridin-3-yl)(1-(methylsulfonyl)piperidin-4-yl)methanone (0.006 g, 0.013 mmol) in THE (1.0 mL), $NaBH_4$ (0.001 g, 0.026 mmol) was added and stirred for 2 h at 0° C. Completion of reaction was monitored by TLC. On completion, quenched with water, extracted with 10% MeOH in DCM. The organic layer was washed with water, brine, dried over sodium sulphate and concentrated under reduced pressure to obtained (6-(4-(3H-imidazo[4,5-b]pyridin-7-yl)-1H-pyrazol-1-yl)pyridin-3-yl)(1-(methylsulfonyl)piperidin-4-yl)methanol (0.03 g, 50.00%) as off white solid.

MS: 454.0 [M+1]

Synthesis of Compound No. 1166: 2-(6-(4-(3H-imidazo[4,5-b]pyridin-7-yl)-1H-pyrazol-1-yl)pyridin-3-yl)-2-(1,1-dioxidothiomorpholino)acetonitrile

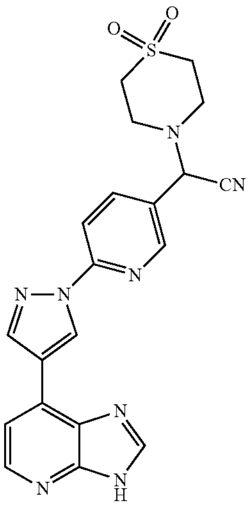 [SMILES: N#CC(c1ccc(-n2cc(-c3ccnc4[nH]cnc34)cn2)nc1)N1CCS(=O)(=O)CC1]

Step-1: Synthesis of 6-bromopyridine-3-carbaldehyde

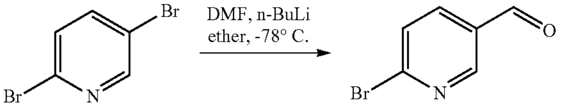

95 96

To a stirred solution of 2,5-dibromopyridine (26.0 g, 109.75 mmol) in diethyl ether (500 mL) at −78° C. was added n-Butyl lithium (2.5M in hexane) (66 mL, 164.63 mmol) under nitrogen and stirred for 1 h at same temperature. DMF (13 mL, 164.63 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 4% ethyl acetate in hexane as eluent to obtain 6-bromopyridine-3-carbaldehyde (12.20 g, 59.8%) as yellow oil.

MS: 187.0 [M+1]

Step-2: Synthesis of 6-(4-(2-amino-3-nitropyridin-4-yl)-1H-pyrazol-1-yl)pyridine-3-carbaldehyde

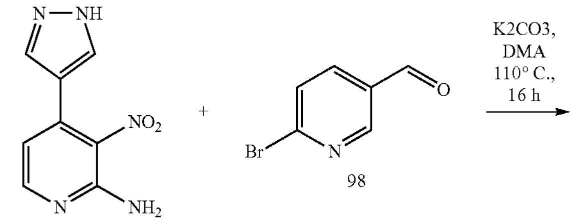

97 98

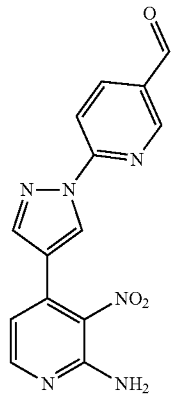

99

To a stirred solution of 3-nitro-4-(1H-pyrazol-4-yl)pyridin-2-amine (0.075 g, 0.36 mmol) and compound 6-bromopyridine-3-carbaldehyde (0.075 g, 0.40 mmol) in DMA (5 ml) was added $K_2CO_3$ (0.124 g, 0.90 mmol) and reaction heated at 110° C. for 16 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 1% to 3% MeOH/DCM to obtained 6-(4-(2-amino-3-nitropyridin-4-yl)-1H-pyrazol-1-yl)pyridine-3-carbaldehyde (0.065 g, 51.58%) as yellow solid.

MS: 311[M+1]

Step-3: 2-(6-(4-(2-amino-3-nitropyridin-4-yl)-1H-pyrazol-1-yl)pyridin-3-yl)-2-(1,1-dioxidothiomorpholino)acetonitrile

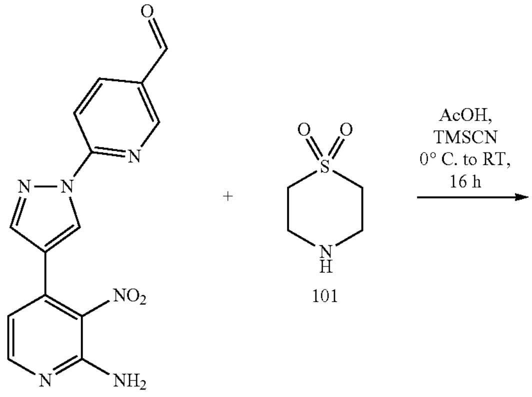

100 101

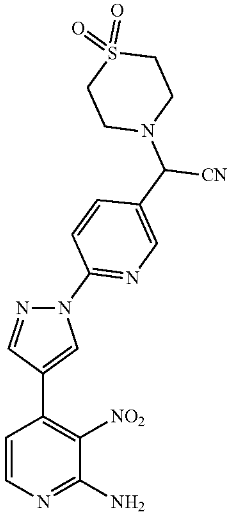

102

To a stirred solution of 6-(4-(2-amino-3-nitropyridin-4-yl)-1H-pyrazol-1-yl)pyridine-3-carbaldehyde (0.065 g, 0.20 mmol) in AcOH (5 mL), Trimethyl silylcynide (TMSCN) (0.031 g, 0.31 mmol) and TMSCN (0.051 g, 0.38 mmol) in AcOH (1 mL) was added at 0° C. and allow to warm to RT. Stirred for 16 h. Reaction was monitored by TLC. On completion reaction mixture was quenched with bi-carbonate water and extracted with ethyl acetate. The organic layer was washed with water, brine, dried over sodium sulphate and concentrated under reduced pressure. Crude was purified by silica gel (100-200 mesh) column chromatography using 2-3% MeOH in DCM as eluent to obtain obtained 2-(6-(4-(2-amino-3-nitropyridin-4-yl)-1H-pyrazol-1-yl)pyridin-3-yl)-2-(1,1-dioxidothiomorpholino)acetonitrile (0.045 g, 47.36%) as yellow solid.

MS: 454 [M+1]

Step-4: 2-(6-(4-(2,3-diaminopyridin-4-yl)-1H-pyrazol-1-yl)pyridin-3-yl)-2-(1,1-dioxidothiomorpholino)acetonitrile

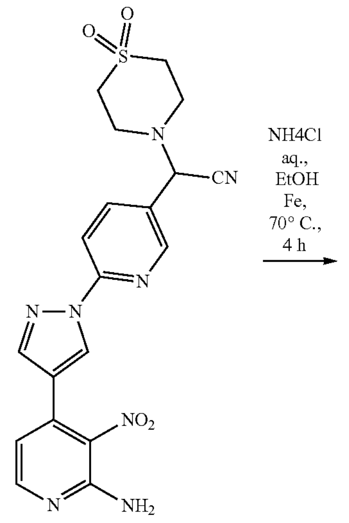

103 104

To a stirred solution of 2-(6-(4-(2-amino-3-nitropyridin-4-yl)-1H-pyrazol-1-yl)pyridin-3-yl)-2-(1,1-dioxidothiomorpholino)acetonitrile (0.045 g, 0.09 mmol) in EtOH (10 mL), $NH_4Cl$ (2.5 mL) was added at room temperature. To resultant reaction mixture, Fe powder (0.027 g, 0.49 mmol) was added and stirred for 4 h at 70° C. Completion of reaction was monitored by TLC. On completion, reaction mixture was diluted with $H_2O$:EtOAc 5:5 (50 mL) and pass over celite to remove inorganic impurities from the reaction mixture. The aqueous layer was extracted with ethyl acetate. The organic layer was washed with water, brine, dried over sodium sulphate and concentrated under reduced pressure to obtained pure 2-(6-(4-(2,3-diaminopyridin-4-yl)-1H-pyrazol-1-yl)pyridin-3-yl)-2-(1,1-dioxidothiomorpholino)acetonitrile (0.016 g, 37.20%) as dark brown solid mass.

MS: 425.1 [M+1]

Step-5: 2-(6-(4-(3H-imidazo[4,5-b]pyridin-7-yl)-1H-pyrazol-1-yl)pyridin-3-yl)-2-(1,1-dioxidothiomorpholino)acetonitrile

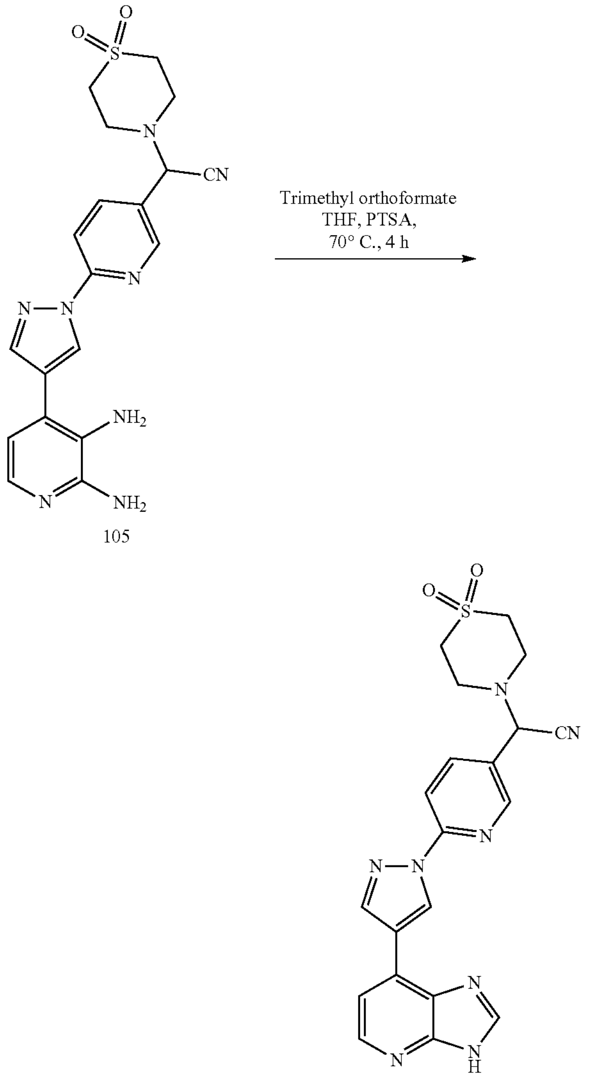

105

1166

To a stirred solution of 2-(6-(4-(2,3-diaminopyridin-4-yl)-1H-pyrazol-1-yl)pyridin-3-yl)-2-(1,1-dioxidothiomorpholino)acetonitrile (0.016 g, 0.037 mmol) in THF (3.0 mL), Trimethyl orthoformate (1.5 mL) was added. To resultant reaction mixture, PTSA (0.003 g, 0.07 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure. Crude was purified by silica gel (100-200 mesh) column chromatography using 4-6% MeOH in DCM as eluent to obtained 2-(6-(4-(3H-imidazo[4,5-b]pyridin-7-yl)-1H-pyrazol-1-yl)pyridin-3-yl)-2-(1,1-dioxidothiomorpholino)acetonitrile (0.03 g, 58.82%) as off white solid.

MS: 435.2 [M+1]

Synthesis of Compound No. 1116: 2-(6-(4-(3H-imidazo[4,5-b]pyridin-7-yl)-1H-pyrazol-1-yl)pyridin-3-yl)-4-(methyl sulfonyl) butanenitrile

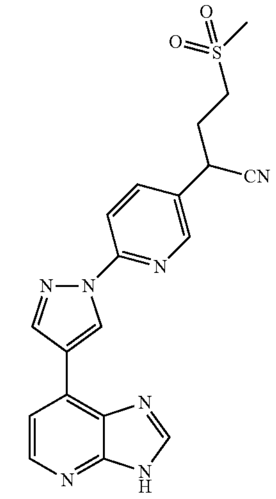 [SMILES: CS(=O)(=O)CCC(C#N)c1ccc(-n2cc(-c3ccnc4[nH]cnc34)cn2)nc1]

Step-1: Synthesis of 1-(6-bromopyridin-3-yl)-3-(methylthio)propan-1-ol

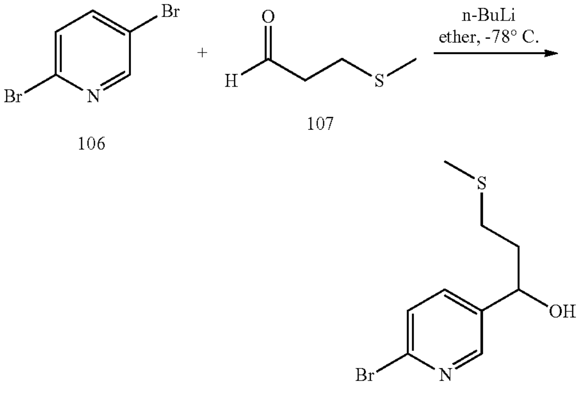

106 107 108

To a stirred solution of 2,5-dibromopyridine (1.5 g, 6.32 mmol) in diethyl ether (25 mL) at −78° C. was added n-Butyl lithium (2.5M in hexane) (2.5 mL, 6.32 mmol) under nitrogen and stirred for 1 h at same temperature. 3-(methylthio)propanal (0.73 g, 6.965 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 4% ethyl acetate in hexane as eluent to obtain 1-(6-bromopyridin-3-yl)-3-(methylthio)propan-1-ol (0.580 g, 35.15%) as colourless oil.

MS: 264.0 [M+1]

Step-2: Synthesis of 1-(6-bromopyridin-3-yl)-3-(methylsulfonyl)propan-1-ol

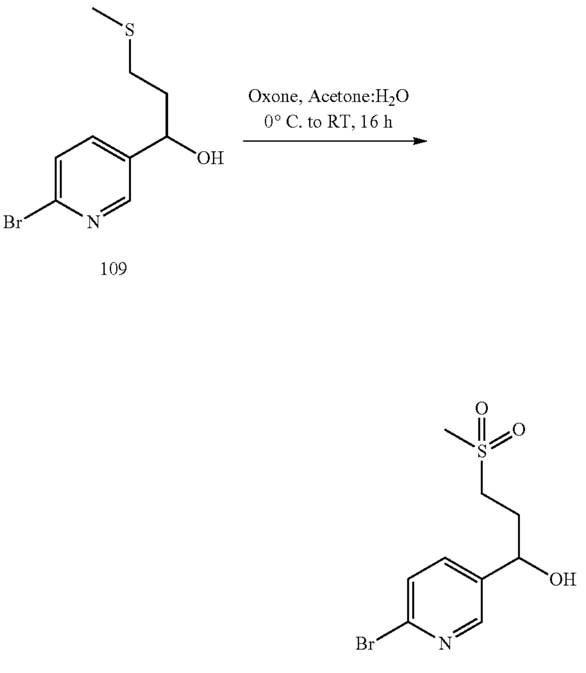

109 110

To a stirred solution of 1-(6-bromopyridin-3-yl)-3-(methylthio)propan-1-ol (0.58 g, 2.19 mmol) in Acetone:$H_2O$ (50 mL, 7:3) at 0° C. was added oxone (1.68 g, 5.49 mmol) under nitrogen and stirred for 16 h at same temperature. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 3% MeOH in DCM as eluent to obtain 1-(6-bromopyridin-3-yl)-3-(methylsulfonyl)propan-1-ol (0.60 g, 93.02%) as colourless oil.

MS: 296.0 [M+1]

Step-3: Synthesis of 1-(6-bromopyridin-3-yl)-3-(methylsulfonyl)propyl methanesulfonate

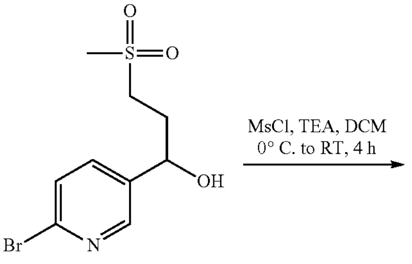

111

-continued

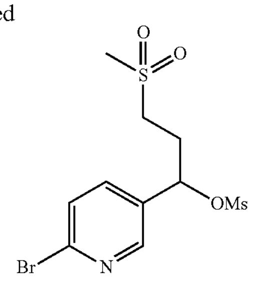

112

To a stirred solution of 2,5-dibromopyridine (0.30 g, 1.02 mmol) in DCM (5.0 mL) at 0° C. was added MsCl (0.151 g, 1.32 mmol) under nitrogen. To resultant reaction mixture TEA (0.153 g, 1.52 mmol) solution in DCM (1.0 mL) was added drop wise, stirred for 15 min at 0° C. Allow reaction mixture to increase temperature slowly to RT and progress of reaction was monitored by TLC. On completion, quenched with water, extracted with ethyl acetate. The aqueous layer was basified with bicarbonate till basic to pH-paper, and then extracted with ethyl acetate, dried over sodium sulphate, concentrated under reduced pressure obtained 1-(6-bromopyridin-3-yl)-3-(methylsulfonyl)propyl methanesulfonate (0.320 g, 84.43%) as crude yellow oily mass.

MS: 374.02 [M+1]

Step-4: Synthesis of 2-(6-bromopyridin-3-yl)-4-(methylsulfonyl)butanenitrile

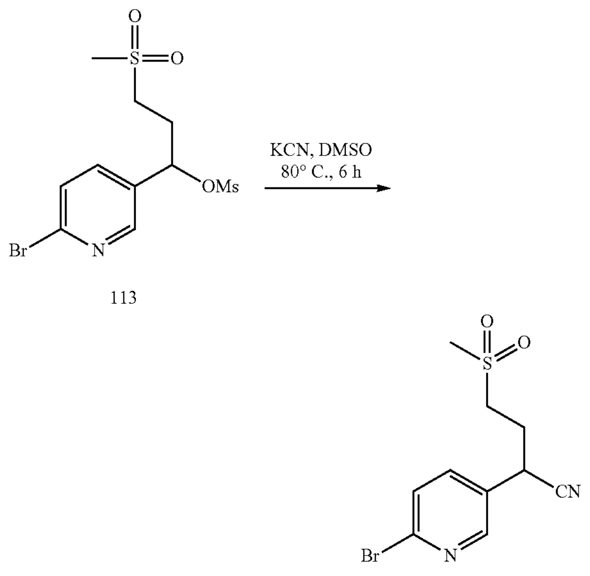

113

114

To a stirred solution of 2,5-dibromopyridine (0.320 g, 8.56 mmol) in DMSO (1.5 mL) at RT was added potassium cyanide (0.067 g, 10.27 mmol) under nitrogen and stirred for 1 h at 80° C. Progress of reaction was monitored by TLC. After completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 2-3% MeOH in DCM as eluent to obtain 2-(6-bromopyridin-3-yl)-4-(methylsulfonyl)butanenitrile (0.120 g, 46.15%) as dark brown sticky mass.

MS: 305.01 [M+1]

Step-5: Synthesis of 2-(6-(4-(2-amino-3-nitropyridin-4-yl)-1H-pyrazol-1-yl)pyridin-3-yl)-4-(methylsulfonyl)butanenitrile

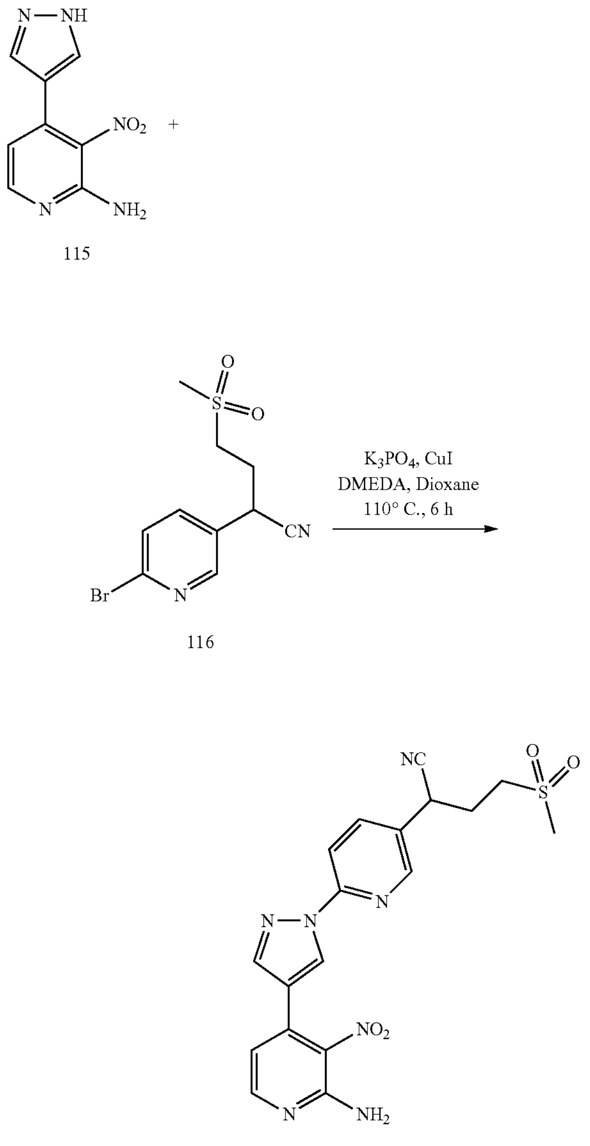

115

116

117

To a stirred solution of 3-nitro-4-(1H-pyrazol-4-yl)pyridin-2-amine (0.07 g, 0.34 mmol) and compound 2-(6-bromopyridin-3-yl)-4-(methylsulfonyl)butanenitrile (0.155 g, 0.51 mmol) in Dioxane (5 ml) was added $K_3PO_4$ (0.166 g, 0.78 mmol) followed by CuI (0.006 g, 0.034 mmol) and DMEDA (0.015 g, 0.175 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 2-3% MeOH in DCM to obtained 2-(6-(4-(2-amino-3-nitropyridin-4-yl)-1H-pyrazol-1-yl)pyridin-3-yl)-4-(methylsulfonyl)butanenitrile (0.030 g, 20.54%) as yellow solid.

MS: 428.1 [M+1]

Step-6: Synthesis of 2-(6-(4-(2,3-diaminopyridin-4-yl)-1H-pyrazol-1-yl)pyridin-3-yl)-4-(methylsulfonyl)butanenitrile

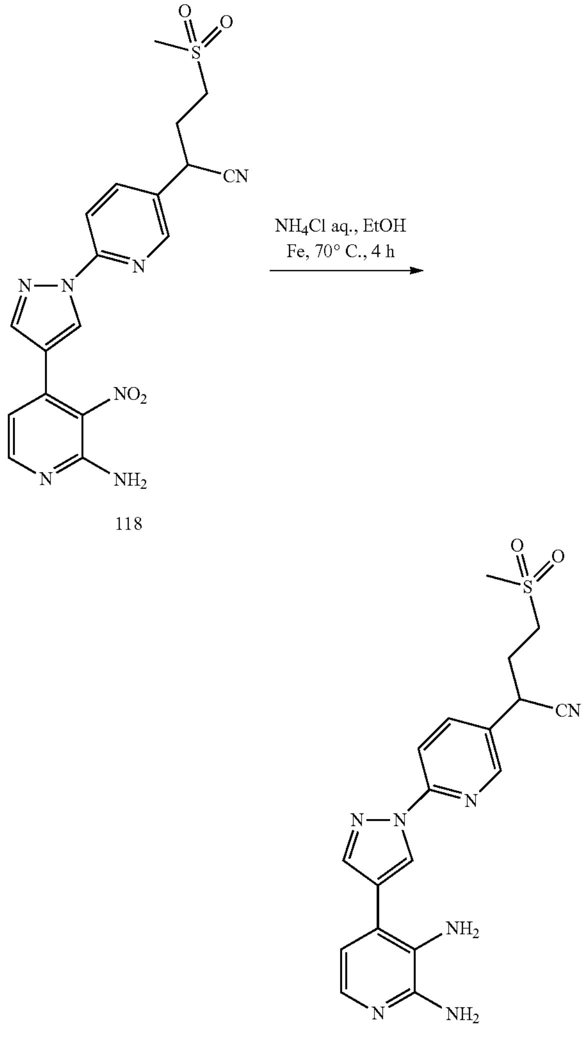

118

119

To a stirred solution of 2-(6-(4-(2-amino-3-nitropyridin-4-yl)-1H-pyrazol-1-yl)pyridin-3-yl)-4-(methylsulfonyl)butanenitrile (0.030 g, 0.070 mmol) in EtOH (3.0 mL), $NH_4Cl$ (1.5 mL) was added at room temperature. To resultant reaction mixture, Fe powder (0.019 g, 0.35 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 4-(1-(5-(2,2,2-trifluoro-1-methoxy ethyl)pyridin-2-yl)-1H-pyrazol-4-yl)pyridine-2,3-diamine (0.015 g, 53.57%) as dark brown solid mass.

MS: 398.2 [M+1]

Step-7: Synthesis of 2-(6-(4-(3H-imidazo[4,5-b]pyridin-7-yl)-1H-pyrazol-1-yl)pyridin-3-yl)-4-(methylsulfonyl)butanenitrile

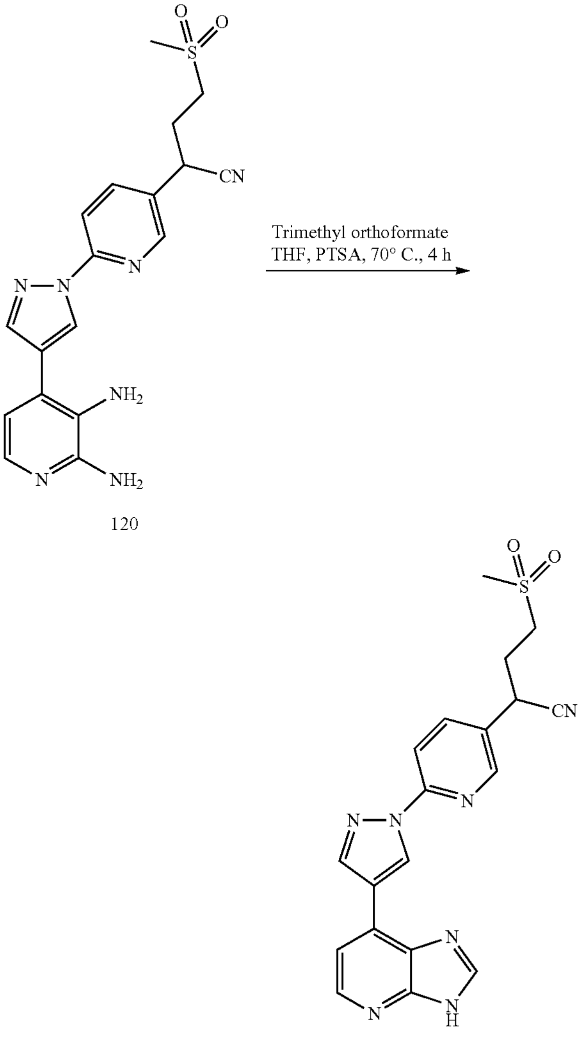

120

1116

To a stirred solution of 4-(1-(5-(2,2,2-trifluoro-1-methoxy ethyl)pyridin-2-yl)-1H-pyrazol-4-yl)pyridine-2,3-diamine (0.015 g, 0.037 mmol) in THF (1.0 mL), Trimethyl orthoformate (1.5 mL) was added. To resultant reaction mixture, PTSA (0.0012 g, 0.018 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 3% to 5% MeOH in DCM to obtained 2-(6-(4-(3H-imidazo[4,5-b]pyridin-7-yl)-1H-pyrazol-1-yl)pyridin-3-yl)-4-(methylsulfonyl)butanenitrile (0.004 g, 25.92%) as off white solid.

MS: 408.0 [M+1]

Synthesis of Compound No. 1089: 1-(6-(4-(3H-imidazo[4,5-b]pyridin-7-yl)-1H-pyrazol-1-yl)nicotinoyl)azetidine-3-carbonitrile

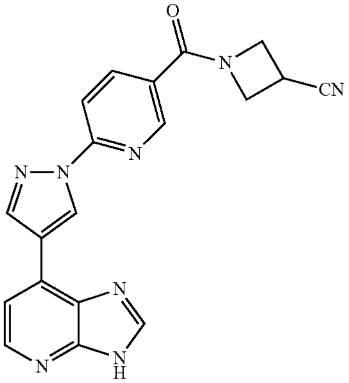 [SMILES: N#CC1CN(C(=O)c2ccc(-n3cc(-c4ccnc5[nH]cnc45)cn3)nc2)C1]

Step-1: Synthesis of Methyl 6-bromopyridine-3-carboxylate

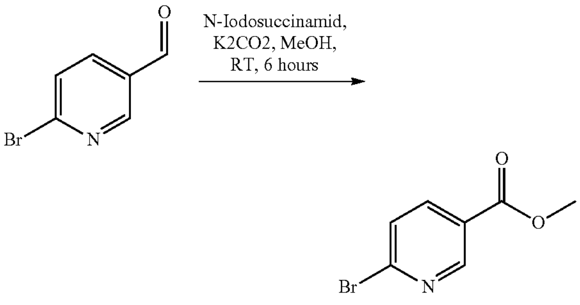

122

To a stirred solution of 6-bromopyridine-3-carbaldehyde (1.5 g, 0.810 mmol) in methanol (45 mL) at RT was added N-Iodosuccinimide (2.72 g, 1.210 mmol) and base potassium carbonate (1.66 g, 1.210 mmol) under dark and stirred for 6 h at same temperature. Progress of reaction was monitored by TLC. After reaction completion reaction mass was quenched with ice cold water. Phases separated and aqueous layer was extracted with ethyl acetate. The organic layer was washed with saturated sodium thiosulfate solution, dried over sodium sulphate and concentrated under reduced pressure. Crude was purified by silica gel (100-200 mesh) column chromatography using 8-12% ethyl acetate in hexane as eluent to obtain Methyl 6-bromopyridine-3-carboxylate (1.05 g, 59.8%) as white solid.

MS: 215.0 [M+1]

Step-2: Synthesis of methyl 6-(4-(2-amino-3-nitropyridin-4-yl)-1H-pyrazol-1-yl)pyridine-3-carboxylate

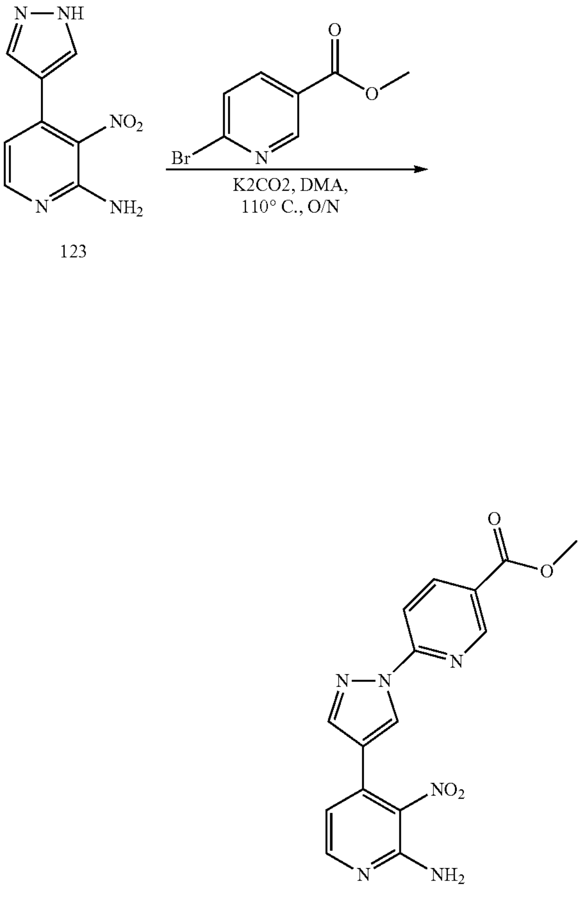

123

124

To a stirred solution of 3-nitro-4-(1H-pyrazol-4-yl)pyridin-2-amine (0.300 g, 0.138 mmol) and compound Methyl 6-bromopyridine-3-carboxylate (0.44 g, 0.207 mmol) in DMA (7 ml) was added $K_2CO_3$ (0.381 g, 0.276 mmol) at RT. Reaction was heated at 110° C. for 16 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 40-60% acetone in n-hexane to obtained methyl 6-(4-(2-amino-3-nitropyridin-4-yl)-1H-pyrazol-1-yl)pyridine-3-carboxylate (0.210 g, 42.85%) as yellow solid.

MS: 341.09 [M+1]

Step-3: 6-(4-(2-amino-3-nitropyridin-4-yl)-1H-pyrazol-1-yl)pyridine-3-carboxylic acid

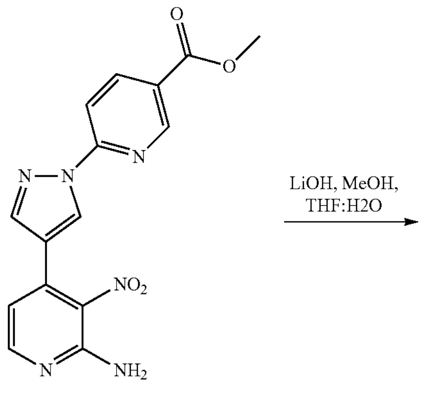

125

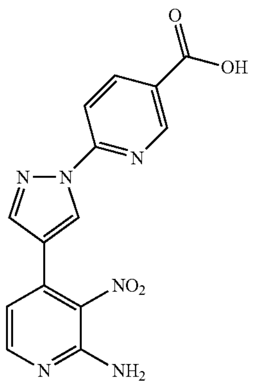

126

To a stirred solution of methyl 6-(4-(2-amino-3-nitropyridin-4-yl)-1H-pyrazol-1-yl)pyridine-3-carboxylate (0.2 g, 0.058 mmol) in mixture of THF:MeOH:$H_2O$ (18 mL, 5:3:1) was added LiOH (0.044 g, 0.117 mmol). And allowed to stir for 2 h at room temperature. On completion, all volatiles were evaporated under reduced pressure. Reaction mass diluted with water, acidify with 6N HCl adjusted pH at 6 and extracted with EtOAc. Organic portions were combined, dried over $Na_2SO_4$, evaporated under reduced pressure to obtain 6-(4-(2-amino-3-nitropyridin-4-yl)-1H-pyrazol-1-yl) pyridine-3-carboxylic acid (0.170 g, 89%) as yellow solid.

MS: 327[M+1]

Step-4: 1-(6-(4-(2-amino-3-nitropyridin-4-yl)-1H-pyrazol-1-yl)nicotinoyl)azetidine-3-carbonitrile

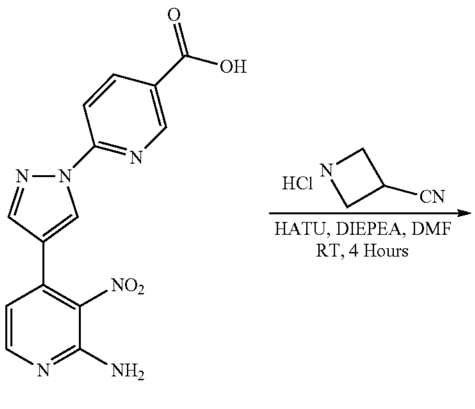

127

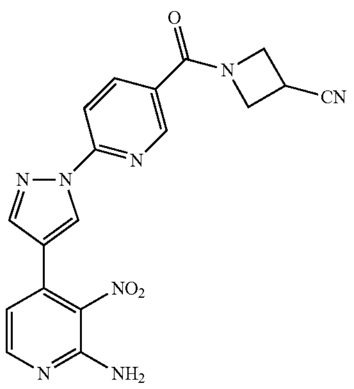

128

To a stirred solution of 6-(4-(2-amino-3-nitropyridin-4-yl)-1H-pyrazol-1-yl)pyridine-3-carboxylic acid (0.080 g, 0.0271 mmol) and Azetidine-3-carbonitrile hydrochloride (0.039 g, 0.049 mmol) in DMF (3 mL) were added HATU (0.139 g, 0.036 mmol, and DIPEA (0.063 g, 0.049 mmol). Then reaction mixture was stirred at room temperature for 6 h. Reaction was monitored by TLC. On completion, reaction was quenched with water, extracted with ethyl acetate. Organic layer was washed with water, brine, dried over sodium sulphate and evaporated under reduced pressure to give crude product. Purification of the crude was done by silica gel (100-200 Mesh) column chromatography; eluent 4% MeOH in DCM to obtain 1-(6-(4-(2-amino-3-nitropyridin-4-yl)-1H-pyrazol-1-yl)nicotinoyl)azetidine-3-carbonitrile (0.055 g, 58%) as light yellow solid.

MS: 391.09[M+1]

Step-5: 1-(6-(4-(2,3-diaminopyridin-4-yl)-1H-pyrazol-1-yl)nicotinoyl)azetidine-3-carbonitrile

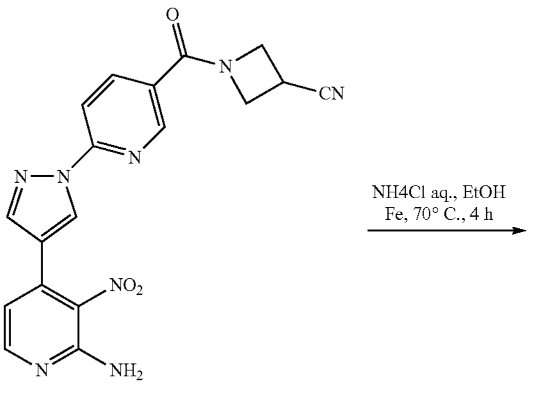

129

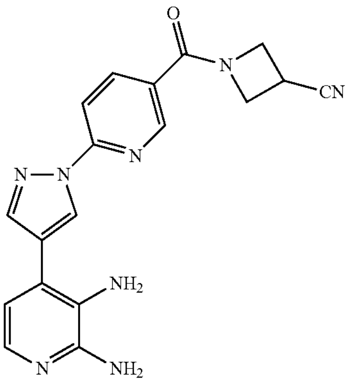

130

To a stirred solution of 1-(6-(4-(2-amino-3-nitropyridin-4-yl)-1H-pyrazol-1-yl)nicotinoyl)azetidine-3-carbonitrile (0.050 g, 0.012 mmol) in EtOH (3.0 mL), $NH_4Cl$ (2.5 mL) was added at room temperature. To resultant reaction mixture, Fe powder (0.033 g, 0.064 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained 1-(6-(4-(2,3-diaminopyridin-4-yl)-1H-pyrazol-1-yl)nicotinoyl)azetidine-3-carbonitrile (0.035 g, 76%) as dark brown solid mass.

MS: 361.2 [M+1]

Step-6: 1-(6-(4-(3H-imidazo[4,5-b]pyridin-7-yl)-1H-pyrazol-1-yl)nicotinoyl)azetidine-3-carbonitrile

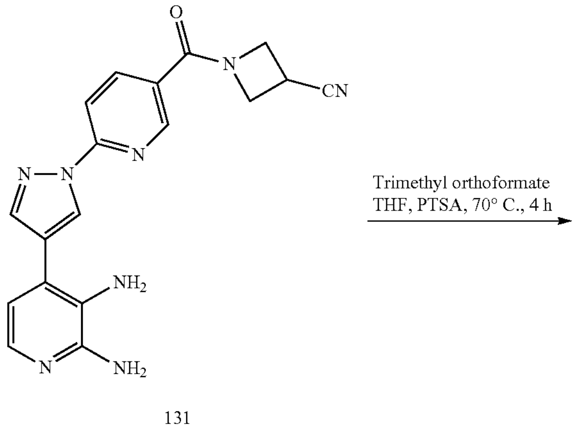

131

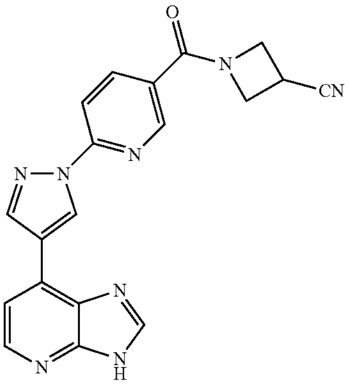

1089

To a stirred solution of 1-(6-(4-(2,3-diaminopyridin-4-yl)-1H-pyrazol-1-yl)nicotinoyl)azetidine-3-carbonitrile (0.035 g, 0.097 mmol) in THF (1.0 mL), trimethyl orthoformate (1.5 mL) was added. To resultant reaction mixture, PTSA (0.003 g, 0.0017 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 5% to 6% MeOH in DCM to obtained 1-(6-(4-(3H-imidazo[4,5-b]pyridin-7-yl)-1H-pyrazol-1-yl)nicotinoyl)azetidine-3-carbonitrile (0.018 g, 51.42%) as off white solid.

MS: 371.1[M+1]

Synthesis of Compound No. 1107: 2-(6-(4-(3H-imidazo[4,5-b]pyridin-7-yl)-1H-pyrazol-1-yl)pyridin-3-yl)propanenitrile

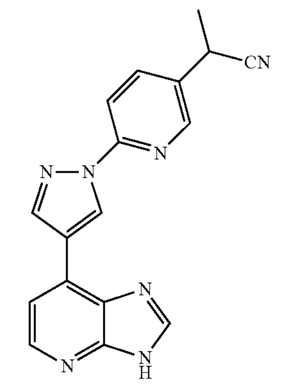

Step-1: Synthesis of 2-(6-bromopyridin-3-yl)propanenitrile

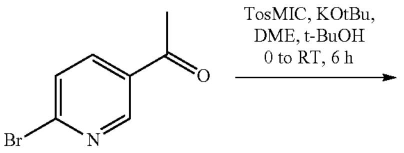

132

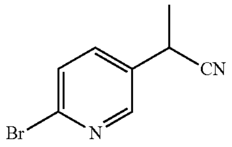

133

To a stirred solution of 1-(6-bromopyridin-3-yl)ethanone (0.4 g, 0.20 mmol) in DME (12 mL) at 0° C. under inert condition was added TosMIC (0.585 g 0.30 mmol). A solution of base potassium ter-butoxide (0.336 g, 0.30 mmol) in tert-butanol was then added drop wise to the reaction mixture. After addition mixture was stirred for 6 h at room temperature. Progress of reaction was monitored by TLC. After completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 15% ethyl acetate in hexane as eluent to obtain 2-(6-bromopyridin-3-yl)propanenitrile (0.240 g, 57.14%) as colourless oil.

MS: 211 [M+1]

Step-2: Synthesis of 2-(6-bromopyridin-3-yl)propanamide

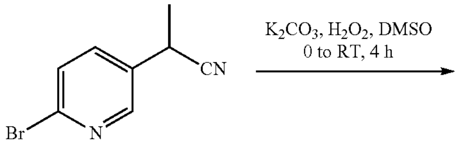

134

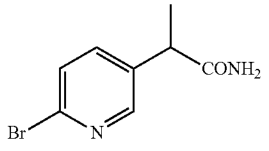

135

To a stirred solution of 2-(6-bromopyridin-3-yl)propanenitrile (0.240 g, 0.114 mmol) and DMSO (4 ml) at 0° C. under $N_2$ added base potassium carbonate (0.315 g, 0.228 mmol). Added hydrogen peroxide (0.7 ml) dropwise at 0° C. and the resultant mixture was stirred at RT for 4 h. Reaction was monitored by TLC. On completion reaction mixture was quenched with water and extracted with ethyl acetate. The organic layer was washed with water, brine, dried over sodium sulphate and concentrated under reduced pressure to give pure product 2-(6-bromopyridin-3-yl)propanamide (0.230 g, 88.46%) as off white solid.

MS: 228 [M+1]

Step-3: Synthesis of 2-(6-(4-(2-amino-3-nitropyridin-4-yl)-1H-pyrazol-1-yl)pyridin-3-yl)propanamide

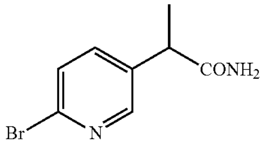

136

+

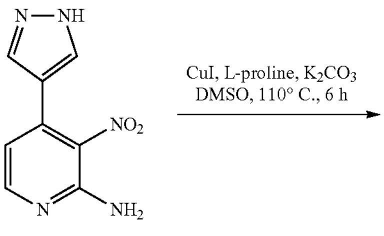

137

-continued

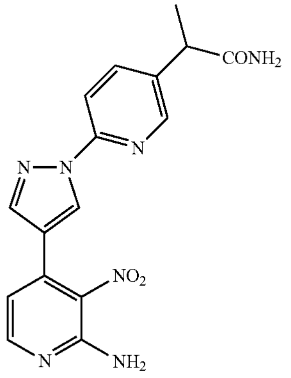

138

-continued

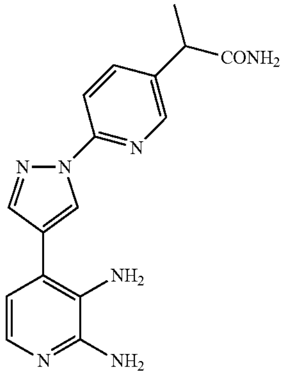

140

To a stirred solution of 3-nitro-4-(1H-pyrazol-4-yl)pyridin-2-amine (0.160 g, 0.078 mmol) and compound 2-(6-bromopyridin-3-yl)propanamide (0.200 g, 0.078 mmol) in DMSO (5 ml) was added $K_2CO_3$ (0.215 g, 0.156 mmol) followed by CuI (0.029 g, 0.00156 mmol) and L-proline (0.017 g, 0.00156 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 6-7% MeOH in DCM to obtained 2-(6-(4-(2-amino-3-nitropyridin-4-yl)-1H-pyrazol-1-yl) pyridin-3-yl)propanamide (0.140 g, 45.45%) as yellow solid.

MS: 354.1 [M+1]

Step-4: Synthesis of 2-(6-(4-(2,3-diaminopyridin-4-yl)-1H-pyrazol-1-yl)pyridin-3-yl)propanamide

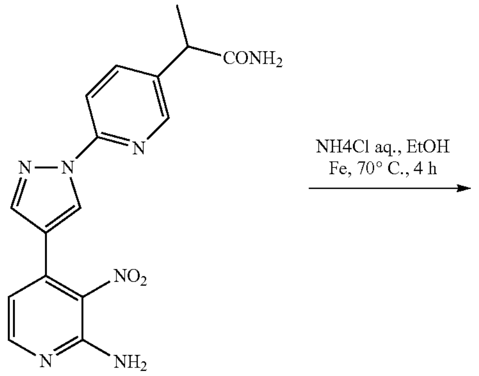

139

141

To a stirred solution of 2-(6-(4-(2-amino-3-nitropyridin-4-yl)-1H-pyrazol-1-yl)pyridin-3-yl)propanamide (0.140 g, 0.039 mmol) in EtOH (7.0 mL), $NH_4Cl$ (2.0 mL) was added at room temperature. To the resultant reaction mixture, Fe powder (0.105 g, 0.198 mmol) was added and stirred for 4 h at 70° C. Completion of reaction was monitored by TLC. On completion, reaction mixture was diluted with $H_2O$: EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 2-(6-(4-(2,3-diaminopyridin-4-yl)-1H-pyrazol-1-yl)pyridin-3-yl)propanamide (0.090 g, 70%) as dark brown solid mass.

MS: 324.2 [M+1]

Step-5: Synthesis of 2-(6-(4-(3H-imidazo[4,5-b]pyridin-7-yl)-1H-pyrazol-1-yl)pyridin-3-yl)propanamide

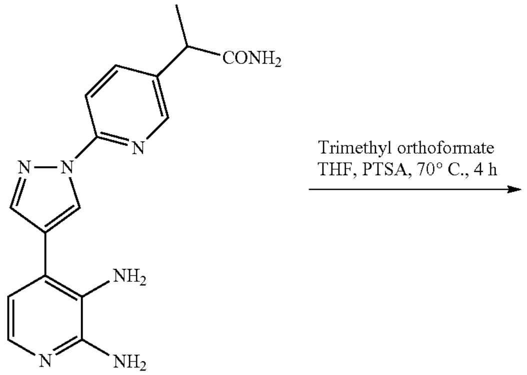

-continued

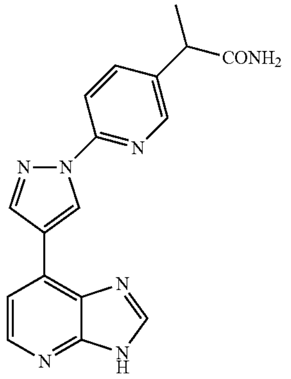

142

To a stirred solution of 2-(6-(4-(2,3-diaminopyridin-4-yl)-1H-pyrazol-1-yl)pyridin-3-yl)propanamide (0.090 g, 0.0278 mmol) in THE (1.0 mL), Trimethyl orthoformate (1.5 mL) was added. To resultant reaction mixture, PTSA (0.0095 g, 0.0055 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained 2-(6-(4-(3H-imidazo[4,5-b]pyridin-7-yl)-1H-pyrazol-1-yl)pyridin-3-yl)propanamide (0.048 g, 52.17%) as off white solid.

MS: 334.1 [M+1]

Step-6: Synthesis of 2-(6-(4-(3H-imidazo[4,5-b]pyridin-7-yl)-1H-pyrazol-1-yl)pyridin-3-yl)propanenitrile

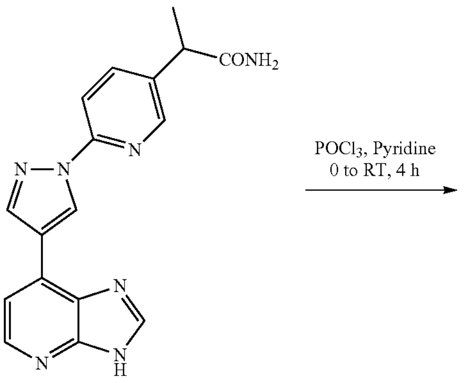

143

-continued

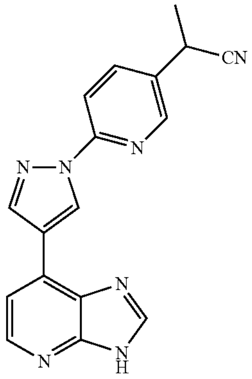 [SMILES: CC(C#N)c1ccc(-n2cc(-c3ccnc4[nH]cnc34)cn2)nc1]

1107

To a stirred solution of 2-(6-(4-(3H-imidazo[4,5-b]pyridin-7-yl)-1H-pyrazol-1-yl)pyridin-3-yl)propanamide (0.040 g, 0.0120 mmol) in pyridine (3.0 mL), added $POCl_3$ (0.091 g, 0.60 mmol) dropwise at 0° C. After addition stirred for 4 h at room temperature. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 4 to 6% MeOH in DCM to obtained 2-(6-(4-(3H-imidazo[4,5-b]pyridin-7-yl)-1H-pyrazol-1-yl)pyridin-3-yl)propanenitrile (0.021 g, 56.7%) as off white solid.

MS: 316.1 [M+1]

Synthesis of Compound No. 1167: 2-(6-(4-(3H-imidazo[4,5-b]pyridin-7-yl)-1H-pyrazol-1-yl)pyridin-3-yl)-2-cyclopropyl-N-(2,2,2-trifluoroethyl)acetamide

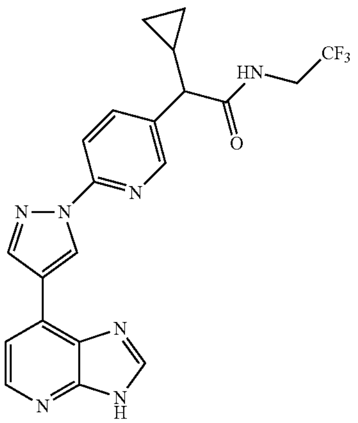

Step-1: Synthesis of 2-(6-bromopyridin-3-yl)-2-cyclopropylacetonitrile

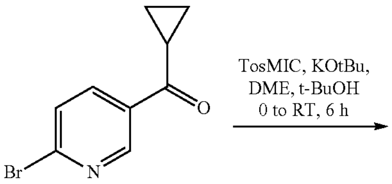

144

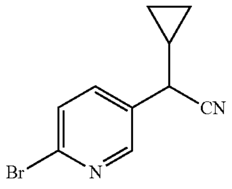

145

To a stirred solution of (6-bromopyridin-3-yl)(cyclopropyl)methanone (1.0 g, 0.442 mmol) in DME (12 mL) at 0° C. under inert condition was added TosMIC (1.29 g 0.663 mmol). A solution of base potassium ter-butoxide (0.991 g, 0.884 mmol) in tert-butanol (1.0 ml) was then added drop wise to the reaction mixture. After addition mixture was stirred for 6 h at room temperature. Progress of reaction was monitored by TLC. After completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 15% ethyl acetate in hexane as eluent to obtain 2-(6-bromopyridin-3-yl)-2-cyclopropylacetonitrile (0.6 g, 56.60%) as colourless oil.

MS: 239 [M+2]

Step-2: Synthesis of 2-(6-bromopyridin-3-yl)-2-cyclopropylacetic acid

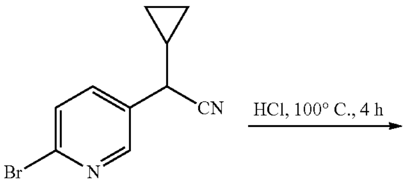

146

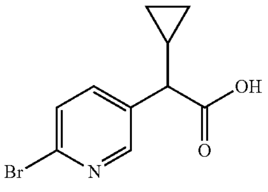

147

To a stirred solution of 2-(6-bromopyridin-3-yl)-2-cyclopropylacetonitrile (0.500 g, 0.210 mmol) was added 4M HCl (5.0 mL) at room temperature. The resultant reaction mixture was stirred for 4 h at 100° C. Completion of reaction was monitored by TLC. On completion, quenched with water, extracted with ethyl acetate. The combined organic layer was washed with water, brine, dried over sodium sulphate and concentrated under reduced pressure to give pure desired product 2-(6-bromopyridin-3-yl)-2-cyclopropylacetic acid (0.320 g, 59.25%) as sticky oil.

MS: 258 [M+2]

Step-3: Synthesis of 2-(6-bromopyridin-3-yl)-2-cyclopropyl-N-(2,2,2-trifluoroethyl)acetamide

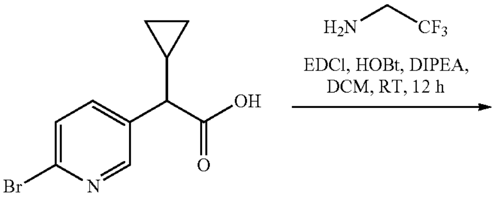

148

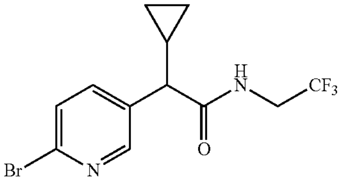

149

To a stirred solution of 2-(6-bromopyridin-3-yl)-2-cyclopropylacetic acid (0.32 g, 0.125 mmol) and Azetidine-3-carbonitrile hydrochloride (0.185 g, 0.187 mmol) in DMF (3 mL) were added EDCI (0.357 g, 0.187 mmol), HOBT (0.252 g, 0.187 mmol) and DIPEA (0.322 g, 0.250 mmol). Then reaction mixture was stirred at room temperature for 12 h. Reaction was monitored by TLC. On completion, reaction was quenched with water, extracted with ethyl acetate. Organic layer was washed with water, brine, dried over sodium sulphate and evaporated under reduced pressure to give crude product. Purification of the crude was done by silica gel (100-200 Mesh) column chromatography; eluent 30% ethyl acetate in hexane to obtain 2-(6-bromopyridin-3-yl)-2-cyclopropyl-N-(2,2,2-trifluoroethyl)acetamide (0.260 g, 61.90%) as off white solid.

MS: 339.09[M+2]

Step-4: Synthesis of 2-(6-(4-(2-amino-3-nitropyridin-4-yl)-1H-pyrazol-1-yl)pyridin-3-yl)-2-cyclopropyl-N-(2,2,2-trifluoroethyl)acetamide

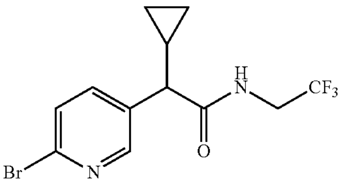

+

150

-continued

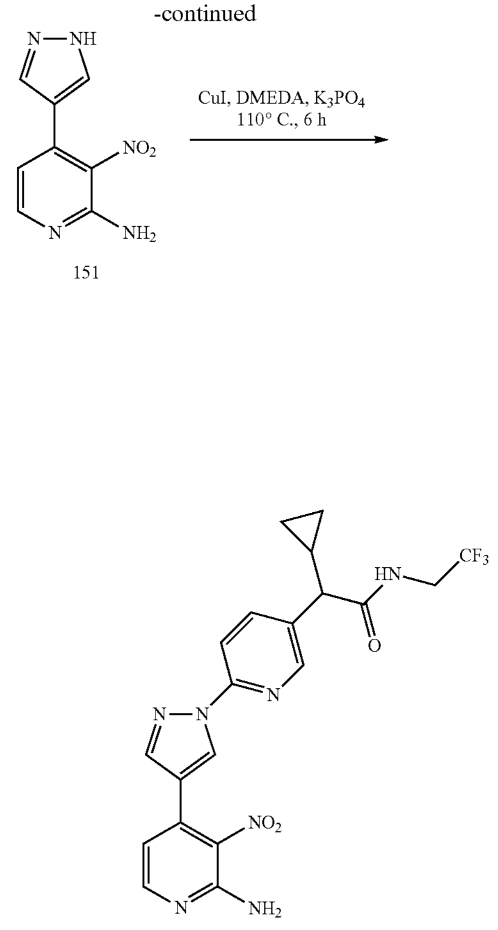

151

152

To a stirred solution of 3-nitro-4-(1H-pyrazol-4-yl)pyridin-2-amine (0.100 g, 0.0487 mmol) and compound 2-(6-bromopyridin-3-yl)-2-cyclopropyl-N-(2,2,2-trifluoroethyl) acetamide (0.163 g, 0.0487 mmol) in Dioxane (5 ml) was added $K_3PO_4$ (0.206 g, 0.0974 mmol) followed by CuI (0.018 g, 0.00974 mmol) and DMEDA (0.085 g, 0.0974 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 4-6% MeOH in DCM to obtained 2-(6-(4-(2-amino-3-nitropyridin-4-yl)-1H-pyrazol-1-yl)pyridin-3-yl)-2-cyclopropyl-N-(2,2,2-trifluoroethyl)acetamide (0.130 g, 59%) as yellow solid.

MS: 462.1 [M+1]

Step-5: Synthesis 2-(6-(4-(2,3-diaminopyridin-4-yl)-1H-pyrazol-1-yl)pyridin-3-yl)-2-cyclopropyl-N-(2,2,2-trifluoroethyl)acetamide

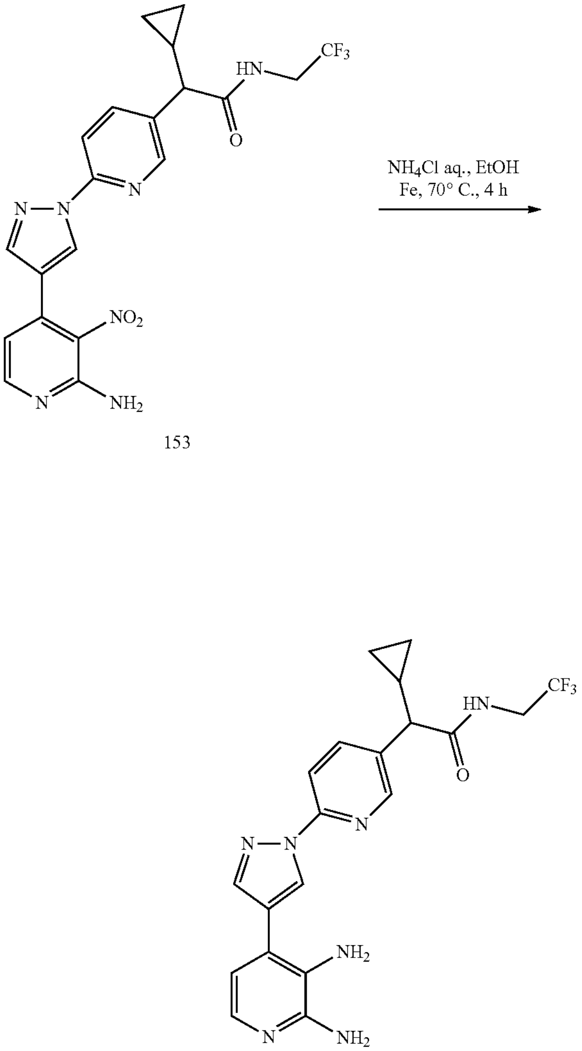

153

154

To a stirred solution of 2-(6-(4-(2-amino-3-nitropyridin-4-yl)-1H-pyrazol-1-yl)pyridin-3-yl)-2-cyclopropyl-N-(2,2,2-trifluoroethyl)acetamide (0.080 g, 0.0173 mmol) in EtOH (7.0 mL), $NH_4Cl$ (2.0 mL) was added at room temperature. To the resultant reaction mixture, Fe powder (0.045 g, 0.0867 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 2-(6-(4-(2,3-diaminopyridin-4-yl)-1H-pyrazol-1-yl)pyridin-3-yl)-2-cyclopropyl-N-(2,2,2-trifluoroethyl)acetamide (0.061 g, 82.43%) as dark brown solid mass.

MS: 432.2 [M+1]

Step-6: Synthesis of 2-(6-(4-(3H-imidazo[4,5-b]pyridin-7-yl)-1H-pyrazol-1-yl)pyridin-3-yl)-2-cyclopropyl-N-(2,2,2-trifluoroethyl)acetamide

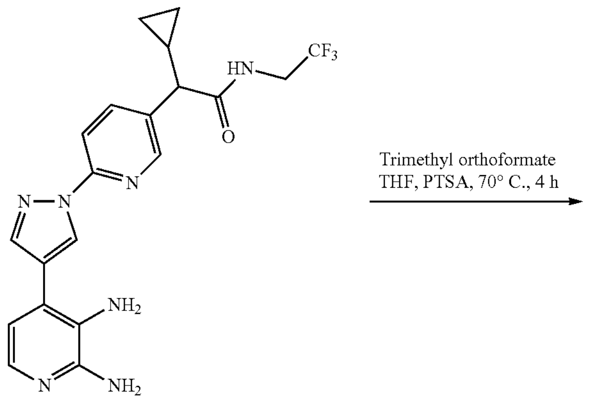

155

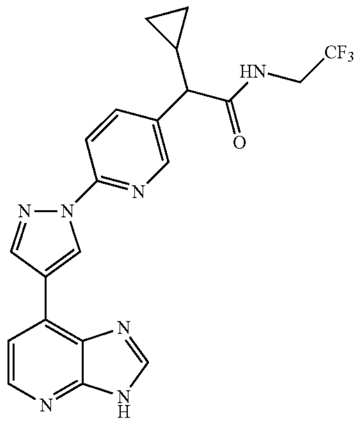 [SMILES: O=C(NCC(F)(F)F)C(c1ccc(-n2cc(-c3ccnc4[nH]cnc34)cn2)nc1)C1CC1]

1167

To a stirred solution of 2-(6-(4-(2,3-diaminopyridin-4-yl)-1H-pyrazol-1-yl)pyridin-3-yl)-2-cyclopropyl-N-(2,2,2-trifluoroethyl)acetamide ((0.060 g, 0.0139 mmol) in THF (1.0 mL), Trimethyl orthoformate (1.5 mL) was added. To resultant reaction mixture, PTSA (0.0046 g, 0.0027 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 7 to 8% MeOH in DCM to obtained 2-(6-(4-(3H-imidazo[4,5-b]pyridin-7-yl)-1H-pyrazol-1-yl)pyridin-3-yl)-2-cyclopropyl-N-(2,2,2-trifluoroethyl)acetamide (0.035 g, 57.37%) as off white solid.

MS: 442.1 [M+1]

Synthesis of Compound No. 1136: -7-(1-(5-(2,2,2-trifluoro-1-(oxetan-3-yl)ethyl)pyridin-2-yl)-1H-pyrazol-4-yl)-3H-imidazo[4,5-b]pyridine

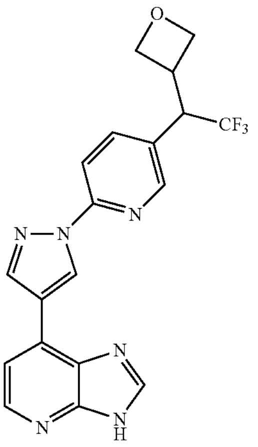 [SMILES: FC(F)(F)C(c1ccc(-n2cc(-c3ccnc4[nH]cnc34)cn2)nc1)C1COC1]

Step-1: Synthesis of 1-(6-bromopyridin-3-yl)-2,2,2-trifluoroethanol

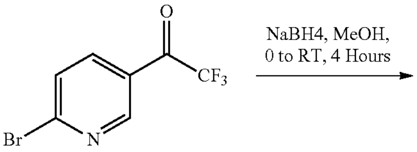

156

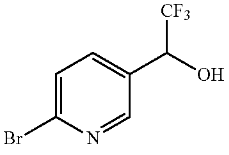

157

To a stirred solution of 1-(6-bromopyridin-3-yl)-2,2,2-trifluoroethanone (2.5 g, 0.984 mmol) in MeOH (50 mL), $NaBH_4$ (0.744 g, 1.962 mmol) was added at 0° C. Reaction was allowed to stir at room temperature for 4 h. Reaction was monitored by TLC. On completion, reaction was quenched with water, extracted with EtOAc. The organic layer was washed with water, dried over $Na_2SO_4$, evaporated under reduced pressure to give 1-(6-bromopyridin-3-yl)-2,2,2-trifluoroethanol (2.3 g, 91%) as white solid.

MS: 256.2 [M+1]

Step-2: Synthesis of 1-(6-bromopyridin-3-yl)-2,2,2-trifluoroethyl trifluoromethanesulfonate

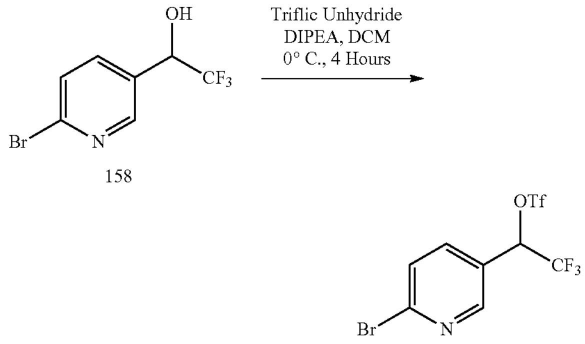

158

159

To a stirred solution of 1-(6-bromopyridin-3-yl)-2,2,2-trifluoroethanol (2.3 g, 0.898 mmol) in DCM (46 mL), DIPEA (2.31 g, 1.796 mmol) was added at 0° C. To resultant reaction mass triflic anhydride (3.7 g, 1.347 mmol) was added dropwise at 0° C. in 10 minute and stirred reaction mixture at same temperature 4 h. Completion of reaction was monitored by TLC. On completion, quenched with water, extracted with DCM. The organic layer was washed with water, brine, dried over sodium sulphate, concentrated under reduced pressure to obtained crude reaction mass. Purification of the crude was done via silica gel (100-200 Mesh) column chromatography and desired compound eluted at 10% acetone/n-Hexane to obtained 1-(6-bromopyridin-3-yl)-2,2,2-trifluoroethyl trifluoromethanesulfonate (2.5 g, 72%) as white solid.

MS: 388 [M+1]

Step-3: Synthesis of diethyl 2-(1-(6-bromopyridin-3-yl)-2,2,2-trifluoroethyl)malonate

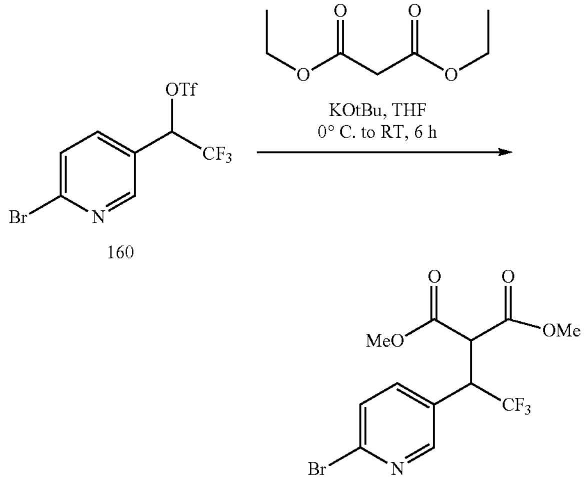

160

161

To a stirred solution of 1-(6-bromopyridin-3-yl)-2,2,2-trifluoroethyl trifluoromethanesulfonate (2.4 g, 0.620 mmol) in THE (50 mL), Diethyl malonate (1.63 g, 1.240 mmol) was added at room temperature and cooled it to 10° C. Added base potassium ter-butoxide (1.38 g, 1.240 mmol) lot wise at 10° C. and stirring continued at room temperature for 6 h. Completion of reaction was monitored by TLC. On completion, quenched with water, extracted with ethyl acetate. The organic layer was washed with water, brine, dried over sodium sulphate, concentrated under reduced pressure to obtained crude reaction mass. Purification of the crude was done via silica gel (100-200 Mesh) column chromatography and desired compound eluted at 15% ethyl acetate/n-Hexane to obtained diethyl 2-(1-(6-bromopyridin-3-yl)-2,2,2-trifluoroethyl)malonate (1.6 g, 70%) as yellow oil.

MS: 398.2[M+1]

Step-4: Synthesis of 2-(1-(6-bromopyridin-3-yl)-2,2,2-trifluoroethyl)propane-1,3-diol

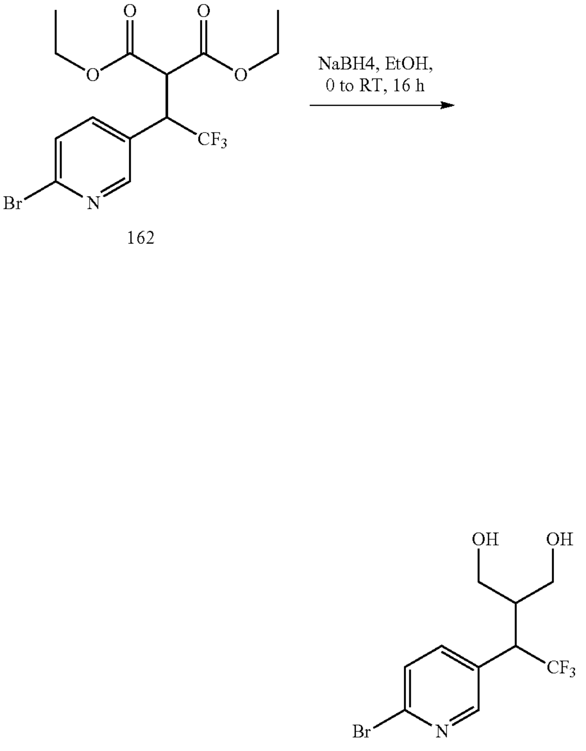

162

163

To a stirred solution of diethyl 2-(1-(6-bromopyridin-3-yl)-2,2,2-trifluoroethyl)malonate (1.6 g, 0.402 mmol) in EtOH (32 mL), $NaBH_4$ (0.450 g, 1.206 mmol) was added at 0° C. Reaction was allowed to stir at room temperature for 16 h. Reaction was monitored by TLC. On completion, reaction was quenched with water, extracted with EtOAc. The organic layer was washed with water, dried over $Na_2SO_4$, evaporated under reduced pressure to obtain crude reaction mass. Purification of the crude was done via silica gel (100-200 Mesh) column chromatography and desired compound eluted at 30% acetone/n-Hexane to obtained 2-(1-(6-bromopyridin-3-yl)-2,2,2-trifluoroethyl)propane-1,3-diol (0.460 g, 35%) as clear oil.

MS: 314 [M+1]

Step-5: Synthesis of 2-bromo-5-(2,2,2-trifluoro-1-(oxetan-3-yl)ethyl)pyridine

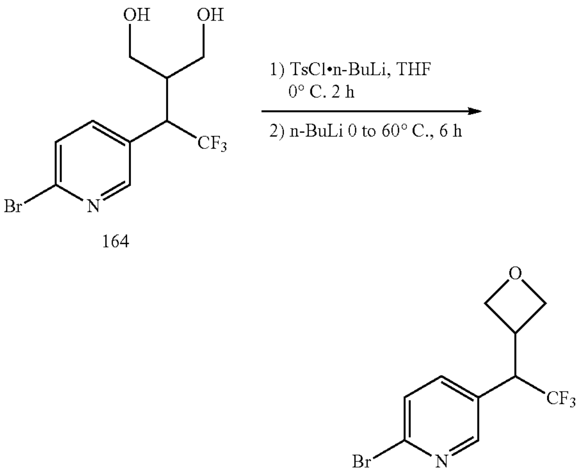

164

165

To a stirred solution of 2-(1-(6-bromopyridin-3-yl)-2,2,2-trifluoroethyl)propane-1,3-diol (0.450 g, 0.143 mmol) in anhydrous THE (20 mL) at 0° C. under $N_2$. Added n-Butyl lithium (1.6M in hexane) (0.890 mL, 0.143 mmol) dropwise at 0° C. and stirred it for 30 minute. A solution of p-toluenesulfonyl chloride (0.271 g. 0.143 mmol) in anhydrous THE was added slowly. The mixture was stirred at 0° C. for 1 h, and a second batch of n-Butyl lithium (1.6M in hexane) (0.890 mL, 0.143 mmol) was added dropwise. After addition the mixture was heated at 60° C. and stirred for 4 h. Completion of reaction was monitored by TLC. After reaction completion reaction mass was quenched with ice cold water. Phases separated and aqueous layer was extracted with ethyl acetate. Combined organic layer was dried over sodium sulphate, concentrated under reduced pressure obtained crude product. Purification of the crude was done via silica gel (100-200 Mesh) column chromatography and desired compound eluted at 10% acetone/n-Hexane to obtained 2-bromo-5-(2,2,2-trifluoro-1-(oxetan-3-yl)ethyl) pyridine (0.130 g, 31%) as clear oil.

MS: 296.1 [M+1]

Step-6: Synthesis of 4-(1-(5-(2,2,2-trifluoro-1-(oxetan-3-yl)ethyl)pyridin-2-yl)-1H-pyrazol-4-yl)-3-nitropyridin-2-amine

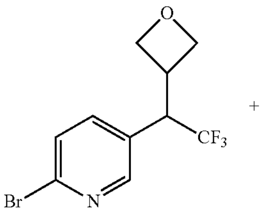

+

-continued

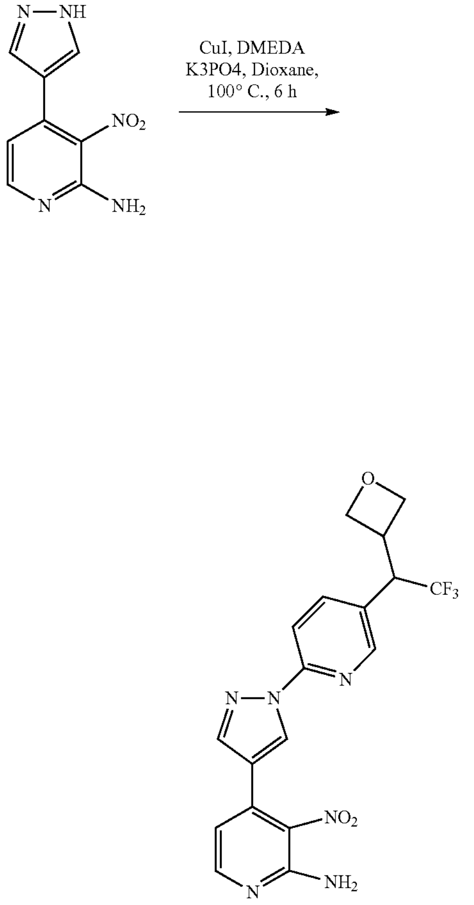

To a stirred solution of 3-nitro-4-(1H-pyrazol-4-yl)pyridin-2-amine (0.088 g, 0.0429 mmol) and compound 2-bromo-5-(2,2,2-trifluoro-1-(oxetan-3-yl)ethyl)pyridine (0.128 g, 0.0429 mmol) in Dioxane (5 ml) was added $K_3PO_4$ (0.182 g, 0.0864 mmol) followed by CuI (0.016 g, 0.00864 mmol) and DMEDA (0.076 g, 0.0864 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 4-5% MeOH in DCM to obtained 4-(1-(5-(2,2,2-trifluoro-1-(oxetan-3-yl)ethyl)pyridin-2-yl)-1H-pyrazol-4-yl)-3-nitropyridin-2-amine (0.085 g, 47.22%) as yellow solid.

MS: 421.1 [M+1]

Step-7: Synthesis of 4-(1-(5-(2,2,2-trifluoro-1-(oxetan-3-yl)ethyl)pyridin-2-yl)-1H-pyrazol-4-yl)pyridine-2,3-diamine

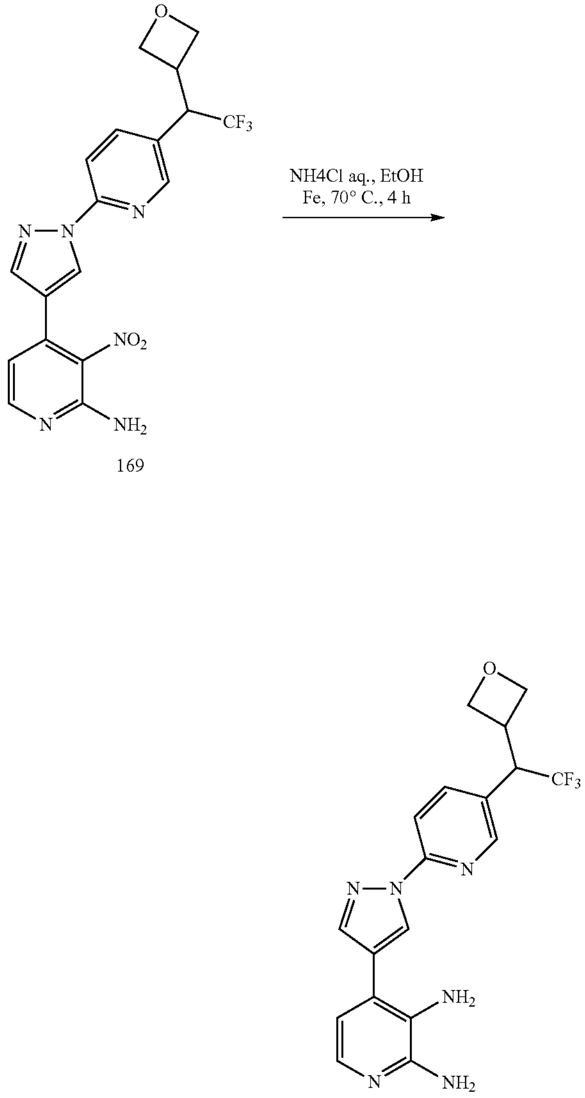

169

170

To a stirred solution of 4-(1-(5-(2,2,2-trifluoro-1-(oxetan-3-yl)ethyl)pyridin-2-yl)-1H-pyrazol-4-yl)-3-nitropyridin-2-amine (0.050 g, 0.0119 mmol) in EtOH (3.0 mL), $NH_4Cl$ (1.5 mL) was added at room temperature. To resultant reaction mixture, Fe powder (0.031 g, 0.0591 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 4-(1-(5-(2,2,2-trifluoro-1-(oxetan-3-yl)ethyl)pyridin-2-yl)-1H-pyrazol-4-yl)pyridine-2,3-diamine (0.032 g, 69.56%) as dark brown solid mass.

MS: 391.2 [M+1]

Step-8: Synthesis of 7-(1-(5-(2,2,2-trifluoro-1-(oxetan-3-yl)ethyl)pyridin-2-yl)-1H-pyrazol-4-yl)-3H-imidazo[4,5-b]pyridine

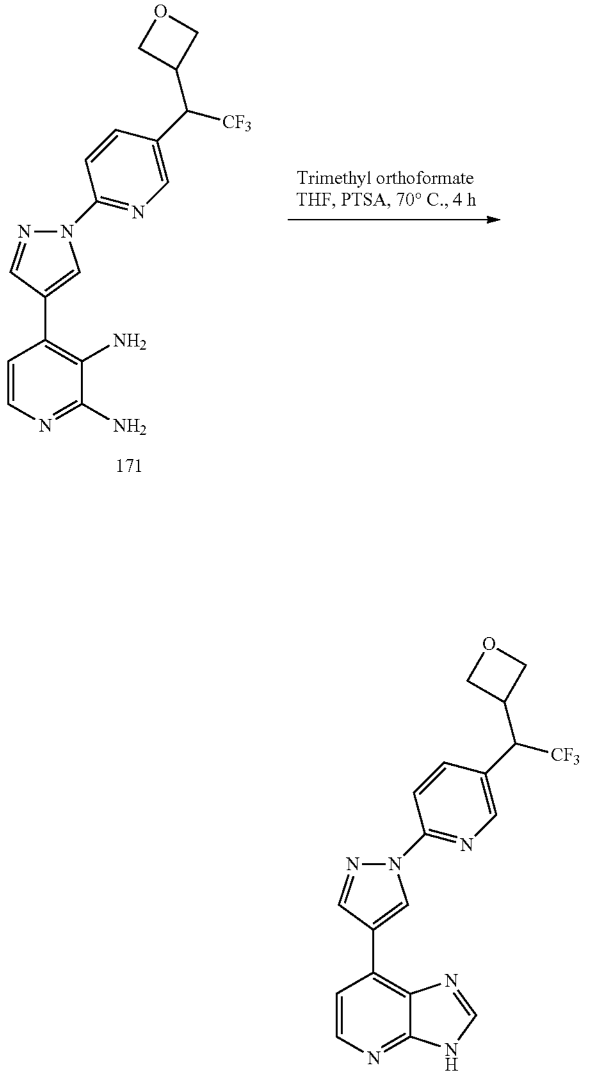

171

1136

To a stirred solution of 4-(1-(5-(2,2,2-trifluoro-1-(oxetan-3-yl)ethyl)pyridin-2-yl)-1H-pyrazol-4-yl)pyridine-2,3-diamine (0.030 g, 0.0076 mmol) in THF (1.0 mL), Trimethyl orthoformate (1.5 mL) was added. To resultant reaction mixture, PTSA (0.004 g, 0.0015 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 3% to 5% MeOH in DCM to obtained 7-(1-(5-(2,2,2-trifluoro-1-(oxetan-3-yl)ethyl)pyridin-2-yl)-1H-pyrazol-4-yl)-3H-imidazo[4,5-b]pyridine (0.021 g, 70%) as off white solid.

MS: 401.0 [M+1]

Synthesis of Compound No. 1158:7-(1-(5-(1-(methylsulfonyl)ethyl)pyridin-2-yl)-1H-pyrazol-4-yl)-3H-imidazo[4,5-b]pyridine

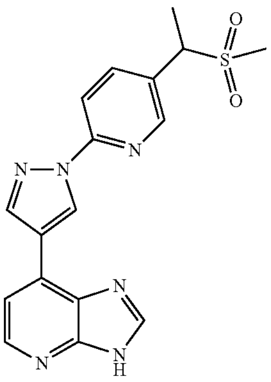 [SMILES: CC(c1ccc(-n2cc(-c3ccnc4[nH]cnc34)cn2)nc1)S(C)(=O)=O]

Step-1: Synthesis of 1-(6-bromopyridin-3-yl)ethanol

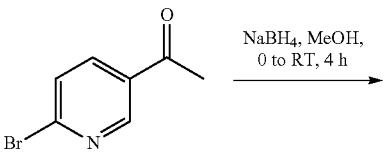

172

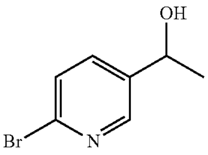

173

To a stirred solution of 1-(6-bromopyridin-3-yl)ethanone (0.5 g, 0.250 mmol) in MeOH (20 mL), $NaBH_4$ (0.190 g, 0.500 mmol) was added at 0° C. Reaction was allowed to stir at room temperature for 4 h. Reaction was monitored by TLC. On completion, reaction was quenched with water, extracted with EtOAc. The organic layer was washed with water, dried over $Na_2SO_4$, evaporated under reduced pressure to obtain crude reaction mass. Purification of the crude was done via silica gel (100-200 Mesh) column chromatography and desired compound eluted at 25% ethyl acetate/n-Hexane to obtained 1-(6-bromopyridin-3-yl)ethanol (0.450 g, 89.10%) as clear oil.

MS: 202.1 [M+1]

Step-2: Synthesis of 2-bromo-5-(1-bromoethyl)pyridine

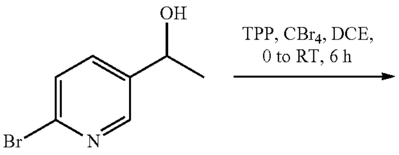

174

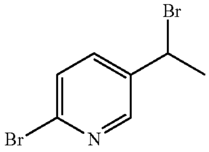

175

To a stirred solution of 1-(6-bromopyridin-3-yl)ethanol (0.400 g, 0.198 mmol) in DCE (20 mL), TPP (0.778 g, 0.297 mmol) was added and then added carbontetrabromide (0.932 g, 0.297 mmol) portion-wise at 0° C. The resultant reaction mixture was stirred at room temperature for 6 h. Completion of reaction was monitored by TLC. After completion reaction mass was quenched with ice cold water. Phases separated and aqueous layer was extracted with DCM. The organic layer was washed with brine, dried over sodium sulphate and concentrated under reduced pressure. Crude product was purified by silica gel (100-200 mesh) column chromatography using 12% ethyl acetate in hexane as eluent to obtain 2-bromo-5-(1-bromoethyl)pyridine (0.290 g, 55.98%) as white solid.

MS: 263.1 [M+1]

Step-3: Synthesis of 2-bromo-5-(1-(methylsulfonyl)ethyl)pyridine

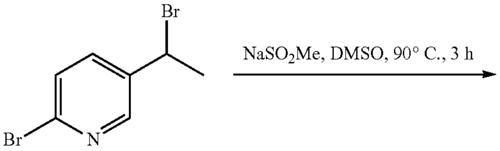

176

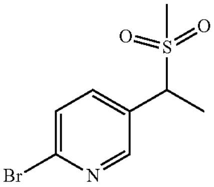

177

To a stirred solution of 2-bromo-5-(1-bromoethyl)pyridine (0.280 g, 0.106 mmol) in DMSO (3.0 mL), sodium mathanesulfinate (0.163 g, 0160 mmol) was added. To resultant reaction mixture was added stirred for 3 h at 90° C. Completion of reaction was monitored by TLC. On completion, quenched with bicarbonate water, extracted with ethyl acetate. The organic layer was washed with water, brine, dried over sodium sulphate and concentrated under reduced pressure to give pure desired product 2-bromo-5-(1-(methylsulfonyl)ethyl)pyridine (0.155 g, 55.35%) as clear oil.

MS: 263 [M+1]

Step-4: Synthesis of 4-(1-(5-(1-(methylsulfonyl)ethyl)pyridin-2-yl)-1H-pyrazol-4-yl)-3-nitropyridin-2-amine

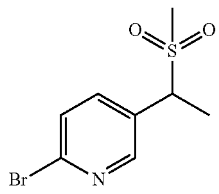

+

178

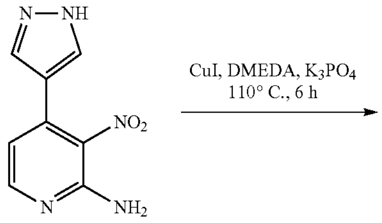

179

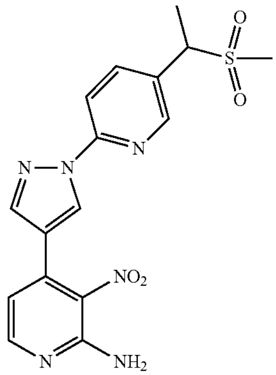

180

To a stirred solution of 3-nitro-4-(1H-pyrazol-4-yl)pyridin-2-amine (0.117 g, 0.057 mmol) and compound 2-bromo-5-(1-(methylsulfonyl)ethyl)pyridine (0.150 g, 0.057 mmol) in Dioxane (7 ml) was added $K_3PO_4$ (0.241 g, 0.114 mmol) followed by CuI (0.021 g, 0.0114 mmol) and DMEDA (0.100 g, 0.114 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 5-6% MeOH in DCM to obtained 4-(1-(5-(1-(methylsulfonyl)ethyl)pyridin-2-yl)-1H-pyrazol-4-yl)-3-nitropyridin-2-amine (0.095 g, 42.79%) as yellow solid.

MS: 389.1 [M+1]

Step-5: Synthesis of 4-(1-(5-(1-(methylsulfonyl)ethyl)pyridin-2-yl)-1H-pyrazol-4-yl)pyridine-2,3-diamine

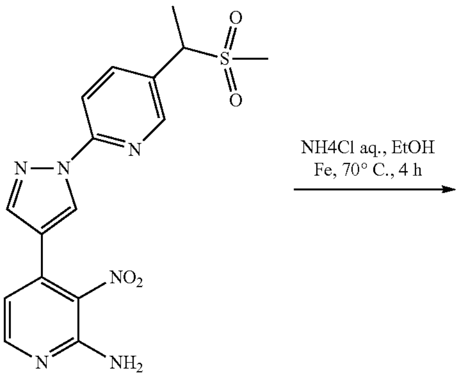

181

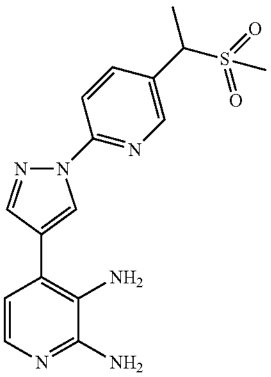

182

To a stirred solution of 4-(1-(5-(1-(methylsulfonyl)ethyl)pyridin-2-yl)-1H-pyrazol-4-yl)-3-nitropyridin-2-amine (0.095 g, 0.024 mmol) in EtOH (7.0 mL), $NH_4Cl$ (2.0 mL) was added at room temperature. To the resultant reaction mixture, Fe powder (0.064 g, 0.122 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 4-(1-(5-(1-(methylsulfonyl)ethyl)pyridin-2-yl)-1H-pyrazol-4-yl)pyridine-2,3-diamine (0.060 g, 68.96%) as dark brown solid mass.

MS: 359.2 [M+1]

Step-6: Synthesis of 7-(1-(5-(1-(methylsulfonyl) ethyl)pyridin-2-yl)-1H-pyrazol-4-yl)-3H-imidazo[4, 5-b]pyridine

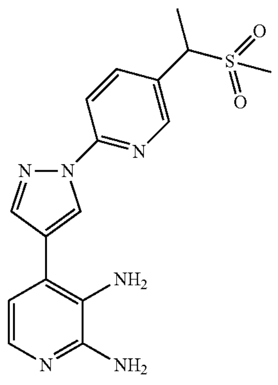

183

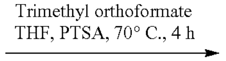

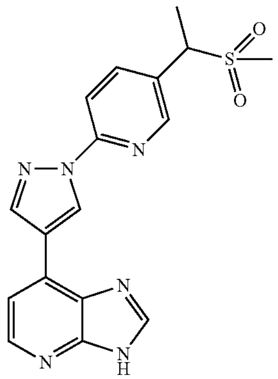

1158

To a stirred solution of 4-(1-(5-(1-(methylsulfonyl)ethyl) pyridin-2-yl)-1H-pyrazol-4-yl)pyridine-2,3-diamine (0.060 g, 0.0136 mmol) in THF (1.0 mL), Trimethyl orthoformate (1.5 mL) was added. To resultant reaction mixture, PTSA (0.0046 g, 0.0027 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 7 to 8% MeOH in DCM to obtained 7-(1-(5-(1-(methylsulfonyl)ethyl)pyridin-2-yl)-1H-pyrazol-4-yl)-3H-imidazo[4,5-b]pyridine (0.027 g, 44.26%) as off white solid.

MS: 369.1 [M+1]

Synthesis of Compound No. 1142: 3-(6-(4-(3H-imidazo[4,5-b]pyridin-7-yl)-1H-pyrazol-1-yl)pyridin-3-yl)-4,4,4-trifluoro-N-methylbutane-1-sulfonamide

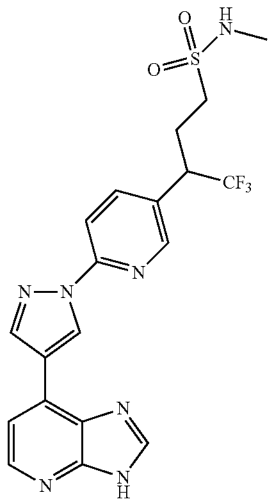 [SMILES: CNS(=O)(=O)CCC(c1ccc(-n2cc(-c3ccnc4[nH]cnc34)cn2)nc1)C(F)(F)F]

Step-1: Synthesis of S-3-(6-bromopyridin-3-yl)-4,4,4-trifluorobutyl ethanethioate

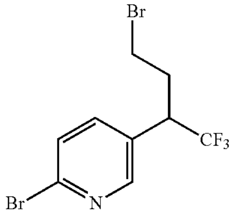

184

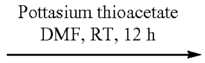

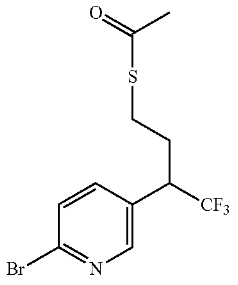

185

To a stirred solution of 2-bromo-5-(4-bromo-1,1,1-trifluorobutan-2-yl)pyridine (0.300 g, 0.086 mmol) in DMF (5 mL) was added potassium tioacetate (0.197, 0.172 mmol) under nitrogen and stirred for 12 h at room temperature. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh)

column chromatography using 18% ethyl acetate in hexane as eluent to obtain S-3-(6-bromopyridin-3-yl)-4,4,4-trifluorobutyl ethanethioate (0.200 g, 68.96%) as black solid.

Step-2: Synthesis of 3-(6-bromopyridin-3-yl)-4,4,4-trifluorobutane-1-sulfonyl chloride

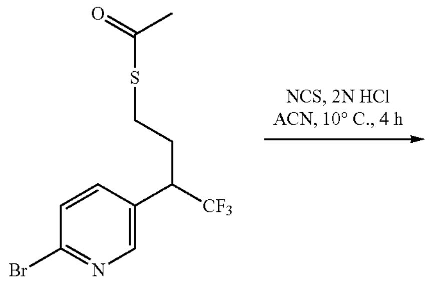

186

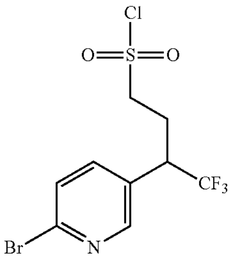

187

To a stirred solution of N-chlorosuccinamide (0.470 g, 0.350 mmol) and 2N HCl (0.5 ml) in ACN at 0° C. under $N_2$ added solution of S-3-(6-bromopyridin-3-yl)-4,4,4-trifluorobutyl ethanethioate (0.300 g, 0.877 mmol) in ACN dropwise. The resultant mixture was stirred at RT for 4 h at room temperature. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 9 to 15% EA/Hexane to 3-(6-bromopyridin-3-yl)-4,4,4-trifluorobutane-1-sulfonyl chloride (0.225 g, 72.58%) as yellow oil.

MS: 366 [M+1]

Step-3: Synthesis of 3-(6-bromopyridin-3-yl)-4,4,4-trifluoro-N-methylbutane-1-sulfonamide

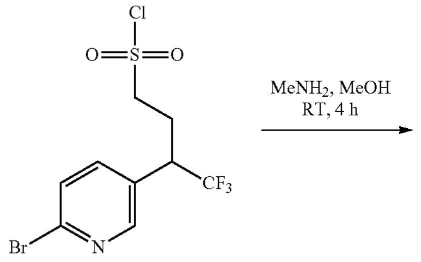

188

-continued

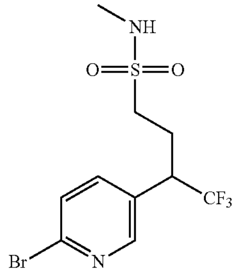

189

To a stirred solution of 3-(6-bromopyridin-3-yl)-4,4,4-trifluorobutane-1-sulfonyl chloride (0.150 g, 0.0409 mmol) in MeOH (7 mL), base trimethylamine (0.124 g, 0.122 mmol) was added. Then add methylamine. HCl (0.082 g, 0.122 mmol) was added at room temperature. Reaction was stirred at room temperature for 4 h. Reaction was monitored by TLC. On completion, reaction was quenched with water, extracted with EtOAc. The organic layer was washed with water, dried over $Na_2SO_4$, evaporated under reduced pressure to obtain pure compound 3-(6-bromopyridin-3-yl)-4,4,4-trifluoro-N-methylbutane-1-sulfonamide (0.130 g, 87.83%) as clear oil.

MS: 361 [M+1]

Step-4: Synthesis of 3-(6-(4-(2-amino-3-nitropyridin-4-yl)-1H-pyrazol-1-yl)pyridin-3-yl)-4,4,4-trifluoro-N-methylbutane-1-sulfonamide

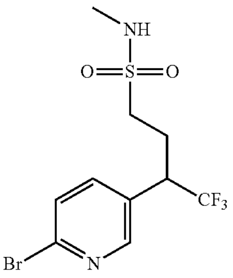

190

+

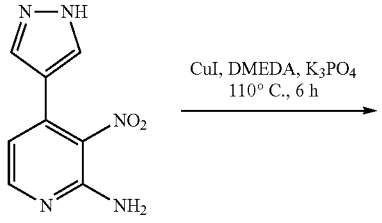

191

-continued

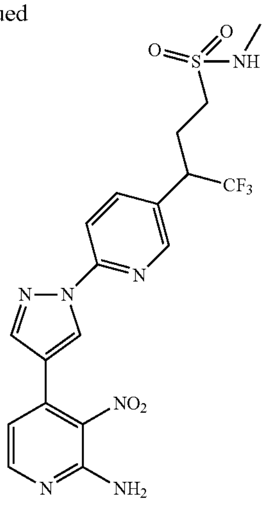

192

To a stirred solution of 3-nitro-4-(1H-pyrazol-4-yl)pyridin-2-amine (0.073 g, 0.036 mmol) and compound 3-(6-bromopyridin-3-yl)-4,4,4-trifluoro-N-methylbutane-1-sulfonamide (0.130 g, 0.036 mmol) in Dioxane (5 ml) was added $K_3PO_4$ (0.152 g, 0.072 mmol) followed by CuI (0.013 g, 0.0072 mmol) and DMEDA (0.0066 g, 0.072 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 6-7% MeOH in DCM to obtained 3-(6-(4-(2-amino-3-nitropyridin-4-yl)-1H-pyrazol-1-yl)pyridin-3-yl)-4,4,4-trifluoro-N-methylbutane-1-sulfonamide (0.09 g, 45%) as yellow solid.

MS: 486.1 [M+1]

Step-5: Synthesis of 3-(6-(4-(2,3-diaminopyridin-4-yl)-1H-pyrazol-1-yl)pyridin-3-yl)-4,4,4-trifluoro-N-methylbutane-1-sulfonamide

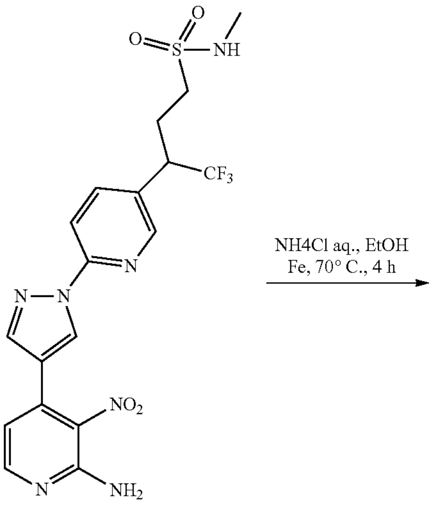

193

-continued

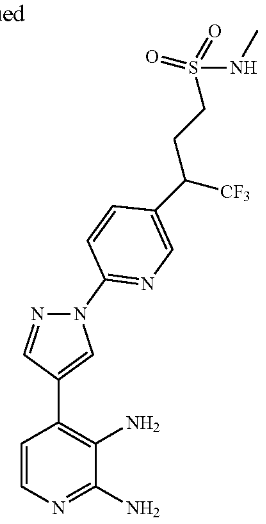

194

To a stirred solution of 3-(6-(4-(2-amino-3-nitropyridin-4-yl)-1H-pyrazol-1-yl)pyridin-3-yl)-4,4,4-trifluoro-N-methylbutane-1-sulfonamide (0.070 g, 0.0144 mmol) in EtOH (7.0 mL), $NH_4Cl$ (2.0 mL) was added at room temperature. To the resultant reaction mixture, Fe powder (0.40 g, 0.76 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 3-(6-(4-(2,3-diaminopyridin-4-yl)-1H-pyrazol-1-yl)pyridin-3-yl)-4,4,4-trifluoro-N-methylbutane-1-sulfonamide (0.045 g, 69.23%) as dark brown solid mass.

MS: 456.2 [M+1]

Step-6: Synthesis of 3-(6-(4-(3H-imidazo[4,5-b]pyridin-7-yl)-1H-pyrazol-1-yl)pyridin-3-yl)-4,4,4-trifluoro-N-methylbutane-1-sulfonamide

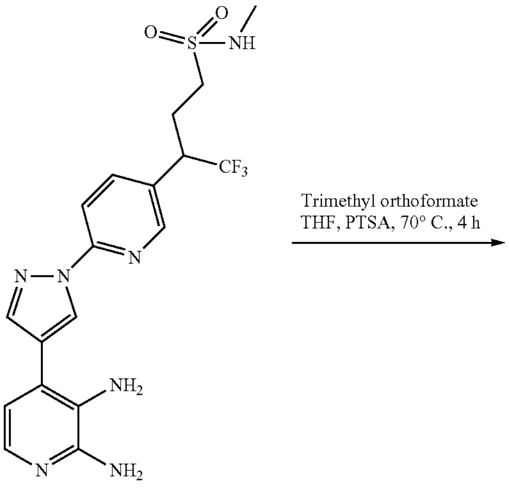

195

-continued

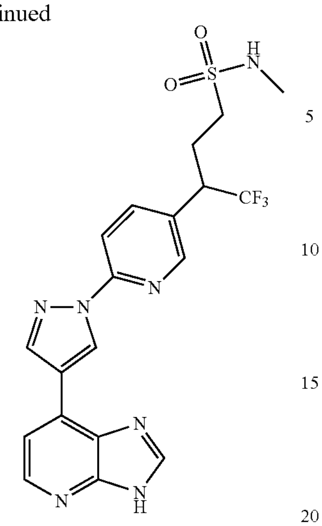

1142

To a stirred solution of 3-(6-(4-(2,3-diaminopyridin-4-yl)-1H-pyrazol-1-yl)pyridin-3-yl)-4,4,4-trifluoro-N-methylbutane-1-sulfonamide (0.045 g, 0.0098 mmol) in THF (1.0 mL), Trimethyl orthoformate (1.5 mL) was added. To resultant reaction mixture, PTSA (0.0034 g, 0.0019 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained 3-(6-(4-(3H-imidazo[4,5-b]pyridin-7-yl)-1H-pyrazol-1-yl)pyridin-3-yl)-4,4,4-trifluoro-N-methylbutane-1-sulfonamide (0.021 g, 46.66%) as off white solid.

MS: 466.1 [M+1]

Synthesis of Compound No. 1160: 7-(1-(5-(3-(methylsulfonyl)-1-(oxetan-3-yl)propyl)pyridin-2-yl)-1H-pyrazol-4-yl)-3H-imidazo[4,5-b]pyridine

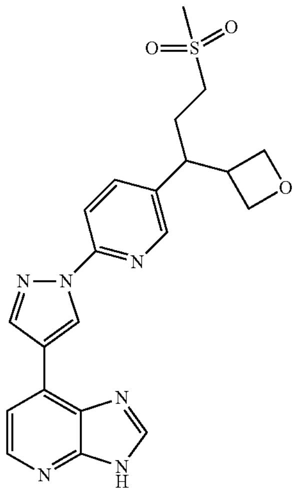 [SMILES: CS(=O)(=O)CCC(c1ccc(-n2cc(-c3ccnc4[nH]cnc34)cn2)nc1)C1COC1]

Step-1: Synthesis of 2-bromo-5-(1-bromo-3-(methylthio)propyl)pyridine

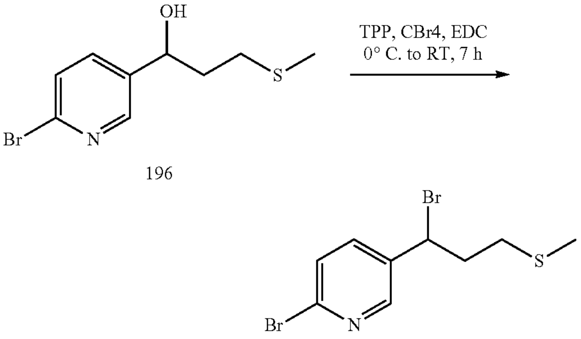

196

197

To a stirred solution of 1-(6-bromopyridin-3-yl)-3-(methylthio)propan-1-ol (3.5 g, 1.33 mmol) in DCE (70 mL), TPP (4.5 g, 1.73 mmol) was added and then added carbontetrabromide (5.7 g, 1.73 mmol) portion-wise at 0° C. The resultant reaction mixture was stirred at room temperature for 7 h. Completion of reaction was monitored by TLC. After reaction completion reaction mass was quenched with ice cold water. Phases separated and aqueous layer was extracted with DCM. The organic layer was washed with brine, dried over sodium sulphate and concentrated under reduced pressure. Crude product was purified by silica gel (100-200 mesh) column chromatography using 4% ethyl acetate in hexane as eluent to obtain 2-bromo-5-(1-bromo-3-(methylthio)propyl)pyridine (2.65 g, 61.05%) as yellow oil.

MS: 326.1 [M+1]

Step-2: Synthesis of diethyl 2-(1-(6-bromopyridin-3-yl)-3-(methylthio)propyl)malonate

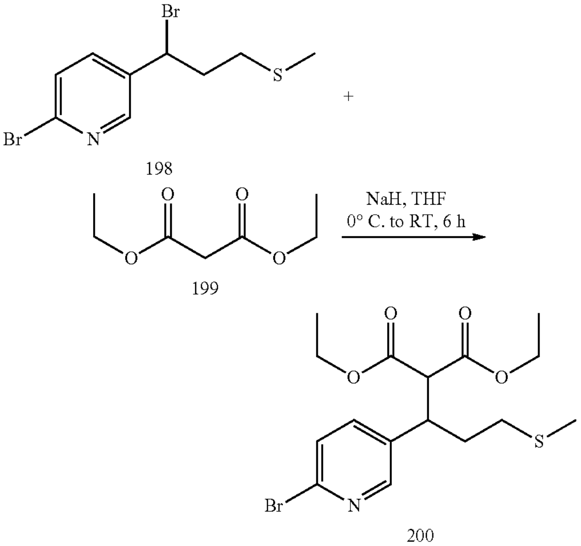

198

199

200

To a stirred solution of 2-bromo-5-(1-bromo-3-(methylthio)propyl)pyridine (2.34 g, 0.720 mmol) in THE (50 mL), Diethyl malonate (1.72 g, 1.08 mmol) was added at room temperature and cooled it to 10° C. Added base sodium hydride (0.420 g, 1.08 mmol) lot wise at 10° C. and stirring continued at room temperature for 6 h. Completion of reaction was monitored by TLC. On completion, quenched with water, extracted with ethyl acetate. The organic layer was washed with water, brine, dried over sodium sulphate, concentrated under reduced pressure to obtained crude reaction mass. Purification of the crude was done via silica gel (100-200 Mesh) column chromatography and desired compound eluted at 15% ethyl acetate/n-Hexane to obtained diethyl 2-(1-(6-bromopyridin-3-yl)-3-(methylthio)propyl) malonate (1.05 g, 37.5%) as yellow oil.

MS: 404.2[M+1]

Step-3: Synthesis of 2-(1-(6-bromopyridin-3-yl)-3-(methylthio)propyl)propane-1,3-diol

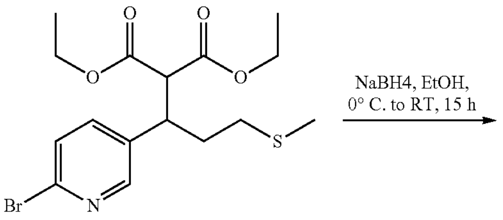

201

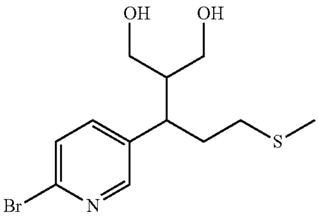

202

To a stirred solution of diethyl 2-(1-(6-bromopyridin-3-yl)-3-(methylthio)propyl)malonate (1.05 g, 0.259 mmol) in EtOH (20 mL), $NaBH_4$ (0.290 g, 0.777 mmol) was added at 0° C. Reaction was allowed to stir at room temperature for 16 h. Reaction was monitored by TLC. On completion, reaction was quenched with water, extracted with EtOAc. The organic layer was washed with water, dried over $Na_2SO_4$, evaporated under reduced pressure to obtain crude reaction mass. Purification of the crude was done via silica gel (100-200 Mesh) column chromatography and desired compound eluted at 30% acetone/n-Hexane to obtained 2-(1-(6-bromopyridin-3-yl)-3-(methylthio)propyl)propane-1,3-diol_(0.500 g, 60.16%) as clear oil.

MS: 320 [M+1]

Step-4: Synthesis of 2-bromo-5-(3-(methylthio)-1-(oxetan-3-yl)propyl)pyridine

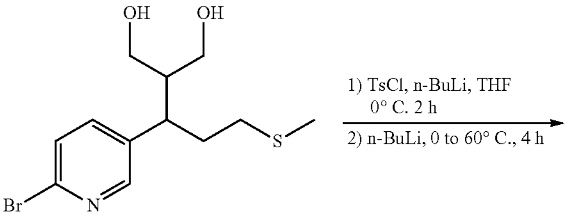

203

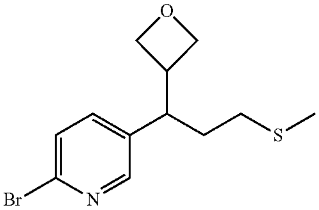

204

To a stirred solution of 2-(1-(6-bromopyridin-3-yl)-3-(methylthio)propyl)propane-1,3-diol (0.470 g, 0.146 mmol) in anhydrous THE (30 mL) at 0° C. under $N_2$. Added n-Butyl lithium (1.6M in hexane) (0.908 mL, 0.146 mmol) dropwise at 0° C. and stirred it for 30 minute. A solution of p-toluenesulfonyl chloride (0.277 g. 0.146 mmol) in anhydrous THE was added slowly. The mixture was stirred at 0° C. for 1 h, and a second batch of n-Butyl lithium (1.6M in hexane) (0.908 mL, 0.146 mmol) was added dropwise. After addition the mixture was heated at 60° C. and stirred for 4 h. Completion of reaction was monitored by TLC. After reaction completion reaction mass was quenched with ice cold water. Phases separated and aqueous layer was extracted with ethyl acetate. Combined organic layer was dried over sodium sulphate, concentrated under reduced pressure obtained crude product. Purification of the crude was done via silica gel (100-200 Mesh) column chromatography and desired compound eluted at 11% acetone/n-Hexane to obtained 2-bromo-5-(3-(methylthio)-1-(oxetan-3-yl)propyl) pyridine (0.160 g, 36.1%) as clear oil.

MS: 302.1 [M+1]

Step-5: Synthesis of 2-bromo-5-(3-(methylsulfonyl)-1-(oxetan-3-yl)propyl)pyridine

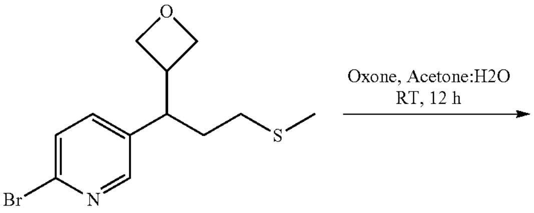

205

-continued

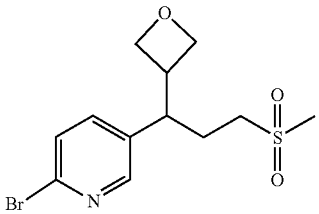

206

To a stirred solution of 2-bromo-5-(3-(methylthio)-1-(oxetan-3-yl)propyl)pyridine (0.160 g, 0.0520 mmol) in Acetone:$H_2O$ (20 mL, 7:3) at 0° C. was added oxone (0.487 g, 0.158 mmol) under nitrogen and stirred for 12 h at same temperature. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 3% MeOH in DCM as eluent to obtain 2-bromo-5-(3-(methylsulfonyl)-1-(oxetan-3-yl)propyl)pyridine (0.130 g, 73.86%) as colourless oil.

MS: 334.0 [M+1]

Step-6: Synthesis of 4-(1-(5-(3-(methylsulfonyl)-1-(oxetan-3-yl)propyl)pyridin-2-yl)-1H-pyrazol-4-yl)-3-nitropyridin-2-amine

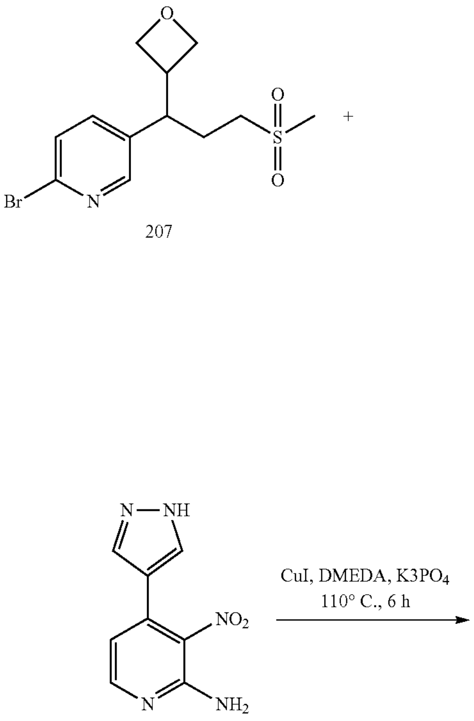

208

-continued

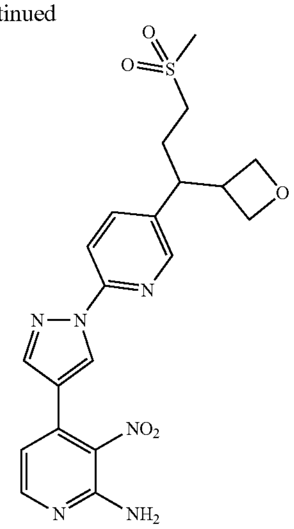

209

To a stirred solution of 3-nitro-4-(1H-pyrazol-4-yl)pyridin-2-amine (0.079 g, 0.0389 mmol) and compound 2-bromo-5-(3-(methylsulfonyl)-1-(oxetan-3-yl)propyl)pyridine (0.130 g, 0.0389 mmol) in Dioxane (5 ml) was added $K_3PO_4$ (0.164 g, 0.0778 mmol) followed by CuI (0.014 g, 0.0077 mmol) and DMEDA (0.068 g, 0.0778 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 4-5% MeOH in DCM to obtained 4-(1-(5-(3-(methylsulfonyl)-1-(oxetan-3-yl)propyl)pyridin-2-yl)-1H-pyrazol-4-yl)-3-nitropyridin-2-amine (0.085 g, 47.22%) as yellow solid.

MS: 459.1 [M+1]

Step-7: Synthesis of 4-(1-(5-(3-(methylsulfonyl)-1-(oxetan-3-yl)propyl)pyridin-2-yl)-1H-pyrazol-4-yl) pyridine-2,3-diamine

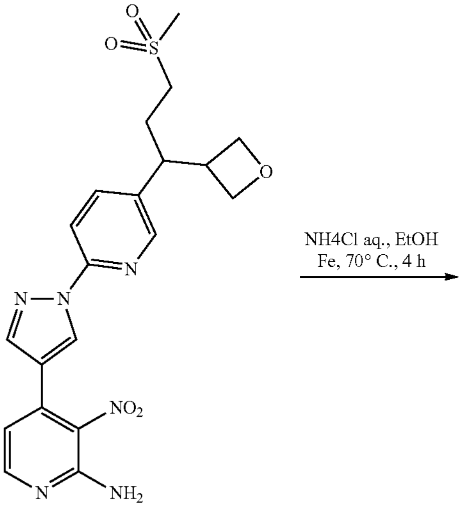

210

-continued

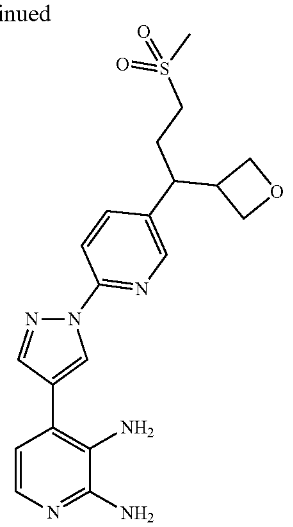

211

To a stirred solution of 4-(1-(5-(3-(methylsulfonyl)-1-(oxetan-3-yl)propyl)pyridin-2-yl)-1H-pyrazol-4-yl)-3-nitropyridin-2-amine (0.060 g, 0.0131 mmol) in EtOH (7.0 mL), $NH_4Cl$ (2.0 mL) was added at room temperature. To the resultant reaction mixture, Fe powder (0.034 g, 0.06591 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 4-(1-(5-(3-(methylsulfonyl)-1-(oxetan-3-yl)propyl)pyridin-2-yl)-1H-pyrazol-4-yl)pyridine-2,3-diamine (0.045 g, 80.35%) as dark brown solid mass.

MS: 429.2 [M+1]

Step-8: Synthesis of 7-(1-(5-(3-(methylsulfonyl)-1-(oxetan-3-yl)propyl)pyridin-2-yl)-1H-Pyrazol-4-yl)-3H-imidazo[4,5-b]pyridine

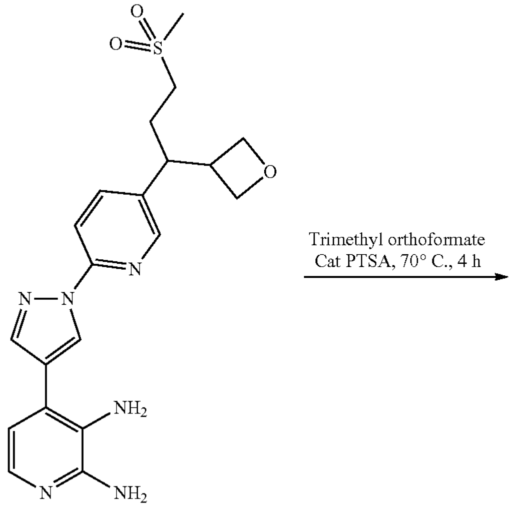

212

-continued

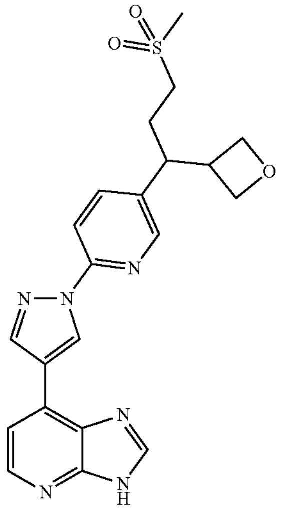

1160

To a stirred solution of 4-(1-(5-(3-(methylsulfonyl)-1-(oxetan-3-yl)propyl)pyridin-2-yl)-1H-pyrazol-4-yl)pyridine-2,3-diamine (0.045 g, 0.0105 mmol) in THF (1.0 mL), Trimethyl orthoformate (1.5 mL) was added. To resultant reaction mixture, PTSA (0.0036 g, 0.0021 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 6 to 7% MeOH in DCM to obtained 7-(1-(5-(3-(methylsulfonyl)-1-(oxetan-3-yl)propyl)pyridin-2-yl)-1H-pyrazol-4-yl)-3H-imidazo[4,5-b]pyridine (0.025 g, 54%) as off white solid.

MS: 439.0 [M+1]

Synthesis of Compound No. 1175: 7-(1-(6-(1,1,1-trifluoro-4-(methylsulfonyl)butan-2-yl)pyridin-2-yl)-1H-pyrazol-4-yl)-3H-imidazo[4,5-b]pyridine

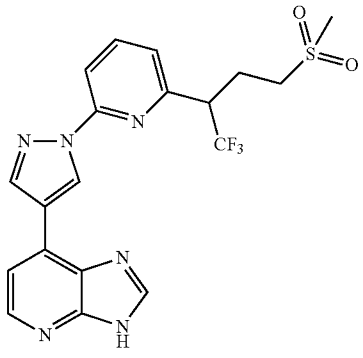 [SMILES: CS(=O)(=O)CCC(c1cccc(-n2cc(-c3ccnc4[nH]cnc34)cn2)n1)C(F)(F)F]

Step-1: Synthesis of 1-(6-bromopyridin-2-yl)-2,2,2-trifluoroethanone

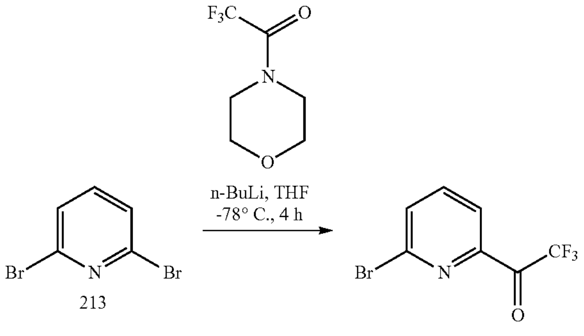

213

214

To a stirred solution of 2,6-dibromopyridine (5.0 g, 2.12 mmol) in THF (50 mL) at −78° C. was added n-Butyl lithium (2.5M in hexane) (12.5 mL, 3.18 mmol) under nitrogen and stirred for 1 h at same temperature. 2,2,2-trifluoro-1-morpholinoethanone (5.06 g, 2.76 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 18% ethyl acetate in hexane as eluent to obtain 1-(6-bromopyridin-2-yl)-2,2,2-trifluoroethanone (3.5 g, 64.81%) as colourless oil.

Step-2: Synthesis of (E/Z)-ethyl 3-(6-bromopyridin-2-yl)-4,4,4-trifluorobut-2-enoate

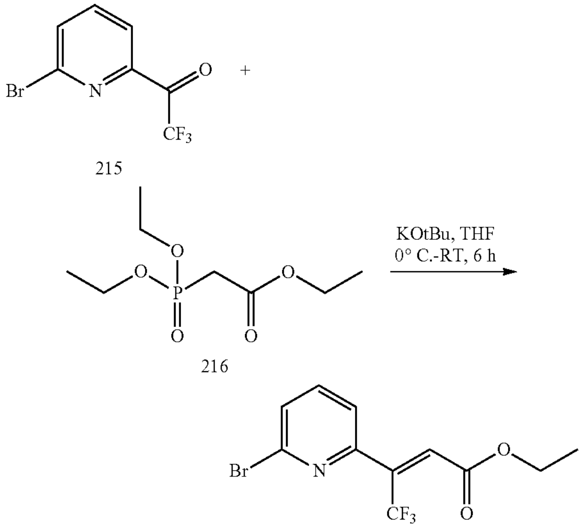

215

216

217

To a stirred solution of Triethyl phosphonoacetate (3.9 g, 1.77 mmol) and THE (60 ml) at 0° C. under $N_2$ added base potassium ter-butoxide (1.98 g, 1.77 mmol) lotwise. The resultant mixture was stirred at RT for 1 h for anion generation. A solution of 1-(6-bromopyridin-2-yl)-2,2,2-trifluoroethanone (3.0 g, 1.18 mmol) in THE (15 ml) was added slowly. After addition stirred mixture for 6 h at RT. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 9 to 15% EA/Hexane to obtained (E/Z)-ethyl 3-(6-bromopyridin-2-yl)-4,4,4-trifluorobut-2-enoate (1.5 g, 40%) as yellow oil.

MS: 324 [M+1]

Step-3: Synthesis of 3-(6-bromopyridin-2-yl)-4,4,4-trifluorobutan-1-ol

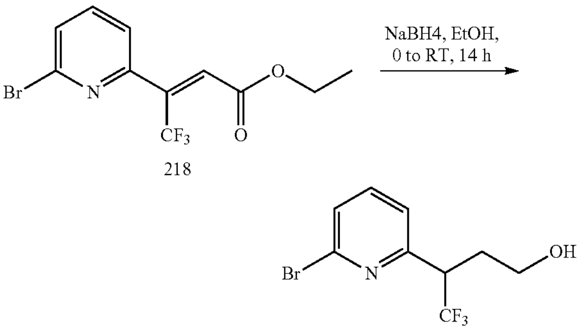

218

219

To a stirred solution of (E/Z)-ethyl 3-(6-bromopyridin-2-yl)-4,4,4-trifluorobut-2-enoate (1.5 g, 462 mmol) in EtOH (30 mL), $NaBH_4$ (0.520 g, 1380 mmol) was added at 0° C. Reaction was allowed to stir at room temperature for 14 h. Reaction was monitored by TLC. On completion, reaction was quenched with water, extracted with EtOAc. The organic layer was washed with water, dried over $Na_2SO_4$, evaporated under reduced pressure to obtain crude reaction mass. Purification of the crude was done via silica gel (100-200 Mesh) column chromatography and desired compound eluted at 30% ethyl acetate/n-Hexane to obtained 3-(6-bromopyridin-2-yl)-4,4,4-trifluorobutan-1-ol (0.610 g, 46.5%) as clear oil.

MS: 284 [M+1]

Step-4: Synthesis of 3-(6-(4-(2-amino-3-nitropyridin-4-yl)-1H-pyrazol-1-yl)pyridin-2-yl)-4,4,4-trifluorobutan-1-ol

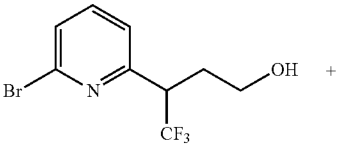

220

-continued

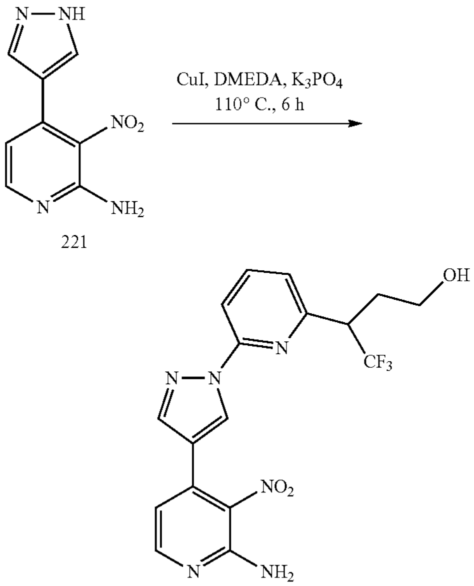

221

222

-continued

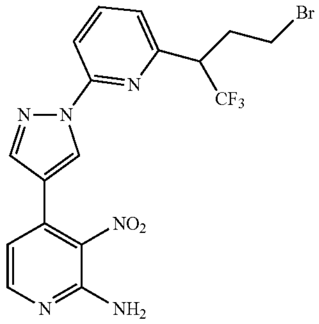

224

To a stirred solution of 3-nitro-4-(1H-pyrazol-4-yl)pyridin-2-amine (0.253 g, 123 mmol) and compound 3-(6-bromopyridin-2-yl)-4,4,4-trifluorobutan-1-ol (0.350 g, 123 mmol) in Dioxane (5 ml) was added $K_3PO_4$ (0.521 g, 246 mmol) followed by CuI (0.046 g, 0.246 mmol) and DMEDA (0.216 g, 246 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 6-7% MeOH in DCM to obtained 3-(6-(4-(2-amino-3-nitropyridin-4-yl)-1H-pyrazol-1-yl)pyridin-2-yl)-4,4,4-trifluorobutan-1-ol (0.250 g, 50%) as yellow solid.

MS: 409.1 [M+1]

Step-5: Synthesis of 4-(1-(6-(4-bromo-1,1,1-trifluorobutan-2-yl)pyridin-2-yl)-1H-pyrazol-4-yl)-3-nitropyridin-2-amine To a stirred solution of 3-(6-(4-(2-amino-3-nitropyridin-4-yl)-1H-pyrazol-1-yl)pyridin-2-yl)-4,4,4-trifluorobutan-1-ol (0.120 g, 0.29 mmol) in DCE (10 mL), TPP (0.115 g, 0.44 mmol) was added and then added carbontetrabromide (0.145 g, 0.44 mmol) portion-wise at 0° C. The resultant reaction mixture was stirred at room temperature for 7 h. Completion of reaction was monitored by TLC. After completion reaction mass was quenched with ice cold water. Phases separated and aqueous layer was extracted with DCM. The organic layer was washed with brine, dried over sodium sulphate and concentrated under reduced pressure. Crude product was purified by silica gel (100-200 mesh) column chromatography using 2 to 3% methanol in DCMA as eluent to obtain 4-(1-(6-(4-bromo-1,1,1-trifluorobutan-2-yl)pyridin-2-yl)-1H-pyrazol-4-yl)-3-nitropyridin-2-amine (0.065 g, 47.05%) as yellow solid.

MS: 471.1 [M+1]

Step-6: Synthesis of 4-(1-(6-(1,1,1-trifluoro-4-(methylsulfonyl)butan-2-yl)pyridin-2-yl)-1H-pyrazol-4-yl)-3-nitropyridin-2-amine

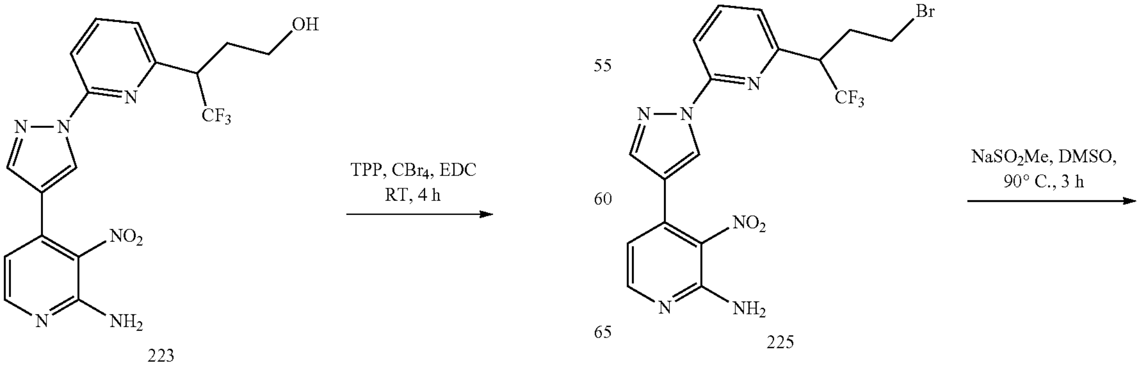

223

225

-continued

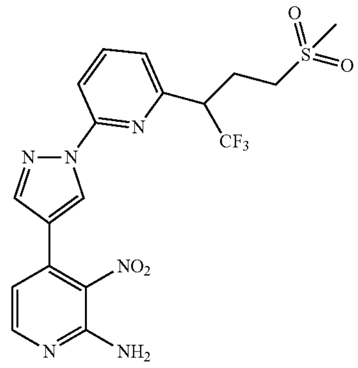

226

To a stirred solution of 4-(1-(6-(4-bromo-1,1,1-trifluorobutan-2-yl)pyridin-2-yl)-1H-pyrazol-4-yl)-3-nitropyridin-2-amine (0.065 g, 0.130 mmol) in DMSO (3.0 mL), sodium mathanesulfinate (0.027 g, 0.20 mmol) was added. To resultant reaction mixture was added stirred for 3 h at 90° C. Completion of reaction was monitored by TLC. On completion, quenched with bicarbonate water, extracted with ethyl acetate. The organic layer was washed with water, brine, dried over sodium sulphate and concentrated under reduced pressure to give crude desired product that was purified by silica gel (100 to 200 Mesh) column chromatography: eluent at 6 to 7% MeOH/DCM to obtained 4-(1-(6-(1,1,1-trifluoro-4-(methylsulfonyl)butan-2-yl)pyridin-2-yl)-1H-pyrazol-4-yl)-3-nitropyridin-2-amine (0.052 g, 81.20%) as yellow solid.

MS: 471[M+1]

Step-7: Synthesis of 4-(1-(6-(1,1,1-trifluoro-4-(methylsulfonyl)butan-2-yl)pyridin-2-yl)-1H-pyrazol-4-yl)pyridine-2,3-diamine

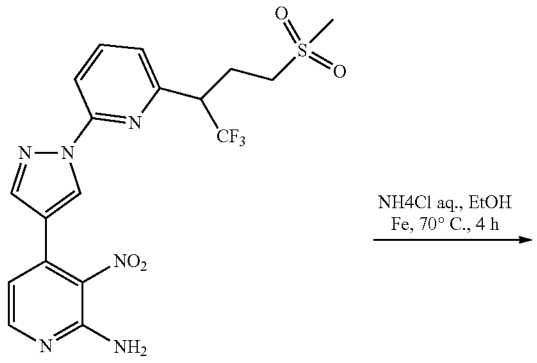

227

229

-continued

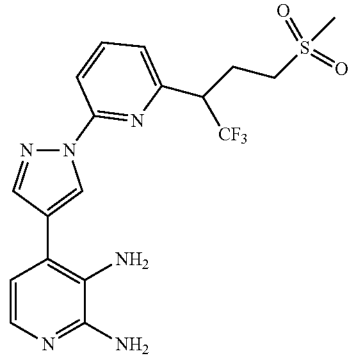

228

To a stirred solution of 4-(1-(6-(1,1,1-trifluoro-4-(methylsulfonyl)butan-2-yl)pyridin-2-yl)-1H-pyrazol-4-yl)-3-nitropyridin-2-amine (0.052 g, 0.11 mmol) in EtOH (7.0 mL), $NH_4Cl$ (2.0 mL) was added at room temperature. To the resultant reaction mixture, Fe powder (0.029 g, 0.55 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 4-(1-(6-(1,1,1-trifluoro-4-(methylsulfonyl)butan-2-yl)pyridin-2-yl)-1H-pyrazol-4-yl)pyridine-2,3-diamine (0.036 g, 75%) as dark brown solid mass.

MS: 441.2 [M+1]

Step-8: Synthesis of 7-(1-(6-(1,1,1-trifluoro-4-(methylsulfonyl)butan-2-yl)pyridin-2-yl)-1H-pyrazol-4-yl)-3H-imidazo[4,5-b]pyridine

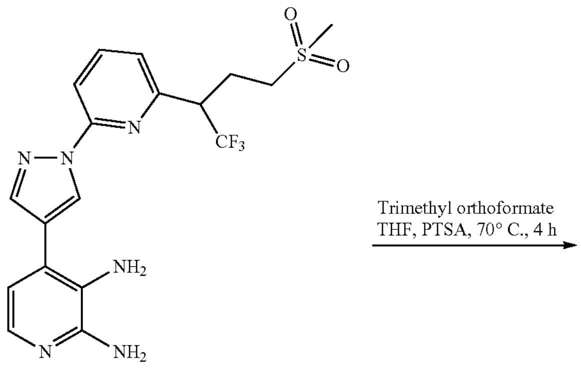

-continued

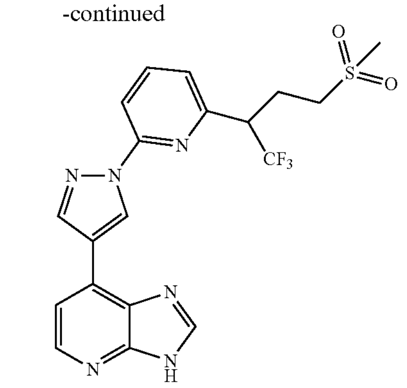

1175

To a stirred solution of 4-(1-(6-(1,1,1-trifluoro-4-(methylsulfonyl)butan-2-yl)pyridin-2-yl)-1H-pyrazol-4-yl)pyridine-2,3-diamine (0.035 g, 0.079 mmol) in THF (1.0 mL), Trimethyl orthoformate (1.5 mL) was added. To resultant reaction mixture, PTSA (0.0027 g, 0.015 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained 7-(1-(6-(1,1,1-trifluoro-4-(methylsulfonyl)butan-2-yl)pyridin-2-yl)-1H-pyrazol-4-yl)-3H-imidazo[4,5-b]pyridine (0.021 g, 60%) as off white solid.

MS: 451.1 [M+1]

Synthesis of Compound No. 1176: 7-(1-(4-(1,1,1-trifluoro-4-(methylsulfonyl)butan-2-yl)pyridin-2-yl)-1H-pyrazol-4-yl)-3H-imidazo[4,5-b]pyridine

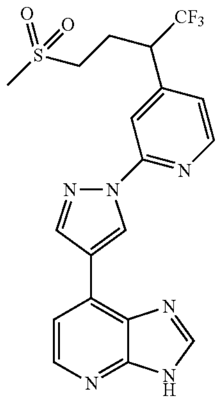 [SMILES: CS(=O)(=O)CCC(c1ccnc(-n2cc(-c3ccnc4[nH]cnc34)cn2)c1)C(F)(F)F]

Step-1: Synthesis of 1-(2-bromopyridin-4-yl)-2,2,2-trifluoroethanone

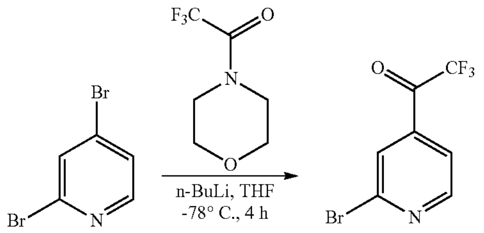

230 231

To a stirred solution of 2,4-dibromopyridine (5.0 g, 2.12 mmol) in THF (50 mL) at −78° C. was added n-Butyl lithium (2.5M in hexane) (12.5 mL, 3.18 mmol) under nitrogen and stirred for 1 h at same temperature. 2,2,2-trifluoro-1-morpholinoethanone (5.06 g, 2.76 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 18% ethyl acetate in hexane as eluent to obtain 1-(2-bromopyridin-4-yl)-2,2,2-trifluoroethanone (3.5 g, 64.81%) as colourless oil.

Step-2: Synthesis of (E/Z)-ethyl 3-(2-bromopyridin-4-yl)-4,4,4-trifluorobut-2-enoate

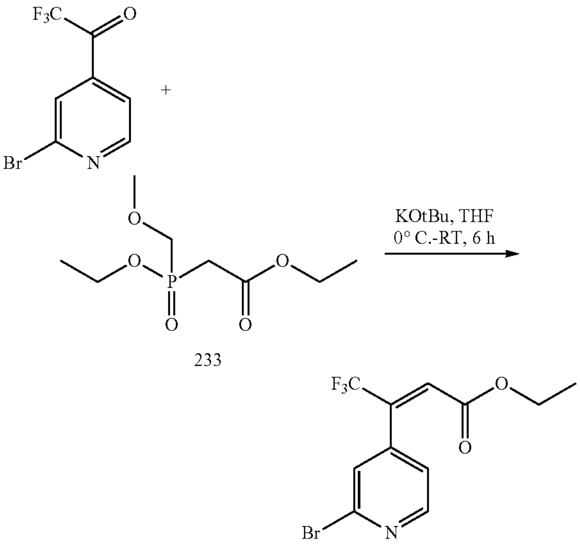

233

234

To a stirred solution of Triethyl phosphonoacetate (3.9 g, 1.77 mmol) and THE (60 ml) at 0° C. under $N_2$ added base potassium ter-butoxide (1.98 g, 1.77 mmol) lotwise. The resultant mixture was stirred at RT for 1 h for anion generation. A solution of 1-(2-bromopyridin-4-yl)-2,2,2-trifluoroethanone (3.0 g, 1.18 mmol) in THE (15 ml) was added slowly. After addition stirred mixture for 6 h at RT. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 9 to 15% EA/Hexane to obtained (E/Z)-ethyl 3-(2-bromopyridin-4-yl)-4,4,4-trifluorobut-2-enoate (1.5 g, 40%) as yellow oil.

MS: 324 [M+1]

Step-3: Synthesis of 3-(2-bromopyridin-4-yl)-4,4,4-trifluorobutan-1-ol

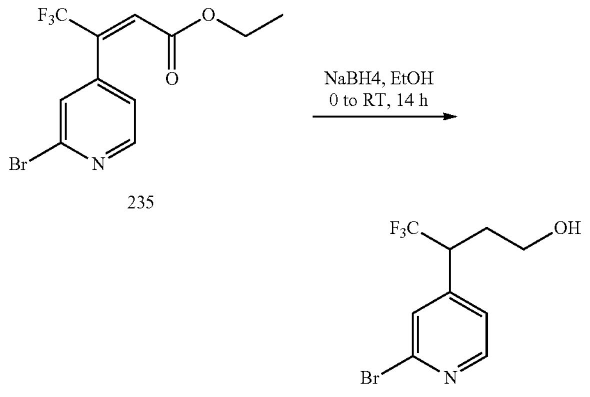

235

236

To a stirred solution of (E/Z)-ethyl 3-(6-bromopyridin-3-yl)-4,4,4-trifluorobut-2-enoate (1.5 g, 462 mmol) in EtOH (30 mL), $NaBH_4$ (0.520 g, 1380 mmol) was added at 0° C. Reaction was allowed to stir at room temperature for 14 h. Reaction was monitored by TLC. On completion, reaction was quenched with water, extracted with EtOAc. The organic layer was washed with water, dried over $Na_2SO_4$, evaporated under reduced pressure to obtain crude reaction mass. Purification of the crude was done via silica gel (100-200 Mesh) column chromatography and desired compound eluted at 30% ethyl acetate/n-Hexane to obtained 3-(2-bromopyridin-4-yl)-4,4,4-trifluorobutan-1-ol (0.610 g, 46.5%) as clear oil.

MS: 284 [M+1]

Step-4: Synthesis of 3-(2-(4-(2-amino-3-nitropyridin-4-yl)-1H-pyrazol-1-yl)pyridin-4-yl)-4,4,4-trifluorobutan-1-ol

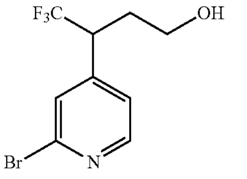

237

+

-continued

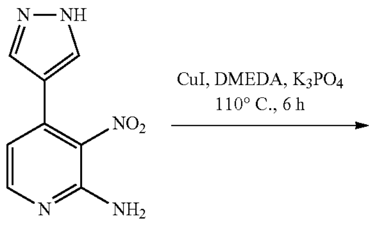

238

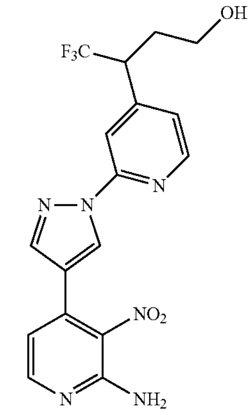

239

To a stirred solution of 3-nitro-4-(1H-pyrazol-4-yl)pyridin-2-amine (0.253 g, 123 mmol) and compound 3-(2-bromopyridin-4-yl)-4,4,4-trifluorobutan-1-ol (0.350 g, 123 mmol) in Dioxane (5 ml) was added $K_3PO_4$ (0.521 g, 246 mmol) followed by CuI (0.046 g, 0.246 mmol) and DMEDA (0.216 g, 246 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 6-7% MeOH in DCM to obtained 3-(2-(4-(2-amino-3-nitropyridin-4-yl)-1H-pyrazol-1-yl)pyridin-4-yl)-4,4,4-trifluorobutan-1-ol (0.250 g, 50%) as yellow solid.

MS: 409.1 [M+1]

Step-5: Synthesis of 4-(1-(4-(4-bromo-1,1,1-trifluorobutan-2-yl)pyridin-2-yl)-1H-pyrazol-4-yl)-3-nitropyridin-2-amine

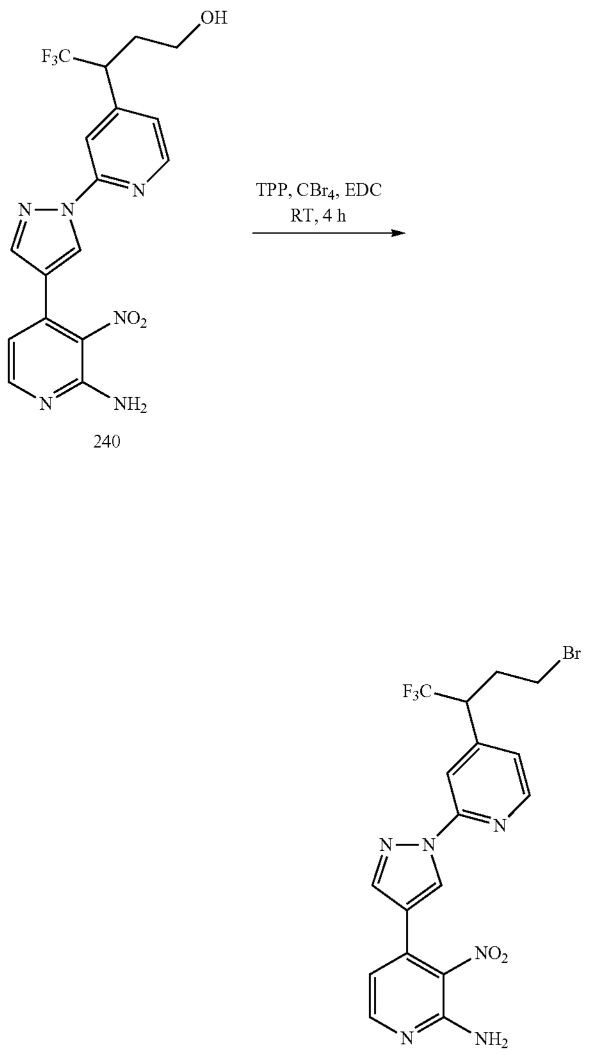

240

241

To a stirred solution of 3-(2-(4-(2-amino-3-nitropyridin-4-yl)-1H-pyrazol-1-yl)pyridin-4-yl)-4,4,4-trifluorobutan-1-ol (0.120 g, 0.29 mmol) in DCE (10 mL), TPP (0.115 g, 0.44 mmol) was added and then added carbontetrabromide (0.145 g, 0.44 mmol) portion-wise at 0° C. The resultant reaction mixture was stirred at room temperature for 7 h. Completion of reaction was monitored by TLC. After completion reaction mass was quenched with ice cold water. Phases separated and aqueous layer was extracted with DCM. The organic layer was washed with brine, dried over sodium sulphate and concentrated under reduced pressure. Crude product was purified by silica gel (100-200 mesh) column chromatography using 2 to 3% methanol in DCMA as eluent to obtain 4-(1-(4-(4-bromo-1,1,1-trifluorobutan-2-yl)pyridin-2-yl)-1H-pyrazol-4-yl)-3-nitropyridin-2-amine (0.065 g, 47.05%) as yellow solid.

MS: 471.1 [M+1]

Step-6: Synthesis of 4-(1-(4-(1,1,1-trifluoro-4-(methylsulfonyl)butan-2-yl)pyridin-2-yl)-1H-pyrazol-4-yl)-3-nitropyridin-2-amine

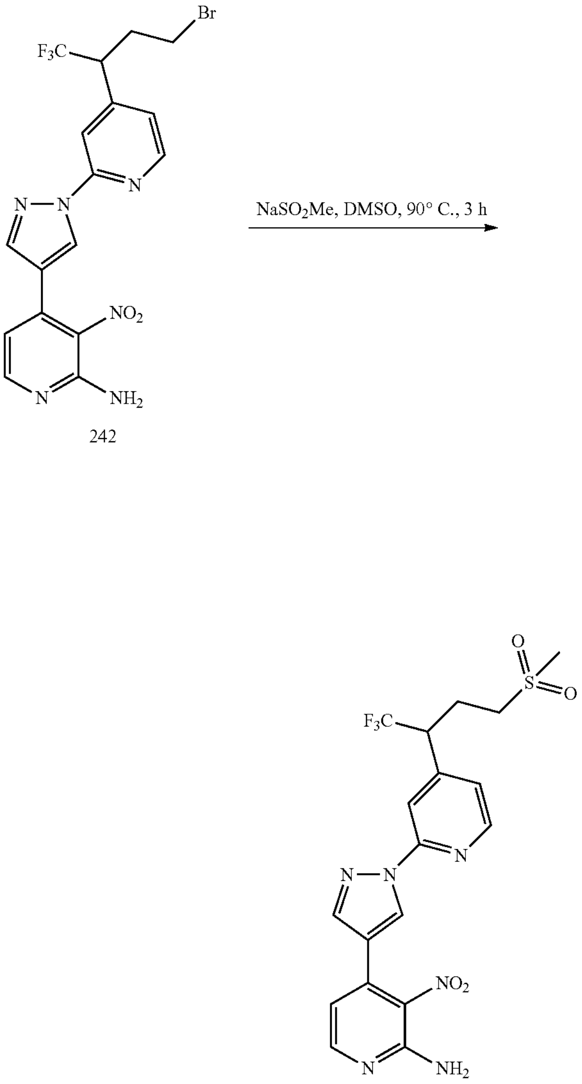

242

243

To a stirred solution of 4-(1-(4-(4-bromo-1,1,1-trifluorobutan-2-yl)pyridin-2-yl)-1H-pyrazol-4-yl)-3-nitropyridin-2-amine (0.065 g, 0.130 mmol) in DMSO (3.0 mL), sodium mathanesulfinate (0.027 g, 0.20 mmol) was added. To resultant reaction mixture was added stirred for 3 h at 90° C. Completion of reaction was monitored by TLC. On completion, quenched with bicarbonate water, extracted with ethyl acetate. The organic layer was washed with water, brine, dried over sodium sulphate and concentrated under reduced pressure to give crude desired product that was purified by silica gel (100 to 200 Mesh) column chromatography: eluent at 6 to 7% MeOH/DCM to obtained 4-(1-(4-(1,1,1-trifluoro-4-(methylsulfonyl)butan-2-yl)pyridin-2-yl)-1H-pyrazol-4-yl)-3-nitropyridin-2-amine (0.052 g, 81.20%) as yellow solid.

MS: 471[M+1]

Step-7: Synthesis of 4-(1-(4-(1,1,1-trifluoro-4-(methylsulfonyl)butan-2-yl)pyridin-2-yl)-1H-pyrazol-4-yl)pyridine-2,3-diamine

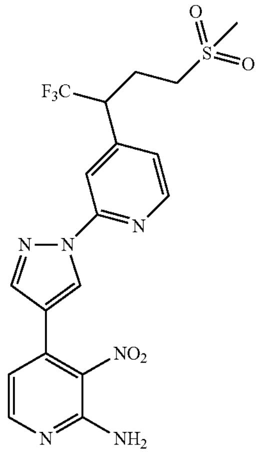

244

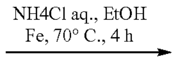

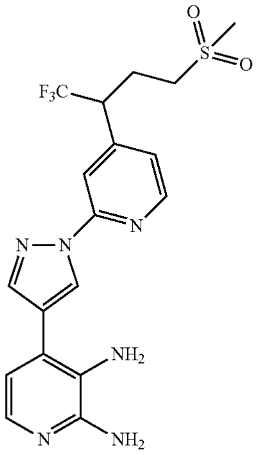

245

To a stirred solution of 4-(1-(4-(1,1,1-trifluoro-4-(methylsulfonyl)butan-2-yl)pyridin-2-yl)-1H-pyrazol-4-yl)-3-nitropyridin-2-amine (0.052 g, 0.11 mmol) in EtOH (7.0 mL), $NH_4Cl$ (2.0 mL) was added at room temperature. To the resultant reaction mixture, Fe powder (0.029 g, 0.55 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 4-(1-(4-(1,1,1-trifluoro-4-(methylsulfonyl)butan-2-yl)pyridin-2-yl)-1H-pyrazol-4-yl)pyridine-2,3-diamine (0.036 g, 75%) as dark brown solid mass.

MS: 441.2 [M+1]

Step-8: Synthesis of 7-(1-(4-(1,1,1-trifluoro-4-(methylsulfonyl)butan-2-yl)pyridin-2-yl)-1H-pyrazol-4-yl)-3H-imidazo[4,5-b]pyridine

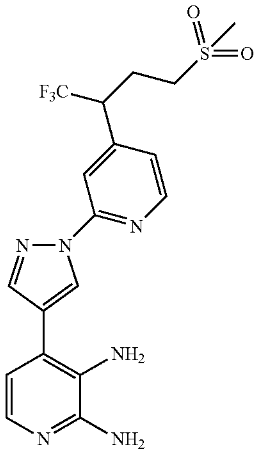

246

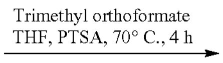

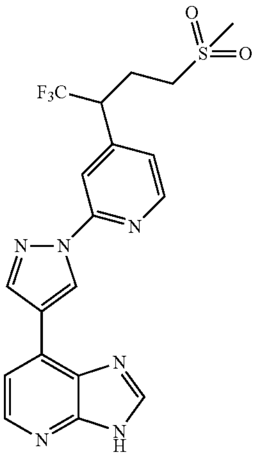

1176

To a stirred solution of 4-(1-(5-(1,1,1-trifluoro-4-(methylsulfonyl)butan-2-yl)pyridin-2-yl)-1H-pyrazol-4-yl)pyridine-2,3-diamine ((0.035 g, 0.079 mmol) in THE (1.0 mL), Trimethyl orthoformate (1.5 mL) was added. To resultant reaction mixture, PTSA (0.0027 g, 0.015 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained 7-(1-(4-(1,1,1-trifluoro-4-(methylsulfonyl)butan-2-yl)pyridin-2-yl)-1H-pyrazol-4-yl)-3H-imidazo[4,5-b]pyridine (0.021 g, 60%) as off white solid.

MS: 451.1 [M+1]

Synthesis of Compound No. 1178: 1-(1-(6-(4-(3H-imidazo[4,5-b]pyridin-7-yl)-1H-Pyrazol-1-yl)pyridin-3-yl)-2,2,2-trifluoroethyl)-3-cyclopropylurea

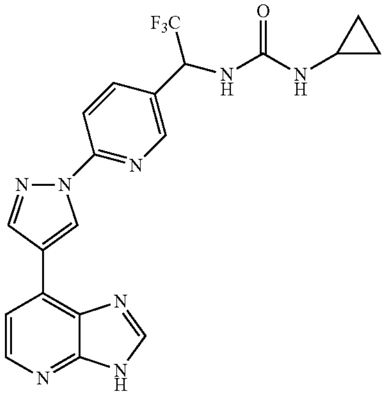 [SMILES: O=C(NC1CC1)NC(c1ccc(-n2cc(-c3ccnc4[nH]cnc34)cn2)nc1)C(F)(F)F]

Step-1: Synthesis of 4-nitrophenyl cyclopropylcarbamate

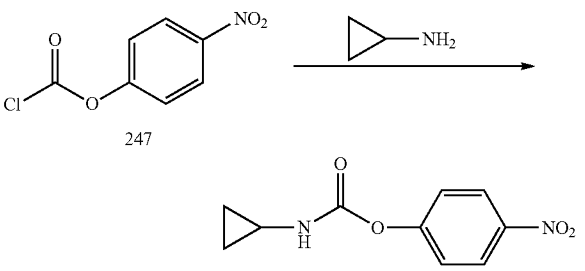

247

248

To a stirred solution of cyclopropanamine (2.0 g, 3.508 mmol) in DCM (60.0 mL), trimethylamine (5.3 g, 5.26 mmol) was added followed by 4-nitrophenyl chloroformate (9.1 g, 4.55 mmol) at 0° C. The resultant reaction mixture was stirred for 6 h at room temperature. Completion of reaction was monitored by TLC. On completion solid fall out was directly filtered on buckner and then washed with DCM to obtained pure product (1.2 g, 15.58%) as white solid

MS: 223 [M+1]

Step-2: Synthesis of 1-(6-bromopyridin-3-yl)-2,2,2-trifluoroethanamine

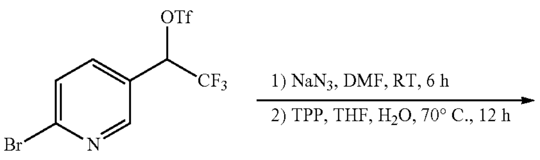

249

-continued

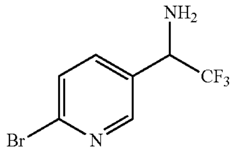

250

To a stirred solution of 1-(6-bromopyridin-3-yl)-2,2,2-trifluoroethyl trifluoromethanesulfonate (0.650 g, 0.167 mmol) in DMF (5 ml) was added sodium azide (0.108 g, 0.167 mmol) at room temperature. Stirred reaction mixture at same temperature for 6 h. On completion reaction mixture was quenched with water and extracted with ethyl acetate. The organic layer was washed with water, brine, dried over sodium sulphate and concentrated under reduced pressure to give pure intermediate. To solution of Azide intermediate (0.550 g, 0.192 mmol) was added TPP (0.512 g, 0.192 mmol) in THF:$H_2O$ (8:2 ml) at RT and then stirring continued at 60° C. for 12 h. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 20-30% acetone in hexane to obtained 1-(6-bromopyridin-3-yl)-2,2,2-trifluoroethanamine (0.160 g, 32%) as yellow oil.

MS: 255.1 [M+1]

Step-3: Synthesis 1-(1-(6-bromopyridin-3-yl)-2,2,2-trifluoroethyl)-3-cyclopropylurea

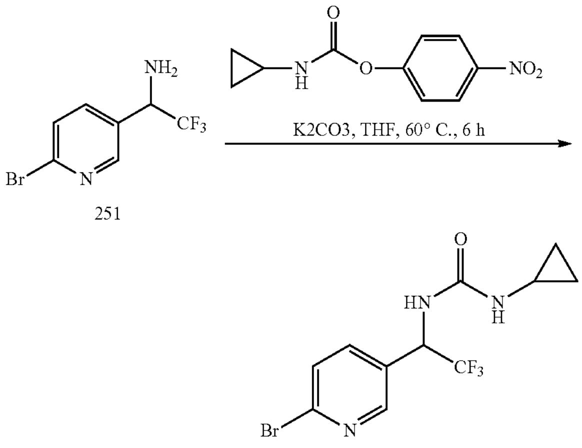

251

252

To a stirred solution of 1-(6-bromopyridin-3-yl)-2,2,2-trifluoroethanamine (0.200 g, 0.078 mmol) in THE (10.0 mL), potassium carbonate (0.107 g, 0.078 mmol) was added followed by 4-nitrophenyl cyclopropylcarbamate (0.248 g, 0.011 mmol). The resultant reaction mixture was stirred for 6 h at 60° C. Completion of reaction was monitored by TLC. On completion, quenched with water, extracted with ethyl acetate. The combined organic layer was washed with water, brine, dried over sodium sulphate and concentrated under reduced pressure to give crude desired product that was purified by silica gel (100 to 200 Mesh) column chromatography: eluent at 15 to 20% Acetone/Hexane to obtained (0.120 g, 50.84%) as white solid.

MS: 338[M+1]

Step-4: Synthesis of 1-(1-(6-(4-(2-amino-3-nitropyridin-4-yl)-1H-pyrazol-1-yl)pyridin-3-yl)-2,2,2-trifluoroethyl)-3-cyclopropylurea

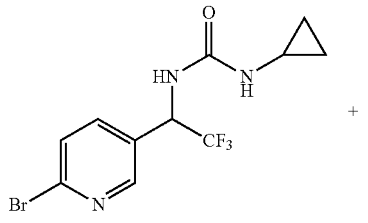

253

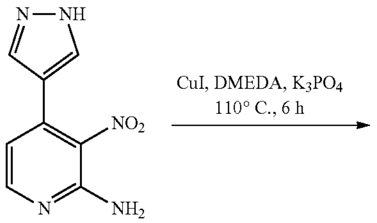

254

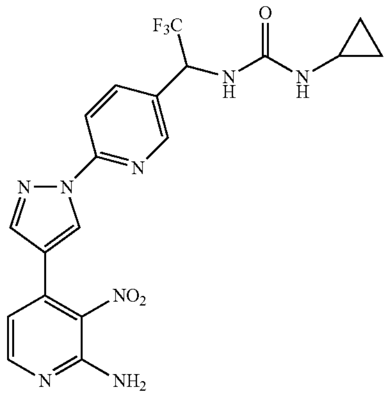

255

To a stirred solution of 3-nitro-4-(1H-pyrazol-4-yl)pyridin-2-amine (0.090 g, 0.0443 mmol) and compound 1-(1-(6-bromopyridin-3-yl)-2,2,2-trifluoroethyl)-3-cyclopropylurea (0.150 g, 0.0443 mmol) in Dioxane (5 ml) was added $K_3PO_4$ (0.122 g, 0.0886 mmol) followed by CuI (0.016 g, 0.00886 mmol) and DMEDA (0.077 g, 0.0886 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 9-10% MeOH in DCM to obtained 1-(1-(6-(4-(2-amino-3-nitropyridin-4-yl)-1H-pyrazol-1-yl)pyridin-3-yl)-2,2,2-trifluoroethyl)-3-cyclopropylurea (0.090 g, 45%) as yellow solid.

MS: 463.1 [M+1]

Step-5: Synthesis 1-(1-(6-(4-(2,3-diaminopyridin-4-yl)-1H-pyrazol-1-yl)pyridin-3-yl)-2,2,2-trifluoroethyl)-3-cyclopropylurea

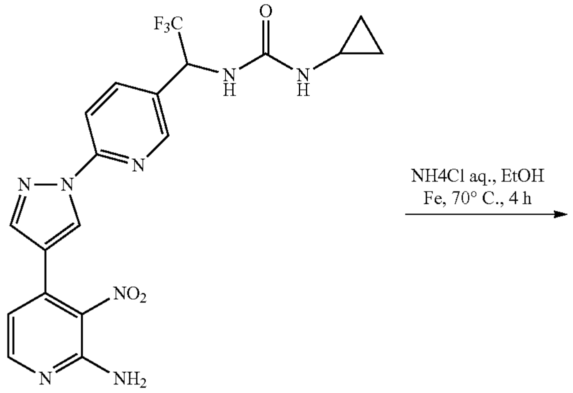

256

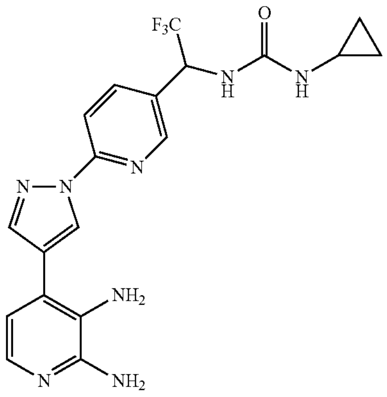

257

To a stirred solution of 1-(1-(6-(4-(2-amino-3-nitropyridin-4-yl)-1H-pyrazol-1-yl)pyridin-3-yl)-2,2,2-trifluoroethyl)-3-cyclopropylurea (0.085 g, 0.0183 mmol) in EtOH (7.0 mL), $NH_4Cl$ (2.0 mL) was added at room temperature. To the resultant reaction mixture, Fe powder (0.048 g, 0.0919 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 1-(1-(6-(4-(2,3-diaminopyridin-4-yl)-1H-pyrazol-1-yl)pyridin-3-yl)-2,2,2-trifluoroethyl)-3-cyclopropylurea (0.045 g, 56.96%) as dark brown solid mass.

MS: 433.2 [M+1]

Step-6: Synthesis of 1-(1-(6-(4-(3H-imidazo[4,5-b]pyridin-7-yl)-1H-pyrazol-1-yl)pyridin-3-yl)-2,2,2-trifluoroethyl)-3-cyclopropylurea

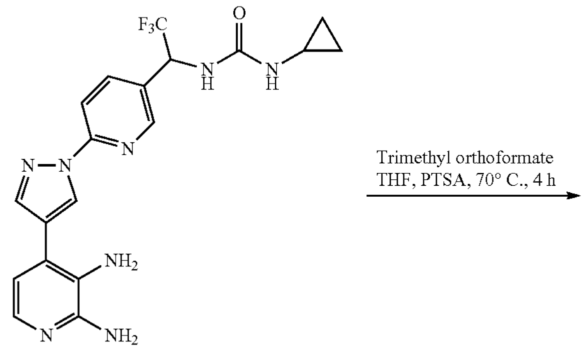

258

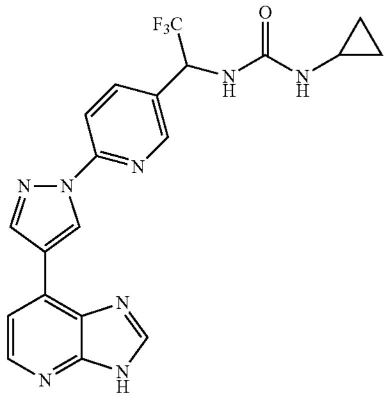

1178

To a stirred solution of 1-(1-(6-(4-(2,3-diaminopyridin-4-yl)-1H-pyrazol-1-yl)pyridin-3-yl)-2,2,2-trifluoroethyl)-3-cyclopropylurea ((0.045 g, 0.0104 mmol) in THE (1.0 mL), Trimethyl orthoformate (1.5 mL) was added. To resultant reaction mixture, PTSA (0.0035 g, 0.0020 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 10 to 11% MeOH in DCM to obtained 1-(1-(6-(4-(3H-imidazo[4,5-b]pyridin-7-yl)-1H-pyrazol-1-yl)pyridin-3-yl)-2,2,2-trifluoroethyl)-3-cyclopropylurea (0.023 g, 51%) as off white solid.

MS: 443.1 [M+1]

Synthesis of Compound No. 1179: 1-(3-(6-(4-(3H-imidazo[4,5-b]pyridin-7-yl)-1H-Pyrazol-1-yl)pyridin-3-yl)-4,4,4-trifluorobutyl)-3-cyclopropylurea

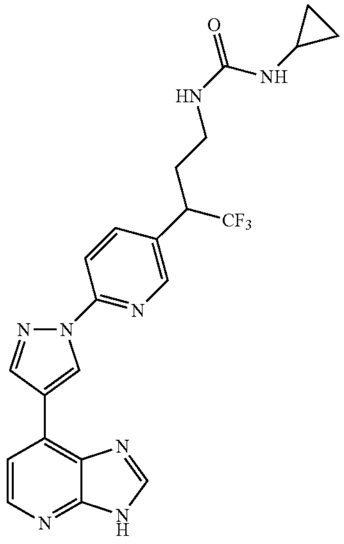 [SMILES: O=C(NCCC(c1ccc(-n2cc(-c3ccnc4[nH]cnc34)cn2)nc1)C(F)(F)F)NC1CC1]

Step-1: Synthesis of 1-(3-(6-bromopyridin-3-yl)-4,4,4-trifluorobutyl)-3-cyclopropylurea

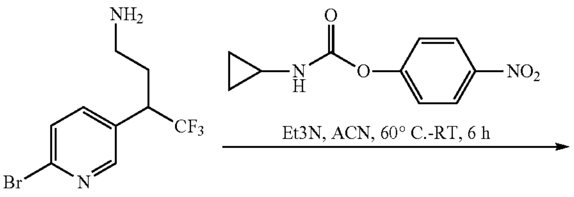

259

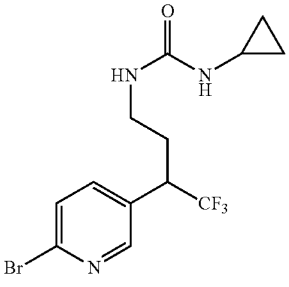

260

To a stirred solution of 3-(6-bromopyridin-3-yl)-4,4,4-trifluorobutan-1-amine (0.130 g, 0.045 mmol) in ACN (10.0 mL), trimethylamine (0.136 g, 0.135 mmol) was added followed by 4-nitrophenyl cyclopropylcarbamate (0.152 g, 0.068 mmol). The resultant reaction mixture was stirred for 6 h at 60° C. Completion of reaction was monitored by TLC. On completion, quenched with water, extracted with ethyl acetate. The combined organic layer was washed with water, brine, dried over sodium sulphate and concentrated under reduced pressure to give crude desired product that was purified by silica gel (100 to 200 Mesh) column chromatography: eluent at 25 to 30% Acetone/Hexane to obtained (0.140 g, 83.83%) as sticky oil.

MS: 367[M+2]

Step-2: Synthesis of 1-(3-(6-(4-(2-amino-3-nitropyridin-4-yl)-1H-pyrazol-1-yl)pyridin-3-yl)-4,4,4-trifluorobutyl)-3-cyclopropylurea

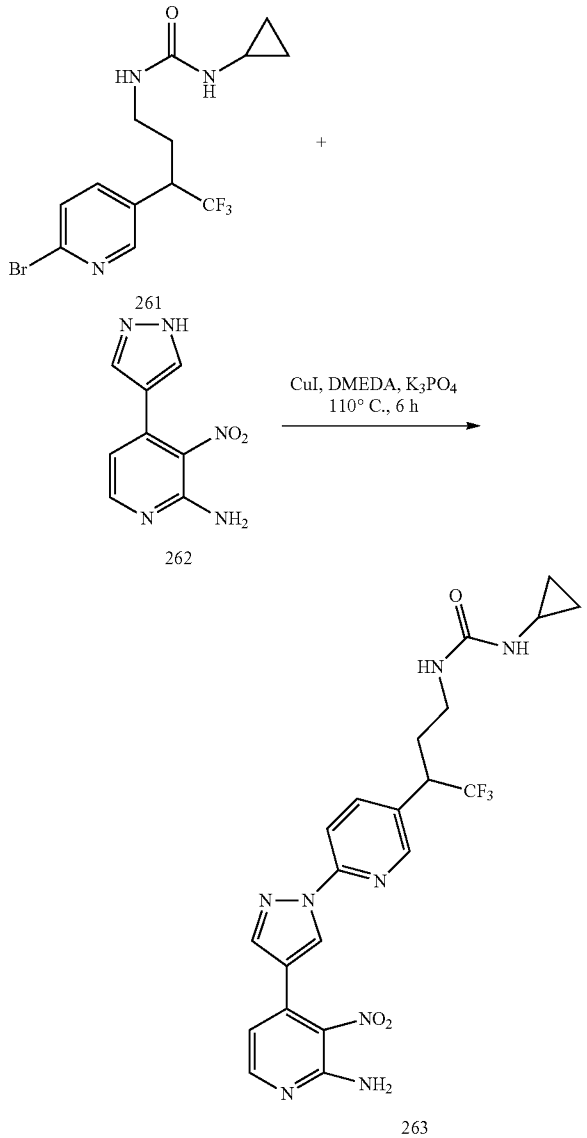

261

262

263

To a stirred solution of 3-nitro-4-(1H-pyrazol-4-yl)pyridin-2-amine (0.073 g, 0.0356 mmol) and compound 1-(3-(6-bromopyridin-3-yl)-4,4,4-trifluorobutyl)-3-cyclopropylurea_(0.130 g, 0.0356 mmol) in Dioxane (5 ml) was added $K_3PO_4$ (0.150 g, 0.0712 mmol) followed by CuI (0.013 g, 0.00712 mmol) and DMEDA (0.062 g, 0.0712 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 7-8% MeOH in DCM to obtained 1-(3-(6-(4-(2-amino-3-nitropyridin-4-yl)-1H-pyrazol-1-yl)pyridin-3-yl)-4,4,4-trifluorobutyl)-3-cyclopropylurea (0.080 g, 45.97%) as yellow solid.

MS: 491.1 [M+1]

Step-3: Synthesis 1-(3-(6-(4-(2,3-diaminopyridin-4-yl)-1H-pyrazol-1-yl)pyridin-3-yl)-4,4,4-trifluorobutyl)-3-cyclopropylurea

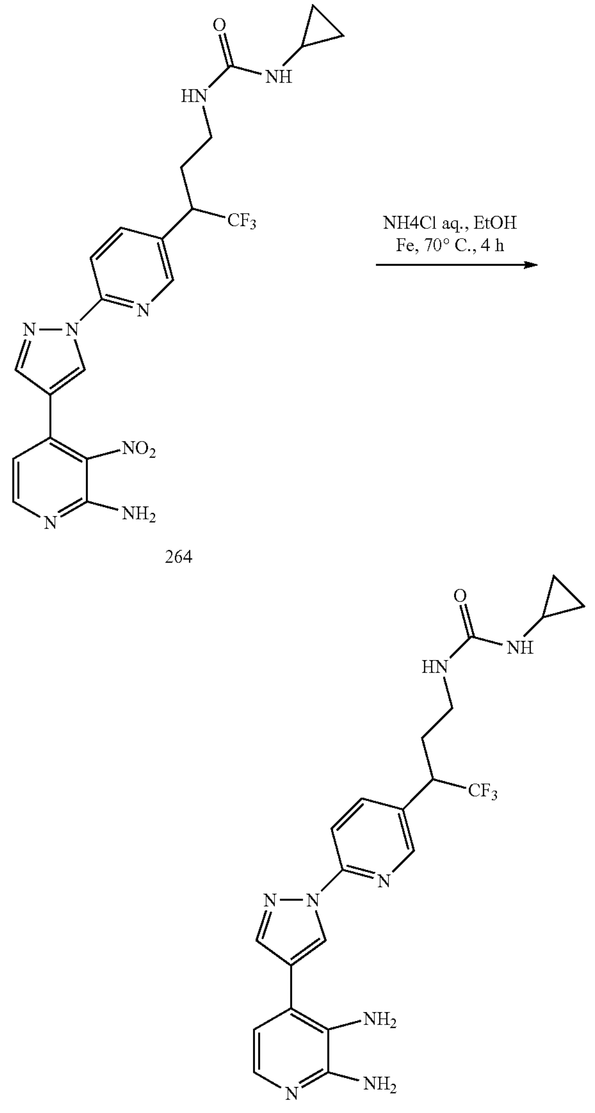

264

265

To a stirred solution of 1-(3-(6-(4-(2-amino-3-nitropyridin-4-yl)-1H-pyrazol-1-yl)pyridin-3-yl)-4,4,4-trifluorobutyl)-3-cyclopropylurea (0.060 g, 0.0122 mmol) in EtOH (7.0 mL), $NH_4Cl$ (2.0 mL) was added at room temperature. To the resultant reaction mixture, Fe powder (0.032 g, 0.0612 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 1-(3-(6-(4-(2,3-diamino-pyridin-4-yl)-1H-pyrazol-1-yl)pyridin-3-yl)-4,4,4-trifluorobutyl)-3-cyclopropylurea (0.042 g, 75%) as dark brown solid mass.

MS: 461.2 [M+1]

Step-4: Synthesis of 1-(3-(6-(4-(3H-imidazo[4,5-b]pyridin-7-yl)-1H-pyrazol-1-yl)pyridin-3-yl)-4,4,4-trifluorobutyl)-3-cyclopropylurea

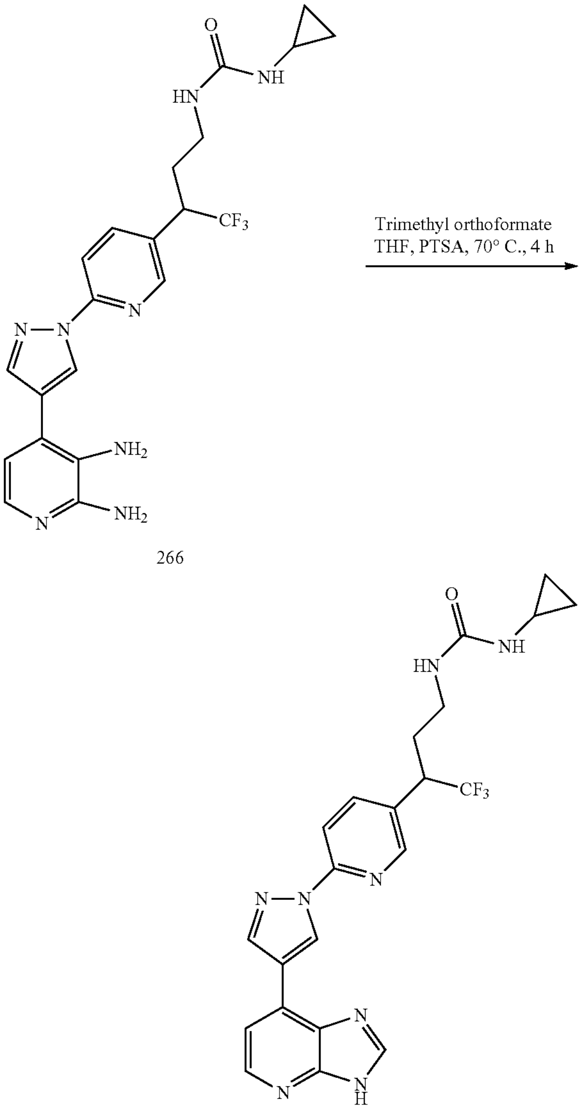

266

1179

To a stirred solution of 1-(3-(6-(4-(2,3-diaminopyridin-4-yl)-1H-pyrazol-1-yl)pyridin-3-yl)-4,4,4-trifluorobutyl)-3-cyclopropylurea ((0.042 g, 0.0091 mmol) in THF (1.0 mL), Trimethyl orthoformate (1.5 mL) was added. To resultant reaction mixture, PTSA (0.0031 g, 0.0018 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained 1-(3-(6-(4-(3H-imidazo[4,5-b]pyridin-7-yl)-1H-pyrazol-1-yl)pyridin-3-yl)-4,4,4-trifluorobutyl)-3-cyclopropylurea (0.021 g, 48.83%) as off white solid.

MS: 471.1 [M+1]

Synthesis of Compound No. 1075: 2-(2-(4-(3H-imidazo[4,5-b]pyridin-7-yl)-1H-pyrazol-1-yl)oxazol-4-yl)acetonitrile

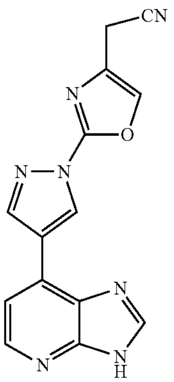 [SMILES: N#CCc1coc(-n2cc(-c3ccnc4[nH]cnc34)cn2)n1]

Step-1: Synthesis of ethyl 2-aminooxazole-4-carboxylate

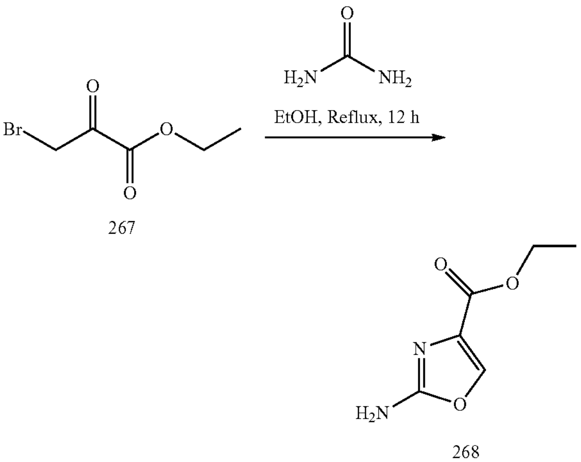

267

268

To a stirred solution of ethyl 3-bromo-2-oxopropanoate (1.0 g, 5.128 mmol) in ethanol (20 mL), urea (0.462 g, 7.692 mmol) was added at room temperature. The resultant reaction mixture was stirred at reflux temperature for overnight. Completion of reaction was monitored by TLC. On completion, quenched with ice water, extracted with ethyl acetate. The organic layer was washed with water, brine, dried over sodium sulphate, concentrated under reduced pressure obtained crude reaction mass. Purification of the crude was done via silica gel (100-200 Mesh) column chromatography and desired compound eluted at 40% ethyl acetate/n-Hexane to obtained ethyl 2-aminooxazole-4-carboxylate (0.700 g, 87.5%) as cream colour solid.

MS: 157.2 [M+1]

Step-2: Synthesis of ethyl 2-chlorooxazole-4-carboxylate

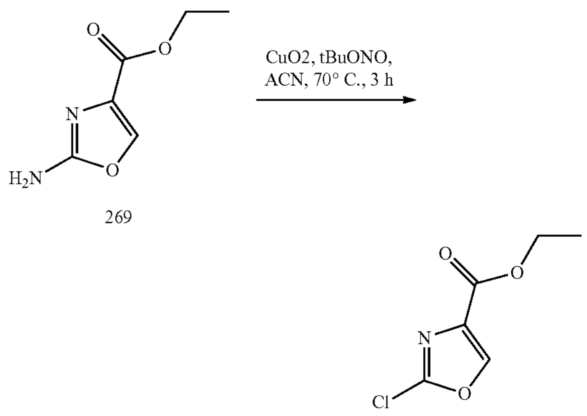

269

270

To a stirred solution of $CuCl_2$ (1.29 g, 9.609 mmol) in ACN (20 mL), ter-butylnitrile (0.991 g, 9.609 mmol) was added at room temperature. To resultant reaction mass was heated at 65° C. Added compound ethyl 2-aminooxazole-4-carboxylate (1.0 g, 6.406 mmol) was added portion wise at 65° C. and stirring continued for 2 h. Completion of reaction was monitored by TLC. Reaction mixture was cooled to 0° C. and acidify with 6N HCl and extracted with ether. The organic layer was washed with water, brine, dried over sodium sulphate, concentrated under reduced pressure to obtained crude reaction mass. Purification of the crude was done via silica gel (100-200 Mesh) column chromatography and desired compound eluted at 18% ethyl acetate/n-Hexane to obtained ethyl 2-chlorooxazole-4-carboxylate (0500 g, 44.6%) as brown solid.

MS: 176 [M+1]

Step-3: Synthesis of (2-chlorooxazol-4-yl) methanol

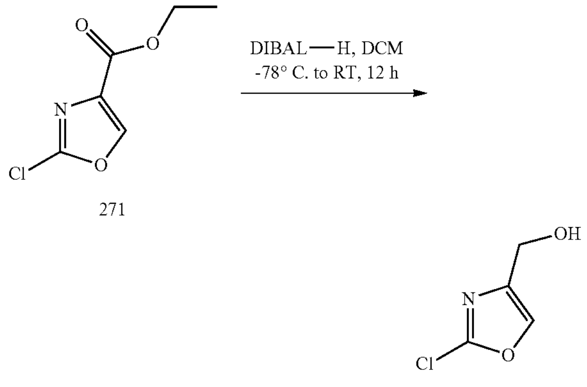

271

272

To a stirred solution of ethyl 2-chlorooxazole-4-carboxylate (0.400 g, 2.271 mmol) in DCM (10 mL) cooled it to −78° C. under inert condition. Added DIBAL-H (3.4 ml, 3.410 mmol) at −78° C. and stirring continued for 1 h for same temperature. After that stirred it at room temperature for 16 h. Completion of reaction was monitored by TLC. Reaction mixture was quenched with crushed ice, followed by 1N HCl, extracted with ether. The organic layer was washed with water, brine, dried over sodium sulphate, concentrated under reduced pressure to obtained crude (2-chlorooxazol-4-yl)methanol (0.250 g, 82.5%) as yellow liquid, which is used as such for next step.

MS: 134.1[M+1]

Step-4: Synthesis of (2-chlorooxazol-4-yl)methyl methanesulfonate

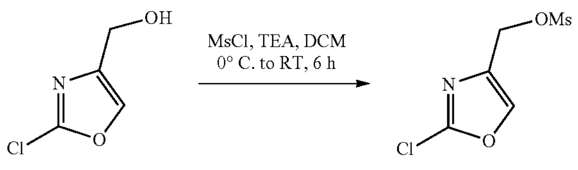

273

274

To a stirred solution of (2-chlorooxazol-4-yl) methanol (0.10 g, 0.749 mmol) in DCM (10 mL), base triethylamine (0.114 g, 1.123 mmol) was added at room temperature and cooled it to 0° C. Added mesyl chloride (0.103 g, 0.898 mmol) dropwise at 0° C. and stirring continued for 6 h. Completion of reaction was monitored by TLC. On completion, quenched with water, extracted with DCM. Combine organic layer was dried over sodium sulphate, concentrated under reduced pressure obtained pure (2-chlorooxazol-4-yl) methyl methanesulfonate (0.155 g, 97.77%) as off white solid.

MS: 211.1 [M+1]

Step-5: Synthesis of 2-(2-chlorooxazol-4-yl)acetonitrile

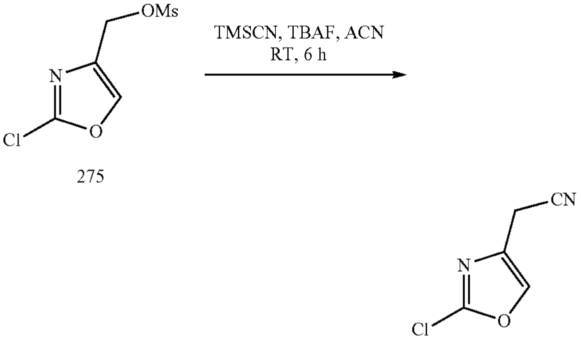

275

276

To a stirred solution of (2-chlorooxazol-4-yl)methyl methanesulfonate (0.500 g, 2.362 mmol) in ACN (10 mL), TBAF 1M in THE (4.72 ml, 4.725 mmol) was added at room temperature and then added TMSCN (0.469 g, 4.725 mmol). Stirred resultant reaction mixture for 6 h at room temperature. Completion of reaction was monitored by TLC. On completion, quenched with water, extracted with ethyl acetate, dried over sodium sulphate, concentrated under reduced pressure to obtained crude reaction mass. Purification of the crude was done via silica gel (100-200 Mesh) column chromatography and desired compound eluted at 18% ethyl acetate/n-Hexane to obtained pure 2-(2-chlorooxazol-4-yl)acetonitrile (0.210 g, 62.31%) as white solid.

MS: 143.2 [M+1]

Step-6: Synthesis of 2-(2-(4-(2-amino-3-nitropyridin-4-yl)-1H-pyrazol-1-yl)oxazol-4-yl)acetonitrile

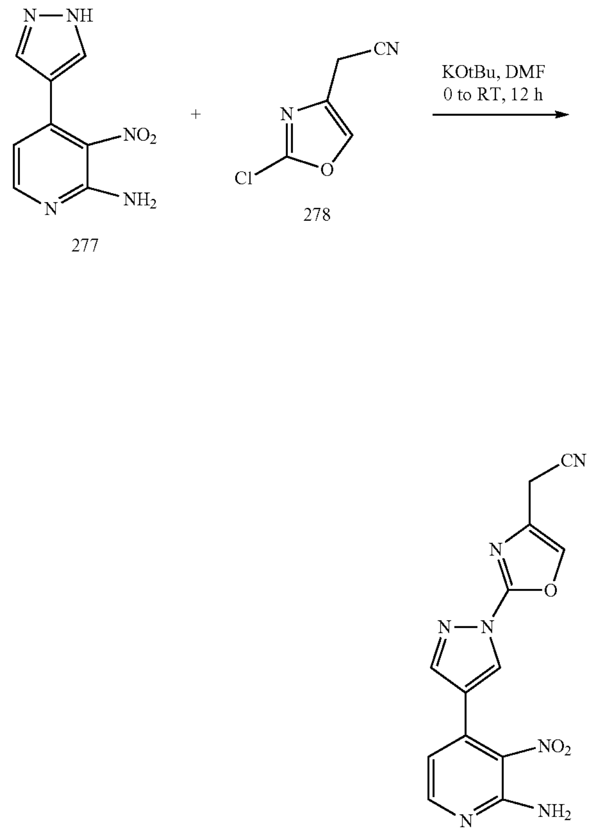

277 278 279

To a stirred solution of 3-nitro-4-(1H-pyrazol-4-yl)pyridin-2-amine (0.040 g, 0.195 mmol), DMF (4 ml), potassium ter-butoxide (0.022 g, 0.195 mmol) and compound 2-(2-chlorooxazol-4-yl)acetonitrile (0.028 g, 0.39 mmol) was added at room temperature. Reaction was heated at 80° C. for 12 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 5-6% MeOH in DCM to obtained 2-(2-(4-(2-amino-3-nitropyridin-4-yl)-1H-pyrazol-1-yl)oxazol-4-yl)acetonitrile (0.030 g, 49.45%) as yellow solid.

MS: 312.1 [M+1]

Step-7 Synthesis of 2-(2-(4-(2,3-diaminopyridin-4-yl)-1H-pyrazol-1-yl)oxazol-4-yl)acetonitrile

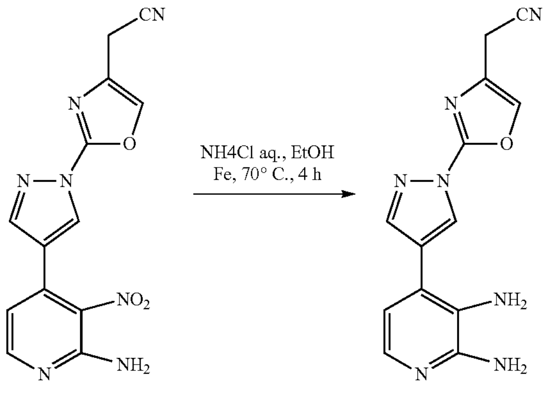

280 281

To a stirred solution of 2-(2-(4-(2-amino-3-nitropyridin-4-yl)-1H-pyrazol-1-yl)oxazol-4-yl)acetonitrile (0.030 g, 0.096 mmol) in EtOH (3.0 mL), $NH_4Cl$ (2.5 mL) was added at room temperature. To resultant reaction mixture, Fe powder (0.017 g, 0.48 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained 2-(2-(4-(2,3-diaminopyridin-4-yl)-1H-pyrazol-1-yl)oxazol-4-yl)acetonitrile (0.025 g, 92%) as dark brown solid mass.

MS: 283.2 [M+1]

Step-8: Synthesis of 2-(2-(4-(3H-imidazo[4,5-b]pyridin-7-yl)-1H-pyrazol-1-yl)oxazol-4-yl)acetonitrile

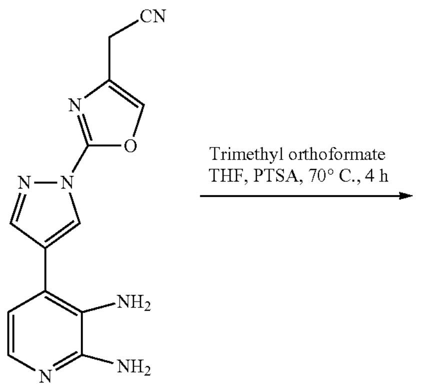

282

-continued

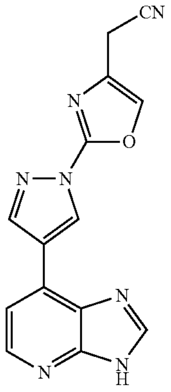

1075

To a stirred solution of 2-(2-(4-(2,3-diaminopyridin-4-yl)-1H-pyrazol-1-yl)oxazol-4-yl)acetonitrile (0.025 g, 0.088 mmol) in THF (1.0 mL), trimethyl orthoformate (1.5 mL) was added. To resultant reaction mixture, PTSA (0.003 g, 0.0017 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 6 to 7% MeOH in DCM to obtained 2-(2-(4-(3H-imidazo[4,5-b]pyridin-7-yl)-1H-pyrazol-1-yl)oxazol-4-yl)acetonitrile (0.011 g, 44%) as off white solid.

MS: 293.1[M+1]

Synthesis of Compound No. 1078: 2-(6-(4-(3H-imidazo[4,5-b]pyridin-7-yl)-1H-pyrazol-1-yl)pyridin-3-yl)acetonitrile

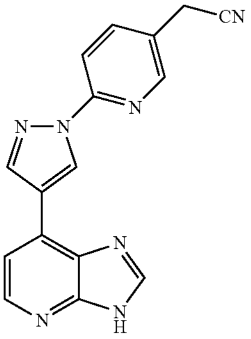 [SMILES: N#CCc1ccc(-n2cc(-c3ccnc4[nH]cnc34)cn2)nc1]

Step-1: Synthesis of (6-(4-(2-amino-3-nitropyridin-4-yl)-1H-pyrazol-1-yl)pyridin-3-yl)methanol

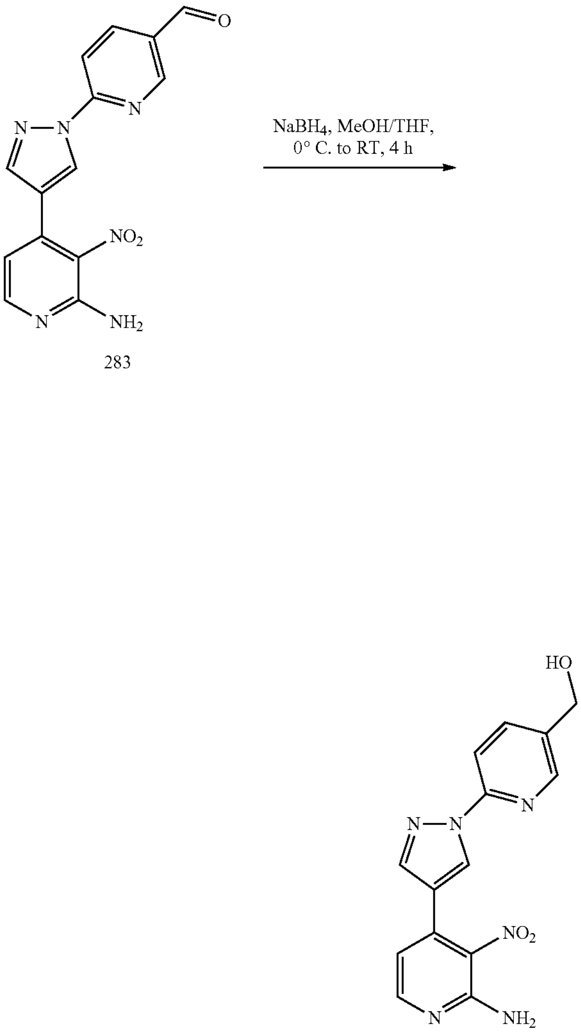

283

284

To a stirred solution of 6-(4-(2-amino-3-nitropyridin-4-yl)-1H-pyrazol-1-yl)pyridine-3-carbaldehyde (0.50 g, 1.612 mmol) in methanol/THF (10 mL, 1:1) was added sodium borohydride (0.069 g, 1.612 mmol) at 0° C. and the mixture was stirred at room temperature for 3 h. Progress of reaction was monitored by TLC. After reaction completion water (10 mL) was added to the reaction mixture and the product extracted with ethyl acetate. The organic layer was dried over sodium sulphate, concentrated under reduced pressure to give (6-(4-(2-amino-3-nitropyridin-4-yl)-1H-pyrazol-1-yl)pyridin-3-yl)methanol (0.5 g, 100%) as yellow solid.

MS: 313.28 [M+1]

Step-2: Synthesis of (6-(4-(2-amino-3-nitropyridin-4-yl)-1H-pyrazol-1-yl)pyridin-3-yl)methyl methanesulfonate

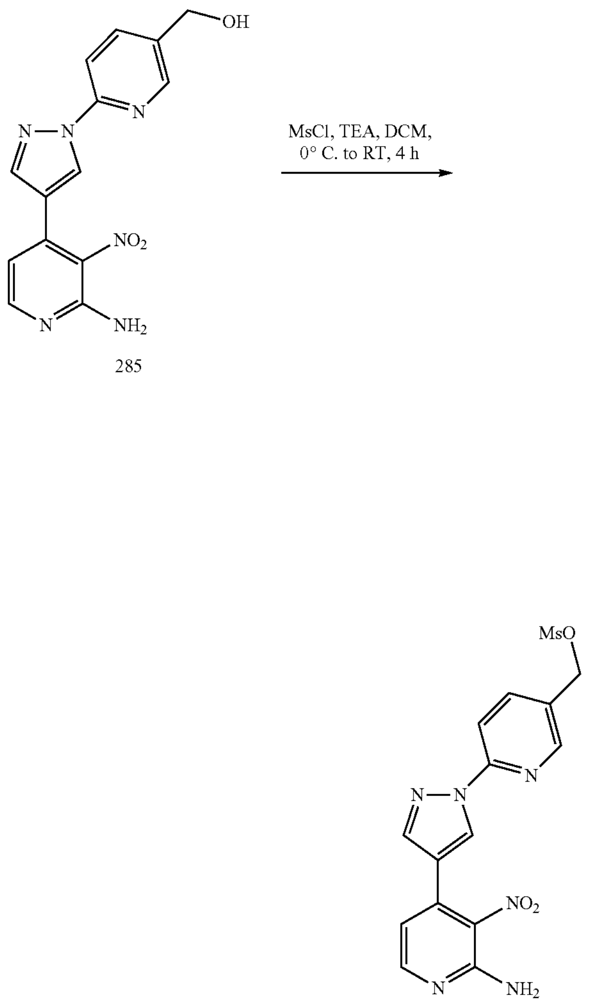

285

286

To a stirred solution of (6-(4-(2-amino-3-nitropyridin-4-yl)-1H-pyrazol-1-yl)pyridin-3-yl)methanol (0.15 g, 0.480 mmol) in DCM (5.0 mL) at 0° C. was added MsCl (0.06 g, 0.528 mmol) under nitrogen. To resultant reaction mixture TEA (0.063 g, 0.629 mmol) solution in DCM (1.0 mL) was added drop wise, stirred for 15 min at 0° C. and then warmed to RT and progress of reaction was monitored by TLC. On completion, quenched with water, extracted with ethyl acetate. Organic layer was dried over sodium sulphate, concentrated under reduced pressure to obtain (6-(4-(2-amino-3-nitropyridin-4-yl)-1H-pyrazol-1-yl)pyridin-3-yl) methyl methanesulfonate (0.19 g, 100%) as crude yellow oily mass.

MS: 391.37 [M+1]

Step-3: Synthesis of 2-(6-(4-(2-amino-3-nitropyridin-4-yl)-1H-pyrazol-1-yl)pyridin-3-yl)acetonitrile

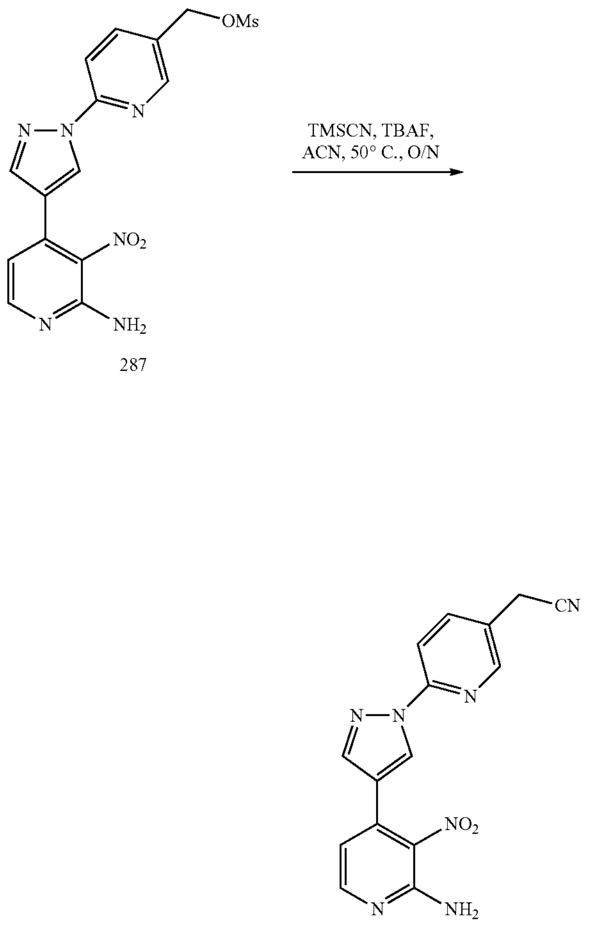

287

288

To a stirred solution of (6-(4-(2-amino-3-nitropyridin-4-yl)-1H-pyrazol-1-yl)pyridin-3-yl)methyl methanesulfonate (0.25 g, 0.641 mmol) in ACN (5 mL) at 0° C. was added TMSCN (0.13 g, 1.282 mmol) under nitrogen followed by TBAF (1M solution in THF, 1.3 mL, 1.282 mmol) and the resulted solution heated overnight at 50° C. Progress of reaction was monitored by TLC. After reaction completion reaction mass was cooled to 0° C. and quenched with 1M HCl. Product was extracted with ethyl acetate. The organic layer was washed with brine, dried over sodium sulphate and concentrated under reduced pressure. Crude was purified by silica gel (100-200 mesh) column chromatography using 1% MeOH/DCM as eluent to obtain 2-(6-(4-(2-amino-3-nitropyridin-4-yl)-1H-pyrazol-1-yl)pyridin-3-yl)acetonitrile (0.08 g, 40%) as yellow oil.

MS: 322.29 [M+1]

Step-4: Synthesis of 2-(6-(4-(2,3-diaminopyridin-4-yl)-1H-pyrazol-1-yl)pyridin-3-yl)acetonitrile

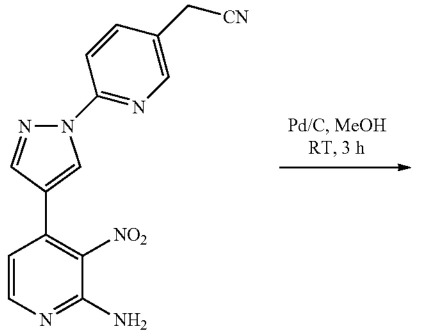

289

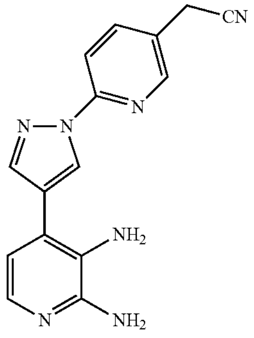

290

To a stirred solution of 2-(6-(4-(2-amino-3-nitropyridin-4-yl)-1H-pyrazol-1-yl)pyridin-3-yl)acetonitrile (0.05 g, 0.1557 mmol) in methanol (5 mL) was hydrogenated by 10% Pd/C (0.005 g, 10% wt/wt) using hydrogen balloon. Progress of the reaction was monitored by TLC. After reaction completion reaction mass filtered through celite and filtrate was evaporated under reduced pressure to give 2-(6-(4-(2,3-diaminopyridin-4-yl)-1H-pyrazol-1-yl)pyridin-3-yl)acetonitrile (0.044 g, 99%) as brown solid.

MS: 292.31 [M+1]

Step-5: Synthesis of 2-(6-(4-(3H-imidazo[4,5-b]pyridin-7-yl)-1H-pyrazol-1-yl)pyridin-3-yl)acetonitrile

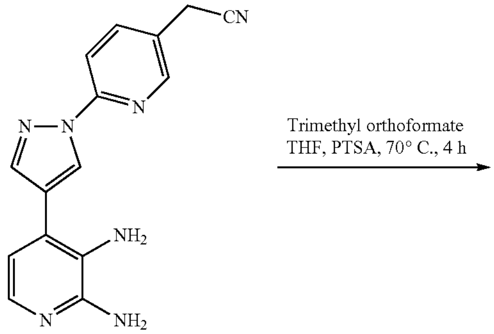

291

-continued

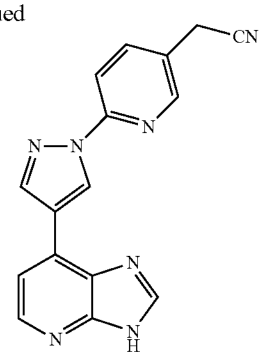

1078

To a stirred solution of 2-(6-(4-(2,3-diaminopyridin-4-yl)-1H-pyrazol-1-yl)pyridin-3-yl)acetonitrile (0.045 g, 0.1512 mmol) in THF (1.0 mL), trimethyl orthoformate (1.0 mL) was added. To resultant reaction mixture, PTSA (0.005 g, 0.0302 mmol) was added and stirred for 4 h at 70° C. Completion of reaction was monitored by TLC. On completion, quenched with aq. sodium bicarbonate solution, extracted with ethyl acetate. The organic layer was washed with water, brine, dried over sodium sulphate and concentrated under reduced pressure to give crude desired product that was purified by silica gel (100 to 200 Mesh) column chromatography: eluent at 3% to 5% MeOH in DCM to obtain 2-(6-(4-(3H-imidazo[4,5-b]pyridin-7-yl)-1H-pyrazol-1-yl)pyridin-3-yl)acetonitrile (0.05 g, 10%) as off white solid.

MS: 302.31 [M+1]

Synthesis of Compound No. 1094: N-(2,2,2-trifluoroethyl)-4-(2-phenyl-3H-imidazo[4,5-b]pyridin-7-yl)-1H-pyrazole-1-carboxamide

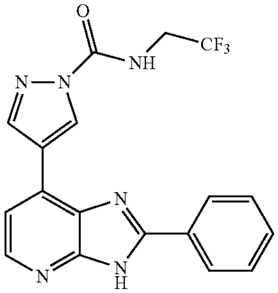 [SMILES: O=C(NCC(F)(F)F)n1cc(-c2ccnc3[nH]c(-c4ccccc4)nc23)cn1]

Step-1: Synthesis of N-(2,2,2-trifluoroethyl)-4-(2-phenyl-3H-imidazo[4,5-b]pyridin-7-yl)-1H-pyrazole-1-carboxamide

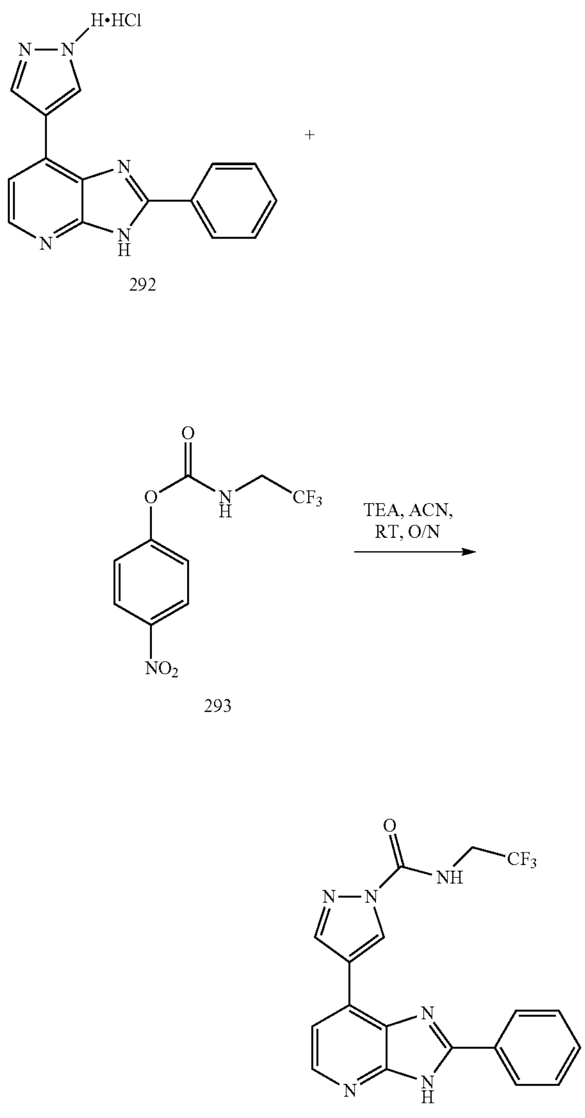

292

293

1094

To a stirred solution of tert-butyl 2-phenyl-7-(1H-pyrazol-4-yl)-3H-imidazo[4,5-b]pyridine hydrochloride (0.015 g, 0.05042 mmol) and 4-nitrophenyl 2,2,2-trifluoroethylcarbamate (0.013 g, 0.05042 mmol) in anhydrous ACN (3 mL) was added triethylamine (0.01 g, 0.1008 mmol) and stirred at RT overnight. Progress of reaction was monitored by TLC. After reaction completion reaction mass was quenched with ice cold water and extracted with ethyl acetate. The organic layer was dried over sodium sulphate and concentrated under reduced pressure. Crude was purified by silica gel (100-200 mesh) column chromatography using 2% methanol in DCM as eluent to yield N-(2,2,2-trifluoroethyl)-4-(2-phenyl-3H-imidazo[4,5-b]pyridin-7-yl)-1H-pyrazole-1-carboxamide (0.004 g, 20%) as white solid.

MS: 387.33 [M+1]

Synthesis of Compound No. 1180: 3-cyclopentyl-3-(4-(2-phenyl-3H-imidazo[4,5-b]pyridin-7-yl)-1H-pyrazol-1-yl)propanenitrile

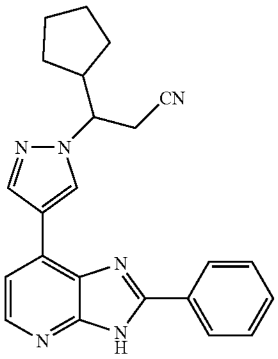 [SMILES: N#CCC(C1CCCC1)n1cc(-c2ccnc3[nH]c(-c4ccccc4)nc23)cn1]

Step-1: Synthesis of tert-butyl 4-(2-amino-3-nitropyridin-4-yl)-1H-pyrazole-1-carboxylate

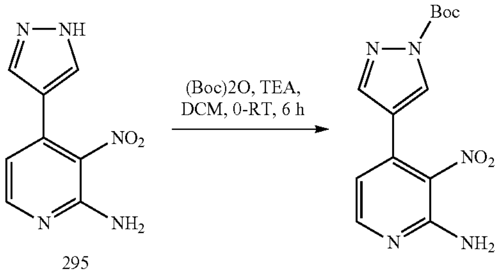

295

296

To a stirred solution of 3-nitro-4-(1H-pyrazol-4-yl)pyridin-2-amine (1 g, 4.878 mmol) in DCM (10 mL) was added TEA (2.0 mL, 14.634 mmol) dropwise at room temperature and reaction allowed to stir for 15 min. After 15 min Boc anhydride (1.59 g, 7.317 mmol) was added it and stirred for 6 h. Reaction was monitored by TLC. On completion reaction was quenched with water, extracted with DCM. The organic layer was washed with water, $NaHCO_3$, brine, dried over $Na_2SO_4$, evaporated under reduced pressure. Crude was purified by silica gel (100 to 200 Mesh) column chromatography: eluent at 1% MeOH in DCM to obtain tert-butyl 4-(2-amino-3-nitropyridin-4-yl)-1H-pyrazole-1-carboxylate (1.2 g, 81.0%) as yellow solid.

MS: 306.29 [M+1]

Step-2: Synthesis of tert-butyl 4-(2,3-diaminopyridin-4-yl)-1H-pyrazole-1-carboxylate

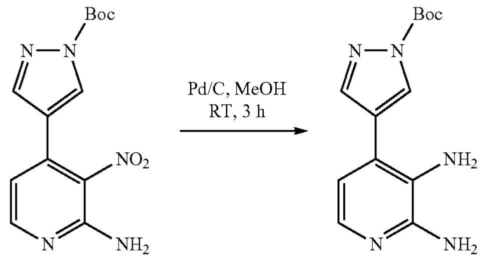

296 297

To a stirred solution of tert-butyl 4-(2-amino-3-nitropyridin-4-yl)-1H-pyrazole-1-carboxylate (0.5 g, 1.639 mmol) in methanol (5 mL) was hydrogenated by 10% Pd/C (0.05 g, 10% wt/wt) using hydrogen balloon. Progress of the reaction was monitored by TLC. After reaction completion reaction mass filtered through celite and filtrate was evaporated under reduced pressure to give tert-butyl 4-(2,3-diaminopyridin-4-yl)-1H-pyrazole-1-carboxylate (0.45 g, 99.8%) as brown solid.

MS: 276.31 [M+1]

Step-3: Synthesis of tert-butyl 4-(2-phenyl-3H-imidazo[4,5-b]pyridin-7-yl)-1H-pyrazole-1-carboxylate

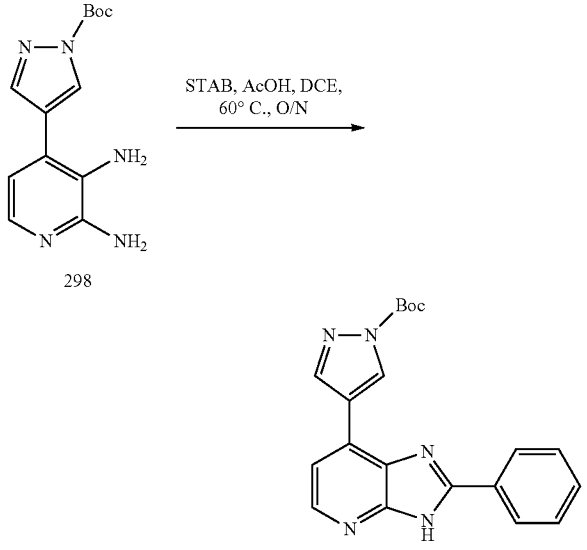

298

299

To a stirred solution of tert-butyl 4-(2,3-diaminopyridin-4-yl)-1H-pyrazole-1-carboxylate (0.4 g, 1.452 mmol) and benzaldehyde (0.15 g, 1.452 mmol) in DCE (5 mL) at 0° C. was added AcOH (0.4 mL) and stirred for 30 min. Sodium triacetoxyborohydride (0.13 g, 2.179 mmol) was then added and the resulting mixture was heated overnight at 60° C. Progress of reaction was monitored by TLC. After reaction completion reaction mass was cooled to 0° C. and quenched with ice water. Product was extracted with ethyl acetate. The organic layer was washed with brine, dried over sodium sulphate and concentrated under reduced pressure. Crude was purified by silica gel (100-200 mesh) column chromatography using 1% MeOH/DCM as eluent to obtain tert-butyl 4-(2-phenyl-3H-imidazo[4,5-b]pyridin-7-yl)-1H-pyrazole-1-carboxylate (0.3 g, 57.1%) as white solid.

MS: 362.4 [M+1]

Step-4: Synthesis of tert-butyl 2-phenyl-7-(1H-pyrazol-4-yl)-3H-imidazo[4,5-b]pyridine hydrochloride

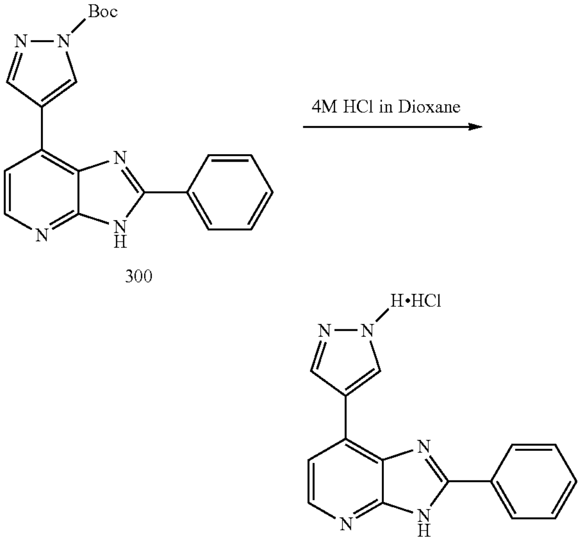

300

301

To tert-butyl 4-(2-phenyl-3H-imidazo[4,5-b]pyridin-7-yl)-1H-pyrazole-1-carboxylate (0.3 g, 0.831 mmol) was added 4 M HCl in Dioxane (3 mL) and stirred at room temperature for 3 h. Progress of reaction was monitored by TLC. After reaction completion reaction mass was concentrated under reduced pressure, washed with diethyl ether and dried to give tert-butyl 2-phenyl-7-(1H-pyrazol-4-yl)-3H-imidazo[4,5-b]pyridine hydrochloride (0.25 g, 100%) as white solid.

MS: 298.4 [M+1]

Step-5: Synthesis of 3-cyclopentyl-3-(4-(2-phenyl-3H-imidazo[4,5-b]pyridin-7-yl)-1H-pyrazol-1-yl)propanenitrile

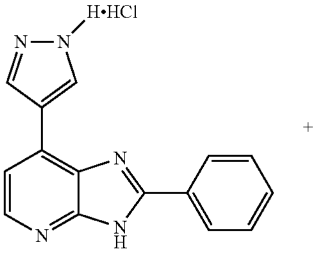

302

-continued

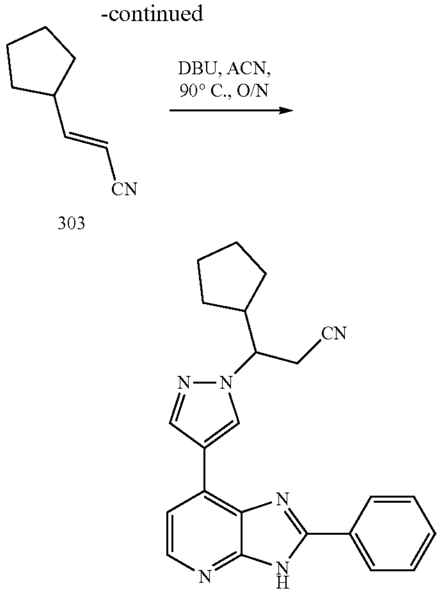

303

1180

To a stirred solution of tert-butyl 2-phenyl-7-(1H-pyrazol-4-yl)-3H-imidazo[4,5-b]pyridine hydrochloride (0.03 g, 0.115 mmol) and 3-cyclopentylacrylonitrile (0.015 g, 0.126 mmol) in anhydrous ACN (5 mL) was added DBU (0.052 g, 0.3448 mmol) and heated overnight at 90° C. Progress of reaction was monitored by TLC. After reaction completion reaction mass was quenched with ice cold water and extracted with ethyl acetate. The organic layer was dried over sodium sulphate and concentrated under reduced pressure. Crude was purified by silica gel (100-200 mesh) column chromatography using 3% methanol in DCM as eluent to yield 3-cyclopentyl-3-(4-(2-phenyl-3H-imidazo[4,5-b]pyridin-7-yl)-1H-pyrazol-1-yl)propanenitrile (0.005 g, 11.3%) as white solid.

MS: 383.46 [M+1]

Synthesis of Compound No. 1174: 7-(1-(6-(1,1,1-trifluoro-4-(methylsulfonyl)butan-2-yl)pyridin-2-yl)-1H-pyrazol-4-yl)-3H-imidazo[4,5-b]pyridine

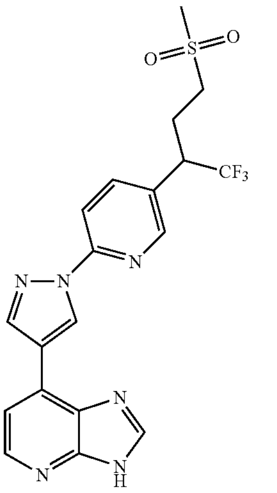 [SMILES: CS(=O)(=O)CCC(c1ccc(-n2cc(-c3ccnc4[nH]cnc34)cn2)nc1)C(F)(F)F]

Step-1: Synthesis of (E/Z)-ethyl 3-(6-bromopyridin-3-yl)-4,4,4-trifluorobut-2-enoate

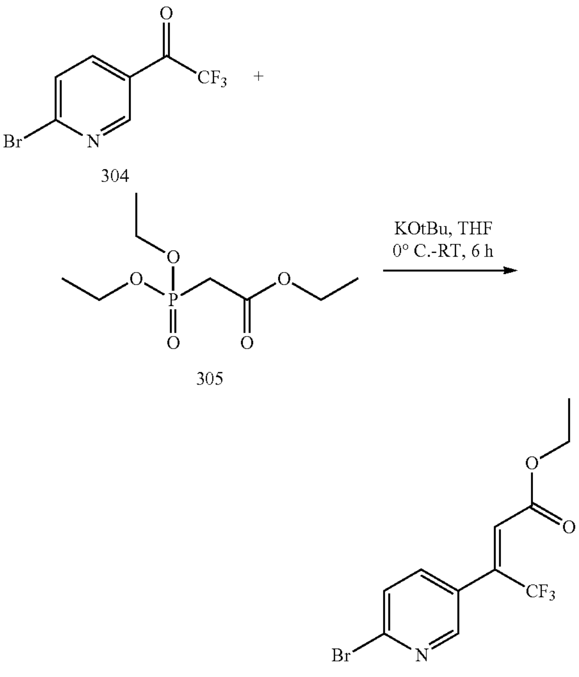

304

305

306

To a stirred solution of Triethyl phosphonoacetate (3.9 g, 1.77 mmol) and THE (60 ml) at 0° C. under $N_2$ added base potassium ter-butoxide (1.98 g, 1.77 mmol) lotwise. The resultant mixture was stirred at RT for 1 h for anion generation. A solution of 1-(6-bromopyridin-3-yl)-2,2,2-trifluoroethanone (3.0 g, 1.18 mmol) in THE (15 ml) was added slowly. After addition stirred mixture for 6 h at RT. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 9 to 15% EA/Hexane to obtained (E/Z)-ethyl 3-(6-bromopyridin-2-yl)-4,4,4-trifluorobut-2-enoate (1.5 g, 40%) as yellow oil.

MS: 324 [M+1]

Step-2: Synthesis of 3-(6-bromopyridin-3-yl)-4,4,4-trifluorobutan-1-ol

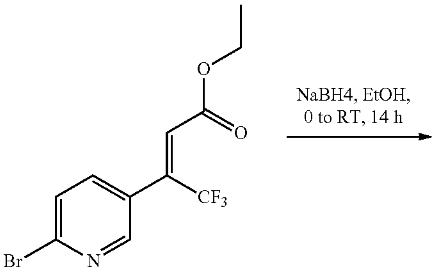

307

-continued

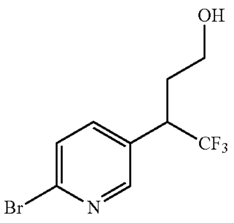

308

To a stirred solution of (E/Z)-ethyl 3-(6-bromopyridin-3-yl)-4,4,4-trifluorobut-2-enoate (1.5 g, 462 mmol) in EtOH (30 mL), $NaBH_4$ (0.520 g, 1380 mmol) was added at 0° C. Reaction was allowed to stir at room temperature for 14 h. Reaction was monitored by TLC. On completion, reaction was quenched with water, extracted with EtOAc. The organic layer was washed with water, dried over $Na_2SO_4$, evaporated under reduced pressure to obtain crude reaction mass. Purification of the crude was done via silica gel (100-200 Mesh) column chromatography and desired compound eluted at 30% ethyl acetate/n-Hexane to obtained 3-(6-bromopyridin-3-yl)-4,4,4-trifluorobutan-1-ol (0.610 g, 46.5%) as clear oil.

MS: 284 [M+1]

Step-3: Synthesis of 3-(6-(4-(2-amino-3-nitropyridin-4-yl)-1H-pyrazol-1-yl)pyridin-3-yl)-4,4,4-trifluorobutan-1-ol

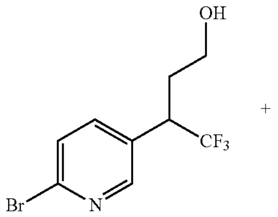

309

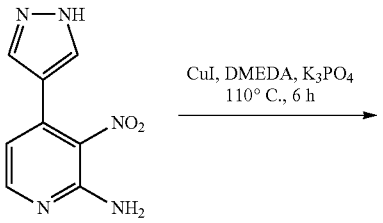

310

-continued

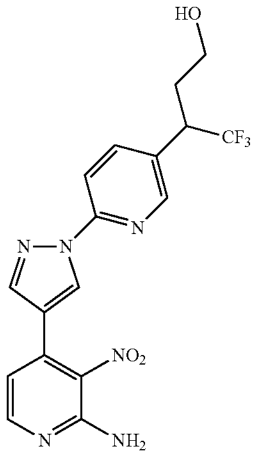

311

To a stirred solution of 3-nitro-4-(1H-pyrazol-4-yl)pyridin-2-amine (0.253 g, 123 mmol) and compound 3-(6-bromopyridin-3-yl)-4,4,4-trifluorobutan-1-ol (0.350 g, 123 mmol) in Dioxane (5 ml) was added $K_3PO_4$ (0.521 g, 246 mmol) followed by CuI (0.046 g, 0.246 mmol) and DMEDA (0.216 g, 246 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 6-7% MeOH in DCM to obtained 3-(6-(4-(2-amino-3-nitropyridin-4-yl)-1H-pyrazol-1-yl)pyridin-3-yl)-4,4,4-trifluorobutan-1-ol (0.250 g, 50%) as yellow solid.

MS: 409.1 [M+1]

Step-4: Synthesis of 4-(1-(5-(4-bromo-1,1,1-trifluorobutan-2-yl)pyridin-2-yl)-1H-pyrazol-4-yl)-3-nitropyridin-2-amine

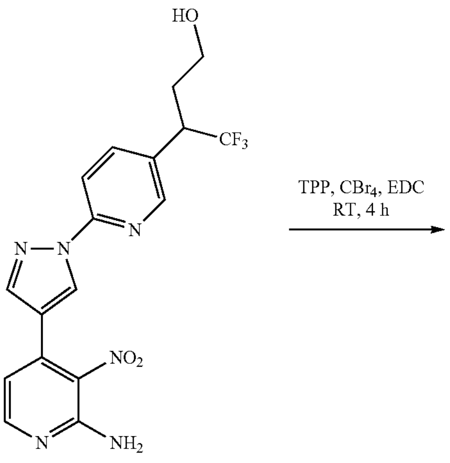

312

-continued

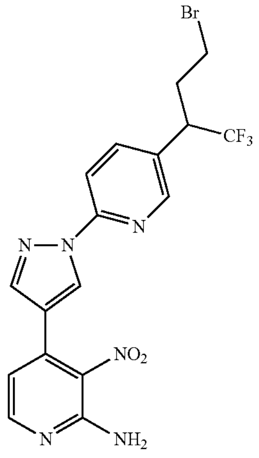

313

To a stirred solution of 3-(6-(4-(2-amino-3-nitropyridin-4-yl)-1H-pyrazol-1-yl)pyridin-3-yl)-4,4,4-trifluorobutan-1-ol (0.120 g, 0.29 mmol) in DCE (10 mL), TPP (0.115 g, 0.44 mmol) was added and then added carbontetrabromide (0.145 g, 0.44 mmol) portion-wise at 0° C. The resultant reaction mixture was stirred at room temperature for 7 h. Completion of reaction was monitored by TLC. After completion reaction mass was quenched with ice cold water. Phases separated and aqueous layer was extracted with DCM. The organic layer was washed with brine, dried over sodium sulphate and concentrated under reduced pressure. Crude product was purified by silica gel (100-200 mesh) column chromatography using 2 to 3% methanol in DCMA as eluent to obtain 4-(1-(5-(4-bromo-1,1,1-trifluorobutan-2-yl)pyridin-2-yl)-1H-pyrazol-4-yl)-3-nitropyridin-2-amine (0.065 g, 47.05%) as yellow solid.

MS: 471.1 [M+1]

Step-5: Synthesis of 4-(1-(5-(1,1,1-trifluoro-4-(methylsulfonyl)butan-2-yl)pyridin-2-yl)-1H-pyrazol-4-yl)-3-nitropyridin-2-amine -continued

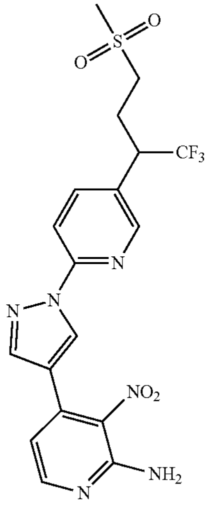

315

To a stirred solution of 4-(1-(5-(4-bromo-1,1,1-trifluorobutan-2-yl)pyridin-2-yl)-1H-pyrazol-4-yl)-3-nitropyridin-2-amine (0.065 g, 0.130 mmol) in DMSO (3.0 mL), sodium mathanesulfinate (0.027 g, 0.20 mmol) was added. To resultant reaction mixture was added stirred for 3 h at 90° C. Completion of reaction was monitored by TLC. On completion, quenched with bicarbonate water, extracted with ethyl acetate. The organic layer was washed with water, brine, dried over sodium sulphate and concentrated under reduced pressure to give crude desired product that was purified by silica gel (100 to 200 Mesh) column chromatography: eluent at 6 to 7% MeOH/DCM to obtained 4-(1-(5-(1,1,1-trifluoro-4-(methylsulfonyl)butan-2-yl)pyridin-2-yl)-1H-pyrazol-4-yl)-3-nitropyridin-2-amine (0.052 g, 81.20%) as yellow solid.

MS: 471[M+1]

Step-6: Synthesis of 4-(1-(5-(1,1,1-trifluoro-4-(methylsulfonyl)butan-2-yl)pyridin-2-yl)-1H-pyrazol-4-yl)pyridine-2,3-diamine

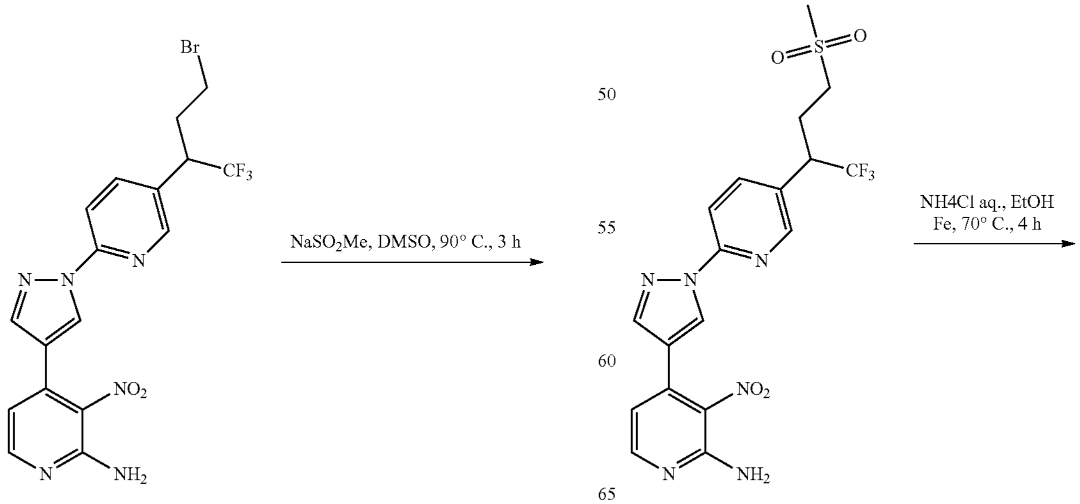

313

316

-continued

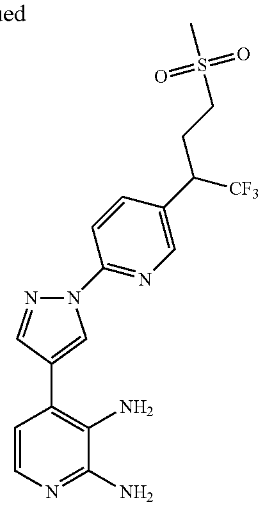

317

To a stirred solution of 4-(1-(5-(1,1,1-trifluoro-4-(methylsulfonyl)butan-2-yl)pyridin-2-yl)-1H-pyrazol-4-yl)-3-nitropyridin-2-amine (0.052 g, 0.11 mmol) in EtOH (7.0 mL), $NH_4Cl$ (2.0 mL) was added at room temperature. To the resultant reaction mixture, Fe powder (0.029 g, 0.55 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure 4-(1-(5-(1,1,1-trifluoro-4-(methylsulfonyl)butan-2-yl)pyridin-2-yl)-1H-pyrazol-4-yl)pyridine-2,3-diamine (0.036 g, 75%) as dark brown solid mass.

MS: 441.2 [M+1]

Step-7: Synthesis of 7-(1-(5-(1,1,1-trifluoro-4-(methylsulfonyl)butan-2-yl)pyridin-2-yl)-1H-pyrazol-4-yl)-3H-imidazo[4,5-b]pyridine

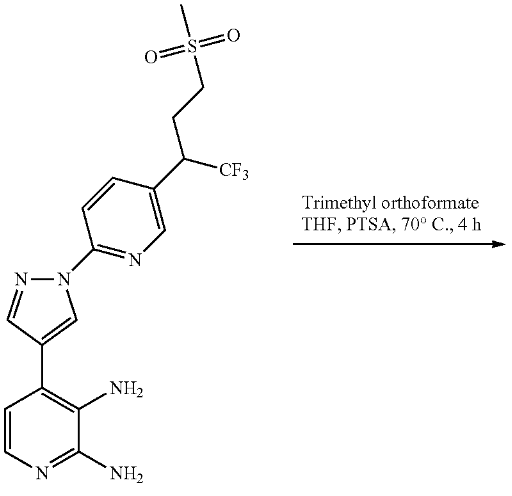

318

-continued

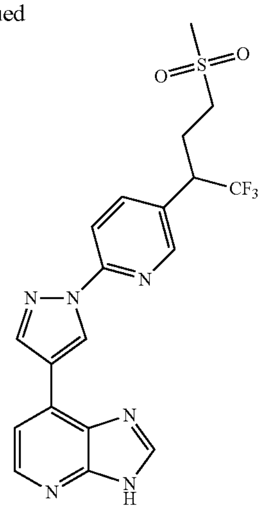

1174

To a stirred solution of 4-(1-(5-(1,1,1-trifluoro-4-(methylsulfonyl)butan-2-yl)pyridin-2-yl)-1H-pyrazol-4-yl)pyridine-2,3-diamine (0.035 g, 0.079 mmol) in THF (1.0 mL), Trimethyl orthoformate (1.5 mL) was added. To resultant reaction mixture, PTSA (0.0027 g, 0.015 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained 7-(1-(5-(1,1,1-trifluoro-4-(methylsulfonyl)butan-2-yl)pyridin-2-yl)-1H-pyrazol-4-yl)-3H-imidazo[4,5-b]pyridine (0.021 g, 60%) as off white solid.

MS: 451.1 [M+1]

Synthesis of Compound No. 1157: 2-(1-(6-(4-(3H-imidazo[4,5-b]pyridin-7-yl)-1H-pyrazol-1-yl)pyridin-3-yl)-2,2,2-trifluoroethoxy)acetonitrile

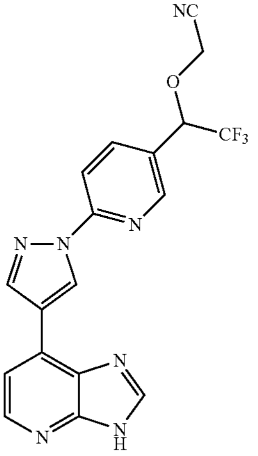 [SMILES: N#CCOC(c1ccc(-n2cc(-c3ccnc4[nH]cnc34)cn2)nc1)C(F)(F)F]

Step-1: Synthesis of 1-(6-(4-(2-amino-3-nitropyridin-4-yl)-1H-pyrazol-1-yl)pyridin-3-yl)-2,2,2-trifluoroethanol

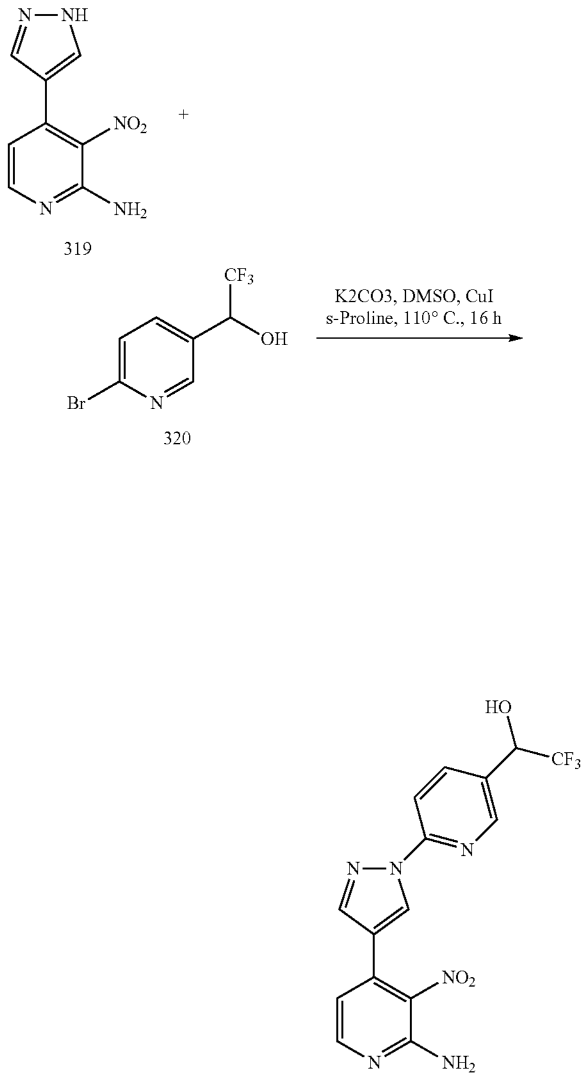

319

320

321

To a stirred solution of 3-nitro-4-(1H-pyrazol-4-yl)pyridin-2-amine (0.500 g, 2.439 mmol) and compound 1-(6-bromopyridin-3-yl)-2,2,2-trifluoroethanol (0.68 g, 2.682 mmol) in DMSO (5 ml) was added $K_2CO_3$ (1.0 g, 7.317 mmol) followed by CuI (0.045 g, 0.243 mmol) and s-Proline (0.146 g, 1.219 mmol). Reaction was heated at 110° C. for 16 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 2-3% MeOH in DCM to obtained 1-(6-(4-(2-amino-3-nitropyridin-4-yl)-1H-pyrazol-1-yl)pyridin-3-yl)-2,2,2-trifluoroethanol (0.35 g, 37.8%) as yellow solid.

MS: 381.28 [M+1]

Step-2: Synthesis of 2-(1-(6-(4-(2-amino-3-nitropyridin-4-yl)-1H-pyrazol-1-yl)pyridin-3-yl)-2,2,2-trifluoroethoxy)acetonitrile

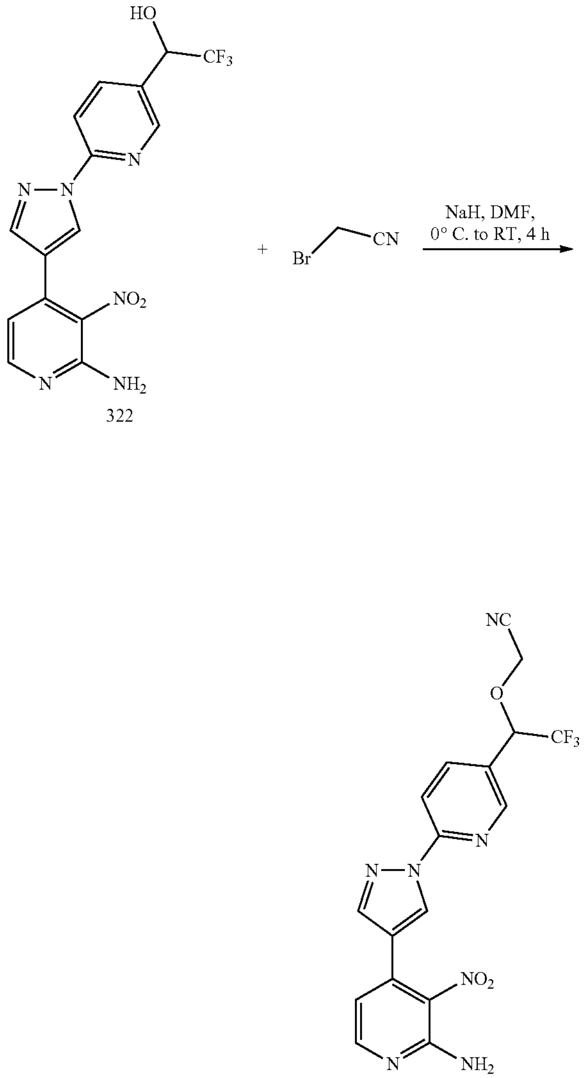

322

323

To a stirred solution of 1-(6-(4-(2-amino-3-nitropyridin-4-yl)-1H-pyrazol-1-yl)pyridin-3-yl)-2,2,2-trifluoroethanol (0.3 g, 0.7894 mmol) in DMF (10 mL) at 0° C. was added NaH (0.31 g, 0.7894 mmol) under nitrogen and stirred for 30 min. at same temperature. To resultant reaction mass 2-bromoacetonitrile (0.094 g, 0.7894 mmol) was added and stirred for 4 h at RT. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 1% Methanol in DCM as eluent to obtain 2-(1-(6-(4-(2-amino-3-nitropyridin-4-yl)-1H-pyrazol-1-yl)pyridin-3-yl)-2,2,2-trifluoroethoxy)acetonitrile (0.14 g, 42.4%) as yellow solid.

MS: 420.32 [M+1]

Step-3: Synthesis of 2-(1-(6-(4-(2,3-diaminopyridin-4-yl)-1H-pyrazol-1-yl)pyridin-3-yl)-2,2,2-trifluoroethoxy)acetonitrile

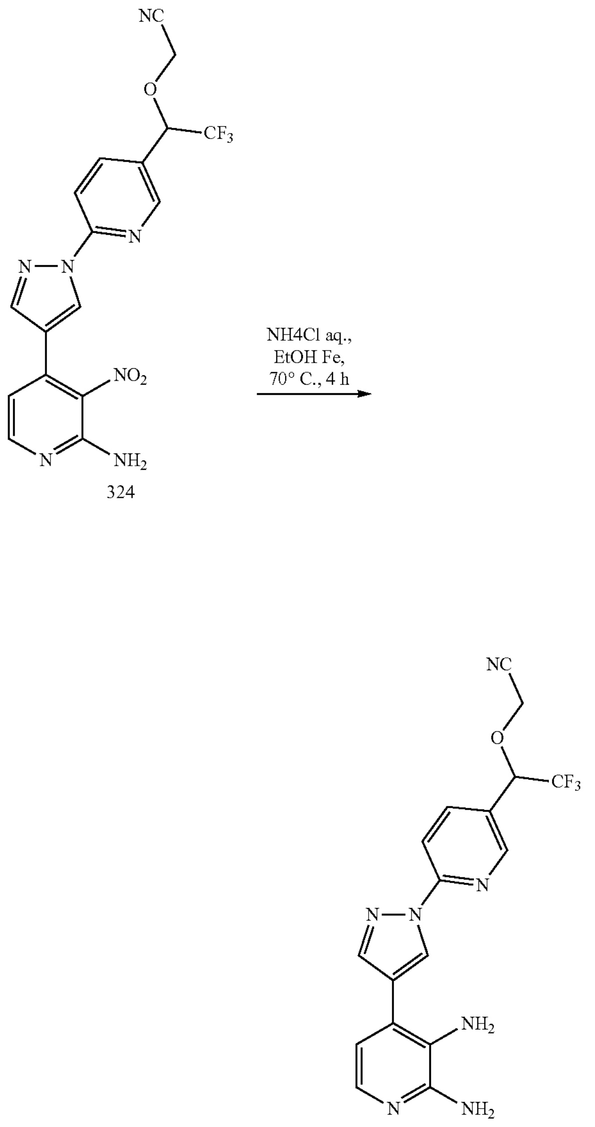

324

325

To a stirred solution of 2-(1-(6-(4-(2-amino-3-nitropyridin-4-yl)-1H-pyrazol-1-yl)pyridin-3-yl)-2,2,2-trifluoroethoxy)acetonitrile (0.050 g, 0.119 mmol) in EtOH (10 mL), $NH_4Cl$ (2.5 mL) was added at room temperature. To resultant reaction mixture, Fe powder (0.033 g, 0.59 mmol) was added and stirred for 4 h at 70° C. Completion of reaction was monitored by TLC. On completion, reaction mixture was diluted with $H_2O$:EtOAc (50 mL, 5:5) and filtered through celite to remove inorganic impurities from the reaction mixture. The aqueous layer was extracted with ethyl acetate. The organic layer was washed with water, brine, dried over sodium sulphate and concentrated under reduced pressure to obtained pure 2-(1-(6-(4-(2,3-diaminopyridin-4-yl)-1H-pyrazol-1-yl)pyridin-3-yl)-2,2,2-trifluoroethoxy)acetonitrile (0.040 g, 86.9%) as dark brown solid mass.

MS: 389.33 [M+1]

Step-4: Synthesis of 2-(1-(6-(4-(3H-imidazo[4,5-b]pyridin-7-yl)-1H-pyrazol-1-yl)pyridin-3-yl)-2,2,2-trifluoroethoxy)acetonitrile

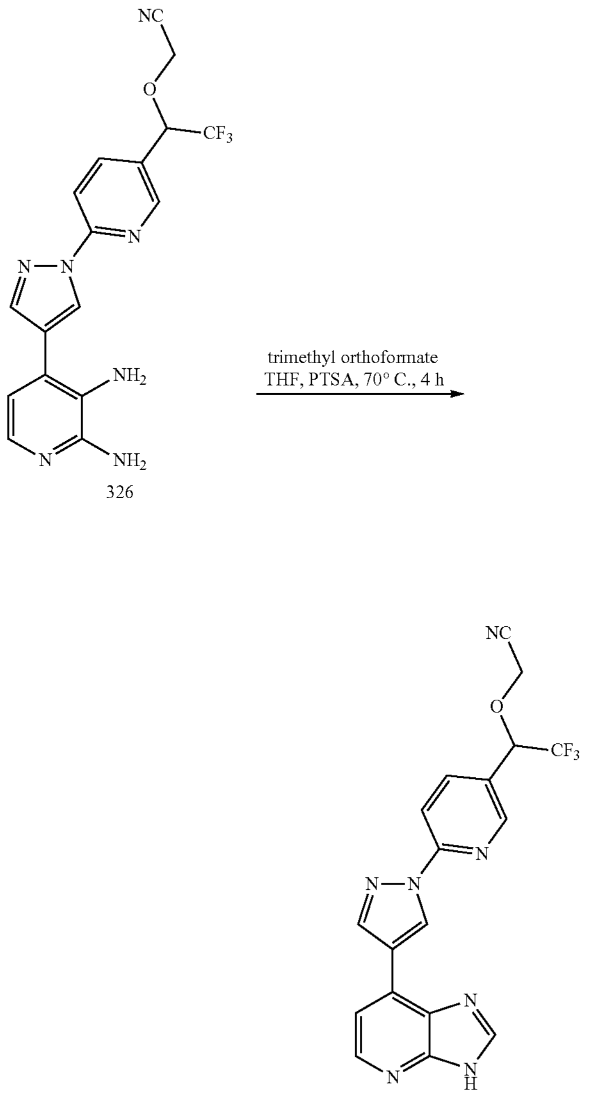

326

1157

To a stirred solution of 2-(1-(6-(4-(2,3-diaminopyridin-4-yl)-1H-pyrazol-1-yl)pyridin-3-yl)-2,2,2-trifluoroethoxy)acetonitrile (0.040 g, 0.102 mmol) in THF (3.0 mL), trimethyl orthoformate (1.5 mL) was added. To resultant reaction mixture, PTSA (0.003 g, 0.0205 mmol) was added and stirred for 4 h at 70° C. Completion of reaction was monitored by TLC. On completion, quenched with bicarbonate water, extracted with ethyl acetate. The organic layer was washed with water, brine, dried over sodium sulphate and concentrated under reduced pressure to give crude desired product that was purified by silica gel (100 to 200 Mesh) column chromatography using 3% to 5% MeOH in DCM as eluent to obtain 2-(1-(6-(4-(3H-imidazo[4,5-b]pyridin-7-yl)-1H-pyrazol-1-yl)pyridin-3-yl)-2,2,2-trifluoroethoxy)acetonitrile (0.008 g, 19.5%) as off white solid.

MS: 400.33 [M+1]

Synthesis of Compound No. 1150: 4-(6-(4-(3H-imidazo[4,5-b]pyridin-7-yl)-1H-pyrazol-1-yl)pyridin-3-yl)-N-cyclopropyl-5,5,5-trifluoropentanamide

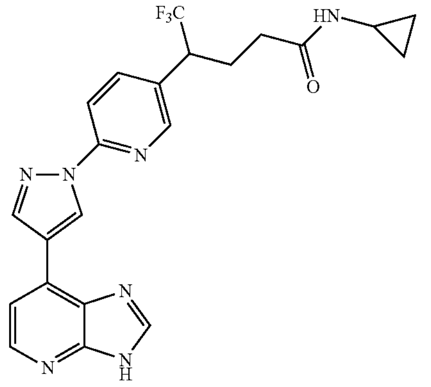 [SMILES: O=C(CCC(c1ccc(-n2cc(-c3ccnc4[nH]cnc34)cn2)nc1)C(F)(F)F)NC1CC1]

Step-1: Synthesis of 4-(6-bromopyridin-3-yl)-5,5,5-trifluoropentanenitrile

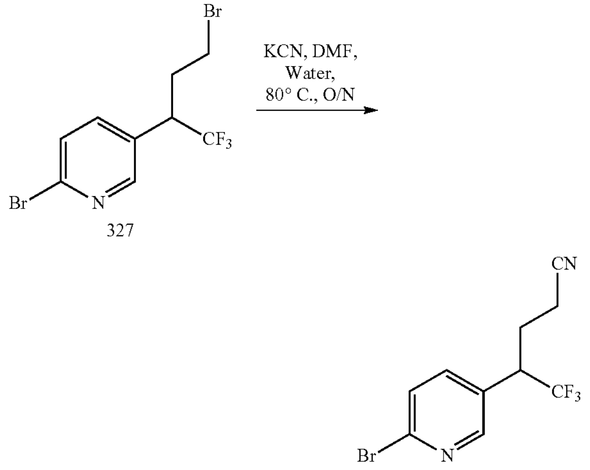

327

328

To a stirred solution of 2-bromo-5-(4-bromo-1,1,1-trifluorobutan-2-yl)pyridine (2.0 g, 5.797 mmol) in DMSO (10 mL) and water (2 mL) at RT was added potassium cyanide (0.75 g, 11.594 mmol) under nitrogen and heated overnight at 80° C. Progress of reaction was monitored by TLC. After completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) column chromatography using 15% acetone in hexane as eluent to obtain 4-(6-bromopyridin-3-yl)-5,5,5-trifluoropentanenitrile (1.1 g, 65.08%) as dark brown sticky mass.

MS: 293.08 [M+1]

Step-2: Synthesis of 4-(6-bromopyridin-3-yl)-5,5,5-trifluoropentanoic acid

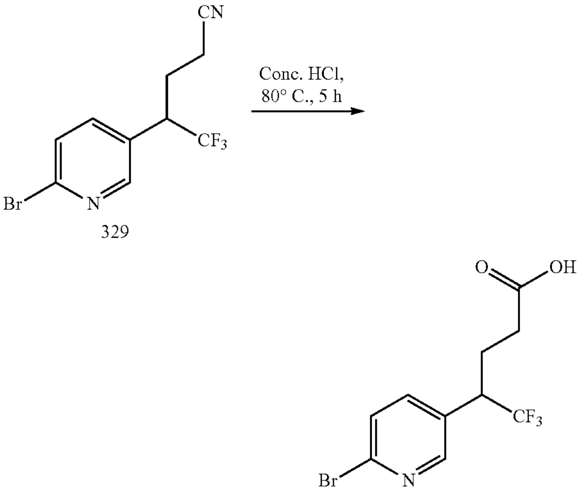

329

330

Conc. HCl (10 mL) was added to 4-(6-bromopyridin-3-yl)-5,5,5-trifluoropentanenitrile (1.0 g, 3.412 mmol) in a sealed tube and heated to 80° C. for 5 h. Progress of reaction was monitored by TLC. After completion reaction mass was quenched with ice cold water. Phases separated and aqueous layer was extracted with ethyl acetate. The organic layer was washed with brine, dried over sodium sulphate and concentrated under reduced pressure to obtain 4-(6-bromopyridin-3-yl)-5,5,5-trifluoropentanoic acid (0.6 g, 56.6%) as dark brown sticky mass.

MS: 312.08 [M+1]

Step-3: Synthesis of 4-(6-bromopyridin-3-yl)-N-cyclopropyl-5,5,5-trifluoropentanamide

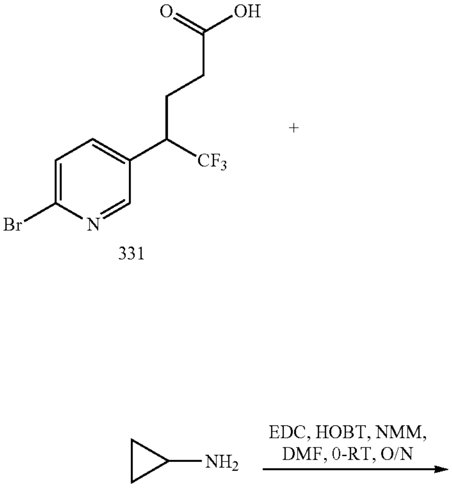

331

332

-continued

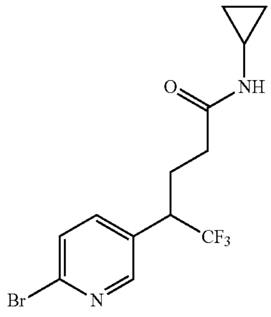

333

To a stirred solution of 4-(6-bromopyridin-3-yl)-5,5,5-trifluoropentanoic acid (0.15 g, 0.4823 mmol) and cyclopropylamine (0.033 g, 0.5787 mmol) in DMF (5 mL) was added EDCI (0.110 g, 0.5787 mmol), HOBT (0.097 g, 0.723 mmol) and NMM (0.146 g, 1.446 mmol) at 10° C. The resulting reaction mixture was stirred at room temperature for 16 h. Reaction was monitored by TLC. On completion reaction was quenched with water, extracted with ethyl acetate. Organic layer was washed with water, brine, dried over sodium sulphate, concentrated under reduced pressure to obtain 4-(6-bromopyridin-3-yl)-N-cyclopropyl-5,5,5-trifluoropentanamide as crude (0.150 g, 88.8%) as yellow oil.

MS: 351.16 [M+1]

Step-4: Synthesis of 4-(6-(4-(2-amino-3-nitropyridin-4-yl)-1H-pyrazol-1-yl)pyridin-3-yl)-N-cyclopropyl-5,5,5-trifluoropentanamide

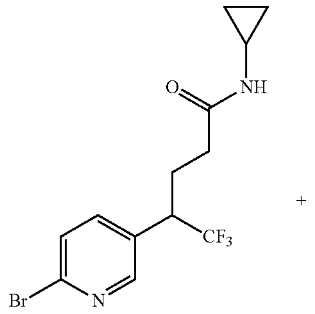

334

+

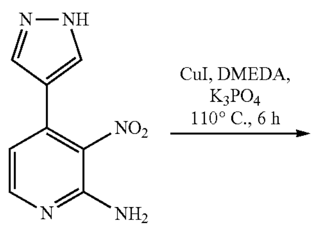

335

-continued

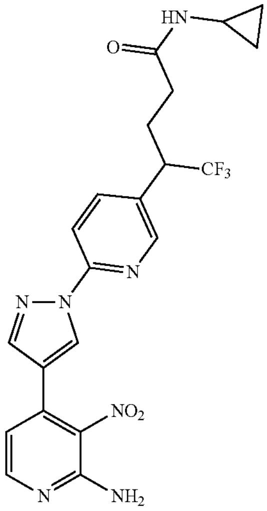

336

To a stirred solution of 3-nitro-4-(1H-pyrazol-4-yl)pyridin-2-amine (0.06 g, 0.292 mmol) and compound 4-(6-bromopyridin-3-yl)-N-cyclopropyl-5,5,5-trifluoropentanamide (0.150 g, 0.536 mmol) in Dioxane (5 ml) was added $K_3PO_4$ (0.124 g, 0.585 mmol) followed by CuI (0.011 g, 0.0585 mmol) and DMEDA (0.128 g, 1.463 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography using 2% MeOH in DCM as eluent to obtain 4-(6-(4-(2-amino-3-nitropyridin-4-yl)-1H-pyrazol-1-yl)pyridin-3-yl)-N-cyclopropyl-5,5,5-trifluoropentanamide (0.05 g, 35.9%) as yellow solid.

MS: 476.42 [M+1]

Step-5: Synthesis of 4-(6-(4-(2,3-diaminopyridin-4-yl)-1H-pyrazol-1-yl)pyridin-3-yl)-N-cyclopropyl-5,5,5-trifluoropentanamide

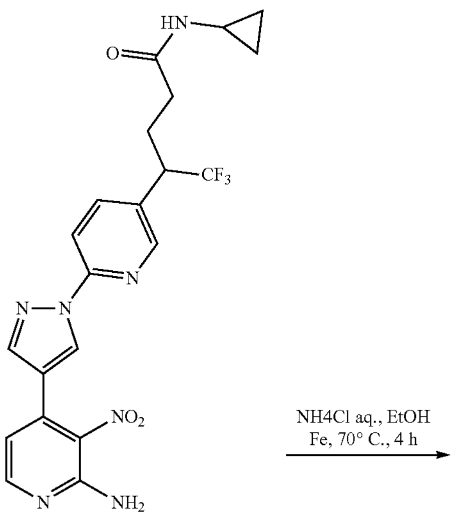

337

-continued

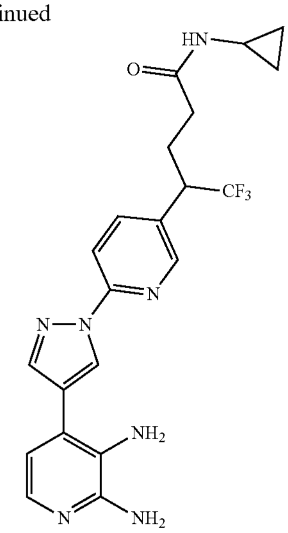

338

-continued

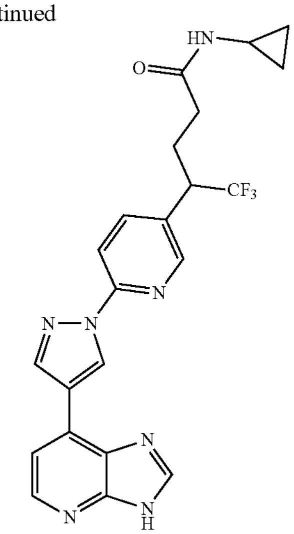

1150

To a stirred solution of 4-(6-(4-(2-amino-3-nitropyridin-4-yl)-1H-pyrazol-1-yl)pyridin-3-yl)-N-cyclopropyl-5,5,5-trifluoropentanamide (0.050 g, 0.105 mmol) in EtOH (10 mL), NH4Cl (2.5 mL) was added at room temperature. To resultant reaction mixture, Fe powder (0.029 g, 0.526 mmol) was added and stirred for 4 h at 70° C. Completion of reaction was monitored by TLC. On completion, reaction mixture was diluted with $H_2O$:EtOAc (50 mL, 5:5) and filtered through celite to remove inorganic impurities from the reaction mixture. The aqueous layer was extracted with ethyl acetate. The organic layer was washed with water, brine, dried over sodium sulphate and concentrated under reduced pressure to obtained pure 4-(6-(4-(2,3-diaminopyridin-4-yl)-1H-pyrazol-1-yl)pyridin-3-yl)-N-cyclopropyl-5,5,5-trifluoropentanamide (0.040 g, 85.4%) as dark brown solid mass.

MS: 446.44 [M+1]

Step-6: Synthesis of 4-(6-(4-(3H-imidazo[4,5-b]pyridin-7-yl)-1H-pyrazol-1-yl)pyridin-3-yl)-N-cyclopropyl-5,5,5-trifluoropentanamide

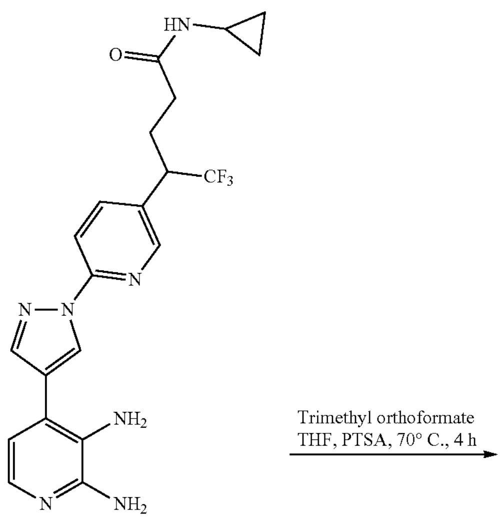

339

To a stirred solution of 4-(6-(4-(2,3-diaminopyridin-4-yl)-1H-pyrazol-1-yl)pyridin-3-yl)-N-cyclopropyl-5,5,5-trifluoropentanamide (0.040 g, 0.0898 mmol) in THF (3.0 mL), trimethyl orthoformate (1.5 mL) was added. To resultant reaction mixture, PTSA (0.003 g, 0.0179 mmol) was added and stirred for 4 h at 70° C. Completion of reaction was monitored by TLC. On completion, quenched with bicarbonate water, extracted with ethyl acetate. The organic layer was washed with water, brine, dried over sodium sulphate and concentrated under reduced pressure to give crude desired product that was purified by silica gel (100 to 200 Mesh) column chromatography using 3% to 5% MeOH in DCM as eluent to obtain 4-(6-(4-(3H-imidazo[4,5-b]pyridin-7-yl)-1H-pyrazol-1-yl)pyridin-3-yl)-N-cyclopropyl-5,5,5-trifluoropentanamide (0.020 g, 49.0%) as off white solid.

MS: 456.44 [M+1]

Synthesis of Compound No. 1131: 1-(4-(1-(6-(4-(3H-imidazo[4,5-b]pyridin-7-yl)-1H-pyrazol-1-yl)pyridin-3-yl)-2,2,2-trifluoro-1-hydroxyethyl)piperidin-1-yl)ethanone

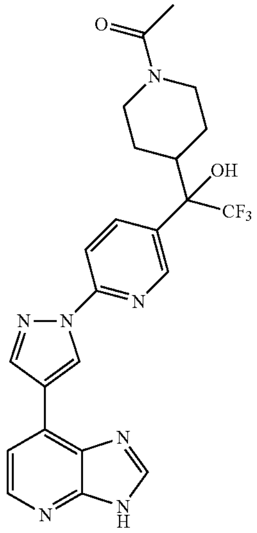 [SMILES: CC(=O)N1CCC(C(O)(c2ccc(-n3cc(-c4ccnc5[nH]cnc45)cn3)nc2)C(F)(F)F)CC1]

Step-1: Synthesis of N-methoxy-N-methyl cyclopropane carboxamide

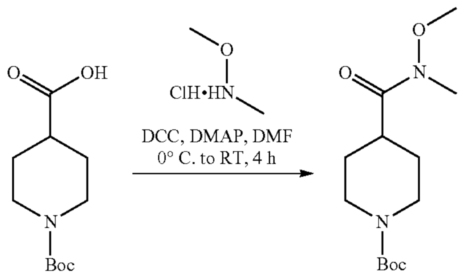

340 341

To a stirred solution of 1-(tert-butoxy carbonyl)piperidine-4-carboxylic acid (10.0 g, 43.66 mmol) and N-methoxy methanamine hydrochloride (5.56 g, 56.76 mmol) in DMF (35 mL), DCC (13.51 g, 65.49 mmol) and DMAP (1.60 g, 13.98 mmol) was added successively at 0° C. and allow to stirred for 30 min. Resultant reaction mass was allow to warm to RT and stirred for 4 h. Completion of reaction was monitored by TLC. On completion, quenched reaction mixture with 1N HCl water and extracted with EtOAc. The organic layer was washed with bicarbonate water, brine, dried over sodium sulphate and concentrated under reduced pressure to give crude desired product that was purified by silica gel (100 to 200 Mesh) column chromatography: eluent at 20% acetone in n-hexane to obtained tert-butyl 4-(N-methoxy-N-methylcarbamoyl)piperidine-1-carboxylate (7.45 g, 60%) as colourless oily mass.

MS: 273.1 [M+1]

Step-2: Synthesis of tert-butyl 4-(6-bromonicotinoyl)piperidine-1-carboxylate

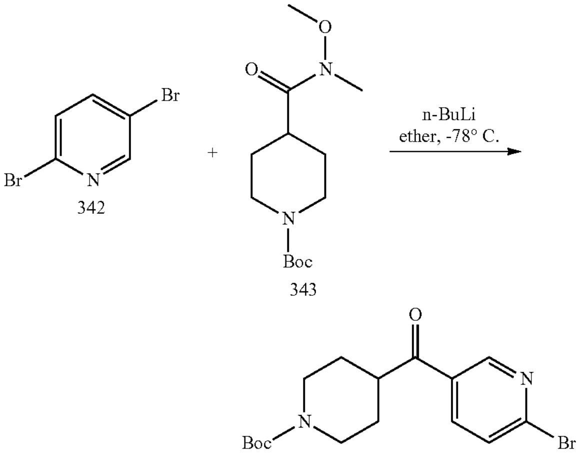

342 343 344

To a stirred solution of 2,5-dibromopyridine (5.0 g, 21.18 mmol) in diethyl ether (100 mL) at −78° C. was added n-Butyl lithium (2.5M in hexane) (8.47 mL, 21.18 mmol) under nitrogen and stirred for 1 h at same temperature. tert-butyl 4-(N-methoxy-N-methylcarbamoyl)piperidine-1-carboxylate (6.36 g, 23.29 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with 10% MeOH in DCM. The organic layer was washed with brine, dried over sodium sulphate and concentrated under reduced pressure to obtained tert-butyl 4-(6-bromonicotinoyl)piperidine-1-carboxylate (5.8 g, 67.12%) as colourless oily mass.

MS: 371.0 [M+1]

Step-3: Synthesis of tert-butyl 4-(1-(6-bromopyridin-3-yl)-2,2,2-trifluoro-1-hydroxyethyl)piperidine-1-carboxylate

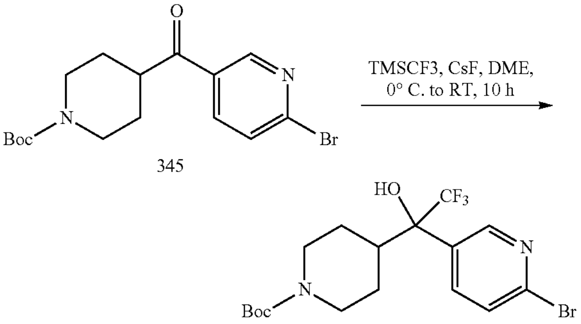

345 346

To a stirred solution of tert-butyl 4-(6-bromonicotinoyl)piperidine-1-carboxylate (1 g, 2.71 mmol) in DME (50 mL), TMSCF3 (0.77 g, 5.43 mmol) was added at 0° C. under nitrogen followed by CsF (0.82 g, 5.43 mmol) added portion wise to reaction mixture. Allow to warm reaction mixture to RT and stirred for 10 h. On completion, reaction mixture quenched with 0.1 N HCL and extracted with ethyl acetate. The organic layer was washed with brine, dried over sodium sulphate and concentrated under reduced pressure. Crude was purified by silica gel (100-200 mesh) column chromatography using 10% Acetone in Hexane as eluent to obtain tert-butyl 4-(1-(6-bromopyridin-3-yl)-2,2,2-trifluoro-1-hydroxyethyl)piperidine-1-carboxylate (0.52 g, 45.45%) as white colour solid.

MS: 440 [M+2]

Step-4: Synthesis of tert-butyl 4-(1-(6-(4-(2-amino-3-nitropyridin-4-yl)-1H-pyrazol-1-yl)pyridin-3-yl)-2,2,2-trifluoro-1-hydroxyethyl)piperidine-1-carboxylate

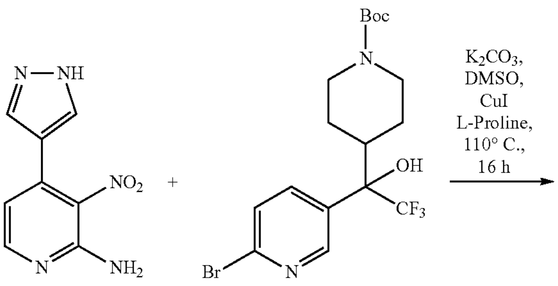

347 348

-continued

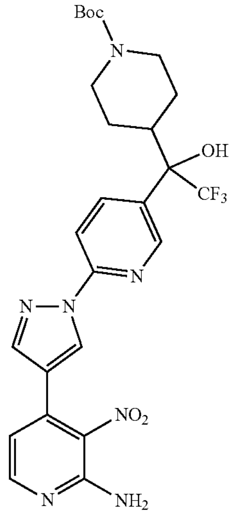

349

To a stirred solution of 3-nitro-4-(1H-pyrazol-4-yl)pyridin-2-amine (0.20 g, 0.975 mmol) and compound 4-(1-(6-bromopyridin-3-yl)-2,2,2-trifluoro-1-hydroxyethyl)piperidine-1-carboxylate (0.428 g, 0.975 mmol) in DMSO (6 ml) was added $K_2CO_3$ (0.403 g, 2.92 mmol) followed by CuI (0.016 g, 0.0975 mmol) and L-Proline (0.056 g, 0.487 mmol). Reaction was heated at 110° C. for 16 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 40-60% acetone in n-hexane to obtained tert-butyl 4-(1-(6-(4-(2-amino-3-nitropyridin-4-yl)-1H-pyrazol-1-yl)pyridin-3-yl)-2,2,2-trifluoro-1-hydroxyethyl)piperidine-1-carboxylate (0.075 g, 15.12%) as yellow solid

MS: 564.02 [M+1]

Step-5: Synthesis of 1-(6-(4-(2-amino-3-nitropyridin-4-yl)-1H-pyrazol-1-yl)pyridin-3-yl)-2,2,2-trifluoro-1-(piperidin-4-yl)ethanol

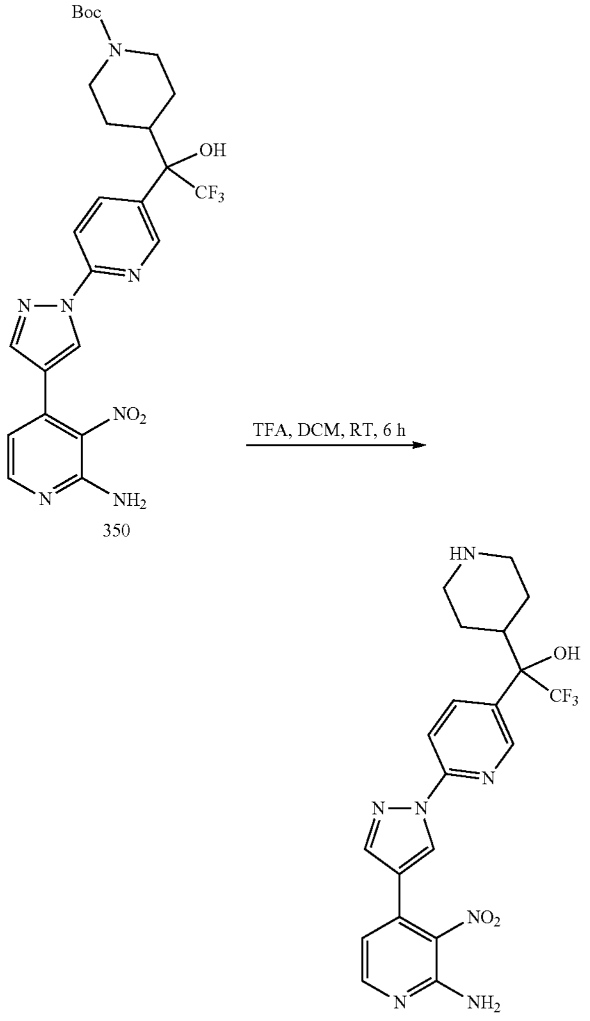

350

351

To a stirred solution of tert-butyl 4-(1-(6-(4-(2-amino-3-nitropyridin-4-yl)-1H-pyrazol-1-yl)pyridin-3-yl)-2,2,2-trifluoro-1-hydroxyethyl)piperidine-1-carboxylate (0.075 g, 13.51 mmol) in DCM (50 mL), TFA (0.2 g, 13.51 mmol) was added dropwise at RT under nitrogen. Allow to warm reaction mixture to RT and stirred for 6 h. On completion, reaction mixture quenched with bicarbonate solution and extracted with 10% MeOH in DCM. The organic layer was washed with brine, dried over sodium sulphate and concentrated under reduced pressure. Crude was purified by silica gel (100-200 mesh) column chromatography using 4-5% MeOH in DCM as eluent to obtain (6-bromopyridin-3-yl)(piperidin-4-yl)methanone (43 g, 74.52%) as yellow solid.

MS: 364.16 [M+1]

Step-6: Synthesis of 1-(4-(1-(6-(4-(2-amino-3-nitropyridin-4-yl)-1H-pyrazol-1-yl)pyridin-3-yl)-2,2,2-trifluoro-1hydroxyethyl)piperidin-1-yl)ethanone

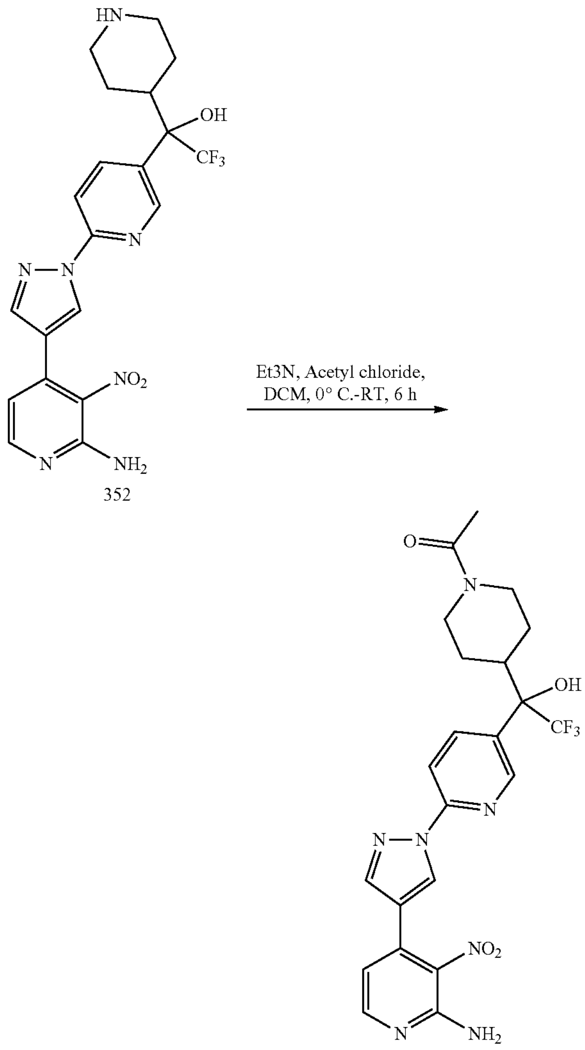

352

353

To a stirred solution of (6-bromopyridin-3-yl)(piperidin-4-yl)methanone1-(6-(4-(2-amino-3-nitropyridin-4-yl)-1H-pyrazol-1-yl)pyridin-3-yl)-2,2,2-trifluoro-1-(piperidin-4-yl) ethanol (0.040 g, 0.109 mmol) in dry DCM (5 mL) at 0° C. was added Et3N (0.033 g, 0.329 mmol) under nitrogen. To resultant reaction mixture Acetyl Chloride (0.005 g, 0.109 mmol) was added drop wise to the reaction mixture, stirred for 1 h at 0° C. Allow to warm to RT and Stirred for 1 h. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) on flash column chromatography using 2-3% MeOH in DCM as eluent to obtain 1-(4-(1-(6-(4-(2-amino-3-nitropyridin-4-yl)-1H-pyrazol-1-yl)pyridin-3-yl)-2,2,2-trifluoro-1-hydroxyethyl)piperidin-1-yl)ethanone (0.035 g, 63.63%) as yellow solid.

MS: 506.01 [M+1]

Step-7: Synthesis of 1-(4-(1-(6-(4-(2,3-diaminopyridin-4-yl)-1H-pyrazol-1-yl)pyridin-3-yl)-2,2,2-trifluoro-1-hydroxyethyl)piperidin-1-yl)ethenone

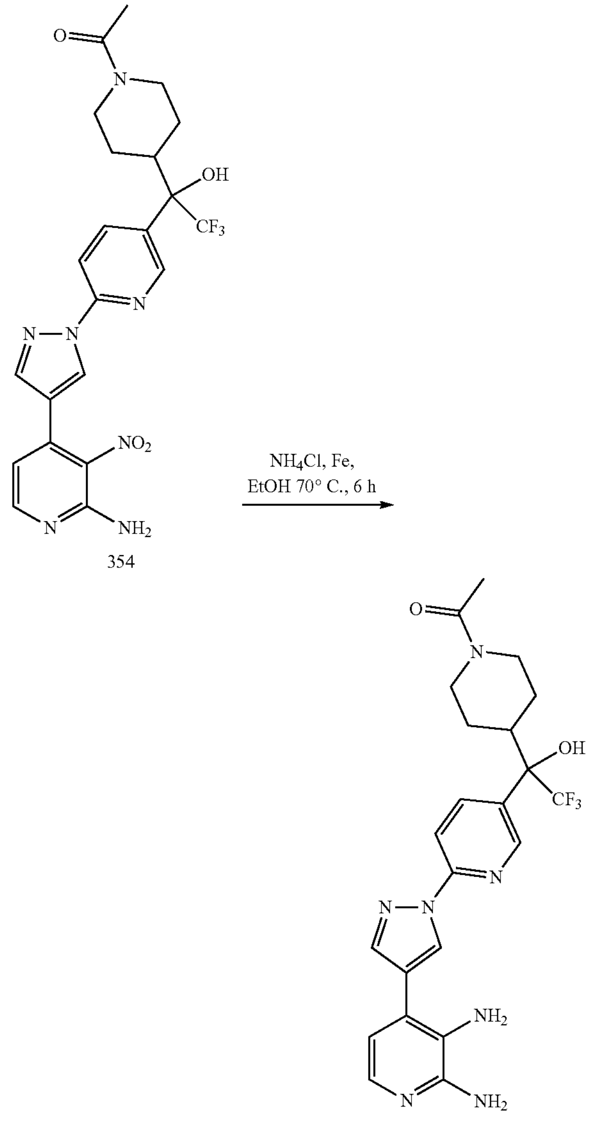

354

355

To a stirred solution of 1-(4-(1-(6-(4-(2-amino-3-nitropyridin-4-yl)-1H-pyrazol-1-yl)pyridin-3-yl)-2, 2, 2-trifluoro-1-hydroxyethyl) piperidin-1-yl) ethanone (0.035 g, 0.0693 mmol) in EtOH (3.0 mL), $NH_4Cl$ (2.5 mL) was added at room temperature. To resultant reaction mixture, Fe powder (0.019 g, 0.346 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained 1-(4-(1-(6-(4-(2, 3-diaminopyridin-4-yl)-1H-pyrazol-1-yl)pyridin-3-yl)-2,2, 2-trifluoro-1-hydroxyethyl)piperidin-1-yl)ethanone (0.025 g, 78.12%) as dark brown solid mass.

MS: 476.19 [M+1]

Step-8: Synthesis of 1-(4-(1-(6-(4-(3H-imidazo[4,5-b]pyridin-7-yl)-1H-pyrazol-1-yl)pyridin-3-yl)-2,2,2-trifluoro-1-hydroxyethyl)piperidin-1-yl)ethenone

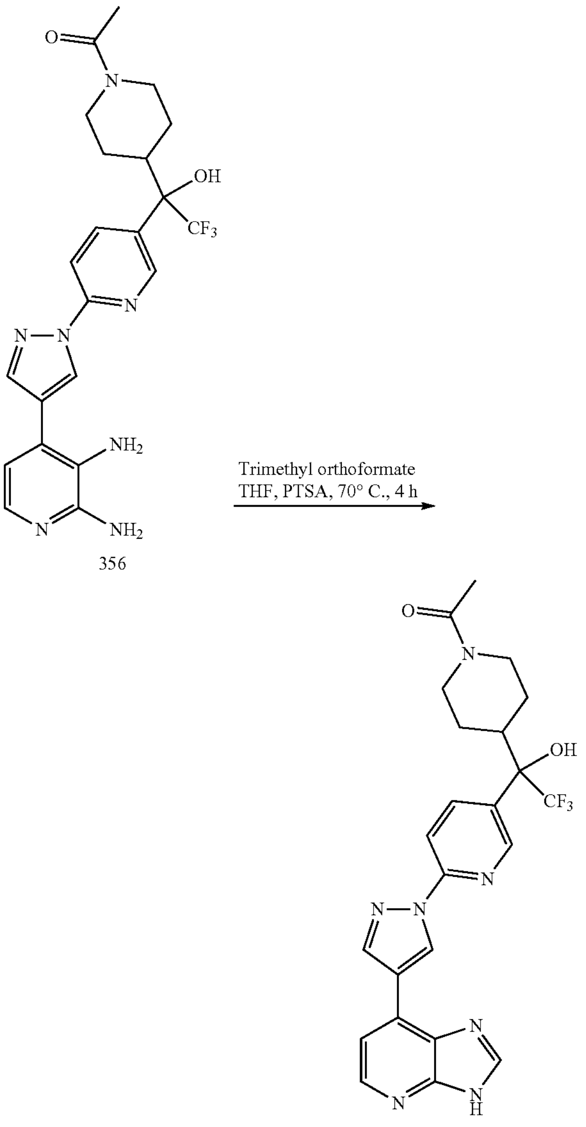

356

1131

To a stirred solution 1-(4-(1-(6-(4-(2, 3-diaminopyridin-4-yl)-1H-pyrazol-1-yl)pyridin-3-yl)-2, 2, 2-trifluoro-1-hydroxyethyl) piperidin-1-yl) ethanone 0.025 g, 0.05263 mmol) in THF (1.0 mL), trimethyl orthoformate (1.5 mL) was added. To resultant reaction mixture, PTSA (0.003 g, 0.0052 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure. Crude was purified by silica gel (100-200 mesh) on flash column chromatography using 5-6% MeOH in DCM as eluent to obtained 1-(4-(1-(6-(4-(3H-imidazo[4, 5-b]pyridin-7-yl)-1H-pyrazol-1-yl)pyridin-3-yl)-2,2,2-trifluoro-1-hydroxyethyl)piperidin-1-yl)ethanone (0.006 g, 17.41%) as off white solid.

MS: 486.02 [M+1]

Synthesis of Compound No. 1133: 1-(6-(4-(3H-imidazo[4,5-b]pyridin-7-yl)-1H-pyrazol-1-yl)pyridin-3-yl)-2,2,2-trifluoro-1-(1-methylpiperidin-4-yl) ethanol

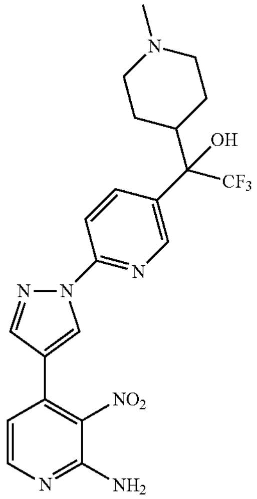 [SMILES: CN1CCC(C(O)(c2ccc(-n3cc(-c4ccnc(N)c4[N+](=O)[O-])cn3)nc2)C(F)(F)F)CC1]

Step-1: Synthesis of 1-(6-(4-(2-amino-3-nitropyridin-4-yl)-1H-pyrazol-1-yl)pyridin-3-yl)-2,2,2-trifluoro-1-(1-methylpiperidin-4-yl)ethanol

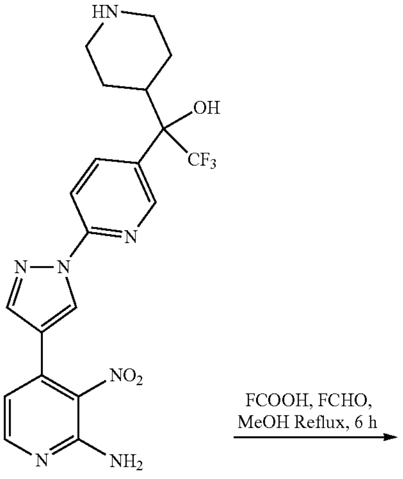

357

-continued

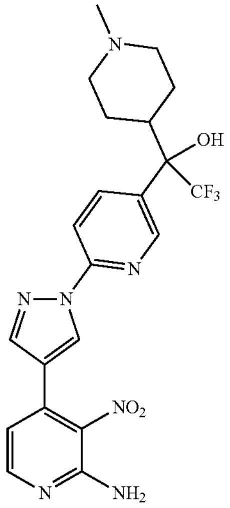

358

To a stirred solution of 1-(6-(4-(2-amino-3-nitropyridin-4-yl)-1H-pyrazol-1-yl)pyridin-3-yl)-2,2,2-trifluoro-1-(piperidin-4-yl)ethanol (0.110 g, 0.023 mmol) in dry methanol (5 mL) at room temperature was added formic acid (0.030 g, 0.071 mmol) and formaldehyde (0.021 g, 0.071 mmol) under nitrogen. Stirred reaction mixture at 70° C. for 6 h. Progress of reaction was monitored by TLC. After reaction completion reaction mass was quenched with ice cold water. Phases separated and aqueous layer was extracted with ethyl acetate. The organic layer was washed with brine, dried over sodium sulphate and concentrated under reduced pressure. Crude was purified by silica gel (100-200 mesh) on flash column chromatography using 5-6% MeOH in DCM as eluent to obtain 1-(6-(4-(2-amino-3-nitropyridin-4-yl)-1H-pyrazol-1-yl)pyridin-3-yl)-2,2,2-trifluoro-1-(1-methylpiperidin-4-yl)ethanol (0.060 g, 53.63%) as yellow solid.

MS: 478.01 [M+1]

Step-2: 1-(6-(4-(2,3-diaminopyridin-4-yl)-1H-pyrazol-1-yl)pyridin-3-yl)-2,2,2-trifluoro-1-(1-methylpiperidin-4-yl)ethanol

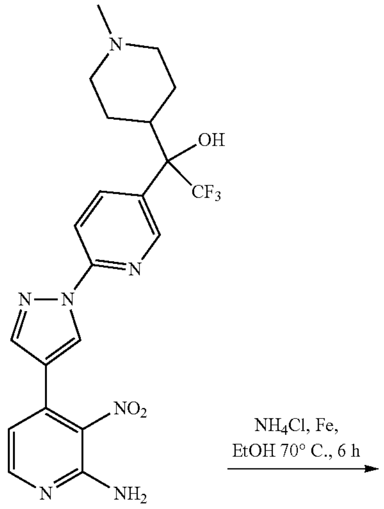

359

-continued

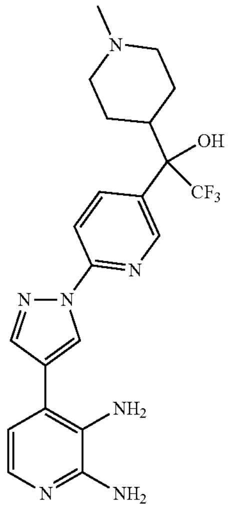

360

To a stirred solution of 1-(6-(4-(2-amino-3-nitropyridin-4-yl)-1H-pyrazol-1-yl)pyridin-3-yl)-2,2,2-trifluoro-1-(1-methylpiperidin-4-yl)ethanol (0.060 g, 0.0125 mmol) in EtOH (7.0 mL), $NH_4Cl$ (2.5 mL) was added at room temperature. To resultant reaction mixture, Fe powder (0.033 g, 0.062 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained 1-(6-(4-(2,3-diaminopyridin-4-yl)-1H-pyrazol-1-yl)pyridin-3-yl)-2,2,2-trifluoro-1-(1-methylpiperidin-4-yl)ethanol (0.040 g, 71.4%) as dark brown solid mass.

MS: 448.19 [M+1]

Step-3: Synthesis of 1-(6-(4-(3H-imidazo[4,5-b]pyridin-7-yl)-1H-pyrazol-1-yl)pyridin-3-yl)-2,2,2-trifluoro-1-(1-methylpiperidin-4-yl)ethanol

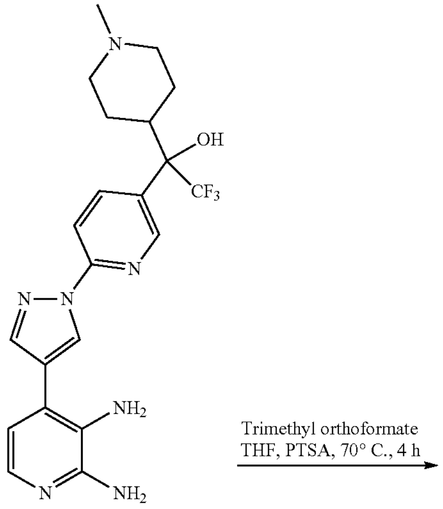

361

-continued

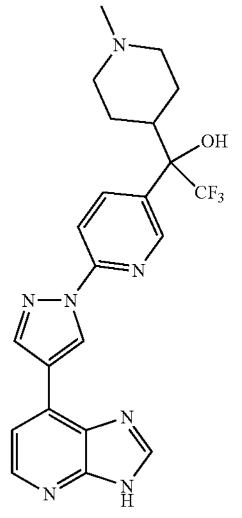

1133

To a stirred solution 1-(6-(4-(2,3-diaminopyridin-4-yl)-1H-pyrazol-1-yl)pyridin-3-yl)-2,2,2-trifluoro-1-(1-methylpiperidin-4-yl)ethanol 0.040 g, 0.0089 mmol) in THE (1.0 mL), trimethyl orthoformate (2.0 mL) was added. To resultant reaction mixture, PTSA (0.003 g, 0.0052 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure. Crude was purified by silica gel (100-200 mesh) on flash column chromatography using 5-6% MeOH in DCM as eluent to obtained 1-(6-(4-(3H-imidazo[4,5-b]pyridin-7-yl)-1H-pyrazol-1-yl)pyridin-3-yl)-2,2,2-trifluoro-1-(1-methylpiperidin-4-yl)ethanol (0.014 g, 34.41%) as off white solid.

MS: 458.02 [M+1]

Synthesis of Compound No. 1146: N-(3-(6-(4-(3H-imidazo[4,5-b]pyridin-7-yl)-1H-pyrazol-1-yl)pyridin-3-yl)-4,4,4-trifluorobutyl)methanesulfonamide

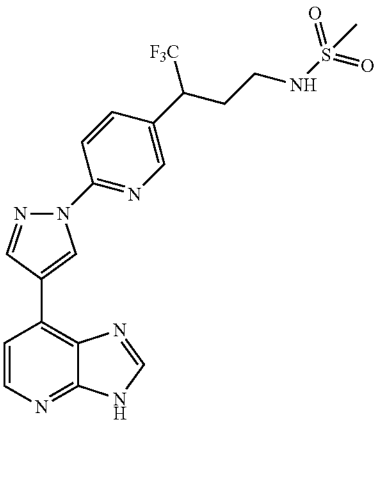 [SMILES: CS(=O)(=O)NCCC(c1ccc(-n2cc(-c3ccnc4[nH]cnc34)cn2)nc1)C(F)(F)F]

Step-1: Synthesis of 1-(6-bromopyridin-3-yl)-2,2,2-trifluoroethanone

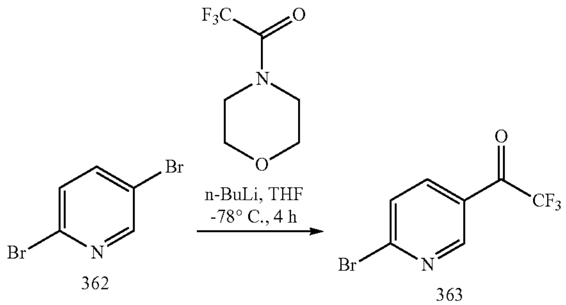

362

363

To a stirred solution of 2,5-dibromopyridine (5.0 g, 2.12 mmol) in THF (50 mL) at −78° C. was added n-Butyl lithium (2.5M in hexane) (12.5 mL, 3.18 mmol) under nitrogen and stirred for 1 h at same temperature. 2,2,2-trifluoro-1-morpholinoethanone (5.06 g, 2.76 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 18% ethyl acetate in hexane as eluent to obtain 1-(6-bromopyridin-2-yl)-2,2,2-trifluoroethanone (3.5 g, 64.81%) as colourless oil.

Step-2: Synthesis of (E/Z)-ethyl 3-(6-bromopyridin-3-yl)-4,4,4-trifluorobut-2-enoate

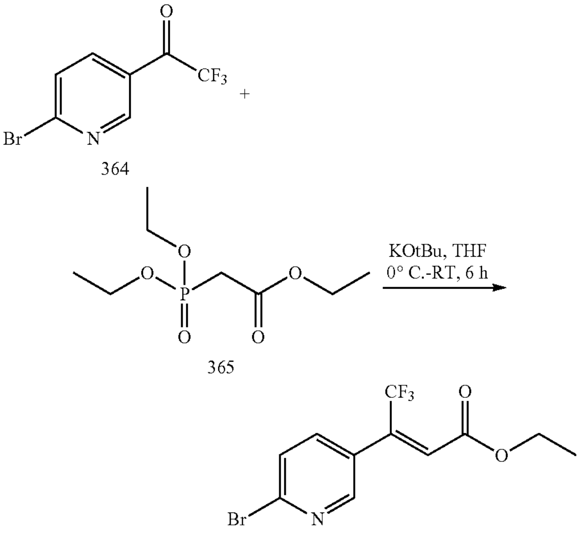

364

365

366

To a stirred solution of Triethyl phosphonoacetate (3.9 g, 1.77 mmol) and THE (60 ml) at 0° C. under $N_2$ added base potassium ter-butoxide (1.98 g, 1.77 mmol) lotwise. The resultant mixture was stirred at RT for 1 h for anion generation. A solution of 1-(6-bromopyridin-3-yl)-2,2,2-trifluoroethanone (3.0 g, 1.18 mmol) in THE (15 ml) was added slowly. After addition stirred mixture for 6 h at RT. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 9 to 15% EA/Hexane to obtained (E/Z)-ethyl 3-(6-bromopyridin-3-yl)-4,4,4-trifluorobut-2-enoate (1.5 g, 40%) as yellow oil.

MS: 324 [M+1]

Step-3: Synthesis of 3-(6-bromopyridin-3-yl)-4,4,4-trifluorobutan-1-ol

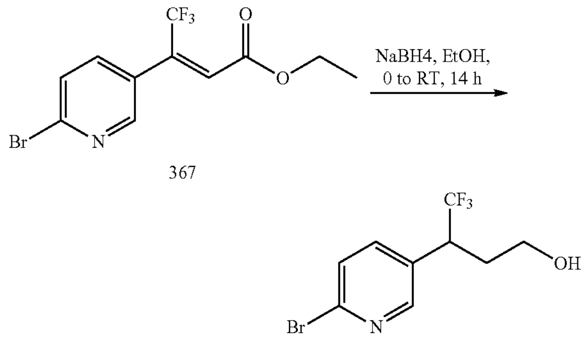

367

368

To a stirred solution of (E/Z)-ethyl 3-(6-bromopyridin-3-yl)-4,4,4-trifluorobut-2-enoate (1.5 g, 462 mmol) in EtOH (30 mL), $NaBH_4$ (0.520 g, 1380 mmol) was added at 0° C. Reaction was allowed to stir at room temperature for 14 h. Reaction was monitored by TLC. On completion, reaction was quenched with water, extracted with EtOAc. The organic layer was washed with water, dried over $Na_2SO_4$, evaporated under reduced pressure to obtain crude reaction mass. Purification of the crude was done via silica gel (100-200 Mesh) column chromatography and desired compound eluted at 30% ethyl acetate/n-Hexane to obtained 3-(6-bromopyridin-3-yl)-4,4,4-trifluorobutan-1-ol (0.610 g, 46.5%) as clear oil.

MS: 284 [M+1]

Step-4: Synthesis of 2-(3-(6-bromopyridin-3-yl)-4,4,4-trifluorobutyl)isoindoline-1,3-dione

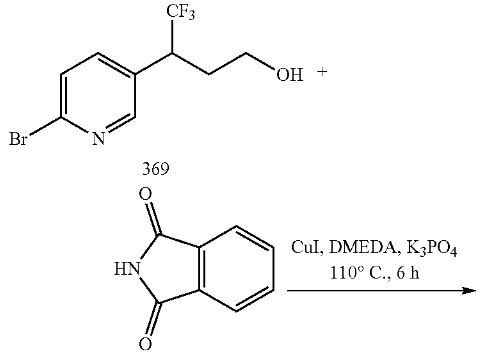

369

370

-continued

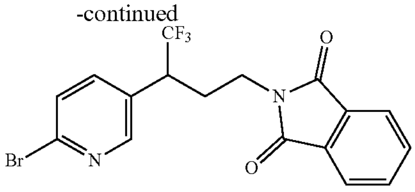

371

To ice cooled a stirred solution of isoindoline-1,3-dione (0.774 g, 5.28 mmol) and compound 3-(6-bromopyridin-2-yl)-4,4,4-trifluorobutan-1-ol (1 g, 3.53 mmol) and TPP (1.3 g, 5.28 mmol) in THE (10 ml) was added DEAD (0.919 g, 5.28 mmol). Reaction was stirred at RT for 16 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 20% Acetone in Hexane to obtained 2-(3-(6-bromopyridin-3-yl)-4,4,4-trifluorobutyl)isoindoline-1,3-dione (0.600 g, 42%) as yellowish colour free flow solid.

MS: 409.1 [M+1]

Step-5: Synthesis of 3-(6-bromopyridin-3-yl)-4,4,4-trifluorobutan-1-amine

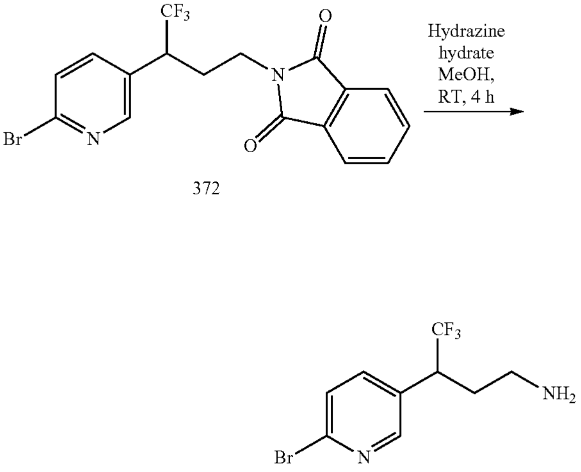

372

373

To a stirred solution of 2-(3-(6-bromopyridin-3-yl)-4,4-trifluorobutyl) isoindoline-1,3-dione (0.500 g, 0.29 mmol) in MeOH (10 mL), Hydrazine hydrate (3 ml) was added dropwise at 0° C. The resultant reaction mixture was stirred at room temperature for 4 h. Completion of reaction was monitored by TLC. After completion reaction mass was quenched with 1N NaOH solution. Phases separated and aqueous layer was extracted with DCM. The organic layer was washed with brine, dried over sodium sulphate and concentrated under reduced pressure. Obtain 3-(6-bromopyridin-3-yl)-4,4,4-trifluorobutan-1-amine (0.200 g, 47.05%) as reddish semi solid used as such in next step.

MS: 284.09 [M+1]

Step-: 6 Synthesis of

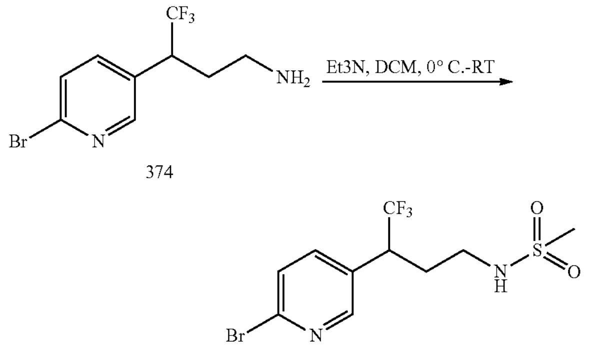

374

375

To an ice cooled stirred solution of 3-(6-bromopyridin-3-yl)-4, 4,4-trifluorobutan-1-amine (0.080 g, 0.282 mmol) in DCM (4.0 mL), trimethylamine (0.057 ml, 0.424 mmol) was added followed by MsCl (0.035 g, 0.252 mmol). To resultant reaction mixture was added stirred for 3 h at RT. Completion of reaction was monitored by TLC. On completion, quenched with bicarbonate water, extracted with dichloromethane. The organic layer was washed with water, brine, dried over sodium sulphate and concentrated under reduced pressure to give crude desired product that was purified by silica gel (100 to 200 Mesh) column chromatography: eluent at 10 to 15% Acetone/Hexane to obtained (0.070 g, 81.20%) as reddish semi solid.

MS: 363[M+2]

Step-7: Synthesis of N-(3-(6-(4-(2-amino-3-nitropyridin-4-yl)-1H-pyrazol-1-yl)pyridin-3-yl)-4,4,4-trifluorobutyl)methanesulfonamide

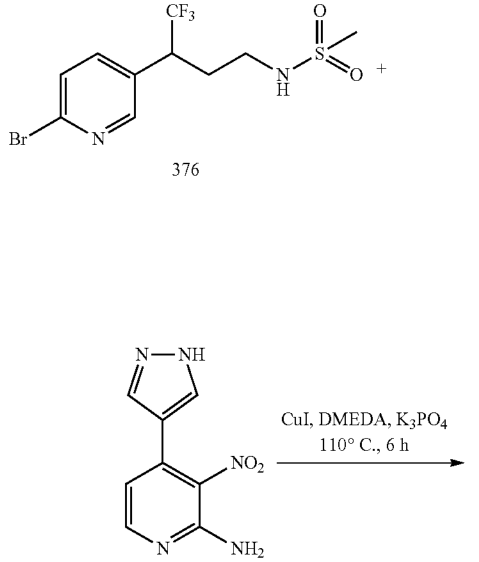

376

377

-continued

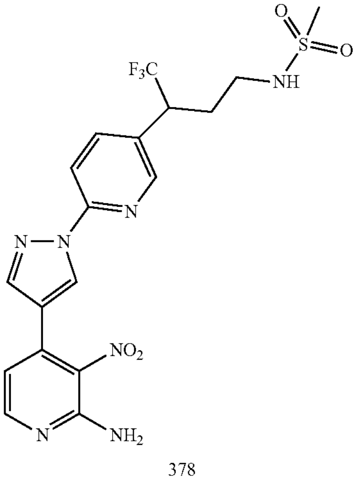

378

To a stirred solution of 3-nitro-4-(1H-pyrazol-4-yl)pyridin-2-amine (0.040 g, 0.195 mmol) and compound N-(3-(6-bromopyridin-3-yl)-4,4,4-trifluorobutyl)methanesulfonamide (0.070 g, 0.195 mmol) in Dioxane (5 ml) was added $K_3PO_4$ (0.080 g, 0.585 mmol) followed by CuI (0.005 g, 0.0195 mmol) and DMEDA (0.017 g, 0.195 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 6-7% MeOH in DCM to obtained N-(3-(6-(4-(2-amino-3-nitropyridin-4-yl)-1H-pyrazol-1-yl)pyridin-3-yl)-4,4,4-trifluorobutyl)methanesulfonamide (0.035 g, 50%) as yellow solid.

MS: 466.1 [M+1]

Step-8: Synthesis of N-(3-(6-(4-(2,3-diaminopyridin-4-yl)-1H-pyrazol-1-yl)pyridin-3-yl)-4,4,4-trifluorobutyl)methanesulfonamide

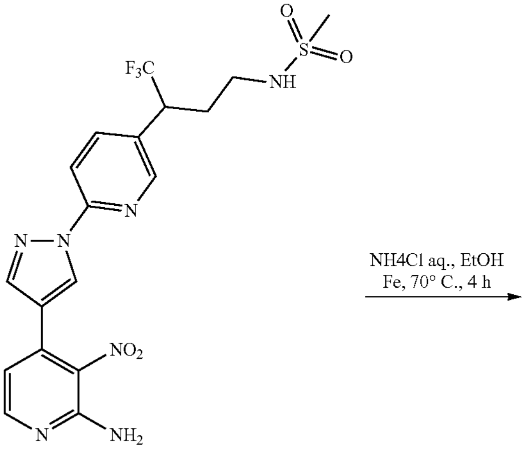

379

-continued

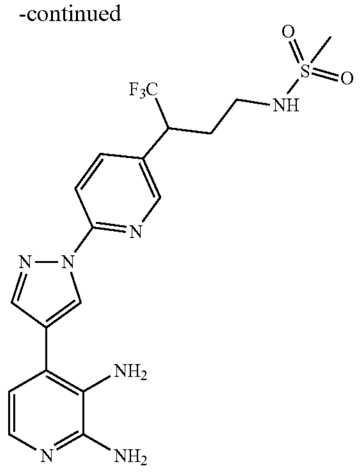

380

To a stirred solution of N-(3-(6-(4-(2-amino-3-nitropyridin-4-yl)-1H-pyrazol-1-yl)pyridin-3-yl)-4,4,4-trifluorobutyl)methanesulfonamide (0.035 g, 0.11 mmol) in EtOH (7.0 mL), $NH_4Cl$ (2.0 mL) was added at room temperature. To the resultant reaction mixture, Fe powder (0.029 g, 0.55 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure N-(3-(6-(4-(2,3-diaminopyridin-4-yl)-1H-pyrazol-1-yl)pyridin-3-yl)-4,4,4-trifluorobutyl)methanesulfonamide (0.025 g, 75%) as dark brown solid mass.

MS: 456.2 [M+1]

Step-9: Synthesis of N-(3-(6-(4-(3H-imidazo[4,5-b]pyridin-7-yl)-1H-pyrazol-1-yl)pyridin-3-yl)-4,4,4-trifluorobutyl)methanesulfonamide

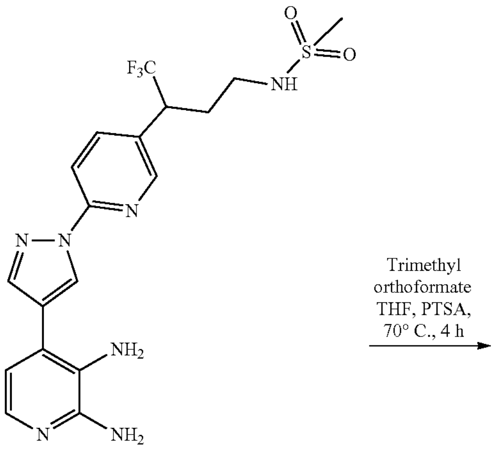

381

-continued

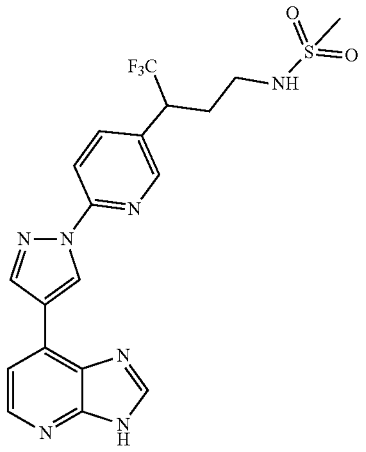

1146

To a stirred solution of N-(3-(6-(4-(2,3-diaminopyridin-4-yl)-1H-pyrazol-1-yl)pyridin-3-yl)-4,4,4-trifluorobutyl)methanesulfonamide ((0.025 g, 0.079 mmol) in THF (1.0 mL), Trimethyl orthoformate (1.5 mL) was added. To resultant reaction mixture, PTSA (0.0027 g, 0.015 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained N-(3-(6-(4-(3H-imidazo[4,5-b]pyridin-7-yl)-1H-pyrazol-1-yl)pyridin-3-yl)-4,4,4-trifluorobutyl)methanesulfonamide (0.006 g, 60%) as off white solid.

MS: 466.45 [M+1]

Synthesis of Compound No. 1152: 3-(6-(4-(3H-imidazo[4,5-b]pyridin-7-yl)-1H-pyrazol-1-yl)pyridin-3-yl)-4,4,4-trifluoro-N-methylbutan-1-amine

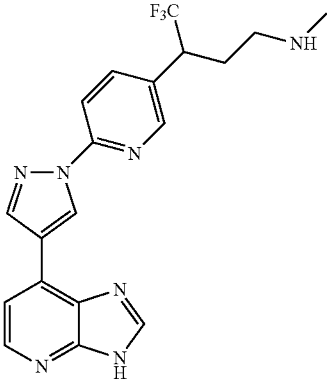

Step-1: Synthesis of 1-(6-bromopyridin-3-yl)-2,2,2-trifluoroethanone

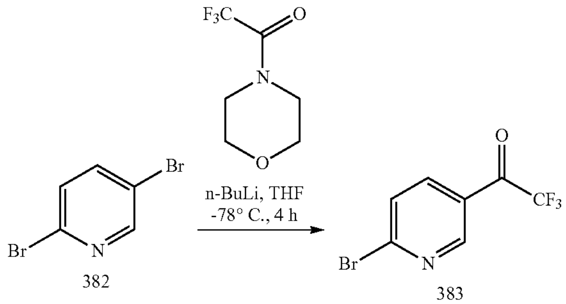

382 383

To a stirred solution of 2, 5-dibromopyridine (5.0 g, 2.12 mmol) in THE (50 mL) at −78° C. was added n-Butyl lithium (2.5M in hexane) (12.5 mL, 3.18 mmol) under nitrogen and stirred for 1 h at same temperature. 2,2,2-trifluoro-1-morpholinoethanone (5.06 g, 2.76 mmol) was then added drop wise to the reaction mixture, stirred for 1 h at −78° C. Progress of reaction was monitored by TLC. After reaction completion reaction mass was quenched with ice cold water. Phases separated and aqueous layer was extracted with diethyl ether. The organic layer was washed with brine, dried over sodium sulphate and concentrated under reduced pressure. Crude was purified by silica gel (100-200 mesh) column chromatography using 18% ethyl acetate in hexane as eluent to obtain 1-(6-bromopyridin-2-yl)-2,2,2-trifluoroethanone (3.5 g, 64.81%) as colourless oil.

Step-2: Synthesis of (E/Z)-ethyl 3-(6-bromopyridin-3-yl)-4,4,4-trifluorobut-2-enoate

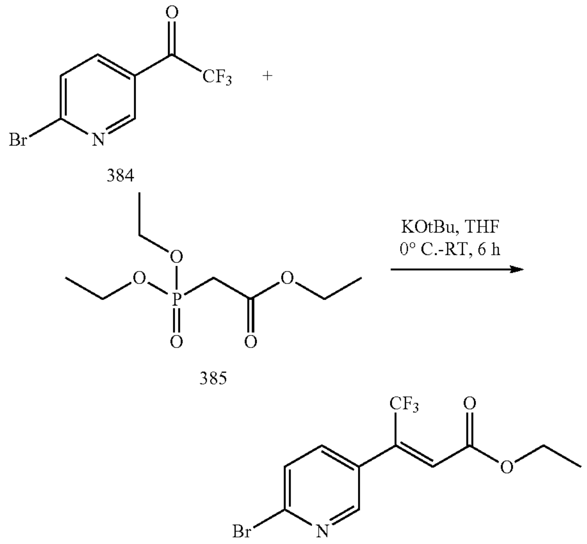

384

385

386

To a stirred solution of Triethyl phosphonoacetate (3.9 g, 1.77 mmol) and THE (60 ml) at 0° C. under $N_2$ added base potassium ter-butoxide (1.98 g, 1.77 mmol) lotwise. The resultant mixture was stirred at RT for 1 h for anion generation. A solution of 1-(6-bromopyridin-3-yl)-2,2,2-trifluoroethanone (3.0 g, 1.18 mmol) in THE (15 ml) was added slowly. After addition stirred mixture for 6 h at RT. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 9 to 15% EA/Hexane to obtained (E/Z)-ethyl 3-(6-bromopyridin-3-yl)-4,4,4-trifluorobut-2-enoate (1.5 g, 40%) as yellow oil.

MS: 254 [M+2]

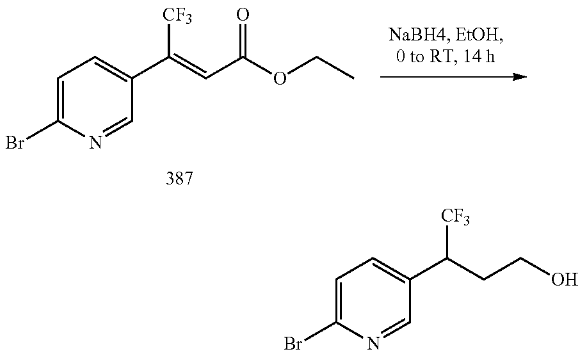

387

388

Step-3: Synthesis of 3-(6-bromopyridin-3-yl)-4,4,4-trifluorobutan-1-ol

To a stirred solution of (E/Z)-ethyl 3-(6-bromopyridin-3-yl)-4,4,4-trifluorobut-2-enoate (1.5 g, 462 mmol) in EtOH (30 mL), $NaBH_4$ (0.520 g, 1380 mmol) was added at 0° C. Reaction was allowed to stir at room temperature for 14 h. Reaction was monitored by TLC. On completion, reaction was quenched with water, extracted with EtOAc. The organic layer was washed with water, dried over $Na_2SO_4$, evaporated under reduced pressure to obtain crude reaction mass. Purification of the crude was done via silica gel (100-200 Mesh) column chromatography and desired compound eluted at 30% ethyl acetate/n-Hexane to obtained 3-(6-bromopyridin-3-yl)-4,4,4-trifluorobutan-1-ol (0.610 g, 46.5%) as clear oil.

MS: 284 [M+1]

Step-4: Synthesis of 2-bromo-5-(4-bromo-1,1,1-trifluorobutan-2-yl)pyridine

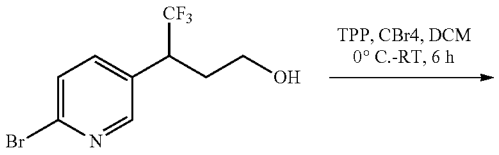

389

-continued

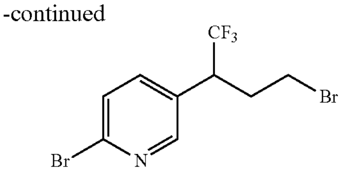

390

To a stirred solution of 3-(6-bromopyridin-3-yl)-4,4,4-trifluorobutan-1-ol (0.500 g, 1.76 mmol) in DCM (20 mL), TPP (0.922 g, 3.52 mmol) was added and then added carbontetrabromide (1.16 g, 3.521 mmol) portion-wise at 0° C. The resultant reaction mixture was stirred at room temperature for 7 h. Completion of reaction was monitored by TLC. After completion reaction mass was quenched with ice cold water. Phases separated and aqueous layer was extracted with DCM. The organic layer was washed with brine, dried over sodium sulphate and concentrated under reduced pressure. Crude product was purified by silica gel (100-200 mesh) column chromatography using 5 to 7% Acetone in Hexane as eluent to obtain 2-bromo-5-(4-bromo-1,1,1-trifluorobutan-2-yl)pyridine (0.300 g, 47.05%) as reddish colour semi solid.

MS: 346.97 [M+1]

Step-5: Synthesis of tert-butyl 3-(6-bromopyridin-3-yl)-4,4,4-trifluorobutylmethylcarbamate

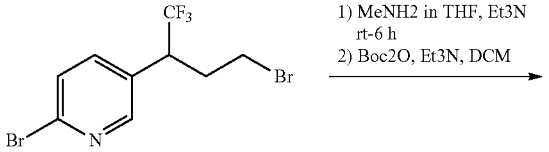

391

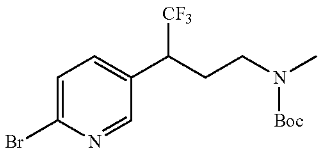

392

To a stirred solution of 2-bromo-5-(4-bromo-1, 1, 1-trifluorobutan-2-yl)pyridine (0.300 g, 0.867 mmol) in THE (10 mL), methyl amine in THE (3 ml) followed by $Et_3N$ (0.262 g, 2.60 mmol) was added at 0° C. The resultant reaction mixture was stirred at room temperature for 4 h. Completion of reaction was monitored by TLC. After completion reaction mass was quenched with water. Phases separated and aqueous layer was extracted with ethyl acetate. The organic layer was washed with brine, dried over sodium sulphate and concentrated under reduced pressure. Obtain 3-(6-bromopyridin-3-yl)-4, 4,4-trifluoro-N-methylbutan-1-amine (93.75%), (0.240 g, 0.8080 mmol) was dissolved in DCM (10 mL), Boc Anhydride (0.264 g, 1.21 mmol) followed by $Et_3N$ (0.204 g, 2.02 mmol) was added at 0° C. The resultant reaction mixture was stirred at room temperature for 6 h. Completion of reaction was monitored by TLC. After completion reaction mass was quenched with water. Phases separated and aqueous layer was extracted with DCM. The organic layer was washed with brine, dried over sodium sulphate and concentrated under reduced pressure. Obtain tert-butyl 3-(6-bromopyridin-3-yl)-4,4,4-trifluorobutylmethylcarbamate (0.200 g, 49.05%) as off white solid used as such in next step.

MS: 397.09 [M+1]

Step-6: Synthesis of tert-butyl 3-(6-(4-(2-amino-3-nitropyridin-4-yl)-1H-pyrazol-1-yl)pyridin-3-yl)-4,4,4-trifluorobutylmethylcarbamate

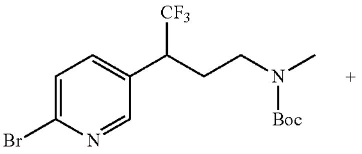

393

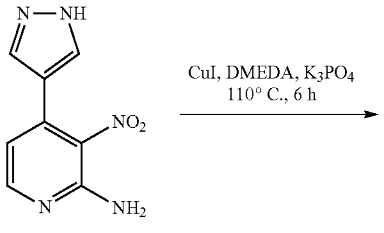

394

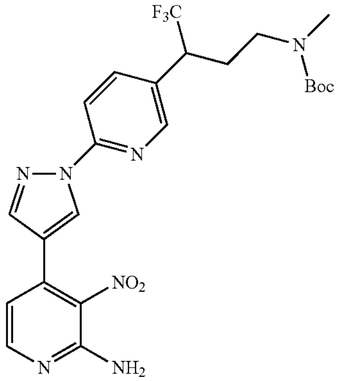

395

To a stirred solution of 3-nitro-4-(1H-pyrazol-4-yl)pyridin-2-amine (0.100 g, 0.487 mmol) and compound tert-butyl 3-(6-bromopyridin-3-yl)-4,4,4-trifluorobutylmethylcarbamate (0.193 g, 0.48 mmol) in Dioxane (5 ml) was added $K_3PO_4$ (0.305 g, 1.44 mmol) followed by CuI (0.009 g, 0.048 mmol) and DMEDA (0.042 g, 0.48 mmol). Reaction was heated at 110° C. for 6 h. Reaction was monitored by TLC. On completion reaction mixture was quenched with water and extracted with ethyl acetate. The organic layer was washed with water, brine, dried over sodium sulphate and concentrated under reduced pressure to give crude desired product that was purified by silica gel (100 to 200 Mesh) column chromatography: eluent at 3-5% MeOH in DCM to obtained tert-butyl 3-(6-(4-(2-amino-3-nitropyridin-4-yl)-1H-pyrazol-1-yl)pyridin-3-yl)-4,4,4-tyrifluorobutylmethylcarbamate (0.070 g, 50%) as yellow solid.

MS: 522.1 [M+1]

Step-7: Synthesis of tert-butyl 3-(6-(4-(2,3-diaminopyridin-4-yl)-1H-pyrazol-1-yl)pyridin-3-yl)-4,4,4-trifluorobutylmethylcarbamate

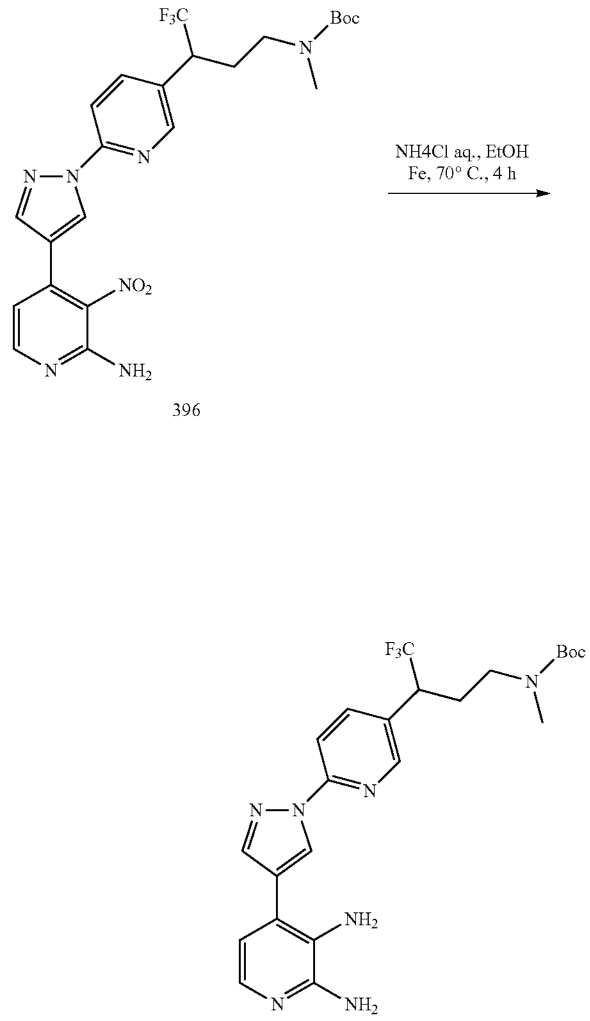

396

397

To a stirred solution tert-butyl 3-(6-(4-(2-amino-3-nitropyridin-4-yl)-1H-pyrazol-1-yl)pyridin-3-yl)-4,4,4-trifluorobutylmethylcarbamate (0.052 g, 1.91 mmol) in EtOH (7.0 mL), $NH_4Cl$ (2.0 mL) was added at room temperature. To the resultant reaction mixture, Fe powder (0.52 g, 9.51 mmol) was added and stirred for 4 h at 70° C. Completion of reaction was monitored by TLC. On completion, reaction mixture was diluted with $H_2O$:EtOAc (50 mL, 5:5) and pass over celite to remove inorganic impurities from the reaction mixture. The aqueous layer was extracted with ethyl acetate. The organic layer was washed with water, brine, dried over sodium sulphate and concentrated under reduced pressure to obtained pure tert-butyl 3-(6-(4-(2,3-diaminopyridin-4-yl)-1H-pyrazol-1-yl)pyridin-3-yl)-4,4,4-trifluorobutylmethylcarbamate (0.036 g, 75%) as dark brown solid mass.

MS: 492.2 [M+1]

Step-8: Synthesis of tert-butyl 3-(6-(4-(3H-imidazo[4,5-b]pyridin-7-yl)-1H-pyrazol-1-yl)pyridin-3-yl)-4,4,4-trifluorobutylmethylcarbamate

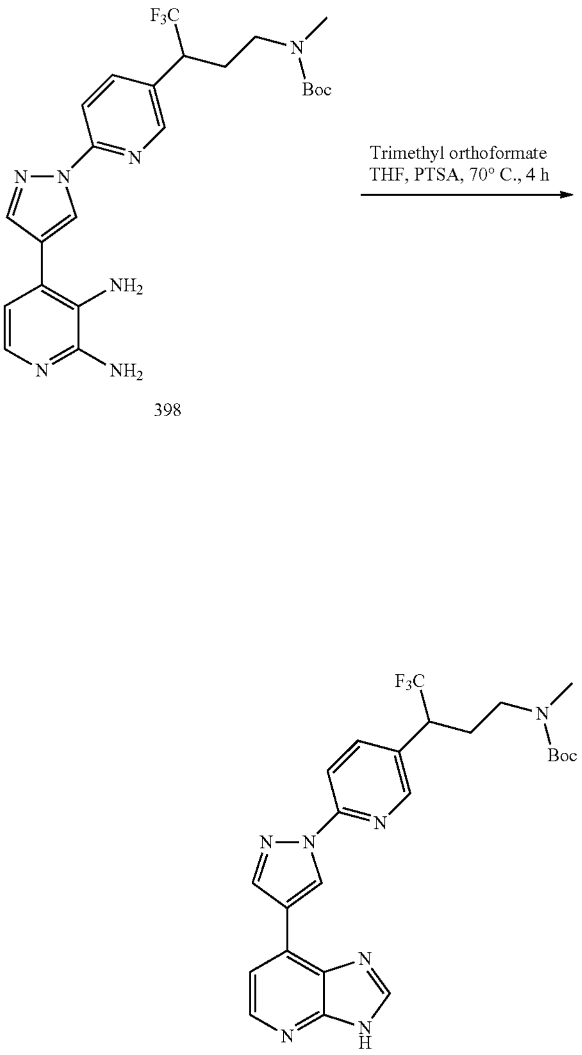

398

399

To a stirred solution of tert-butyl 3-(6-(4-(2,3-diaminopyridin-4-yl)-1H-pyrazol-1-yl)pyridin-3-yl)-4,4,4-trifluorobutylmethylcarbamate (0.035 g, 0.079 mmol) in THF (1.0 mL), Trimethyl orthoformate (1.5 mL) was added. To resultant reaction mixture, PTSA (0.0027 g, 0.015 mmol) was added and stirred for 4 h at 70° C. Completion of reaction was monitored by TLC. On completion, quenched with bicarbonate water, extracted with 10% MeOH in DCM. The organic layer was washed with water, brine, dried over sodium sulphate and concentrated under reduced pressure to give crude desired product that was purified by silica gel (100 to 200 Mesh) column chromatography: eluent at 8 to 9% MeOH in DCM to obtained tert-butyl 3-(6-(4-(3H-imidazo[4,5-b]pyridin-7-yl)-1H-pyrazol-1-yl)pyridin-3-yl)-4,4,4-trifluorobutylmethylcarbamate (0.021 g, 60%) as off white solid.

MS: 502.1 [M+1]

Step-9: Synthesis 3-(6-(4-(3H-imidazo[4,5-b]pyridin-7-yl)-1H-pyrazol-1-yl)pyridin-3-yl)-4,4,4-trifluoro-N-methylbutan-1-amine

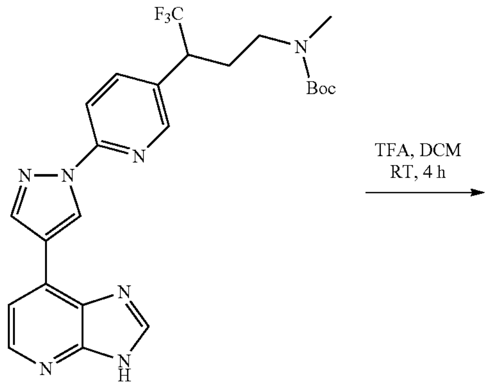

400

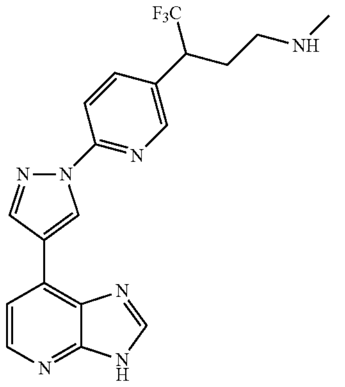 [SMILES: CNCCC(c1ccc(-n2cc(-c3ccnc4[nH]cnc34)cn2)nc1)C(F)(F)F]

1152

To a stirred solution of tert-butyl 3-(6-(4-(3H-imidazo[4, 5-b]pyridin-7-yl)-1H-pyrazol-1-yl)pyridin-3-yl)-4, 4, 4-trifluorobutylmethylcarbamate (0.021 g, 0.0419 mmol) in DCM (50 mL), TFA (0.004 g, 0.0419 mmol) was added dropwise at RT under nitrogen. Allow to warm reaction mixture to RT and stirred for 6 h. On completion, reaction mixture quenched with bicarbonate solution and extracted with 10% MeOH in DCM. The organic layer was washed with brine, dried over sodium sulphate and concentrated under reduced pressure. Crude was purified by silica gel (100-200 mesh) column chromatography using 4-5% MeOH in DCM as eluent to obtain 3-(6-(4-(3H-imidazo[4,5-b]pyridin-7-yl)-1H-pyrazol-1-yl)pyridin-3-yl)-4,4,4-trifluoro-N-methylbutan-1-amine (0.05 g, 31.25%) as off-white solid.

MS: 402.1 [M+1]

The compounds of the present invention were tested for their activity and were found to be active. The assays and results are presented here below.

Biological Example 1: JAK Biochemical Assay

Recombinant JAK1, JAK2, JAK3 and TYK2 (Carna Biosciences) were used to develop biochemical assays in 50 mM HEPES pH 7.5, 1 mM EGTA, 10 mM $MgCl_2$, 2 mM DTT and 0.01% Tween-20. Amount of enzyme, substrate (ULigh-JAK-1 (Tyr1023) Peptide and ATP concentrations to be used was determined for each kinase assay by respective titration and Km studies. Biochemical assay was developed by LANCE Ultra TR-FRET technology (Perkin Elmer). Enzyme and compounds were incubated at 22° C. for 60 minutes in a white 384 well optiplate (Perkin Elmer). Substrate and ATP were added to the above mix and incubated further for 90 minutes. Reaction is terminated by adding EDTA and detection antibody (Europium-anti-phospho-tyrosine (PT66) Antibody) was added. Assay read out was measured in TR-FRET mode in BMG FLUOstar multimode reader. Upon irradiation at 320 nm, the energy from the Eu donor is transferred to the ULight acceptor dye which, in turn, generates light at 665 nm. The intensity of the light emission is proportional to the level of ULight substrate phosphorylation. Compounds which interfere with JAK enzyme activity show a lesser substrate phosphorylation and values are projected in terms of % inhibition in comparison to vehicle control.

Biological Example 2: JAK Cellular Assays—STAT3 and STAT5 Phosphorylation by IL-6 and GMCSF TF-1 cells were starved overnight in OptiMEM medium with 0.5% charcoal stripped fetal bovine serum, 0.1 mM nonessential amino acids (NEAA), 1 mM sodium pyruvate and without phenol red in $CO_2$ incubator maintained at 37° c. Next day, cells were resuspended in RPMI without phenol red and dispensed into a 96 well plate at a final cell density of 1,20,000 cells per well. Compounds were diluted in DMSO and added to cells and incubated for 30 minutes in $CO_2$ incubator maintained at 37° c. Final DMSO concentration in cell based assay was 0.2%. Human recombinant cytokines, IL-6 (30 ng/ml) and GMCSF (5 ng/ml) were added to the plate containing cells along with compound and incubated for 20 minutes with gentle tapping at every 5 minutes once. Compound mediated effects on STAT3 and STAT5 phosphorylation was measured in the lysates prepared by using CISBIO pSTAT3 and pSTAT5 detection kits by HTRF method. Background signal obtained from cells which were not activated with cytokines, was subtracted from vehicle controls and compound treated wells. Percentage inhibition of pSTAT3/5 levels by compounds were calculated from vehicle controls, which were considered as 100% pSTAT3/5 controls.

Biological Example 3: STAT5 Phosphorylation by IL-2

HT-2 cells were starved overnight in RPMI phenol red with 10% fetal bovine serum for 4 hours in $CO_2$ incubator maintained at 37° c. Compounds were diluted in DMSO and added to 96 well plate containing a final density of 1,20,000 cells per well. Cells and compounds are incubated for 30 minutes in $CO_2$ incubator maintained at 37° C. and final DMSO concentration in cell based assay was 0.2%. Human recombinant cytokine, IL-2 (50 U/ml) was added to the plate containing cells and compound and incubated for 20 minutes with gentle tapping/shaking at every 5 minutes once. Compound mediated effects on STAT5 phosphorylation was measured in the lysates prepared by using CISBIO pSTAT5 detection kit by HTRF method. Background signal obtained from cells which were not activated with cytokines, was subtracted from vehicle controls and compound treated wells. Percentage inhibition of pSTAT5 levels by compounds were calculated from vehicle controls, which were considered as 100% pSTAT5 controls.

Biological Example 4: IFN-γ Production in NK 92 Cells by IL-12

NK 92 cells were cultured in medium without IL-2 for overnight. Next day, 5000 cells per well NK 92 cells were seeded in a 96 well plate. Compounds were added to cells and incubated for 1 hour. Later IL-12, 10 U/ml was added to cells and incubated for overnight. Supernatant was collected from the wells and IFN-7 secretion was measured by using human IFN-7 ELISA kit. Absorbance was measured at 450 nm in BMG FLUOstar. Background signal obtained from cells which were not activated with cytokines, was subtracted from vehicle controls and compound treated wells. Percentage inhibition of IFN-7 secretion by compounds were calculated from vehicle controls, which were considered as 100% IFN-7 secretion.

The compounds of the present invention have been tested as per Biological examples 1 to 4 and the result are in Table 2 below

TABLE 2

Activity of the compounds of the present invention.

| | Biochemical Assay (μM) | | | | Cell Based Assay (μM) | | | |
|---|---|---|---|---|---|---|---|---|
| | | | | | TF-1/IL-6/ | TF-1/GMCSF/ | HT-2/IL-2/ | NK-92/IL-2/ |
| S. No. | JAK1 | JAK2 | JAK3 | TYK2 | pSTAT3 | pSTAT5 | pSTAT5 | IFN-γ |
| 1001. | >10 | >10 | >10 | >10 | | | | |
| 1002. | <0.5 | <0.5 | <0.5 | >0.5 | >10 | >10 | | |
| 1003. | 0.021 | 0.036 | 0.175 | 0.182 | >10 | | | |
| 1004. | >10 | >10 | >10 | >10 | | | | |
| 1005. | 0.5 | 0.5 | 0.5 | >1 | >10 | | | |
| 1006. | 0.5 | 0.5 | 0.5 | >1 | | | | |
| 1007. | >0.5 | >0.5 | >1 | >1 | >10 | | | |
| 1008. | >1 | >1 | >1 | >10 | | | | |
| 1009. | >10 | >0.5 | >1 | >10 | | | | |
| 1010. | <0.5 | <0.5 | >0.5 | >1 | | | | |
| 1011. | 0.5 | >1 | >1 | >1 | >10 | >10 | >10 | |
| 1012. | 0.5 | 0.5 | >1 | 1 | | | | |
| 1013. | >10 | >10 | >10 | >10 | | | | |
| 1014. | 0.5 | 1 | >1 | >1 | >10 | >10 | >10 | |
| 1015. | 1 | >1 | >1 | >1 | | | | |
| 1016. | >10 | >10 | >10 | >10 | | | | |
| 1017. | >1 | >1 | >10 | >10 | | | | |
| 1018. | >10 | >10 | >10 | >10 | | | | |
| 1019. | 0.5 | >1 | >1 | >1 | | | | |
| 1020. | >10 | >10 | >10 | >10 | | | | |
| 1021. | 1 | >1 | >1 | >1 | | | | |
| 1022. | <0.5 | <0.5 | <0.5 | <0.5 | >10 | | | |
| 1023. | >10 | >10 | >10 | >10 | | | | |
| 1024. | >1 | >1 | >1 | >1 | | | | |
| 1025. | >10 | >10 | >10 | >10 | | | | |
| 1026. | 0.041 | 0.048 | 0.283 | 0.122 | >1 | >10 | | |
| 1027. | 0.028 | 0.044 | 0.146 | 0.096 | >10 | >10 | >10 | |
| 1028. | >1 | >1 | >1 | >1 | | | | |
| 1029. | >10 | >10 | >10 | >10 | | | | |
| 1030. | 0.039 | 0.066 | 0.43 | 0.093 | 10 | | | |
| 1031. | >1 | >1 | >1 | >1 | | | | |
| 1032. | <0.5 | <0.5 | <0.5 | <0.5 | >10 | | | |
| 1033. | 0.5 | 0.5 | >1 | >1 | | | | |
| 1034. | >1 | >1 | >10 | >10 | | | | |
| 1035. | >10 | >10 | >10 | >10 | >10 | | | |
| 1036. | >10 | >10 | >10 | >10 | | | | |
| 1037. | >0.5 | >1 | >1 | >0.5 | >10 | | | |
| 1038. | >0.5 | >0.5 | >0.5 | >0.5 | 10 | | | |
| 1039. | <0.5 | <0.5 | 0.5 | <0.5 | 10 | | | |
| 1040. | 0.5 | 0.5 | 0.5 | >1 | | | | |
| 1041. | >1 | >1 | >10 | >1 | >10 | | | |
| 1042. | >10 | >1 | >10 | >10 | | | | |
| 1043. | 0.03 | 0.031 | 0.123 | 0.053 | 4.7 | >10 | | |
| 1044. | <0.5 | <0.5 | <0.5 | <0.5 | 10 | | | |
| 1045. | >1 | >1 | >1 | >1 | | | | |
| 1046. | <0.5 | <0.5 | <0.5 | <0.5 | >10 | >10 | | |
| 1047. | <0.5 | <0.5 | <0.5 | <0.5 | 4.9 | 10 | | |
| 1048. | <0.5 | <0.5 | <0.5 | <0.5 | >10 | >10 | | |
| 1049. | <0.5 | <0.5 | <0.5 | <0.5 | <10 | >10 | | |
| 1050. | <0.5 | <0.5 | <0.5 | <0.5 | <10 | >10 | | |
| 1051. | <0.5 | <0.5 | >1 | <0.5 | <10 | >10 | | |
| 1052. | <0.5 | <0.5 | >0.5 | <0.5 | >10 | >10 | | |
| 1053. | <1 | <1 | 1 | >1 | >10 | >10 | | |
| 1054. | >10 | >0.5 | >1 | >1 | >1 | 10 | | |
| 1055. | >1 | <0.5 | >1 | >0.5 | >10 | >10 | | |
| 1056. | <0.5 | <0.5 | <0.5 | >0.5 | >10 | >10 | | |
| 1057. | >0.5 | >0.5 | >0.5 | >1 | | | | |
| 1058. | >1 | >1 | >10 | >10 | >10 | >10 | | |

TABLE 2-continued

Activity of the compounds of the present invention.

| | Biochemical Assay (μM) | | | | Cell Based Assay (μM) | | | |
|---|---|---|---|---|---|---|---|---|
| | | | | | TF-1/IL-6/ | TF-1/GMCSF/ | HT-2/IL-2/ | NK-92/IL-2/ |
| S. No. | JAK1 | JAK2 | JAK3 | TYK2 | pSTAT3 | pSTAT5 | pSTAT5 | IFN-γ |
| 1059. | >1 | >1 | >10 | >10 | | | | |
| 1060. | >0.5 | >0.5 | >0.5 | >1 | | | | |
| 1061. | >1 | 1 | >1 | >1 | >10 | >10 | | |
| 1062. | <0.5 | <0.5 | <0.5 | <0.5 | | | | |
| 1063. | >0.5 | <0.5 | >0.5 | <0.5 | | | | |
| 1064. | <0.5 | <0.5 | <0.5 | <0.5 | >10 | | | |
| 1065. | >0.5 | <0.5 | >0.5 | >0.5 | | | | |
| 1066. | 1 | >0.5 | >0.5 | >0.5 | >10 | | | |
| 1067. | >1 | >0.5 | >0.5 | >10 | >10 | >10 | | |
| 1068. | >1 | >1 | >1 | >1 | >10 | >10 | | |
| 1069. | >10 | >1 | >0.5 | >1 | | | | |
| 1070. | >0.5 | <0.5 | >0.5 | >0.5 | >10 | >10 | | |
| 1071. | >0.5 | >0.5 | >0.5 | >0.5 | >10 | | | |
| 1072. | >0.5 | >0.5 | >0.5 | 1 | >10 | >10 | | |
| 1073. | >1 | >0.5 | >0.5 | >0.5 | >1 | >10 | | |
| 1074. | >10 | >1 | >1 | >1 | >10 | >10 | | |
| 1075. | 0.046 | 0.19 | <0.5 | >1 | 3.1 | >10 | | |
| 1076. | 0.037 | 0.085 | <0.5 | >1 | 6 | >10 | | |
| 1077. | >1 | >1 | >1 | >10 | >10 | >10 | | |
| 1078. | 0.025 | 0.108 | 0.07 | >1 | 1.05 | >10 | >1 | >10 |
| 1079. | >10 | >1 | >1 | >10 | | | | |
| 1080. | 0.068 | <0.5 | <0.5 | >10 | >1 | >10 | | |
| 1081. | <0.5 | >0.5 | <0.5 | >10 | >1 | >10 | | |
| 1082. | <0.5 | <0.5 | <0.5 | >1 | >1 | >10 | | |
| 1083. | >0.5 | >0.5 | <0.5 | >1 | | | | |
| 1084. | NA | NA | NA | NA | >1 | >10 | | |
| 1085. | >1 | >1 | >1 | >10 | | | | |
| 1086. | <0.5 | >0.5 | >0.5 | >10 | >10 | >10 | | |
| 1087. | >0.5 | >1 | >1 | >10 | | | | |
| 1088. | >1 | >1 | >1 | >1 | | | | |
| 1089. | >0.5 | >0.5 | >1 | >1 | | | | |
| 1090. | 0.053 | 0.3 | 0.12 | >1 | >1 | >10 | >1 | |
| 1091. | >0.5 | >1 | >0.5 | >10 | | | | |
| 1092. | >1 | >1 | >1 | >1 | | | | |
| 1093. | >0.5 | <0.5 | <0.5 | >10 | | | | |
| 1094. | <0.5 | <0.5 | <0.5 | <0.5 | >1 | >1 | | |
| 1095. | <1 | <1 | <1 | >10 | | | | |
| 1096. | >10 | >1 | >1 | >10 | | | | |
| 1097. | >10 | >0.5 | >10 | >1 | | | | |
| 1098. | >1 | >1 | >1 | >10 | | | | |
| 1099. | <0.5 | <0.5 | <0.5 | >1 | >1 | >10 | | |
| 1100. | >0.5 | >0.5 | >0.5 | >10 | >10 | >10 | | |
| 1101. | >0.5 | >0.5 | >1 | >10 | >10 | >10 | | |
| 1102. | <0.5 | >0.5 | >0.5 | >1 | >10 | >10 | | |
| 1103. | >0.5 | >0.5 | >10 | >10 | >1 | >10 | | |
| 1104. | >1 | <0.5 | <0.5 | >1 | | | | |
| 1105. | >1 | >0.5 | >0.5 | >10 | | | | |
| 1106. | <0.5 | <0.5 | <0.5 | >1 | >1 | >10 | | |
| 1107. | <0.1 | >0.1 | <0.1 | >1 | >1 | >10 | | |
| 1108. | >0.1 | >0.5 | >0.1 | >1 | >10 | >10 | | |
| 1109. | <0.5 | <0.5 | <0.5 | >10 | >1 | >10 | | |
| 1110. | >0.1 | >0.5 | >0.1 | >1 | | | | |
| 1111. | <0.5 | >0.5 | <0.5 | >10 | >10 | >10 | | |
| 1112. | 0.5 | >0.5 | >1 | >1 | 10 | >10 | | |
| 1113. | >1 | >0.1 | >0.5 | >1 | >10 | >10 | | |
| 1114. | >0.1 | >0.5 | >0.1 | >1 | | | | |
| 1115. | >0.5 | >0.5 | >0.5 | >1 | | | | |
| 1116. | >0.1 | >0.5 | >0.1. | >1 | >1 | >10 | | |
| 1117. | NA | NA | NA | NA | >1 | >10 | | |
| 1118. | >0.5 | >0.5 | >0.5 | >1 | >10 | >10 | | |
| 1119. | 0.03 | 0.2 | 0.07 | >1 | 1.3 | >10 | >1 | 10 |
| 1120. | >0.05 | >0.1 | >0.1 | >1 | >1 | >10 | | |
| 1121. | 0.1 | >0.1 | >0.1 | >1 | | | | |
| 1122. | >0.1 | >0.5 | >0.5 | >1 | >1 | >1 | >1 | |
| 1123. | >0.1 | >0.5 | >0.1 | >1 | >1 | 10 | | |
| 1124. | >1 | >1 | >0.5 | >1 | | | | |
| 1125. | 0.004 | 0.023 | 0.009 | 0.15 | 0.27 | >10 | 0.26 | >10 |
| 1126. | 0.003 | 0.036 | 0.007 | >1 | 0.34 | >1 | <1 | |
| 1127. | >0.5 | >1 | >1 | >1 | >1 | >10 | | |
| 1128. | <0.1 | >0.5 | >0.5 | >1 | >1 | >10 | | |
| 1129. | <0.1 | >0.1 | <0.1 | >1 | >0.5 | >10 | >1 | |

TABLE 2-continued

Activity of the compounds of the present invention.

| | Biochemical Assay (μM) | | | | Cell Based Assay (μM) | | | |
|---|---|---|---|---|---|---|---|---|
| S. No. | JAK1 | JAK2 | JAK3 | TYK2 | TF-1/IL-6/ pSTAT3 | TF-1/GMCSF/ pSTAT5 | HT-2/ IL-2/ pSTAT5 | NK-92/IL-2/ IFN-γ |
| 1130. | >0.1 | >0.1 | >0.1 | >1 | >1 | >10 | | |
| 1131. | 0.053 | 0.38 | 0.11 | >1 | >0.5 | >10 | >1 | |
| 1132. | 0.1 | >0.5 | >0.1 | >1 | | | | |
| 1133. | <0.1 | 0.1 | 0.1 | >1 | 0.6 | >10 | 2.3 | |
| 1134. | <0.1 | 0.5 | <0.1 | >1 | >1 | >10 | | |
| 1135. | <0.1 | <0.1 | <0.1 | <0.1 | >1 | >10 | | |
| 1136. | <0.1 | <0.1 | <0.1 | >1 | 0.7 | >1 | 0.8 | |
| 1137. | 0.5 | >0.5 | >0.5 | >1 | | | | |
| 1138. | <0.1 | >0.1 | >0.1 | >1 | >1 | >10 | | |
| 1139. | >0.5 | >0.5 | >0.1 | >1 | 1 | | | |
| 1140. | <0.1 | <0.1 | <0.1 | >1 | | | | |
| 1141. | <0.1 | <0.1 | <0.1 | >1 | <1 | >10 | | |
| 1142. | <0.1 | 0.1 | <0.1 | >1 | >0.5 | >1 | >0.5 | |
| 1143. | <0.1 | <0.1 | <0.1 | >1 | 0.47 | <1 | 0.67 | |
| 1144. | 0.1 | 0.5 | >0.1 | >1 | >1 | >10 | | |
| 1145. | <0.1 | >0.1 | <0.1 | >1 | >0.5 | >1 | >1 | |
| 1146. | <0.1 | <0.1 | <0.1 | <0.1 | >0.1 | >0.1 | >0.1 | |
| 1147. | >0.5 | >1 | >1 | >1 | | | | |
| 1148. | <0.1 | <0.1 | <0.1 | >1 | >0.5 | | >1 | |
| 1149. | <0.1 | >0.1 | <0.1 | >1 | >0.5 | | >0.5 | |
| 1150. | <0.1 | <0.1 | <0.1 | >1 | >0.5 | >1 | >1 | |
| 1151. | <0.1 | >0.1 | >0.1 | >1 | >0.5 | >1 | >1 | |
| 1152. | <0.1 | <0.1 | <0.1 | >0.5 | >0.1 | | >0.1 | |
| 1153. | <0.1 | <0.1 | <0.1 | >0.5 | 0.36 | >1 | 2.1 | |
| 1154. | <0.1 | <0.1 | <0.1 | >0.5 | >0.5 | >1 | >0.5 | |
| 1155. | >0.1 | >0.5 | >0.1 | >1 | | | | |
| 1156. | >0.1 | >0.5 | >0.5 | >1 | >0.5 | | >1 | |
| 1157. | <0.1 | <0.1 | <0.1 | >0.5 | <1 | >10 | | |
| 1158. | <0.1 | >0.1 | >0.1 | >1 | >1 | >1 | | |
| 1159. | <0.1 | >0.1 | <0.1 | >1 | | | | |
| 1160. | >0.1 | >0.5 | >0.5 | >1 | | | | |
| 1161. | >1 | >1 | >0.5 | >1 | | | | |
| 1162. | >0.5 | >0.5 | >0.5 | >1 | | | | |
| 1163. | >0.5 | >0.5 | >0.5 | >1 | | | | |
| 1164. | >1 | >1 | >1 | >1 | | | | |
| 1165. | >1 | >1 | >1 | >1 | | | | |
| 1166. | >0.5 | >1 | >0.5 | >1 | | | | |
| 1167. | 0.096 | 0.3 | 0.173 | >10 | 10 | >10 | | |
| 1168. | >0.1 | >0.5 | >0.1 | >1 | >1 | | >1 | |
| 1169. | 0.013 | 0.073 | 0.014 | >1 | 0.45 | >10 | <1 | >10 |
| 1170. | >0.1 | >0.1 | >0.05 | >1 | >10 | >10 | | |
| 1171. | >1 | >1 | >1 | >1 | >10 | >10 | | |
| 1172. | 0.5 | 0.5 | <0.1 | >1 | | | | |
| 1173. | <0.1 | <0.1 | <0.1 | >1 | 10 | >10 | | |
| 1174. | 0.018 | 0.108 | 0.055 | >1 | 0.3 | >10 | 1.3 | |
| 1175. | >1 | >1 | >1 | >1 | | | | |
| 1176. | >1 | >1 | >1 | >1 | | | | |
| 1177. | >1 | <0.5 | >1 | >0.5 | >10 | >10 | | |
| 1178. | <0.1 | <0.1 | <0.1 | >1 | >1 | 1 | >1 | |
| 1179 | <0.1 | <0.1 | <0.1 | >1 | >1 | >1 | >1 | |
| 1180 | <1 | <1 | <1 | <1 | >1 | >1 | | |
| 1181 | <0.1 | 0.1 | <0.1 | >1 | >0.5 | >1 | >1 | |
| 1182 | 0.015 | 0.1 | 0.041 | >1 | 0.35 | >1 | 0.9 | >3 |
| 1183 | >0.1 | >0.5 | >0.1 | >1 | 1 | >1 | | |
| 1184 | <0.1 | >0.1 | <0.1 | >1 | >0.8 | >1 | 1.5 | |
| 1185 | <0.1 | >0.1 | >0.1 | >1 | 2 | >1 | >3 | |
| 1186 | <0.1 | >0.1 | >0.1 | >1 | >0.8 | >1 | >1 | |
| 1187 | <0.1 | >0.1 | <0.1 | >1 | >1 | >1 | | |
| 1188 | <0.1 | <0.1 | <0.1 | >1 | >0.5 | >1 | >0.75 | |
| 1189 | >0.5 | >1 | >1 | >1 | | | | |
| 1190 | <0.1 | <0.1 | <0.1 | >1 | 1 | | 3.6 | |
| 1191 | <0.1 | <0.1 | <0.1 | >1 | >1 | >1 | | |
| 1192 | <0.1 | <0.1 | <0.1 | >1 | >0.8 | | >0.8 | |
| 1193 | >0.1 | >0.5 | >0.1 | >1 | | | | |
| 1194 | >0.5 | >0.5 | >0.5 | >1 | | | | |
| 1195 | <0.1 | <0.1 | <0.1 | >1 | >0.5 | >1 | | |
| 1196 | >0.1 | >0.5 | >0.1 | >1 | | | | |
| 1197 | <0.1 | <0.1 | <0.1 | >0.5 | >0.3 | >1 | | |
| 1198 | <0.1 | <0.1 | <0.1 | >0.5 | 0.1 | 1 | 0.6 | |
| 1199 | <0.1 | >0.1 | <0.1 | >0.5 | | | | |
| 1200 | 0.023 | 0.015 | 0.009 | 0.52 | 0.1 | 1 | 0.6 | |

TABLE 2-continued

Activity of the compounds of the present invention.

| | | | | | Cell Based Assay (μM) | | | |
|---|---|---|---|---|---|---|---|---|
| | Biochemical Assay (μM) | | | | TF-1/IL-6/ | TF-1/GMCSF/ | HT-2/IL-2/ | NK-92/IL-2/ |
| S. No. | JAK1 | JAK2 | JAK3 | TYK2 | pSTAT3 | pSTAT5 | pSTAT5 | IFN-γ |
| 1201 | <0.1 | >0.5 | <0.1 | >1 | >0.5 | >1 | | |
| 1202 | <0.1 | >0.1 | <0.1 | >0.5 | >0.5 | >1 | | |
| 1203 | <0.1 | <0.1 | <0.1 | >0.5 | >0.1 | >1 | >0.5 | |
| 1204 | <0.1 | <0.1 | <0.1 | >1 | | | | |
| 1205 | <0.1 | >0.1 | >0.1 | >1 | | | | |
| 1206 | >0.1 | >0.1 | >0.5 | >1 | | | | |
| 1207 | 0.005 | 0.01 | 0.005 | >0.5 | 0.43 | | 1.08 | |
| 1208 | 0.01 | 0.01 | 0.005 | >0.5 | >1 | | | |
| 1209 | <0.1 | <0.1 | <0.1 | >1 | >0.75 | >1 | | |
| 1210 | <0.1 | <0.1 | <0.1 | >1 | >0.75 | >1 | | |
| 1211 | <0.1 | >0.1 | >0.1 | >1 | | | | |
| 1212 | <0.1 | <0.1 | <0.1 | >0.5 | >0.75 | >1 | | |
| 1213 | <0.1 | <0.1 | <0.1 | >0.5 | 0.55 | | 0.7 | |
| 1214 | <0.1 | <0.5 | <0.1 | >1 | >1 | | >1 | |
| 1215 | <0.1 | <0.1 | <0.1 | >1 | 0.32 | | 0.75 | |
| 1216 | <0.1 | <0.1 | <0.1 | >0.5 | 0.28 | | 0.51 | |
| 1217 | 0.0026 | 0.007 | 0.006 | 0.08 | >0.1 | | >0.5 | |
| 1218 | NA | NA | NA | NA | >0.5 | | | |
| 1219 | <0.1 | <0.1 | <0.1 | >0.5 | >0.75 | >1 | | |
| 1220 | <0.1 | <0.1 | <0.1 | >0.5 | >1 | >1 | | |
| 1221 | <0.1 | <0.1 | <0.1 | >0.1 | >0.75 | >1 | | |
| 1222 | NA | NA | NA | NA | >0.8 | >1 | | |
| 1223 | 0.002 | 0.015 | 0.004 | 0.39 | >0.1 | >1 | >0.5 | |
| 1224 | 0.001 | 0.03 | 0.001 | >0.1 | >0.75 | >1 | | |
| 1225 | .0025 | 0.064 | 0.018 | >1 | 0.16 | >1 | 0.47 | >3 |
| 1226 | <0.01 | >0.03 | >0.03 | >1 | >0.5 | >1 | >0.75 | |
| 1227 | <0.1 | <0.1 | <0.1 | >0.1 | >0.1 | >0.75 | >0.5 | |
| 1228 | <0.1 | <0.1 | <0.1 | >0.1 | >0.5 | >1 | >0.5 | |
| 1229 | <0.1 | <0.1 | <0.1 | >1 | >1 | | >1 | |
| 1230 | <0.1 | <0.1 | <0.1 | >0.5 | >0.5 | | >0.5 | |
| 1231 | .0003 | 0.005 | 0.003 | 0.1 | 0.05 | 1.5 | 0.15 | >3 |
| 1232 | 0.003 | 0.023 | 0.015 | 0.2 | 0.09 | >1 | 0.34 | >3 |
| 1233 | <0.1 | <0.1 | <0.1 | <0.5 | 0.21 | >1 | >0.5 | >3 |
| 1234 | 0.006 | 0.03 | 0.035 | 0.67 | 0.14 | >1 | 0.47 | >1 |
| 1235 | 0.001 | >0.03 | 0.001 | >1 | 0.36 | >1 | 0.55 | >1 |
| 1236 | 0.001 | >0.03 | >0.03 | >0.1 | >1 | | >0.75 | |
| 1237 | 0.001 | 0.01 | 0.005 | 0.1 | 0.19 | >1 | >0.5 | >3 |
| 1238 | 0.003 | >0.03 | 0.003 | >0.1 | >0.1 | 1 | >0.1 | |
| 1239 | 0.006 | 0.056 | 0.023 | 0.06 | 0.05 | 0.26 | | |
| 1240 | >0.01 | >0.03 | >0.03 | >1 | >0.5 | >1 | | |
| 1241 | <0.1 | >0.1 | <0.1 | >1 | >0.5 | >1 | >0.75 | |
| 1242 | <0.1 | <0.1 | <0.1 | >1 | >1 | >1 | >1 | |
| 1243 | <0.1 | <0.1 | <0.1 | >1 | >1 | >1 | >1 | |
| 1244 | <0.1 | >0.1 | >0.1 | >1 | >1 | | | |
| 1245 | >.001 | >0.03 | >.003 | >1 | >1 | | | |
| 1246 | 0.006 | 0.034 | 0.006 | 0.79 | 1.5 | | 2 | |
| 1247 | 0.01 | 0.06 | 0.023 | 0.19 | >1 | | >1 | |
| 1248 | <0.1 | <0.1 | <0.1 | >0.5 | >0.75 | | >0.8 | |
| 1249 | >0.5 | >0.5 | >0.5 | >1 | | | | |
| 1250 | <0.1 | <0.1 | <0.1 | >1 | >1 | | >1 | |
| 1251 | <0.1 | <0.1 | <0.1 | >0.5 | 1 | | >2 | |
| 1252 | <0.1 | <0.1 | <0.1 | >0.5 | 1.1 | | 1.63 | |

From Table 2, it can be clearly seen that the compounds of the present invention all possess activity as selective JAK1 inhibitor.

Biological Example 5: Comparison with Existing JAK Inhibitors

By way of illustration, certain exemplary compounds, were tested for their activity in comparison with existing JAK inhibitor. Example 1133, 1181 and 1215 was compared with the results of the existing JAK inhibitor under the same experimental condition, and the results are shown in Table 3

TABLE 3

Comparison of exemplary compounds of the present invention with known JAK inhibitors

| | Biochemical IC50 (nM) | | | | Cell based IC50 (μM) | | | |
|---|---|---|---|---|---|---|---|---|
| Example | JAK1 | JAK2 | JAK3 | TYK2 | TF-1/ IL-6 | TF-1/ GM-CSF | HT-2/ IL-2 | NK-92/ IL-12* |
| 1133 | 8 | 152 | 100 | 850 | 0.6 | >10 | 2.3 | >10 |
| 1181 | 15 | 105 | 42 | >1 | 0.35 | >10 | 0.9 | >10 |
| 1215 | 0.5 | 40 | 11 | >100 | 0.3 | >10 | 0.7 | >10 |
| Filgotinib | 64 | 58 | 750 | 490 | 0.6 | 3.4 | 0.95 | >10 |
| Tofacitinib | 1.2 | 1.7 | 0.34 | 33 | 0.033 | 0.24 | 0.019 | 3 |

*indicates IFN-γ detection from cell supernatants.

Data thus generated for compounds were compared with two reference standards, filgotinib—a JAK1 selective inhibitor, and tofacitinib—pan JAK inhibitor. Example 1133, 1181 and 1215 showed better potency as well as selectivity for JAK1 (7 to 80 fold selective for JAK1 vs JAK2; 3 to 22 fold selective for JAK1 vs JAK3) compared to filgotinib (0.9 fold JAK1 vs JAK2; 12 fold JAK1 vs JAK3). These compounds are also far superior in terms of JAK1 selectivity compared to a pan inhibitor such as tofacitinib.

Biological Example 6: Mouse Model of Rheumatoid Arthritis

Rheumatoid arthritis (RA) is an autoimmune disease that can cause joint pain and damage throughout the body. Several cytokines such as IL-6 and IFN-γ activate the Janus kinase/signal transducers and activators of transcription (JAK/STAT) pathway. Inhibition of JAK/STAT pathway is considered as one of the therapeutic options for treatment of rheumatoid arthritis. Rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis.

Compounds described herein are tested for JAK/STAT pathway inhibition driven efficacy in collagen induced mouse arthritis model. Compounds were orally dosed, QD for 21 days and at the end of the study, clinical symptoms, body weight and histopathology of ankle and paws were measured. Arthritis score was calculated for the compounds as well as reference standard, filgotinib. By way of exemplification, examples 1215, 1181 and 1133 showed very good efficacy and are better or comparable to filgotinib.

Biological Example 7: Mouse Model of Imiquimod Induced Psoriasis

Imiquimod (IMQ) induced dermatitis closely resembles human psoriasis lesions not only with regard to phenotypic and histological characteristics but also in the development of the lesions. IMQ is a ligand for toll-like receptor 7 (TLR7) and TLR8, and is a potent immune activator. IMQ's immunomodulatory effects in triggering psoriasis are attributed to stimulation of TLR7 and TLR8 on plasmacytoid dendritic cells (pDCs) and an upregulated type I interferon pathway. Migration of activated dermal dendritic cells to lymph nodes in skin triggers a sequence of events leading to late phase of psoriasis. Compounds described herein are tested for JAK inhibition driven efficacy in Imiquimod induced dermatitis in mice.

Female BALB/c mice were topically dosed with 3% cream formulation containing test compounds. After four hours of test compound administration, 5% Imiquimod was applied on back skin and right ear for five days. On day 6, post dosing with test compounds, the severity of psoriasis was monitored and graded following Psoriasis Area and Severity Index (PASI). Efficacies of the compounds were evaluated based on PASI score. Redness, thickness and scaling of back skin and ear were assessed among the groups for scoring.

Compounds of the present invention for instance, Example 1133, Example 1215 and filgotinib showed statistically significant decrease in cumulative psoriasis score compared to vehicle. There was a significant decrease in back skin thickness, ear thickness on administration of Example 1133, 1215 and filgotinib (3% topical, QD). Example 1215 showed better efficacy compared to 1133 and reference compound filgotinib. The data is represented by way of a FIG. 1. From the FIGURE, it can be clearly seen that there the exemplary compounds of the present invention show enhanced efficacy when compared to the compounds available in the market such Filgotinib.

Biological Example 9: Murine Model of Oxazolone Induced Colitis

The animal in which the colitis is produced can be any mammal and can include but is not limited to mouse, rat, guinea pig, hamster, rabbit, cat, dog, goat, monkey, and chimpanzee. The colitis can be produced in the animal by any method known in the art. A mouse model of oxazolone induced colitis was utilized to study the efficacy of JAK inhibitors. Oxazolone colitis has a histological resemblance to human ulcerative colitis. Pro-inflammatory cytokines elevated in ulcerative colitis rely on JAK family of tyrosine kinases for signal transduction. It has been proposed that JAK inhibition may be beneficial in the treatment of ulcerative colitis.

Male BALB/c mice were used in the study, 10-12 weeks, on day 1, 4% Oxazolone (in 4:1 acetone:olive oil formulation) or vehicle solution was applied between shoulders to anesthetized animals. Seven days after skin sensitization, mice were fasted for 6 hours prior to intra-rectal administration of 1% oxazolone (in 1:1 ethanol:water formulation). Drug treatment or vehicle administration (PO, BID) was initiated on day 6, a day prior to intra-rectal oxazolone challenge. Animals were dosed with test compounds or vehicle till day 9. Disease activity index (DAI) was graded for each mouse by treatment-blinded experimenters. Body weight loss (0=none, 2=>5-10%, 4=>20%), stool consistency (0=normal, 2=soft without pellet, 4=severe diarrhoea) and rectal bleeding (0=no blood, 2=bloody stool, 4=adhesion of blood to anus& part of tail) were assessed for DAI score.

Below Table 4, mentions the scores of the compounds with respect to disease activity index parameters in comparison with vehicle treated group.

TABLE 4

Testing of exemplary compounds of the present invention in murine model of Oxazolone Induced Colitis:

| | Stool Consistency Index | Rectal Bleeding Index | Body Weight Loss Index | Disease Activity Index |
|---|---|---|---|---|
| Vehicle | 3-3.5 | 2.5-2.8 | 3.5-3.7 | 9-10 |
| 1181 | 1.5-2.0 | 1.5-1.8 | 1.7-1.9 | 2-3 |
| 1215 | 1.0-1.2 | 0.2-0.4 | 0.2-0.3 | 1-2 |
| Filgotinib | 0.9-1.3 | 0.3-0.5 | 0.2-0.3 | 1-2 |

Compounds of the present invention such as example 1181, 1215 and filgotinib showed statistically significant decrease in disease activity index compared to vehicle. There was a significant decrease in stool consistency, rectal bleeding and body weight loss parameters on administration of Example 1181, 1215 and filgotinib (30 mpk, PO, BID). Example 1215 showed better efficacy in comparison to the marketed compound Filgotinib.

We claim:

1. A compound selected from the group consisting of:

1001. N-(2,2,2-trifluoroethyl)-4-(2,3-dihydro-2-oxo-1H-imidazo[4,5-b]pyridin-7-yl)benzamide;
1002. 1-(1,1,1-trifluoropropan-2-yl)-3-(4-(2,3-dihydro-2-oxo-1H-imidazo[4,5-b]pyridin-7-yl)phenyl) urea;
1003. 1-(2,2,2-trifluoroethyl)-3-(4-(2,3-dihydro-2-oxo-1H-imidazo[4,5-b]pyridin-7-yl)phenyl) urea;
1004. 1-(2,2,2-trifluoroethyl)-3-(5-(2,3-dihydro-2-oxo-1H-imidazo[4,5-b]pyridin-7-yl)pyrimidin-2-yl) urea;
1005. 1-(2,2,2-trifluoroethyl)-3-(5-(2,3-dihydro-2-oxo-1H-imidazo[4,5-b]pyridin-7-yl)pyridin-2-yl) urea;
1006. 1-(5-(2-oxo-2,3-dihydro-1H-imidazo[4,5-b]pyridin-7-yl) pyrazin-2-yl)-3-(2,2,2-trifluoroethyl) urea;
1007. N-(4-(2,3-dihydro-2-oxo-1H-imidazo[4,5-b]pyridin-7-yl)phenyl)-3,3-dimethylazetidine-1-carboxamide;
1008. N-(4-(2,3-dihydro-2-oxo-1H-imidazo[4,5-b]pyridin-7-yl)phenyl) morpholine-4-carboxamide;
1009. 1-(4-(2,3-dihydro-2-oxo-1H-imidazo[4,5-b]pyridin-7-yl)phenyl)-3-(pyridin-4-yl) urea;
1010. 1-(4-(3H-imidazo[4,5-b]pyridin-7-yl)phenyl)-3-(2,2,2-trifluoroethyl) urea;
1011. N-(2,2,2-trifluoroethyl)-4-(2,3-dihydro-2-oxo-1H-imidazo[4,5-b]pyridin-7-yl) piperazine-1-carboxamide;
1012. N-(cyanomethyl)-4-(2,3-dihydro-2-oxo-1H-imidazo[4,5-b]pyridin-7-yl) piperazine-1-carboxamide;
1013. 4-(2,3-dihydro-2-oxo-1H-imidazo[4,5-b]pyridin-7-yl)-N-(2-(methylsulfonyl)ethyl) piperazine-1-carboxamide;
1014. 4-(2,3-dihydro-2-oxo-1H-imidazo[4,5-b]pyridin-7-yl)-N-(pyridin-4-yl) piperazine-1-carboxamide;
1015. N-(2-fluoropyridin-4-yl)-4-(2,3-dihydro-2-oxo-1H-imidazo[4,5-b]pyridin-7-yl) piperazine-1-carboxamide;
1016. N-(1-(methylsulfonyl) piperidin-4-yl)-4-(2-oxo-2,3-dihydro-1H-imidazo[4,5-b]pyridin-7-yl) piperazine-1-carboxamide;
1017. N-(cyclopentylmethyl)-4-(2,3-dihydro-2-oxo-1H-imidazo[4,5-b]pyridin-7-yl) piperazine-1-carboxamide;
1018. 7-(4-(1,1-dioxidothiomorpholine-4-carbonyl) piperazin-1-yl)-1,3-dihydro-2H-imidazo[4,5-b]pyridin-2-one;
1019. 4-(2,3-dihydro-2-oxo-1H-imidazo[4,5-b]pyridin-7-yl)-N-(2-methoxypyridin-4-yl) piperazine-1-carboxamide;
1020. N-(1,1-dioxidotetrahydro-2H-thiopyran-4-yl)-4-(2-oxo-2,3-dihydro-1H-imidazo[4,5-b]pyridin-7-yl) piperazine-1-carboxamide;
1021. N-(1,1,1-trifluoropropan-2-yl)-4-(2,3-dihydro-2-oxo-1H-imidazo[4,5-b]pyridin-7-yl) piperazine-1-carboxamide;
1022. N-(2,2,2-trifluoroethyl)-4-(2-phenyl-3H-imidazo[4,5-b]pyridin-7-yl) piperazine-1-carboxamide;
1023. 7-(4-(3,3-dimethylazetidine-1-carbonyl) piperazin-1-yl)-1,3-dihydro-2H-imidazo[4,5-b]pyridin-2-one;
1024. 4-(2,3-dihydro-2-oxo-1H-imidazo[4,5-b]pyridin-7-yl)-N-(2-methyl-4-(methylsulfonyl)phenyl) piperazine-1-carboxamide;
1025. N-(2,2,2-trifluoroethyl)-2-(4-(2,3-dihydro-2-oxo-1H-imidazo[4,5-b]pyridin-7-yl) piperazin-1-yl) acetamide;
1026. N-(2,2,2-trifluoroethyl)-4-(2,3-dihydro-2-oxo-1H-imidazo[4,5-b]pyridin-7-yl)-1H-pyrazole-1-carboxamide;
1027. N-(cyanomethyl)-4-(2,3-dihydro-2-oxo-1H-imidazo[4,5-b]pyridin-7-yl)-1H-pyrazole-1-carboxamide;
1028. N-(2,2,2-trifluoroethyl)-3-(2,3-dihydro-2-oxo-1H-imidazo[4,5-b]pyridin-7-yl)-1H-pyrrole-1-carboxamide;
1029. N-(2,2,2-trifluoroethyl)-4-(2,3-dihydro-1-methyl-2-oxo-1H-imidazo[4,5-b]pyridin-7-yl)-1H-pyrazole-1-carboxamide;
1030. N-(1,1,1-trifluoropropan-2-yl)-4-(2,3-dihydro-2-oxo-1H-imidazo[4,5-b]pyridin-7-yl)-1H-pyrazole-1-carboxamide;
1031. 7-(1-(4,4,4-trifluorobutanoyl)-1H-pyrazol-4-yl)-1H-imidazo[4,5-b]pyridin-2 (3H)-one;
1032. N-(1-cyanocyclopropyl)-4-(2,3-dihydro-2-oxo-1H-imidazo[4,5-b]pyridin-7-yl)-1H-pyrazole-1-carboxamide;
1033. N-(2-cyanopropan-2-yl)-4-(2,3-dihydro-2-oxo-1H-imidazo[4,5-b]pyridin-7-yl)-1H-pyrazole-1-carboxamide;
1034. N-(cyclopentylmethyl)-4-(2,3-dihydro-2-oxo-1H-imidazo[4,5-b]pyridin-7-yl)-1H-pyrazole-1-carboxamide;
1035. N-(cyanomethyl)-4-(2,3-dihydro-2-oxo-1H-imidazo[4,5-b]pyridin-7-yl)-1H-pyrazole-1-carboxamide hydrochloride;

1036. N-(2,2,2-trifluoroethyl)-4-(2,3-dihydro-2-oxo-1H-imidazo[4,5-b]pyridin-7-yl)-1H-pyrazole-1-carboxamide;

1037. 7-(1-(3,3-dimethylazetidine-1-carbonyl)-1H-pyrazol-4-yl)-1,3-dihydro-2H-imidazo[4,5-b]pyridin-2-one;

1038. N-(cyano (cyclopentyl)methyl)-4-(2,3-dihydro-2-oxo-1H-imidazo[4,5-b]pyridin-7-yl)-1H-pyrazole-1-carboxamide;

1039. N-(2-cyano-1-cyclopentylethyl)-4-(2,3-dihydro-2-oxo-1H-imidazo[4,5-b]pyridin-7-yl)-1H-pyrazole-1-carboxamide;

1040. N-(2-cyanobutan-2-yl)-4-(2,3-dihydro-2-oxo-1H-imidazo[4,5-b]pyridin-7-yl)-1H-pyrazole-1-carboxamide;

1041. N-(1-cyclopentyl-2,2,2-trifluoroethyl)-4-(2,3-dihydro-2-oxo-1H-imidazo[4,5-b]pyridin-7-yl)-1H-pyrazole-1-carboxamide;

1042. 4-(1-ethyl-2,3-dihydro-2-oxo-1H-imidazo[4,5-b]pyridin-7-yl)-N-(2,2,2-trifluoroethyl)-1H-pyrazole-1-carboxamide;

1043. N-(cyano (cyclopropyl)methyl)-4-(2,3-dihydro-2-oxo-1H-imidazo[4,5-b]pyridin-7-yl)-1H-pyrazole-1-carboxamide;

1044. N-(1-cyano-2-methylpropyl)-4-(2,3-dihydro-2-oxo-1H-imidazo[4,5-b]pyridin-7-yl)-1H-pyrazole-1-carboxamide;

1045. N-(2,2,2-trifluoroethyl)-4-(2,3-dihydro-2-oxo-1H-imidazo[4,5-b]pyridin-7-yl)-1H-pyrazole-1-carboxamide;

1046. N-(1-cyanopropan-2-yl)-4-(2,3-dihydro-2-oxo-1H-imidazo[4,5-b]pyridin-7-yl)-1H-pyrazole-1-carboxamide;

1047. N—((S)-1-cyano-2-methylpropyl)-4-(2,3-dihydro-2-oxo-1H-imidazo[4,5-b]pyridin-7-yl)-1H-pyrazole-1-carboxamide;

1048. 1-(4-(2-oxo-2,3-dihydro-1H-imidazo[4,5-b]pyridin-7-yl)-1H-pyrazole-1-carbonyl) azetidine-3-carbonitrile;

1049. N—((R)-1-cyano-2-methylpropyl)-4-(2,3-dihydro-2-oxo-1H-imidazo[4,5-b]pyridin-7-yl)-1H-pyrazole-1-carboxamide;

1050. N-(3-cyano-1,1,1-trifluoropropan-2-yl)-4-(2,3-dihydro-2-oxo-1H-imidazo[4,5-b]pyridin-7-yl)-1H-pyrazole-1-carboxamide;

1051. N-(2-cyano-1-cyclopropylethyl)-4-(2,3-dihydro-2-oxo-1H-imidazo[4,5-b]pyridin-7-yl)-1H-pyrazole-1-carboxamide;

1052. N-(1-cyanopropan-2-yl)-4-(2,3-dihydro-2-oxo-1H-imidazo[4,5-b]pyridin-7-yl)-1H-pyrazole-1-carboxamide;

1053. N-(1-cyanopropan-2-yl)-4-(2,3-dihydro-2-oxo-1H-imidazo[4,5-b]pyridin-7-yl)-1H-pyrazole-1-carboxamide;

1054. N—((R)-cyano(cyclopropyl)methyl)-4-(2,3-dihydro-2-oxo-1H-imidazo[4,5-b]pyridin-7-yl)-1H-pyrazole-1-carboxamide;

1055. 1-(4-(2-oxo-2,3-dihydro-1H-imidazo[4,5-b]pyridin-7-yl)-1H-pyrazole-1-carbonyl) pyrrolidine-3-carbonitrile;

1056. N-(3-cyanocyclobutyl)-4-(2,3-dihydro-2-oxo-1H-imidazo[4,5-b]pyridin-7-yl)-1H-pyrazole-1-carboxamide;

1057. 2-(1-(4-(2-oxo-2,3-dihydro-1H-imidazo[4,5-b]pyridin-7-yl)-1H-pyrazole-1-carbonyl) pyrrolidin-3-yl) acetonitrile;

1058. N-(1-(3-cyanoazetidin-1-yl)-1-oxopropan-2-yl)-4-(2-oxo-2,3-dihydro-1H-imidazo[4,5-b]pyridin-7-yl)-1H-pyrazole-1-carboxamide;

1059. N-(2-(3-cyanoazetidin-1-yl)-2-oxoethyl)-4-(2-oxo-2,3-dihydro-1H-imidazo[4,5-b]pyridin-7-yl)-1H-pyrazole-1-carboxamide;

1060. N-(2-(3-cyanoazetidin-1-yl)-2-oxoethyl)-4-(2-oxo-2,3-dihydro-1H-imidazo[4,5-b]pyridin-7-yl)-1H-pyrazole-1-carboxamide;

1061. 3-(1-(4-(2-oxo-2,3-dihydro-1H-imidazo[4,5-b]pyridin-7-yl)-1H-pyrazole-1-carbonyl) pyrrolidin-3-yl) propanenitrile;

1062. N-(2-cyano-1-(tetrahydro-2H-pyran-4-yl)ethyl)-4-(2,3-dihydro-2-oxo-1H-imidazo[4,5-b]pyridin-7-yl)-1H-pyrazole-1-carboxamide;

1063. N-(cyano (phenyl)methyl)-4-(2,3-dihydro-2-oxo-1H-imidazo[4,5-b]pyridin-7-yl)-1H-pyrazole-1-carboxamide;

1064. N-(2,2,2-trifluoroethyl)-4-(3H-imidazo[4,5-b]pyridin-7-yl)-1H-pyrazole-1-carboxamide;

1065. N-(2-cyano-1-(tetrahydro-2H-pyran-4-yl)ethyl)-4-(3H-imidazo[4,5-b]pyridin-7-yl)-1H-pyrazole-1-carboxamide;

1066. N-(2-cyanocyclohexyl)-4-(3H-imidazo[4,5-b]pyridin-7-yl)-1H-pyrazole-1-carboxamide;

1067. 1-(4-(3H-imidazo[4,5-b]pyridin-7-yl)-1H-pyrazole-1-carbonyl) piperidine-4-carbonitrile;

1068. N-(1-(3-cyanoazetidin-1-yl) propan-2-yl)-4-(3H-imidazo[4,5-b]pyridin-7-yl)-1H-pyrazole-1-carboxamide;

1069. N-(1-(4-(3H-imidazo[4,5-b]pyridin-7-yl)-1H-pyrazole-1-carbonyl) pyrrolidin-3-yl) propane-1-sulfonamide;

1070. N-(cyano (phenyl)methyl)-4-(3H-imidazo[4,5-b]pyridin-7-yl)-1H-pyrazole-1-carboxamide;

1071. N-(1-cyano-3-methoxypropyl)-4-(3H-imidazo[4,5-b]pyridin-7-yl)-1H-pyrazole-1-carboxamide;

1072. N-(1-cyano-3-(methylsulfonyl) propyl)-4-(3H-imidazo[4,5-b]pyridin-7-yl)-1H-pyrazole-1-carboxamide;

1073. N—((S)-1-cyano-2-methylpropyl)-4-(3H-imidazo[4,5-b]pyridin-7-yl)-1H-pyrazole-1-carboxamide;

1074. 1-(4-(3H-imidazo[4,5-b]pyridin-7-yl)-1H-pyrazole-1-carbonyl)-4-methylpyrrolidine-3-carbonitrile;

1075. 2-(2-(4-(3H-imidazo[4,5-b]pyridin-7-yl)-1H-pyrazol-1-yl) oxazol-4-yl) acetonitrile;

1076. 2-(2-(4-(3H-imidazo[4,5-b]pyridin-7-yl)-1H-pyrazol-1-yl) thiazol-4-yl) acetonitrile;

1077. 7-(1-((oxazol-5-yl)methyl)-1H-pyrazol-4-yl)-3H-imidazo[4,5-b]pyridine;

1078. 2-(6-(4-(3H-imidazo[4,5-b]pyridin-7-yl)-1H-pyrazol-1-yl)pyridin-3-yl) acetonitrile;

1079. 6-(4-(3H-imidazo[4,5-b]pyridin-7-yl)-1H-pyrazol-1-yl)pyridine-3-carbonitrile;

1080. 7-(1-(5-((methylsulfonyl)methyl)pyridin-2-yl)-1H-pyrazol-4-yl)-3H-imidazo[4,5-b]pyridine;

1081. 7-(1-(5-((oxetan-3-yl)methyl)pyridin-2-yl)-1H-pyrazol-4-yl)-3H-imidazo[4,5-b]pyridine;

1082. 2-(6-(4-(3H-imidazo[4,5-b]pyridin-7-yl)-1H-pyrazol-1-yl)pyridin-3-yl) acetonitrile hydrochloride;

1083. (6-(4-(3H-imidazo[4,5-b]pyridin-7-yl)-1H-pyrazol-1-yl)pyridin-3-yl) methanol;

1084. 7-(1-(5-(2,2,2-trifluoroethyl)pyridin-2-yl)-1H-pyrazol-4-yl)-3H-imidazo[4,5-b]pyridine;

1085. 7-(1-(5-(morpholinomethyl)pyridin-2-yl)-1H-pyrazol-4-yl)-3H-imidazo[4,5-b]pyridine;

1086. 4-((6-(4-(3H-imidazo[4,5-b]pyridin-7-yl)-1H-pyrazol-1-yl)pyridin-3-yl)methyl) thiomorpholine 1,1-dioxide;
1087. 1-((6-(4-(3H-imidazo[4,5-b]pyridin-7-yl)-1H-pyrazol-1-yl)pyridin-3-yl)methyl) azetidine-3-carbonitrile;
1088. 6-(4-(3H-imidazo[4,5-b]pyridin-7-yl)-1H-pyrazol-1-yl)-N-(cyanomethyl)pyridine-3-carboxamide;
1089. N-((6-(4-(3H-imidazo[4,5-b]pyridin-7-yl)-1H-pyrazol-1-yl)pyridin-3-yl)methyl) methanesulfonamide;
1090. N-((6-(4-(3H-imidazo[4,5-b]pyridin-7-yl)-1H-pyrazol-1-yl)pyridin-3-yl)methyl) methanesulfonamide;
1091. N-((6-(4-(3H-imidazo[4,5-b]pyridin-7-yl)-1H-pyrazol-1-yl)pyridin-3-yl)methyl)-2-cyanoacetamide;
1092. 2-(6-(4-(3H-imidazo[4,5-b]pyridin-7-yl)-1H-pyrazol-1-yl)pyridin-3-yl)-N-(2,2,2-trifluoroethyl) acetamide;
1093. 2-(4-(3H-imidazo[4,5-b]pyridin-7-yl)-1H-pyrazol-1-yl)-N-(cyanomethyl)pyrimidine-5-carboxamide;
1094. N-(2,2,2-trifluoroethyl)-4-(2-phenyl-3H-imidazo[4,5-b]pyridin-7-yl)-1H-pyrazole-1-carboxamide;
1095. 4-(2-ethoxy-3H-imidazo[4,5-b]pyridin-7-yl)-N-(2,2,2-trifluoroethyl)-1H-pyrazole-1-carboxamide;
1096. 4-(2-cyclopropyl-3H-imidazo[4,5-b]pyridin-7-yl)-N-(2,2,2-trifluoroethyl)-1H-pyrazole-1-carboxamide;
1097. 3-(4-(2-(4-chloro-3-methoxyphenyl)-3H-imidazo[4,5-b]pyridin-7-yl)-1H-pyrazol-1-yl)-tetrahydro-2H-pyran-4-carbonitrile;
1098. 4-(2-(1-acetylpiperidin-4-yl)-3H-imidazo[4,5-b]pyridin-7-yl)-N-(2,2,2-trifluoroethyl)-1H-pyrazole-1-carboxamide;
1100. 2-(4-(4-(3H-imidazo[4,5-b]pyridin-7-yl)-1H-pyrazol-1-yl)phenyl)-2-cyclopropylacetonitrile;
1101. 2-(4-(4-(3H-imidazo[4,5-b]pyridin-7-yl)-1H-pyrazol-1-yl)phenyl)-2-morpholinoacetonitrile;
1102. N-(4-(4-(3H-imidazo[4,5-b]pyridin-7-yl)-1H-pyrazol-1-yl)phenyl)-2-cyanoacetamide;
1107. 2-(6-(4-(3H-imidazo[4,5-b]pyridin-7-yl)-1H-pyrazol-1-yl)pyridin-3-yl) propanenitrile;
1108. 2-(6-(4-(3H-imidazo[4,5-b]pyridin-7-yl)-1H-pyrazol-1-yl)pyridin-3-yl) propenamide;
1109. 1-(6-(4-(3H-imidazo[4,5-b]pyridin-7-yl)-1H-pyrazol-1-yl)pyridin-3-yl) cyclopropanecarbonitrile;
1110. 2-(6-(4-(3H-imidazo[4,5-b]pyridin-7-yl)-1H-pyrazol-1-yl)pyridin-3-yl)-2-cyclopropylacetonitrile;
1111. 2-(6-(4-(3H-imidazo[4,5-b]pyridin-7-yl)-1H-pyrazol-1-yl)pyridin-3-yl)-2-(3,3-difluoroazetidin-1-yl) acetonitrile;
1112. 2-(6-(4-(3H-imidazo[4,5-b]pyridin-7-yl)-1H-pyrazol-1-yl)pyridin-3-yl)-2-morpholinoacetonitrile;
1113. 2-(6-(4-(3H-imidazo[4,5-b]pyridin-7-yl)-1H-pyrazol-1-yl)pyridin-3-yl)-2-(1,1-dioxidothiomorpholino) acetonitrile;
1114. 2-(6-(4-(3H-imidazo[4,5-b]pyridin-7-yl)-1H-pyrazol-1-yl)pyridin-3-yl)-2-(1-(methylsulfonyl) azetidin-3-yl) acetonitrile;
1115. 2-(6-(4-(3H-imidazo[4,5-b]pyridin-7-yl)-1H-pyrazol-1-yl)pyridin-3-yl)-2-(1-(methylsulfonyl) azetidin-3-yl) acetonitrile;
1116. 2-(6-(4-(3H-imidazo[4,5-b]pyridin-7-yl)-1H-pyrazol-1-yl)pyridin-3-yl)-4-(methylsulfonyl) butanenitrile;
1117. 2-(6-(4-(3H-imidazo[4,5-b]pyridin-7-yl)-1H-pyrazol-1-yl)pyridin-2-yl) acetonitrile;
1118. 2-(2-(4-(3H-imidazo[4,5-b]pyridin-7-yl)-1H-pyrazol-1-yl)pyridin-4-yl) acetonitrile;
1119. 7-(1-(5-(2,2,2-trifluoro-1-methoxyethyl)pyridin-2-yl)-1H-pyrazol-4-yl)-3H-imidazo[4,5-b]pyridine;
1120. 7-(1-(5-(1-chloro-2,2,2-trifluoroethyl)pyridin-2-yl)-1H-pyrazol-4-yl)-3H-imidazo[4,5-b]pyridine;
1121. 1-(6-(4-(3H-imidazo[4,5-b]pyridin-7-yl)-1H-pyrazol-1-yl)pyridin-3-yl)-2,2,2-trifluoro-N,N-dimethylethanamine;
1122. 7-(1-(5-(1,1,1-trifluorobutan-2-yl)pyridin-2-yl)-1H-pyrazol-4-yl)-3H-imidazo[4,5-b]pyridine;
1123. 3-(6-(4-(3H-imidazo[4,5-b]pyridin-7-yl)-1H-pyrazol-1-yl)pyridin-3-yl)-4,4,4-trifluorobutanenitrile;
1124. 7-(1-(5-(2,2,2-trifluoro-1-isopropoxyethyl)pyridin-2-yl)-1H-pyrazol-4-yl)-3H-imidazo[4,5-b]pyridine;
1125. 2-(6-(4-(3H-imidazo[4,5-b]pyridin-7-yl)-1H-pyrazol-1-yl)pyridin-3-yl)-1,1,1-trifluoropropan-2-ol;
1126. 1-(6-(4-(3H-imidazo[4,5-b]pyridin-7-yl)-1H-pyrazol-1-yl)pyridin-3-yl)-1-cyclopropyl-2,2,2-trifluoroethanol;
1127. 7-(1-(5-(1-cyclopropyl-2,2,2-trifluoro-1-methoxyethyl)pyridin-2-yl)-1H-pyrazol-4-yl)-3H-imidazo[4,5-b]pyridine;
1128. 7-(1-(5-(1,1,1,2-tetrafluoropropan-2-yl)pyridin-2-yl)-1H-pyrazol-4-yl)-3H-imidazo[4,5-b]pyridine;
1129. 2-(6-(4-(3H-imidazo[4,5-b]pyridin-7-yl)-1H-pyrazol-1-yl)pyridin-3-yl)-1,1,1-trifluoro-3-methylbutan-2-ol;
1130. 1-(6-(4-(3H-imidazo[4,5-b]pyridin-7-yl)-1H-pyrazol-1-yl)pyridin-3-yl)-1-cyclohexyl-2,2,2-trifluoroethanol;
1131. 1-(4-(1-(6-(4-(3H-imidazo[4,5-b]pyridin-7-yl)-1H-pyrazol-1-yl)pyridin-3-yl)-2,2,2-trifluoro-1-hydroxyethyl) piperidin-1-yl) ethenone;
1132. 1-(6-(4-(3H-imidazo[4,5-b]pyridin-7-yl)-1H-pyrazol-1-yl)pyridin-3-yl)-1-cyclopentyl-2,2,2-trifluoroethanol;
1133. 1-(6-(4-(3H-imidazo[4,5-b]pyridin-7-yl)-1H-pyrazol-1-yl)pyridin-3-yl)-2,2,2-trifluoro-1-(1-methylpiperidin-4-yl) ethanol;
1134. 1-(6-(4-(3H-imidazo[4,5-b]pyridin-7-yl)-1H-pyrazol-1-yl)pyridin-3-yl)-2,2,2-trifluoro-1-(tetrahydro-2H-pyran-4-yl) ethanol;
1135. 1-(6-(4-(3H-imidazo[4,5-b]pyridin-7-yl)-1H-pyrazol-1-yl)pyridin-3-yl)-2,2,2-trifluoro-1-(piperidin-4-yl) ethan-1-ol;
1136. 7-(1-(5-(2,2,2-trifluoro-1-(oxetan-3-yl)ethyl)pyridin-2-yl)-1H-pyrazol-4-yl)-3H-imidazo[4,5-b]pyridine;
1137. 7-(1-(5-(2,2,2-trifluoro-1-morpholinoethyl)pyridin-2-yl)-1H-pyrazol-4-yl)-3H-imidazo[4,5-b]pyridine;
1138. 7-(1-(5-(1,1,1-trifluoro-3-(methylsulfonyl) propan-2-yl)pyridin-2-yl)-1H-pyrazol-4-yl)-3H-imidazo[4,5-b]pyridine;
1139. 7-(1-(5-(4-(cyclopropylsulfonyl)-1,1,1-trifluorobutan-2-yl)pyridin-2-yl)-1H-pyrazol-4-yl)-3H-imidazo[4,5-b]pyridine;
1140. 7-(1-(5-(1-((methylsulfonyl) methoxy)-2,2,2-trifluoroethyl)pyridin-2-yl)-1H-pyrazol-4-yl)-3H-imidazo[4,5-b]pyridine;
1141. 3-(6-(4-(3H-imidazo[4,5-b]pyridin-7-yl)-1H-pyrazol-1-yl)pyridin-3-yl)-4,4,4-trifluorobutane-1-sulfonamide;
1142. 3-(6-(4-(3H-imidazo[4,5-b]pyridin-7-yl)-1H-pyrazol-1-yl)pyridin-3-yl)-4,4,4-trifluoro-N-methylbutane-1-sulfonamide;
1143. N-(3-(6-(4-(3H-imidazo[4,5-b]pyridin-7-yl)-1H-pyrazol-1-yl)pyridin-3-yl)-4,4,4-trifluorobutyl) methanesulfonamide;

1144. 3-(6-(4-(3H-imidazo[4,5-b]pyridin-7-yl)-1H-pyrazol-1-yl)pyridin-3-yl)-4,4,4-trifluoro-N,N-dimethylbutanamide;

1145. 3-(6-(4-(3H-imidazo[4,5-b]pyridin-7-yl)-1H-pyrazol-1-yl)pyridin-3-yl)-4,4,4-trifluoro-N-methylbutanamide;

1146. 1-(1-(6-(4-(3H-imidazo[4,5-b]pyridin-7-yl)-1H-pyrazol-1-yl)pyridin-3-yl)-2,2,2-trifluoroethyl)-3-cyclopropylurea;

1147. 7-(1-(5-(1,1,1-trifluoro-4-(methylsulfonyl) butan-2-yl)pyridin-2-yl)-1H-pyrazol-4-yl)-1H-imidazo[4,5-b] pyridin-2 (3H)-one;

1148. 4-(6-(4-(3H-imidazo[4,5-b]pyridin-7-yl)-1H-pyrazol-1-yl)pyridin-3-yl)-5,5,5-trifluoro-N-methylpentanamide;

1149. N-(3-(6-(4-(3H-imidazo[4,5-b]pyridin-7-yl)-1H-pyrazol-1-yl)pyridin-3-yl)-4,4,4-trifluorobutyl)cyclopropanecarboxamide;

1150. 4-(6-(4-(3H-imidazo[4,5-b]pyridin-7-yl)-1H-pyrazol-1-yl)pyridin-3-yl)-N-cyclopropyl-5,5,5-trifluoropentanamide;

1151. N-(3-(6-(4-(3H-imidazo[4,5-b]pyridin-7-yl)-1H-pyrazol-1-yl)pyridin-3-yl)-4,4,4-trifluorobutyl)cyclopentanecarboxamide;

1152. 3-(6-(4-(3H-imidazo[4,5-b]pyridin-7-yl)-1H-pyrazol-1-yl)pyridin-3-yl)-4,4,4-trifluoro-N-methylbutan-1-amine;

1153. N-(3-(6-(4-(3H-imidazo[4,5-b]pyridin-7-yl)-1H-pyrazol-1-yl)pyridin-3-yl)-4,4,4-trifluorobutyl)cyclopropanamine;

1154. 3-(6-(4-(3H-imidazo[4,5-b]pyridin-7-yl)-1H-pyrazol-1-yl)pyridin-3-yl)-4,4,4-trifluorobutan-1-ol;

1155. 7-(1-(5-(1,1,1-trifluoro-4-methoxybutan-2-yl)pyridin-2-yl)-1H-pyrazol-4-yl)-3H-imidazo[4,5-b]pyridine;

1156. 4-(6-(4-(3H-imidazo[4,5-b]pyridin-7-yl)-1H-pyrazol-1-yl)pyridin-3-yl)-5,5,5-trifluoropentanenitrile;

1157. 2-(1-(6-(4-(3H-imidazo[4,5-b]pyridin-7-yl)-1H-pyrazol-1-yl)pyridin-3-yl)-2,2,2-trifluoroethoxy) acetonitrile;

1158. 7-(1-(5-(1-(methylsulfonyl)ethyl)pyridin-2-yl)-1H-pyrazol-4-yl)-3H-imidazo[4,5-b]pyridine;

1159. (6-(4-(3H-imidazo[4,5-b]pyridin-7-yl)-1H-pyrazol-1-yl)pyridin-3-yl) (cyclopropyl) methanol;

1160. 7-(1-(5-(3-(methylsulfonyl)-1-(oxetan-3-yl) propyl)pyridin-2-yl)-1H-pyrazol-4-yl)-3H-imidazo[4,5-b] pyridine;

1161. 7-(1-(5-(1-methoxy-3-(methylsulfonyl) propyl) pyridin-2-yl)-1H-pyrazol-4-yl)-3H-imidazo[4,5-b] pyridine;

1162. 7-(1-(5-(1-fluoro-3-(methylsulfonyl) propyl)pyridin-2-yl)-1H-pyrazol-4-yl)-3H-imidazo[4,5-b]pyridine;

1163. 7-(1-(5-(4-(methylsulfonyl) butan-2-yl)pyridin-2-yl)-1H-pyrazol-4-yl)-3H-imidazo[4,5-b]pyridine;

1164. (6-(4-(3H-imidazo[4,5-b]pyridin-7-yl)-1H-pyrazol-1-yl)pyridin-3-yl) (1-(methylsulfonyl) piperidin-4-yl) methanol;

1165. (6-(4-(3H-imidazo[4,5-b]pyridin-7-yl)-1H-pyrazol-1-yl)pyridin-3-yl) (1-methylpiperidin-4-yl) methanol;

1166. 2-(6-(4-(3H-imidazo[4,5-b]pyridin-7-yl)-1H-pyrazol-1-yl)pyridin-3-yl)-N-(2,2,2-trifluoroethyl)-2-hydroxyacetamide;

1167. 2-(6-(4-(3H-imidazo[4,5-b]pyridin-7-yl)-1H-pyrazol-1-yl)pyridin-3-yl)-2-cyclopropyl-N-(2,2,2-trifluoroethyl) acetamide;

1168. 2-(6-(4-(3H-imidazo[4,5-b]pyridin-7-yl)-1H-pyrazol-1-yl)pyridin-3-yl)-2-cyano-N-(2,2,2-trifluoroethyl) acetamide;

1169. 1-(6-(4-(3H-imidazo[4,5-b]pyridin-7-yl)-1H-pyrazol-1-yl)pyridin-3-yl)-2,2,2-trifluoroethanol;

1170. 1-(6-(4-(3H-imidazo[4,5-b]pyridin-7-yl)-1H-pyrazol-1-yl)pyridin-2-yl)-2,2,2-trifluoroethanol;

1171. 7-(1-(6-(2,2,2-trifluoro-1-methoxyethyl)pyridin-2-yl)-1H-pyrazol-4-yl)-3H-imidazo[4,5-b]pyridine;

1172. 1-(2-(4-(3H-imidazo[4,5-b]pyridin-7-yl)-1H-pyrazol-1-yl)pyridin-4-yl)-2,2,2-trifluoroethanol;

1173. 1-(5-(4-(3H-imidazo[4,5-b]pyridin-7-yl)-1H-pyrazol-1-yl)pyridin-2-yl)-2,2,2-trifluoroethanol;

1174. 7-(1-(5-(1,1,1-trifluoro-4-(methylsulfonyl) butan-2-yl)pyridin-2-yl)-1H-pyrazol-4-yl)-3H-imidazo[4,5-b] pyridine;

1175. 7-(1-(6-(1,1,1-trifluoro-4-(methylsulfonyl) butan-2-yl)pyridin-2-yl)-1H-pyrazol-4-yl)-3H-imidazo[4,5-b] pyridine;

1176. 7-(1-(4-(1,1,1-trifluoro-4-(methylsulfonyl) butan-2-yl)pyridin-2-yl)-1H-pyrazol-4-yl)-3H-imidazo[4,5-b] pyridine;

1177. 1-(4-(3H-imidazo[4,5-b]pyridin-7-yl)-1H-pyrazole-1-carbonyl) pyrrolidine-3-carbonitrile;

1178. 1-(1-(6-(4-(3H-imidazo[4,5-b]pyridin-7-yl)-1H-pyrazol-1-yl)pyridin-3-yl)-2,2,2-trifluoroethyl)-3-cyclopropylurea;

1179. 1-(3-(6-(4-(3H-imidazo[4,5-b]pyridin-7-yl)-1H-pyrazol-1-yl)pyridin-3-yl)-4,4,4-trifluorobutyl)-3-cyclopropylurea;

1180. 3-cyclopentyl-3-(4-(2-phenyl-3H-imidazo[4,5-b] pyridin-7-yl)-1H-pyrazol-1-yl) propanenitrile;

1181. 7-(1-(5-((S)-1,1,1-trifluoro-4-(methylsulfonyl) butan-2-yl)pyridin-2-yl)-1H-pyrazol-4-yl)-3H-imidazo [4,5-b]pyridine;

1182. 7-(1-(5-((R)-1,1,1-trifluoro-4-(methylsulfonyl) butan-2-yl)pyridin-2-yl)-1H-pyrazol-4-yl)-3H-imidazo [4,5-b]pyridine;

1183. 3-(6-(4-(3H-imidazo[4,5-b]pyridin-7-yl)-1H-pyrazol-1-yl)pyridin-3-yl)-1,1,1-trifluoropropan-2-ol;

1184. 7-(1-(5-((R)-2,2,2-trifluoro-1-(oxetan-3-yl)ethyl) pyridin-2-yl)-1H-pyrazol-4-yl)-3H-imidazo[4,5-b] pyridine;

1185. 7-(1-(5-((S)-2,2,2-trifluoro-1-(oxetan-3-yl)ethyl) pyridin-2-yl)-1H-pyrazol-4-yl)-3H-imidazo[4,5-b] pyridine;

1186. 7-(1-(5-(1,1,1-trifluoro-4-(isopropylsulfonyl) butan-2-yl)pyridin-2-yl)-1H-pyrazol-4-yl)-3H-imidazo [4,5-b]pyridine;

1187. 1-(6-(4-(3H-imidazo[4,5-b]pyridin-7-yl)-(methyl sulfonyl) 1H-pyrazol-1-yl)pyridin-3-yl)-2,2,2-trifluoroethanamine;

1188. 7-(1-(5-(1,1,1-trifluoro-4-(methylsulfonyl) butan-2-yl)pyridin-2-yl)-(cyclopropyl amino sulfonyl) 1H-pyrazol-4-yl)-3H-imidazo[4,5-b]pyridine;

1189. 7-(1-(5-(1,1,1-trifluoro-4-(methylsulfonyl) butan-2-yl)pyridin-2-yl)-1H-pyrazol-4-yl)-1H-imidazo[4,5-b] pyridin-2 (3H)-one;

1190. 7-(1-(4-(1,1,1-trifluoro-4-(methylsulfonyl) butan-2-yl)phenyl)-1H-pyrazol-4-yl)-3H-imidazo[4,5-b]pyridine;

1191. 3-(6-(4-(3H-imidazo[4,5-b]pyridin-7-yl)-1H-pyrazol-1-yl)pyridin-3-yl)-2-(trifluoromethyl) propan-1-ol;

1192. N-(1-(6-(4-(3H-imidazo[4,5-b]pyridin-7-yl)-1H-pyrazol-1-yl)pyridin-3-yl)-2,2,2-trifluoroethyl)-2-cyanoacetamide;

1193. 4-(6-(4-(3H-imidazo[4,5-b]pyridin-7-yl)-1H-pyrazol-1-yl)pyridin-3-yl)-5,5,5-trifluoro-2-methylpentan-2-ol;

1194. 7-(1-(5-(3,3,3-trifluoro-2-((methylsulfonyl)methyl)propyl)pyridin-2-yl)-1H-pyrazol-4-yl)-3H-imidazo[4,5-b]pyridine;

1195. N-(3-(6-(4-(3H-imidazo[4,5-b]pyridin-7-yl)-1H-pyrazol-1-yl)pyridin-3-yl)-4,4,4-trifluorobutyl)-N-methylcyclopropanamine;

1196. 3-(6-(4-(3H-imidazo[4,5-b]pyridin-7-yl)-1H-pyrazol-1-yl)pyridin-3-yl)-4,4,4-trifluoro-2,2-dimethylbutan-1-ol;

1197. N-(2-(1-(6-(4-(3H-imidazo[4,5-b]pyridin-7-yl)-1H-pyrazol-1-yl)pyridin-3-yl)-2,2,2-trifluoroethoxy)ethyl) cyclopropanamine;

1198. 3-(6-(4-(3H-imidazo[4,5-b]pyridin-7-yl)-1H-pyrazol-1-yl)pyridin-3-yl)-4,4,4-trifluoro-N-methylbutan-1-amine;

1199. N-(3-(6-(4-(3H-imidazo[4,5-b]pyridin-7-yl)-1H-pyrazol-1-yl)pyridin-3-yl)-4,4,4-trifluorobutyl)cyclohexanamine;

1200. 3-(6-(4-(3H-imidazo[4,5-b]pyridin-7-yl)-1H-pyrazol-1-yl)pyridin-3-yl)-4,4,4-trifluoro-N-methylbutan-1-amine;

1201. 7-(1-(5-(1,1,1-trifluoro-4-morpholinobutan-2-yl)pyridin-2-yl)-1H-pyrazol-4-yl)-3H-imidazo[4,5-b]pyridine;

1202. 1-(3-(6-(4-(3H-imidazo[4,5-b]pyridin-7-yl)-1H-pyrazol-1-yl)pyridin-3-yl)-4,4,4-trifluorobutyl) azetidine-3-carbonitrile;

1203. 3-(6-(4-(3H-imidazo[4,5-b]pyridin-7-yl)-1H-pyrazol-1-yl)pyridin-3-yl)-4,4,4-trifluoro-N-isopropylbutan-1-amine;

1204. 7-(1-(5-(4-(cyclopropylmethylsulfonyl)-1,1,1-trifluorobutan-2-yl)pyridin-2-yl)-1H-pyrazol-4-yl)-3H-imidazo[4,5-b]pyridine;

1205. 7-(1-(5-(3-(cyclopropylmethylsulfonyl)-1,1,1-trifluoropropan-2-yl)pyridin-2-yl)-1H-pyrazol-4-yl)-3H-imidazo[4,5-b]pyridine;

1206. 7-(1-(5-(1,1,1-trifluoro-3-morpholinopropan-2-yl)pyridin-2-yl)-1H-pyrazol-4-yl)-3H-imidazo[4,5-b]pyridine;

1207. (S)-3-(6-(4-(3H-imidazo[4,5-b]pyridin-7-yl)-1H-pyrazol-1-yl)pyridin-3-yl)-4,4,4-trifluoro-N-isopropylbutan-1-amine;

1208. (R)-3-(6-(4-(3H-imidazo[4,5-b]pyridin-7-yl)-1H-pyrazol-1-yl)pyridin-3-yl)-4,4,4-trifluoro-N-isopropylbutan-1-amine;

1209. 2-(6-(4-(3H-imidazo[4,5-b]pyridin-7-yl)-(Methyl sulfonyl) 1H-pyrazol-1-yl)pyridin-3-yl)-3,3,3-trifluoropropan-1-amine;

1210. 4-(6-(4-(3H-imidazo[4,5-b]pyridin-7-yl)-1H-pyrazol-1-yl)pyridin-3-yl)-5,5,5-trifluoro-N-isopropylpentanamide;

1211. 3-(6-(4-(3H-imidazo[4,5-b]pyridin-7-yl)-1H-pyrazol-1-yl)pyridin-3-yl)-4,4,4-trifluoro-N,N-diisopropylbutan-1-amine;

1212. N-(2-(6-(4-(3H-imidazo[4,5-b]pyridin-7-yl)-1H-pyrazol-1-yl)pyridin-3-yl)-3,3,3-trifluoropropyl)cyclopropanamine;

1213. (R)-3-(6-(4-(3H-imidazo[4,5-b]pyridin-7-yl)-1H-pyrazol-1-yl)pyridin-3-yl)-4,4,4-trifluoro-N-methylbutanamide;

1214. (S)-3-(6-(4-(3H-imidazo[4,5-b]pyridin-7-yl)-1H-pyrazol-1-yl)pyridin-3-yl)-4,4,4-trifluoro-N-methylbutanamide;

1215. (S)-4-(6-(4-(3H-imidazo[4,5-b]pyridin-7-yl)-1H-pyrazol-1-yl)pyridin-3-yl)-5,5,5-trifluoro-N-isopropylpentanamide;

1216. 7-(1-(5-((S)-4-(cyclopropylsulfonyl)-1,1,1-trifluorobutan-2-yl)pyridin-2-yl)-1H-pyrazol-4-yl)-3H-imidazo[4,5-b]pyridine;

1217. (S)-3-(6-(4-(3H-imidazo[4,5-b]pyridin-7-yl)-1H-pyrazol-1-yl)pyridin-3-yl)-4,4,4-trifluoro-N-methylbutan-1-amine, TFA salt;

1218. 2-(6-(4-(3H-imidazo[4,5-b]pyridin-7-yl)-1H-pyrazol-1-yl)pyridin-3-yl)-3,3,3-trifluoro-N-isopropylpropan-1-amine;

1219. 7-(1-(5-(1,1,1-trifluoro-4-(4-methylpiperazin-1-yl)butan-2-yl)pyridin-2-yl)-1H-pyrazol-4-yl)-3H-imidazo[4,5-b]pyridine;

1220. (4-(1-(6-(4-(3H-imidazo[4,5-b]pyridin-7-yl)-1H-pyrazol-1-yl)pyridin-3-yl)-2,2,2-trifluoro-1-hydroxyethyl) piperidin-1-yl) (cyclopropyl) methanone;

1221. 1-(6-(4-(3H-imidazo[4,5-b]pyridin-7-yl)-1H-pyrazol-1-yl)pyridin-3-yl)-1-(1-ethylpiperidin-4-yl)-2,2,2-trifluoroethanol;

1222. 7-(1-(5-(1,1,1-trifluoro-3-(4-methylpiperazin-1-yl)propan-2-yl)pyridin-2-yl)-1H-pyrazol-4-yl)-3H-imidazo[4,5-b]pyridine;

1223. 2-(6-(4-(3H-imidazo[4,5-b]pyridin-7-yl)-1H-pyrazol-1-yl)pyridin-3-yl)-1,1,1-trifluoro-4-(methylsulfonyl) butan-2-ol;

1224. 5-(6-(4-(3H-imidazo[4,5-b]pyridin-7-yl)-1H-pyrazol-1-yl)pyridin-3-yl)-6,6,6-trifluorohexan-2-amine, TFA salt;

1225. (R)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl) ethanol;

1226. (S)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl) ethanol;

1227. 4-(6-(4-(3H-imidazo[4,5-b]pyridin-7-yl)-1H-pyrazol-1-yl)pyridin-3-yl)-5,5,5-trifluoro-4-hydroxypentanenitrile;

1228. 2-(1-(6-(4-(3H-imidazo[4,5-b]pyridin-7-yl)-1H-pyrazol-1-yl)pyridin-3-yl)-2,2,2-trifluoroethoxy)-N-methylethanamine;

1229. 2-(6-(4-(3H-imidazo[4,5-b]pyridin-7-yl)-1H-pyrazol-1-yl)pyridin-3-yl)-1,1,1-trifluoro-3-morpholinopropan-2-ol;

1230. 2-(6-(4-(3H-imidazo[4,5-b]pyridin-7-yl)-1H-pyrazol-1-yl)pyridin-3-yl)-1,1,1-trifluoro-4-morpholinobutan-2-ol;

1231. 1-(6-(4-(3H-imidazo[4,5-b]pyridin-7-yl)-1H-pyrazol-1-yl)pyridin-3-yl)-2,2,2-trifluoro-1-(1-methylazetidin-3-yl) ethanol;

1232. (R)-1-(6-(4-(3H-imidazo[4,5-b]pyridin-7-yl)-1H-pyrazol-1-yl)pyridin-3-yl)-1-(1-ethylpyrrolidin-3-yl)-2,2,2-trifluoroethanol;

1233. (S)-1-(6-(4-(3H-imidazo[4,5-b]pyridin-7-yl)-1H-pyrazol-1-yl)pyridin-3-yl)-1-(1-ethylpyrrolidin-3-yl)-2,2,2-trifluoroethanol;

1234. (S)-1-(6-(4-(3H-imidazo[4,5-b]pyridin-7-yl)-1H-pyrazol-1-yl)pyridin-3-yl)-2,2,2-trifluoro-1-(1-methylpyrrolidin-3-yl) ethanol;

1235. (R)-1-(6-(4-(3H-imidazo[4,5-b]pyridin-7-yl)-1H-pyrazol-1-yl)pyridin-3-yl)-2,2,2-trifluoro-1-(1-methylpyrrolidin-3-yl) ethanol;

1236. 1-(3-(1-(6-(4-(3H-imidazo[4,5-b]pyridin-7-yl)-1H-pyrazol-1-yl)pyridin-3-yl)-2,2,2-trifluoro-1-hydroxyethyl) azetidin-1-yl) ethenone;

1237. 1-(6-(4-(3H-imidazo[4,5-b]pyridin-7-yl)-1H-pyrazol-1-yl)pyridin-3-yl)-2,2,2-trifluoro-1-(1-isopropylazetidin-3-yl) ethanol;

1238. 4-(6-(4-(3H-imidazo[4,5-b]pyridin-7-yl)-1H-pyrazol-1-yl)pyridin-3-yl)-5,5,5-trifluoro-4-hydroxy-N-isopropylpentanamide;

1239. 1-(6-(4-(3H-imidazo[4,5-b]pyridin-7-yl)-1H-pyrazol-1-yl)pyridin-3-yl)-1-(1-ethylazetidin-3-yl)-2,2,2-trifluoroethanol;

1240. 1-(6-(4-(3H-imidazo[4,5-b]pyridin-7-yl)-1H-pyrazol-1-yl)pyridin-3-yl)-2,2,2-trifluoro-1-(1-isopropylpiperidin-4-yl) ethanol;

1241. N-(2-(1-(6-(4-(3H-imidazo[4,5-b]pyridin-7-yl)-1H-pyrazol-1-yl)pyridin-3-yl)-2,2,2-trifluoroethoxy) ethyl) propan-2-amine, TFA salt;

1242. (R)-1-(6-(4-(3H-imidazo[4,5-b]pyridin-7-yl)-1H-pyrazol-1-yl)pyridin-3-yl)-2,2,2-trifluoro-1-(1-(oxetan-3-yl) pyrrolidin-3-yl) ethanol;

1243. (S)-1-(6-(4-(3H-imidazo[4,5-b]pyridin-7-yl)-1H-pyrazol-1-yl)pyridin-3-yl)-2,2,2-trifluoro-1-(1-(oxetan-3-yl) pyrrolidin-3-yl) ethanol;

1244. 7-(1-(5-(2,2,2-trifluoro-1-methoxy-1-(1-methylpiperidin-4-yl)ethyl)pyridin-2-yl)-1H-pyrazol-4-yl)-3H-imidazo[4,5-b]pyridine;

1245. 3-(3-(1-(6-(4-(3H-imidazo[4,5-b]pyridin-7-yl)-1H-pyrazol-1-yl)pyridin-3-yl)-2,2,2-trifluoro-1-hydroxyethyl) azetidin-1-yl)-3-oxopropanenitrile;

1246. 3-(1-(6-(4-(3H-imidazo[4,5-b]pyridin-7-yl)-1H-pyrazol-1-yl)pyridin-3-yl)-2,2,2-trifluoro-1-hydroxyethyl)-N-methylazetidine-1-carboxamide;

1247. N-(3-(6-(4-(3H-imidazo[4,5-b]pyridin-7-yl)-1H-pyrazol-1-yl)pyridin-3-yl)-4,4,4-trifluorobutyl) isobutyramide;

1248. N-(3-(6-(4-(3H-imidazo[4,5-b]pyridin-7-yl)-1H-pyrazol-1-yl)pyridin-3-yl)-4,4,4-trifluorobutyl)-2-cyanoacetamide;

1249. 3-(6-(4-(3H-imidazo[4,5-b]pyridin-7-yl)-1H-pyrazol-1-yl)pyridin-3-yl)-4,4,4-trifluoro-1-morpholinobutan-1-one;

1250. 1-(4-(6-(4-(3H-imidazo[4,5-b]pyridin-7-yl)-1H-pyrazol-1-yl)pyridin-3-yl)-5,5,5-trifluoropentanoyl) azetidine-3-carbonitrile;

1251. (S)-1-(4-(4-(3H-imidazo[4,5-b]pyridin-7-yl)-1H-pyrazol-1-yl)phenyl)-2,2,2-trifluoro-1-(1-isopropylpyrrolidin-3-yl) ethanol; and 1252. (R)-1-(4-(4-(3H-imidazo[4,5-b]pyridin-7-yl)-1H-pyrazol-1-yl)phenyl)-2,2,2-trifluoro-1-(1-isopropylpyrrolidin-3-yl) ethanol, or a pharmaceutically acceptable salt thereof or an isomer thereof.

2. A compound selected from the group consisting of:

1133. 1-(6-(4-(3H-imidazo[4,5-b]pyridin-7-yl)-1H-pyrazol-1-yl)pyridin-3-yl)-2,2,2-trifluoro-1-(1-methylpiperidin-4-yl) ethanol;

1134. 1-(6-(4-(3H-imidazo[4,5-b]pyridin-7-yl)-1H-pyrazol-1-yl)pyridin-3-yl)-2,2,2-trifluoro-1-(tetrahydro-2H-pyran-4-yl) ethanol;

1176. 7-(1-(4-(1,1,1-trifluoro-4-(methylsulfonyl) butan-2-yl)pyridin-2-yl)-1H-pyrazol-4-yl)-3H-imidazo[4,5-b] pyridine;

1181. 7-(1-(5-((S)-1,1,1-trifluoro-4-(methylsulfonyl) butan-2-yl)pyridin-2-yl)-1H-pyrazol-4-yl)-3H-imidazo [4,5-b]pyridine;

1182. 7-(1-(5-((R)-1,1,1-trifluoro-4-(methylsulfonyl) butan-2-yl)pyridin-2-yl)-1H-pyrazol-4-yl)-3H-imidazo [4,5-b]pyridine;

1225. (R)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl) ethanol;

1226. (S)-1-(6-(4-(3H-imidazo[4,5-b]pyridin-7-yl)-1H-pyrazol-1-yl)pyridin-3-yl)-2,2,2-trifluoro-1-(1-isopropylpyrrolidin-3-yl) ethanol; and 1231. 1-(6-(4-(3H-imidazo[4,5-b]pyridin-7-yl)-1H-pyrazol-1-yl)pyridin-3-yl)-2,2,2-trifluoro-1-(1-methylazetidin-3-yl) ethanol, or a pharmaceutically acceptable salt thereof or an isomer thereof.

3. A pharmaceutical composition comprising a compound of claim 1, or pharmaceutically acceptable salt thereof or isomer thereof, and a pharmaceutically acceptable excipient.

4. The pharmaceutical composition of claim 3, which is in the form of a solid, a semi-solid, a lyophilized powder, or a liquid.

5. A method of treating a disease or disorder, comprising administering a therapeutically effective amount of a compound of claim 2, or a pharmaceutically acceptable salt thereof or an isomer thereof, to a subject in need thereof, wherein the disease or disorder is at least one selected from the group consisting of cancer, acquired immunodeficiency syndrome (AIDS), Addison's disease, adult respiratory distress syndrome, allergies, ankylosing spondylitis, amyloidosis, asthma, autoimmune hemolytic anemia, autoimmune thyroiditis, Crohn's disease, episodic lymphopenia with lymphocytotoxins, erythroblastosis fetalis, Goodpasture's syndrome, Graves' disease, Hashimoto's thyroiditis, hypereosinophilia, irritable bowel syndrome, Lupus, myasthenia gravis, myocardial inflammation, pericardial inflammation, pancreatitis, polymyositis, psoriasis, Reiter's syndrome, scleroderma, systemic anaphylaxis, ulcerative colitis, nephritis, gout, arthritis, erythema, dermatitis, dermatomyositis, bronchitis, cholecystitis, sepsis and gastritis.

6. The method of claim 5, wherein the cancer is at least one selected from the group consisting of carcinoma, sarcoma, lymphoma, leukemia, myeloma, a germ cell tumor, a blastoma, a tumor of the central nervous systems, a tumor of the peripheral nervous system, a melanoma, seminoma and Kaposi's sarcoma.

7. The method of claim 5, wherein the nephritis is glomerulonephritis.

8. The method of claim 5, wherein the arthritis is rheumatoid arthritis or osteoarthritis.

9. A pharmaceutical composition comprising a compound of claim 2, or pharmaceutically acceptable salt thereof or isomer thereof, and a pharmaceutically acceptable excipient.

10. The pharmaceutical composition of claim 9, which is in the form of a solid, a semi-solid, a lyophilized powder, or a liquid.

11. A method of treating a disease or disorder, comprising administering a therapeutically effective amount of a compound of claim 5, or a pharmaceutically acceptable salt thereof or an isomer thereof, to a subject in need thereof, wherein the disease or disorder is at least one selected from the group consisting of cancer, acquired immunodeficiency syndrome (AIDS), Addison's disease, adult respiratory distress syndrome, allergies, ankylosing spondylitis, amyloidosis, asthma, autoimmune hemolytic anemia, autoimmune thyroiditis, Crohn's disease, episodic lymphopenia with lymphocytotoxins, erythroblastosis fetalis, Goodpasture's syndrome, Graves' disease, Hashimoto's thyroiditis, hypereosinophilia, irritable bowel syndrome, Lupus, myasthenia gravis, myocardial inflammation, pericardial inflammation, pancreatitis, polymyositis, psoriasis, Reiter's syndrome, scleroderma, systemic anaphylaxis, ulcerative colitis, nephritis, gout, arthritis, erythema, dermatitis, dermatomyositis, bronchitis, cholecystitis, sepsis and gastritis.

12. The method of claim 11, wherein the cancer is at least one selected from the group consisting of carcinoma, sarcoma, lymphoma, leukemia, myeloma, a germ cell tumor, a blastoma, a tumor of the central nervous systems, a tumor of the peripheral nervous system, a melanoma, seminoma and Kaposi's sarcoma.

13. The method of claim 11, wherein the nephritis is glomerulonephritis.

14. The method of claim 11, wherein the arthritis is rheumatoid arthritis or osteoarthritis.

* * * * *